US006361972B1

(12) United States Patent
Harrington et al.

(10) Patent No.: US 6,361,972 B1
(45) Date of Patent: Mar. 26, 2002

(54) COMPOSITIONS AND METHODS FOR NON-TARGETED ACTIVATION OF ENDOGENOUS GENES

(75) Inventors: John J. Harrington, Mentor; Bruce Sherf, Spencer; Stephen Rundlett, Chagrin Falls, all of OH (US)

(73) Assignee: Athersys, Inc., Cleveland, OH (US)

( * ) Notice: Subject to any disclaimer, the term of this patent is extended or adjusted under 35 U.S.C. 154(b) by 0 days.

(21) Appl. No.: 09/481,375

(22) Filed: Jan. 10, 2000

Related U.S. Application Data

(60) Division of application No. 09/276,820, filed on Mar. 26, 1999, which is a continuation-in-part of application No. 09/263,814, filed on Mar. 8, 1999, which is a continuation-in-part of application No. 09/253,022, filed on Feb. 19, 1999, now abandoned, which is a continuation-in-part of application No. 09/159,643, filed on Sep. 24, 1998, now abandoned, which is a continuation-in-part of application No. 08/941,223, filed on Sep. 26, 1997, now abandoned.

(51) Int. Cl.[7] ........................ C12N 15/63; C12N 15/85; C12Q 1/68

(52) U.S. Cl. .......................... 435/69.1; 435/6; 435/455; 435/471; 435/325; 435/243; 435/320.1

(58) Field of Search .............................. 435/320.1, 325, 435/455, 463, 6, 69.1, 243, 471, 70.1; 424/93.21; 514/44

(56) References Cited

U.S. PATENT DOCUMENTS

| | | | | |
|---|---|---|---|---|
| 5,641,670 A | * 6/1997 | Treco et al. | ............. | 435/240.2 |
| 5,707,830 A | 1/1998 | Calos | ........................ | 435/69.1 |
| 5,728,551 A | 3/1998 | Devine et al. | ........... | 435/91.41 |
| 5,733,761 A | 3/1998 | Treco et al. | ............. | 435/172.3 |
| 5,783,385 A | 7/1998 | Treco et al. | ................... | 435/6 |
| 5,789,215 A | 8/1998 | Berns et al. | ............. | 435/172.3 |
| 5,830,698 A | 11/1998 | Reff et al. | ................. | 435/69.1 |
| 5,843,772 A | 12/1998 | Devine et al. | ........... | 435/320.1 |
| 5,912,411 A | * 6/1999 | Bujard et al. | .................. | 800/2 |
| 6,136,566 A | * 10/2000 | Sands et al. | ............... | 435/69.7 |

FOREIGN PATENT DOCUMENTS

| | | |
|---|---|---|
| AU | 71893/94 | 6/1994 |
| EP | 0 742 285 A1 | 11/1996 |
| WO | WO 93/09222 | 5/1993 |
| WO | WO 94/12650 | 6/1994 |
| WO | WO 95/31560 | 11/1995 |
| WO | WO 96/04391 | 2/1996 |
| WO | WO 96/29411 | 9/1996 |
| WO | WO 98/14614 A1 | 4/1998 |
| WO | WO99/07389 A1 | 2/1999 |
| WO | WO 99/15650 A1 | 4/1999 |
| WO | WO 99/50426 | 10/1999 |

OTHER PUBLICATIONS

Chubet et. al.; Vectors for Expression and Secretion of Flag Epitope–Tagged Proteins in Mammalian Cells, 1996, BioTechniques 20: 136–141.*

Schmidt et. al.; The Cytomegalovirus Enhancer: a Pan–Active Control Element in Transgenic Mice; 1990, Molecular and Cellular Biology : 4406–4411.*

<http://www.harcourt.com/dictionary>, Academic Press Online Dictionary fo Science and Technology, accessed by PTO, Jul. 29, 2000.*

Kay, "Gene Therapy", Proc. Natl. Acad. Sci. USA, 94:12744–12746, Nov. 1997.*

Anderson, "Human gene therapy", Nature, 392(Supp.):25–30, Apr. 1998.*

Chu et al., "Retrovirus–mediated gene transfer into human hematopoietic stem cells", J. Mol. Med., 76:184–192, Mar. 1998.*

(List continued on next page.)

*Primary Examiner*—Deborah Crouch
*Assistant Examiner*—Peter Brynovskis
(74) *Attorney, Agent, or Firm*—Shanks & Herbert

(57) ABSTRACT

The present invention is directed generally to activating gene expression or causing over-expression of a gene by recombination methods in situ. The invention also is directed generally to methods for expressing an endogenous gene in a cell at levels higher than those normally found in the cell. In one embodiment of the invention, expression of an endogenous gene is activated or increased following integration into the cell, by non-homologous or illegitimate recombination, of a regulatory sequence that activates expression of the gene. In another embodiment, the expression of the endogenous gene may be further increased by co-integration of one or more amplifiable markers, and selecting for increased copies of the one or more amplifiable markers located on the integrated vector. In another embodiment, the invention is directed to activation of endogenous genes by non-targeted integration of specialized activation vectors, which are provided by the invention, into the genome of a host cell. The invention also provides methods for the identification, activation, isolation, and/or expression of genes undiscoverable by current methods since no target sequence is necessary for integration. The invention also provides methods for isolation of nucleic acid molecules (particularly cDNA molecules) encoding a variety of proteins, including transmembrane proteins, and for isolation of cells expressing such transmembrane proteins which may be heterologous transmembrane proteins. The invention also is directed to isolated genes, gene products, nucleic acid molecules, to compositions comprising such genes, gene products and nucleic acid molecules, and to vectors and host cells comprising such genes and nucleic acid molecules, that may be used in a variety of therapeutic and diagnostic applications. Thus, by the present invention, endogenous genes, including those associated with human disease and development, may be activated and isolated without prior knowledge of the sequence, structure, function, or expression profile of the genes.

58 Claims, 62 Drawing Sheets

OTHER PUBLICATIONS

Havenga et al., "Retroviral stem cell gene therapy", Stem Cells, 15:162–179, 1997.*

Capecchi, "Targeted gene replacement", Sci. Am., 270(3):52–59, Mar. 1994.*

Barker, C.S., et al., "Activation of the Prolactin Receptor Gene by Promoter Insertion in a Moloney Murine Leukemia Virus–Induced Rat Thymoma," *J. Virol.* 66(11):6763–6768 (1992).

Black, A.C., et al., "HTLV–II Rex Binding and Activity Requires an Intact Splice Donor Site and a Specific RNA Secondary Structure," *AIDS Res. & Human Retroviruses* 8:870 (1992).

Brikun, I., et al., "Analysis of CRP–CytR Interactions at the *Escherichia coli* udp Promoter," *J. Bacteriology* 178(6):1614–1622 (Mar. 1996).

Buckler, A.J., et al., "Exon amplification: A strategy to isolate mammalian genes based on RNA spicing," *Proc. Natl. Acad. Sci. USA* 88:4005–4009 (1991).

Butturini, A., et al., "Oncogenes in Human Leukemias," *Acta Haematologica* 78(suppl. 1):2–10 (1987).

Butturini, A., and Gale, R.P., "Oncogenes and Human Leukemias," *Intl. J. Cell Cloning* 6(1):2–24 (1988).

Charkrabory, A.K., et al., "Transforming function of protoras genes depends on heterologous promoters and is enhanced by specific point mutations," *Proc. Natl. Sci. USA* 88:2217–2221 (1991).

Chang, W., et al., "Enrichment of Insertional Mutants Following Retrovirus Gene Trap Selection," *Virol.* 193:737–747 (1993).

Chow, W.–Y., and Berg, D.E., "In5tac1, a derivative of transposon Tn5 that generates conditional mutations," *Proc. Natl. Acad. Sci. USA* 85:6468–6472 (1988).

Church, D.M., et al., "Isolation of genes from complex sources of mammalian genomic DNA using exon amplification," *Nature Genetics* 6:98–105 (1994).

Crabb, B.S., and Cowman, A.F., "Characterization of promoters and stable transfection by homologous and nonhomologous recombination in *Plasmodium falciparum,*" *Proc. Natl. Acad. Sci. USA* 93:7289–7294 (Jul. 1996).

Datson, N.A., et al., "Specific isoloation of 3'–terminal exons of human genes by exon trapping," *Nucl. Acids Res.* 22(20):4148–4153 (1994).

Datson, N.A., et al., "Scanning for genes in large genomic regions: cosmid–based exon trapping of multiple exons in a single product," *Nucl. Acids Res.* 24:1105–1111 (Mar. 1996).

De Benedetti, A., and Rhoads, R.E., "A novel BK virusbased episomal vector for expression of foreign gene in mammalian cells," *Nucl. Acids Res.* 19:1925–1931 (1991).

Dickson, C., et al., "Tumorigenesis by Mouse Mammary Tumor Virus: Proviral Activation of a Cellular Gene in the Common Integration Region int–2," *Cell* 37:529–536 (1984).

Dostatni, N., et al., "Use of Retroviral Vectors for Mapping of Splice Sites in Cottontail Rabbit Papillomavirus," *J. Gen. Virol.* 69:3093–3100 (1988).

Duesberg, P.H., et al., "Cancer Genes by Non–Homologous Recombination," In: *Boudaries between Promotion and Progression during Carcinogenesis*, Sudilovsky, O., et al., eds., Plenum Press, New York, NY, pp. 197–211 (1991).

Duyk, G.M., et al., "Exon trapping: A genetic screen to identify candidate transcribed sequences in cloned mammalian genomic DNA," *Proc. Natl. Acad. Sci. USA* 87:8995–8999 (1990).

Frankel, W., et al., "Retroviral insertional mutagenesis of a target allele in a heterozygous murine cell line," *Proc. Natl. Acad. Sci. USA* 82:6660–6604 (1985).

Fujisawa, J.–I., et al., "Functional activation of the long terminal repeat of human T–cell leukemia virus type I by a trans–acting factor," *Proc. Natl. Acad. Sci. USA* 82:2277–2281 (1985).

Fung, Y.–K.T., et al., "Activation of the Cellular Oncogene c–erbB by LTR Insertion: Molecular Basis for Induction of Erythroblastosis by Avian Leukosis Virus," *Cell* 33:357–368 (1983).

Goff, S.P., "Gene Isolation by Retroviral Tagging," *Meth. Enzymology* 152:469–481 (1987).

Hayward, W.S., et al., "Activation of a cellular onc gene by promoter insertion in ALV–induced lymphoid leukosis," *Nature* 290:475–480 (1981).

Jackson, I.J., "A reappraisal of non–consensus mRNA splice sites," *Nucl. Acids Res.* 19(14):3795–3798 (1991).

Joshi, S., "A Putative Approach for Cloning Silent' Genes Using Retroviral Vectors," *Med. Hypoth.* 36:242–245 (1991).

Joyner, A.L., "Gene Targeting and Gene Trap Screens Using Embryonic Stem Cells: New Approaches to Mammalian Development," *BioEssays* 13:649–656 (1991).

Junejo, F., et al., "Sequence analysis of the herpes simplex virus type 1 strain 17 variants 1704, 1705 and 1706 with respect to their origin and effect on the latency–associated transcript sequence," *J. Gen. Virol.* 72:2311–2315 (1991).

King, W., et al., "Insertion Mutagenesis of Embryonal Carcinoma Cells by Retroviruses," *Science* 228:554–558 (1985).

Kreissig, S., et al., "Expression of peptides encoded by exons in cloned mammalian DNA," *Nucl. Acids Res.* 24:4358–4359 (Nov. 1996).

Lemay, G., and Jolicoeur, P., "Rearrangement of a DNA sequence homologous to a cell–virus junction fragment in several Moloney murine leukemia virus–induced rat thymomas," *Proc. Natl. Acad. Sci. USA* 81:38–42 (1984).

Liang, Y., et al., "Effects of Alternate RNA Splicing on Glucokinase Isoform Activities in the Pancreatic Islet, Liver, and Pituitary," *J. Biol. Chem.* 266(11):6999–7007 (1991).

Lih, C.–J., et al., "Rapid identification and isolation of transcriptionally active regions from mouse genomes," *Gene* 164:289–294 (1995).

Liu, Z., et al., "The E6 Gene of Human Papillomavirus Type 16 Is Sufficient for Transformation of Baby Rat Kidney Cells in Cotransfection with Activated Ha–ras," *Virology* 201:388–396 (1994).

Mölders, H., et al., "Integration of transfected LTR sequences into the c–raf proto–oncogene: activation by promoter insertion," *EMBO J.* 4(3):693–698 (1985).

Moore, R., et al.. "Sequence, Topography and protein coding potential of mous int–2: a putative oncogene activated by mous mammary turmour virus," *EMBO J.* 5(5):919–924 (1986).

Müller, R., and Müller, D., "Co–transfection of normal NIH/3T3 DNA and retroval LTR sequences: a novel strategy for the detection of potential c–onc genes," *EMBO J.* 3(5):1121–1127 (1984).

Muth, K., et al., "Disruption of Genes Regulated During Hematopoietic Differentiation of Mouse Embryonic Stem Cells," *Develop. Dynamics* 212:277–283 (Jun. 1998).

Neel, B.G., et al., "Molecular Analysis of the c–myc Locus in Normal Tissue and in Avian Leukosis Virus–Induced Lymphomas," *J. Virol.* 44(1):158–166 (1982).
Nicolas, J.–F., and Rubenstein, J.L.R., "Retroviral Vectors," In: *Vectors: A Survey of Molecular Cloning Vectors and Their Uses*, Rodriguez, R.L., et al., eds., Butterworths Publs., Stoneham, MA, pp. 493–513 (1988).
Nilsen, T.W., et al., "c–erbB Activation in ALV–Induced Erythroblastosis: Novel RNA Processing and Promoter Insertion Result in Expression of an Amino–Truncated EGF Receptor," *Cell* 41:719–726 (1985).
Niwa, H., et al., "An Efficient Gene–Trap Method Using Poly A Trap Vectors and Characterization of Gene–Trap Events," *J. Biochem.* 113:343–349 (1993).
Nottenburg, C., and Varmus, H.E., "Features of the Chicken c–myc Gene That Influence the Structure of c–myc RNA in Normal Cells and Bursal Lymphomas," *Mol. Cell. Biol.* 6(8):2800–2806 (1986).
Nouvel, P., "The mammalian genome shaping activity of reverse transcriptase," *Genetica* 93:191–201 (1994).
Nusse, R., "The activation of cellular oncogenes by retroviral insertion," *Trends in Genetics* 2:244–247 (1986).
Nusse, R., and Berns, A., "Cellular Oncogene Activation by Insertion of Retroviral DNA; Genes Identified by Provirus Tagging," In: *Cellular Oncogenes Activation*, Klein, G., ed., Marcel Dekker, Inc., New York, NY, pp. 95–119 (1988).
Payne, G.S., et al., "Multiple arrangements of viral DNA and an activated host oncogene in bursal lymphomas," *Nature* 295:209–215 (1982).
Peters, G., et al., "Tumorigenesis by Mouse Mammary Tumor Virus: Evidence for a Common Region for Provirus Integration in Mammary Tumors," *Cell* 33:369–377 (1983).
Petitclerc, D., et al., "The effect of various introns and transcription terminators on the efficiency of expression vectors in various cultured cell lines and in the mammary gland of transgenic mice," *J. Biotechnol.* 40:169–178 (1995).
Reinhart, T.A., et al., "RNA Splice Site Utilization by Simian Immunodeficiency Viruses Derived from Sooty Mangabey Monkeys," *Virology* 224:338–344 (Oct. 1, 1996).
Robinson, W.S., "Molecular Events in the Pathogenesis of Hepadnavirus–Associated Hepatocellular Carcinoma," *Annu. Rev. Med.* 45:297–323 (1994).
Salminen, M., et al., "Efficient Poly A Trap Approach Allows the Capture of Genes Specifically Active in Differentiated Embryonic Stem Cells and in Mouse Embryos," *Develop. Dynamics* 212:326–333 (Jun. 1998).
Segal, D., et al., "Genetic Transformation of Drosophila Cells in Culture by P Element–Mediated Transposition," *Somatic Cell and Mol. Genetics* 22(2):159–165 (Mar. 1996).
Shen–Ong, G.L.C., et al., "Activation of the c–myb Locus by Viral Insertional Mutagenesis in Plasmacytoid Lymphosarcomas," *Science* 226:1077–1080 (1984).
Shen–Ong, G.L.C., et al., "Two Modes of c–myb Activation in Virus–Induced Mouse Myeloid Tumors," *Mol. Cell. Biol.* 6(2):380–392 (1986).
Shin, S., and Steffen, D.L., "Frequent activation of the lck gene by promoter insertion and aberrant splicing in murine leukemia virus–induced rat lymphomas," *Oncogene* 8:141–149 (1993).
Simpson, K., et al., "Stable Episomal Maintenance of Yeast Artificial Chromosomes in Human Cells," *Mol. Cell. Biol.* 16:5117–5126 (Sep. 1996).
Stary, A., and Sarasin, A., "Simian virus 40 (SV40) large T antigen–dependent amplification of an Epstein–Barr virus–SV40 hybrid shuttle vector integrated into the human HeLa cell genome," *J. Gen. Virol.* 73:1679–1685 (1992).
Steffen, D., "Proviruses are adjacent to c–myc in some murine leukemia virus–induced lymphomas," *Proc. Natl. Acad. Sci. USA* 81:2097–2101 (1984).
Sun, T.–Q., et al., "Human artificial episomal chromosomes for cloning large DNA fragments in human cells," *Nature Genetics* 8:33–41 (1994).
Takami, Y., et al., "Cloning and Characterization of Human Papillomavirus Type 52 From Cervical Carcinoma in Indonesia," *Int. J. Cancer* 48:516–522 (1991).
Tashiro, S., et al, "Identification of illegitimate recombination hot spot of the retinoic acid receptor alpha gene involved in 15;17 chromosomal translocation of acute promyelocytic leukemia," *Oncogene* 9:1939–1945 (1994).
Tsichlis, P.N., et al., "A common region for proviral DNA integration in MoMuLV–induced rat thymic lymphomas," *Nature* 302:445–449 (1983).
Unger, R.E., et al., "Simian Immunodeficiency Virus (SIVmac) Exhibits Complex Splicing for tat. rev. and env mRNA," *Virology* 182:177–185 (1991).
van Ooyen, A., and Nusse, R., "Structure and Nucleotide Sequence of the Putative Mammary Oncogene int–1; Proviral Insertions Leave the Protein–Encoding Domain Intact," *Cell* 39:233–240 (1984).
Voss, A.K., et al., "Efficiency Assessment of the Gene Trap Approach," *Develop. Dynamics* 212:171–180 (Jun. 1998).
Westphal, E.M., et al., "A System for Shuttling 200–kb BAC/PAC Clones into Human Cells: Stable Extrachromosomal Persistence and Long–Term Ectopic Gene Activation," *Human Gene Ther.* 9:1863–1873 (Sep. 1998).
Xiong, J.–W., et al., "Large–Scale Screening for Developmental Genes in Embryonic Stem Cells and Embryoid Bodies Using Retroviral Entrapment Vectors," *Develop. Dynamics* 212:181–197 (Jun. 1998).
Zhou, H., and Duesberg, P.H., "A retroviral promoter is sufficient to convert proto–src to a transforming gene that is distinct from the src gene of Rous sarcoma virus," *Proc. Natl. Acad. Sci. USA* 87:9128–9132 (1990).
Dialog File 351, Derwent WPI English language abstract for FR 2 707 091.
Drug Discovery News, "Lexicon Genetics, Inc.," *Genetic Engin. News* 19:35 (Mar. 1999).

* cited by examiner

5′ AGATCTTCAATATTGGCCATTAGCCATATTATTCATTGGTTATATAGCATAAATC
AATATTGGCTATTGGCCATTGCATA
CGTTGTATCTATATCATAATATGTACATTTATATTGGCTCATGTCCAATATGACCG
CCATGTTGGCATTGATTATTGACT
AGTTATTAATAGTAATCAATTACGGGGTCATTAGTTCATAGCCCATATATGGAGT
TCCGCGTTACATAACTTACGGTAAA
TGGCCCGCCTGGCTGACCGCCCAACGACCCCCGCCCATTGACGTCAATAATGACG
TATGTTCCCATAGTAACGCCAATAG
GGACTTTCCATTGACGTCAATGGGTGGAGTATTTACGGTAAACTGCCCACTTGGC
AGTACATCAAGTGTATCATATGCCA
AGTCCGCCCCCTATTGACGTCAATGACGGTAAATGGCCCGCCTGGCATTATGCCC
AGTACATGACCTTACGGGACTTTCC
TACTTGGCAGTACATCTACGTATTAGTCATCGCTATTACCATGGTGATGCGGTTTT
GGCAGTACACCAATGGGCGTGGAT
AGCGGTTTGACTCACGGGGATTTCCAAGTCTCCACCCCATTGACGTCAATGGGAC
TTTGTTTTGGCACCAAAATCAACGG
GACTTTCCAAAATGTCGTAACAACTGCGATCGCCCGCCCCGTTGACGCAAATGGG
CGGTAGGCGTGTACGGTGGGAGGTC
TATATAAGCAGAGCTCGTTTAGTGAACCGTCAGATCACTAGAAGCTTTATTGCGG
TAGTTTATCACAGTTAAATTGCTAA
CGCAGTCAGTGCTTCTGACACAACAGTCTCGAACTTAAGCTGCAGTGACTCTCTT
AATTAACTCCACCAGTCTCACTTCA
GTTCCTTTTGCCTCCACCAGTCTCACTTCAGTTCCTTTTGCATGAAGAGCTCAGAA
TCAAAAGAGGAAACCAACCCCTAA
GATGAGCTTTCCATGTAAATTTGTAGCCAGCTTCCTTCTGATTTTCAATGTTTCTT
CCAAAGGTGCAGTCTCCAAAGAGA
TTACGAATGCCTTGGAAACCTGGGGTGCCTTGGGTCAGGACATCAACTTGGACAT
TCCTAGTTTTCAAATGAGTGATGAT
ATTGACGATATAAATGGGAAAAAACTTCAGACAAGAAAAAGATTGCACAATTCA
GAAAAGAGAAAGAGACTTTCAAGGA
AAAAGATACATATAAGCTATTTAAAAATGGAACTCTGAAAATTAAGCATCTGAAG
ACCGATGATCAGGATATCTACAAGG
TATCAATATATGATACAAAAGGAAAAAATGTGTTGGAAAAAATATTTGATTTGAA
GATTCAAGAGAGGGTCTCAAAACCA
AAGATCTCCTGGACTTGTATCAACACAACCCTGACCTGTGAGGTAATGAATGGAA
CTGACCCCGAATTAAACCTGTATCA
AGATGGGAAACATCTAAAACTTTCTCAGAGGGTCATCACACACAAGTGGACCACC
AGCCTGAGTGCAAATTCAAGTGCA
CAGCAGGGAACAAAGTCAGCAAGGAATCCAGTGTCGAGCCTGTCAGCTGTCCAG
AGAAAGGGATCCAGGTGAGTAGGGCC
CGATCCTTCTAGAGTCGAGCTCTCTTAAGGTAGCAAGGTTACAAGACAGGTTTAA
GGAGACCAATAGAAACTGGGCTTGT
CGAGACAGAGAAGACTCTTGCGTTTCTGATAGGCACCTATTGGTCTTACGCGGCC
GCGAATTCCAAGCTTGAGTATTCTA
TCGTGTCACCTAAATAACTTGGCGTAATCATGGTCATATCTGTTTCCTGTGTGAA
ATTGTTATCCGCTCACAATTCCACA
CAACATACGAGCCGGAAGCATAAAGTGTAAAGCCTGGGGTGCCTAATGAGTGAC
CTAACTCACATTAATTGCGTTGCGCGATGCTTCCATTTTGTGAGGGTTAATGC-

FIG. 5A.

TTCGAGAAGACATGATAAGATACATTGATGAGTTTGGACAAACCACAACAAGAAT
GCAGTGAAAAAAATGCTTTATTTGTGAAATTTGTGATGCTATTGCTTTATTTGTAA
CCATTATAAGCTGCAATAAACA
AGTTAACAACAACAATTGCATTCATTTTATGTTTCAGGTTCAGGGGGAGATGTGG
GAGGTTTTTTAAAGCAAGTAAAACC
TCTACAAATGTGGTAAAATCCGATAAGGATCGATTCCGGAGCCTGAATGGCGAAT
GGACGCGCCCTGTAGCGGCGCATTA
AGCGCGGCGGGTGTGGTGGTTACGCGCACGTGACCGCTACACTTGCCAGCGCCC
TAGCGCCCGCTCCTTTCGCTTTCTTC
CCTTCCTTTCTCGCCACGTTCGCCGGCTTTCCCCGTCAAGCTCTAAATCGGGGG
TCCCTTTAGGGTTCCGATTTAGTGC
TTTACGGCACCTCGACCCCAAAAAACTTGATTAGGGTGATGGTTCACGTAGTGGG
CCATCGCCCTGATAGACGGTTTTTC
GCCCTTTGACGTTGGAGTCCACGTTCTTTAATAGTGGACTCTTGTTCCAAACTGG
AACAACACTCAACCCTATCTCGGTC
TATTCTTTTGATTTATAAGGGATTTTGCCGATTTCGGCCTATTGGTTAAAAAATGA
GCTGATTTAACAAAAATTTAACGC
GAATTTTAACAAAATATTAACGCTTACAATTTCGCCTGTGTACCTTCTGAGGCGG
AAAGAACCAGCTGTGGAATGTGTGT
CAGTTAGGGTGTGGAAAGTCCCCAGGCTCCCCAGCAGGCAGAAGTATGCAAAGC
ATGCATCTCAATTAGTCAGCAACCAG
GTGTGGAAAGTCCCCAGGCTCCCCAGCAGGCAGAAGTATGCAAAGCATGCATCT
CAATTAGTCAGCAACCATAGTCCCGC
CCCTAACTCCGCCCATCCCGCCCCTAACTCCGCCCAGTTCCGCCCATTCTCCGCC
CCATGGCTGACTAATTTTTTTTATT
TATGCAGAGGCCGAGGCCGCCTCGGCCTCTGAGCTATTCCAGAAGTAGTGAGGA
GGCTTTTTTGGAGGCCTAGGCTTTTG
CAAAAAGCTTGATTCTTCTGACACAACAGTCTCGAACTTAAGGCTAGAGCCACCA
TGATTGAACAAGATGGATTGCACGC
AGGTTCTCCGGCCGCTTGGGTGGAGAGGCTATTCGGCTATGACTGGGCACAACAC
ACAATCGGCTGCTCTGATGCCGCCG
TGTTCCGGCTGTCAGCGCAGGGGCGCCCGGTTCTTTTTGTCAAGACCGACCTGTC
CGGTGCCCTGAATGAACTGCAGGAC
GAGGCAGCGCGGCTATCGTGGCTGGCCACGACGGGCGTTCCTTGCGCAGCTGTG
CTCGACGTTGTCACTGAAGCGGGAAG
GGACTGGCTGCTATTGGGCGAAGTGCCGGGGCAGGATCTCCTGTCATCTCACCTT
GCTCCTGCCGAGAAAGTATCCATCA
TGGCTGATGCAATGCGGCGGCTGCATACGCTTGATCCGGCTACCTGCCCATTCGA
CCACCAATGCGAAACATCGCATCGAG
CGAGCACGTACTCGGATGGAAGCCGGTCTTGTCGATCAGGATGATCTGGACGAA
GAGCATCAGGGGCTCGCGCCAGCCGA
ACTGTTCGCCAGGCTCAAGGCGCGCATGCCCGACGGCGAGGATCTCGTCGTGAC
CCATGGCGATGCCTGCTTGCCGAATA
TCATGGTGGAAAATGGCCGCTTTTCTGGATTCATCGACTGTGGCCGGCTGGGTGT
GGCGGACCGCTATCAGGACATAGCG
TTGGCTACCCGTGATATTGCTGAAGAGCTTGGCGGCGAATGGGCTGACCGCTTCC
TCGTGCTTTACGGTATCGCCGCTCC
CGATTCGCAGCGCATCGCCTTCTATCGCCTTCTTGACGAGTTCTTCTGAGCGGGA
CTCTGGGGTTCGAAATGACCGACCAAGCGACGCCCAACCTGCCATCACGATGGC-

FIG. 5B.

CGCAATAAAATATCTTTATTTTCATTACATCTGTGTGTTGGTTTTTTGTGTGAAGA
TCCGCGTA-
TGGTGCACTCTCAGTACAATCTGCTCTGATGCCGCATAGTTAAGCCAGCCCCGAC
ACCCGCCAACAC
CCGCTGACGCGCCCTGACGGGCTTGTCTGCTCCCGGCATCCGCTTACAGACAAGC
TGTGACCGTCTCCGGGAGCTGCATG
TGTCAGAGGTTTTCACCGTCATCACCGAAACGCGCGAGACGAAAGGGCCTCGTGA
TACGCCTATTTTTATAGGTTAATGT
CATGATAATAATGGTTTCTTAGACGTCAGGTGGCACTTTTCGGGGAAATGTGCGC
GGAACCCCTATTTGTTTATTTTTCT
AAATACATTCAAATATGTATCCGCTCATGAGACAATAACCCTGATAAATGCTTCA
ATAATATTGAAAAAGGAAGAGTATG
AGTATTCAACATTTCCGTGTCGCCCTTATTCCCTTTTTTGCGGCATTTTGCCTTCC
TGTTTTTGCTCACCCAGAAACGCT
GGTGAAAGTAAAAGATGCTGAAGATCAGTTGGGTGCACGAGTGGGTTACATCGA
ACTGGATCTCAACAGCGGTAAGATCC
TTGAGAGTTTTCGCCCCGAAGAACGTTTTCCAATGATGAGCACTTTTAAAGTTCT
GCTATGTGGCGCGGTATTATCCCGT
ATTGACGCCGGGCAAGAGCAACTCGGTCGCCGCATACACTATTCTCAGAATGACT
TGGTGAGTACTCACCAGTCACAGA
AAAGCATCTTACGGATGGCATGACAGTAAGAGAATTATGCAGTGCTGCCATAACC
ATGAGTGATAACACTGCGGCCAACT
TACTTCTGACAACGATCGGAGGACCGAAGGAGCTAACCGCTTTTTTGCACAACAT
GGGGGATCATGTAACTCGCCTTGAT
CGTTGGGAACCGGAGCTGAATGAAGCCATACCAAACGACGAGCGTGACACCACG
ATGCCTGTAGCAATGGCAACAACGTT
GCGCAAACTATTAACTGGCGAACTACTTACTCTAGCTTCCCGGCAACAATTAATA
GACTGGATGGAGGCGGATAAAGTTG
CAGGACCACTTCTGCGCTCGGCCCTTCCGGCTGGCTGGTTTATTGCTGATAAATC
TGGAGCCGGTGAGCGTGGGTCTCGC
GGTATCATTGCAGCACTGGGGCCAGATGGTAAGCCCTCCCGTATCGTAGTTATCT
ACACGACGGGGAGTCAGGCAACTAT
GGATGAACGAAATAGACAGATCGCTGAGATAGGTGCCTCACTGATTAAGCATTGG
TAACTGTCAGACCAAGTTTACTCAT
ATATACTTTAGATTGATTTAAAACTTCATTTTTAATTTAAAAGGATCTAGGTGAAG
ATCCTTTTTGATAATCTCATGACC
AAAATCCCTTAACGTGATTTTCGTTCCACTGAGCGTCAGACCCCGTAGAAAAGA
TCAAAGGATCTTCTTGAGATCCTTT
TTTTCTGCGCGTAATCTGCTGCTTGCAAACAAAAAAACCACCGCTACCAGCGGTG
GTTTGTTTGCCGGATCAAGAGCTAC
CAACTCTTTTTCCGAAGGTAACTGGCTTCAGCAGAGCGCAGATACCAAATACTGT
CCTTCTAGTGTAGCCGTAGTTAGGC
CACCACTTCAAGAACTCTGTAGCACCGCCTACATACCTCGCTCTGCTAATCCTGT
TACCAGTGGCTGCTGCCAGTGGCGA
TAAGTCGTGTCTTACCGGGTTGGACTCAAGACGATAGTTACCGGATAAGGCGCAG
CGGTCGGGCTGAACGGGGGGTTCGT
GCACACAGCCCAGCTTGGAGCGAACGACCTACACCGAACTGAGATACCTACAGC
GTGAGCTATGAGAAAGCGCCACGCTT
CCCGAAGGGAGAAAGGCGGACAGGTATCCGGTAAGCGGCAGGGTCGGAACAGG-

FIG. 5C.

AGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGG
GGCGGAGCCTATGGAAAAACGCCAGCAACGCGGCCTTTTTACGGTTCCTGGCCTT
TTGCTGGCCTTTTGCTCACATGGCT
CGAC3′

FIG. 5D.

5'AGATCTTCAATATTGGCCATTAGCCATATTATTCATTGGTTATATAGCATAAATC
AATATTGGCTATTGGCCATTGCAT
ACGTTGTATCTATATCATAATATGTACATTTATATTGGCTCATGTCCAATATGACC
GCCATGTTGGCATTGATTATTGAC
TAGTTATTAATAGTAATCAATTACGGGGTCATTAGTTCATAGCCCATATATGGAC
TTCCGCGTTACATAACTTACGGTAA
ATGGCCCGCCTGGCTGACCGCCCAACGACCCCCGCCCATTGACGTCAATAATGAC
GTATGTTCCCATAGTAACGCCAATA
GGGACTTTCCATTGACGTCAATGGGTGGAGTATTTACGGTAAACTGCCCACTTGG
CAGTACATCAAGTGTATCATATGCC
AAGTCCGCCCCCTATTGACGTCAATGACGGTAAATGGCCCGCCTGGCATTATGCG
CAGTACATGACCTTACGGGACTTTC
CTACTTGGCAGTACATCTACGTATTAGTCATCGCTATTACCATGGTGATGCGGTT
TTGGCAGTACACCAATGGGCGTGGA
TAGCGGTTTGACTCACGGGGATTTCCAAGTCTCCACCCCATTGACGTCAATGGGA
GTTTGTTTTGGCACCAAAATCAACG
GGACTTTCCAAAATGTCGTAACAACTGCGATCGCCCGCCCCGTTGACGCAAATGG
GCGGTAGGCGTGTACGGTGGGAGGT
CTATATAAGCAGAGCTCGTTTAGTGAACCGTCAGATCACTAGAAGCTTTATTGCG
GTAGTTTATCACAGTTAAATTGCTA
ACGCAGTCAGTGCTTCTGACACAACAGTCTCGAACTTAAGCTGCAGTGACTCTCT
TAATTAACTCCACCAGTCTCACTTC
AGTTCCTTTTGCCTCCACCAGTCTCACTTCAGTTCCTTTTGCATGAAGAGCTAGA
ATCAAAAGAGGAAACCAACCCCTA
AGATGAGCTTTCCATGTAAATTTGTAGCCAGCTTCCTTCTGATTTTCAATGTTTCT
TCCAAAGGTGCAGTCTCCAAAGAG
ATTACGAATGCCTTGGAAACCTGGGGTGCCTTGGGTCAGGACATCAACTTGGACA
TTCCTAGTTTTCAAATGAGTGATGA
TATTGACGATATAAAATGGGAAAAAACTTCAGACAAGAAAAAGATTGCACAATTC
AGAAAAGAGAAAGAGACTTTCAAGG
AAAAAGATACATATAAGCTATTTAAAAATGGAACTCTGAAAATTAAGCATCTGAA
GACCGATGATCAGGATATCTACAAG
GTATCAATATATGATACAAAAGGAAAAAATGTGTTGGAAAAAATATTTGATTTGA
AGATTCAAGAGAGGGTCTCAAAACC
AAAGATCTCCTGGACTTGTATCAACACAACCCTGACCTGTGAGGTAATGAATGGA
ACTGACCCCGAATTAAACCTGTATC
AAGATGGGAAACATCTAAAACTTTCTCAGAGGGTCATCACACACAAGTGGACCAC
CAGCCTGAGTGCAAAATTCAAGTGC
ACAGCAGGGAACAAAGTCAGCAAGGAATCCAGTGTCGAGCCTGTCAGCTGTCCA
GAGAAAGGGATCCCAGGTGAGTAGGG
CCCGATCCTTCTAGAGTCGAGCTCTCTTAAGGTAGCAAGGTTACAAGACAGGTTT
AAGGAGACCAATAGAAACTGGGCTT
GTCGAGACAGAGAAGACTCTTGCGTTTCTGATAGGCACCTATTGGTCTTACGCGG
CCGCGAATTCCAAGCTTGAGTATTC
TATCGTGTCACCTAAATAACTTGGCGTAATCATGGTCATATCTGTTTCCTGTGTGA
AATTGTTATCCGCTCACAATTCCA
CACAACATACGAGCCGGAAGCATAAAGTGTAAAGCCTGGGGTGCCTAATGAGTG
AGCTAACTCACATTAATTGCGTTGCG
CGATGCTTCCAATTTTGTGAGGGTTAATGCTTCGAGAAGACATGATAAGATACATT
GATGAGTTTGGACAAACCACAACAAGAATGCAGTGAAAAAAATGCTTTATTTGT-

FIG. 6A.

GAAATTTGTGATGCTATTGCTTTATTTGTAACCATTATAAGCTGCAATAAA
CAAGTTAACAACAACAATTGCATTCATTTTATGTTTCAGGTTCAGGGGGAGATGT
GGGAGGTTTTTTAAAGCAAGTAAA
CCTCTACAAATGTGGTAAAATCCGATAAGGATCGATTCCGGAGCCTGAATGGCGA
ATGGACGCGCCCTGTAGCGGCGCAT
TAAGCGCGGCGGGTGTGGTGGTTACGCGCACGTGACCGCTACACTTGCCAGCGC
CCTAGCGCCCGCTCCTTTCGCTTTCT
TCCCTTCCTTTCTCGCCACGTTCGCCGGCTTTCCCCGTCAAGCTCTAAATCGGGG
GCTCCCTTTAGGGTTCCGATTTAGT
GCTTTACGGCACCTCGACCCCAAAAAACTTGATTAGGGTGATGGTTCACGTAGTG
GGCCATCGCCCTGATAGACGGTTTT
TCGCCCTTTGACGTTGGAGTCCACGTTCTTTAATAGTGGACTCTTGTTCCAAACTG
GAACAACACTCAACCCTATCTCGG
TCTATTCTTTTGATTTATAAGGGATTTTGCCGATTTCGGCCTATTGGTTAAAAAAT
GAGCTGATTTAACAAAAATTTAAC
GCGAATTTTAACAAAATATTAACGCTTACAATTTCGCCTGTGTACCTTCTGAGGC
GGAAAGAACCAGCTGTGGAATGTGT
GTCAGTTAGGGTGTGGAAAGTCCCCAGGCTCCCCAGCAGGCAGAAGTATGCAAA
GCATGCATCTCAATTAGTCAGCAACC
AGGTGTGGAAAGTCCCCAGGCTCCCCAGCAGGCAGAAGTATGCAAAGCATGCAT
CTCAATTAGTCAGCAACCATAGTCCC
GCCCCTAACTCCGCCCATCCCGCCCCTAACTCCGCCCAGTTCCGCCCATTCTCCG
CCCCATGGCTGACTAATTTTTTTTA
TTTATGCAGAGGCCGAGGCCGCCTCGGCCTCTGAGCTATTCCAGAAGTAGTGAGG
AGGCTTTTTTGGAGGCCTAGGCTTT
TGCAAAAAGCTTGATTCTTCTGACACAACAGTCTCGAACTTAAGGCTAGAGCCAC
CATGATTGAACAAGATGGATTGCAC
GCAGGTTCTCCGGCCGCTTGGGTGGAGAGGCTATTCGGCTATGACTGGGCACAAC
AGACAATCGGCTGCTCTGATGCCGC
CGTGTTCCGGCTGTCAGCGCAGGGGCGCCCGGTTCTTTTTGTCAAGACCGACCTG
TCCGGTGCCCTGAATGAACTGCAGG
ACGAGGCAGCGCGGCTATCGTGGCTGGCCACGACGGGCGTTCCTTGCGCAGCTG
TGCTCGACGTTGTCACTGAAGCGGGA
AGGGACTGGCTGCTATTGGGCGAAGTGCCGGGGCAGGATCTCCTGTCATCTCACC
TTGCTCCTGCCGAGAAAGTATCCAT
CATGGCTGATGCAATGCGGCGGCTGCATACGCTTGATCCGGCTACCTGCCCATTC
GACCACCAAGCGAAACATCGCATCG
AGCGAGCACGTACTCGGATGGAAGCCGGTCTTGTCGATCAGGATGATCTGGACG
AAGAGCATCAGGGGCTCGCGCCAGCC
GAACTGTTCGCCAGGCTCAAGGCGCGCATGCCCGACGGCGAGGATCTCGTCGTG
ACCCATGGCGATGCCTGCTTGCCGAA
TATCATGGTGGAAAATGGCCGCTTTTCTGGATTCATCGACTGTGGCCGGCTGGGT
GTGGCGGACCGCTATCAGGACATAGCGTTGGCTACCCGTGATATTGCTGAAGAGC
TTGGCGGCGAATGGGCTGACCGCTTCCTCGTGCTTTACGGTATCGCCGCT
CCCGATTCGCAGCGCATCGCCTTCTATCGCCTTCTTGACGAGTTCTTCTGAGCGG
GACTCTGGGGTTCGAAATGACCGAC
CAAGCGACGCCCAACCTGCCATCACGATGGCCGCAATAAAATATCTTTATTTTCA
TTACATCTGTGTGTTGGTTTTTTGT
GTGAAGATCCGCGTATGGTGCACTCTCAGTACAATCTGCTCTGATGCCGCATAGT
TAAGCCAGCCCCGACACCCGCCAACACCCGCTGACGCGCCCTGACGGGCT-

FIG. 6B.

TGTCTGCTCCCGGCATCCGCTTACAGACAAGCTGTGACCGTCTCCGGGAGCTGCA
TGTGTCAGAGGTTTTCACCGTCATCACCGAAACGCGCGAGACGAAAGGGCCTCGT
GATACGCCTATTTTTATAGGTTAAT
GTCATGATAATAATGGTTTCTTAGACGTCAGGTGGCACTTTTCGGGGAAATGTGC
GCGGAACCCCTATTTGTTTATTTTT
CTAAATACATTCAAATATGTATCCGCTCATGAGACAATAACCCTGATAAATGCTT
CAATAATATTGAAAAAGGAAGAGTA
TGAGTATTCAACATTTCCGTGTCGCCCTTATTCCCTTTTTTGCGGCATTTTGCCTT
CCTGTTTTTGCTCACCCAGAAACG
CTGGTGAAAGTAAAAGATGCTGAAGATCAGTTGGGTGCACGAGTGGGTTACATC
GAACTGGATCTCAACAGCGGTAAGAT
CCTTGAGAGTTTTCGCCCCGAAGAACGTTTTCCAATGATGAGCACTTTTAAAGTT
CTGCTATGTGGCGCGGTATTATCCC
GTATTGACGCCGGGCAAGAGCAACTCGGTCGCCGCATACACTATTCTCAGAATGA
CTTGGTTGAGTACTCACCAGTCACA
GAAAAGCATCTTACGGATGGCATGACAGTAAGAGAATTATGCAGTGCTGCCATAA
CCATGAGTGATAACACTGCGGCCAA
CTTACTTCTGACAACGATCGGAGGACCGAAGGAGCTAACCGCTTTTTTGCACAAC
ATGGGGGATCATGTAACTCGCCTTG
ATCGTTGGGAACCGGAGCTGAATGAAGCCATACCAAACGACGAGCGTGACACCA
CGATGCCTGTAGCAATGGCAACAACG
TTGCGCAAACTATTAACTGGCGAACTACTTACTCTAGCTTCCCGGCAACAATTAA
TAGACTGGATGGAGGCGGATAAAGT
TGCAGGACCACTTCTGCGCTCGGCCCTTCCGGCTGGCTGGTTTATTGCTGATAAA
TCTGGAGCCGGTGAGCGTGGGTCTC
GCGGTATCATTGCAGCACTGGGGCCAGATGGTAAGCCCTCCCGTATCGTAGTTAT
CTACACGACGGGGAGTCAGGCAACT
ATGGATGAACGAAATAGACAGATCGCTGAGATAGGTGCCTCACTGATTAAGCATT
GGTAACTGTCAGACCAAGTTTACTC
ATATATACTTTAGATTGATTTAAAACTTCATTTTTAATTTAAAAGGATCTAGGTGA
AGATCCTTTTTGATAATCTCATGA
CCAAAATCCCTTAACGTGAGTTTTCGTTCCACTGAGCGTCAGACCCCGTAGAAAA
GATCAAAGGATCTTCTTGAGATCCT
TTTTTTCTGCGCGTAATCTGCTGCTTGCAAACAAAAAAACCACCGCTACCAGCGG
TGGTTTGTTTGCCGGATCAAGAGCT
ACCAACTCTTTTTCCGAAGGTAACTGGCTTCAGCAGAGCGCAGATACCAAATACT
GTCCTTCTAGTGTAGCCGTAGTTAG
GCCACCACTTCAAGAACTCTGTAGCACCGCCTACATACCTCGCTCTGCTAATCCT
GTTACCAGTGGCTGCTGCCAGTGGCGATAAGTCGTGTCTTACCGGGTTGGACTCA
AGACGATAGTTACCGGATAAGGCGCAGCGGTCGGGCTGAACGGGGGGTTC
GTGCACACAGCCCAGCTTGGAGCGAACGACCTACACCGAACTGAGATACCTACA
GCGTGAGCTATGAGAAAGCGCCACGC
TTCCCGAAGGGAGAAAGGCGGACAGGTATCCGGTAAGCGGCAGGGTCGGAACAG
GAGAGCGCACGAGGGAGCTTCCAGGG
GGAAACGCCTGGTATCTTTATAGTCCTGTCGGGTTTCGCCACCTCTGACTTGAGC
GTCGATTTTTGTGATGCTCGTCAGG
GGGGCGGAGCCTATGGAAAAACGCCAGCAACGCGGCCTTTTTACGGTTCCTGGC
CTTTTGCTGGCCTTTTGCTCACATGG
CTCGAC3′

FIG. 6C.

5'AGATCTTCAATATTGGCCATTAGCCATATTATTCATTGGTTATATAGCATAAATC
AATATTGGCTATTGGCCATTGCAT
ACGTTGTATCTATATCATAATATGTACATTTATATTGGCTCATGTCCAATATGACC
GCCATGTTGGCATTGATTATTGAC
TAGTTATTAATAGTAATCAATTACGGGGTCATTAGTTCATAGCCCATATATGGAG
TTCCGCGTTACATAACTTACGGTAA
ATGGCCCGCCTGGCTGACCGCCCAACGACCCCCGCCCATTGACGTCAATAATGAC
GTATGTTCCCATAGTAACGCCAATA
GGGACTTTCCATTGACGTCAATGGGTGGAGTATTTACGGTAAACTGCCCACTTGG
CAGTACATCAAGTGTATCATATGCC
AAGTCCGCCCCCTATTGACGTCAATGACGGTAAATGGCCCGCCTGGCATTATGCC
CAGTACATGACCTTACGGGACTTTC
CTACTTGGCAGTACATCTACGTATTAGTCATCGCTATTACCATGGTGATGCGGTT
TTGGCAGTACACCAATGGGCGTGGA
TAGCGGTTTGACTCACGGGGATTTCCAAGTCTCCACCCCATTGACGTCAATGGGA
GTTTGTTTTGGCACCAAAATCAACG
GGACTTTCCAAAATGTCGTAACAACTGCGATCGCCCGCCCCGTTGACGCAAATGG
GCGGTAGGCGTGTACGGTGGGAGGT
CTATATAAGCAGAGCTCGTTTAGTGAACCGTCAGATCACTAGAAGCTTTATTGCG
GTAGTTTATCACAGTTAAATTGCTA
ACGCAGTCAGTGCTTCTGACACAACAGTCTCGAACTTAAGCTGCAGTGACTCTCT
TAATTAACTCCACCAGTCTCACTTC
AGTTCCTTTTGCCTCCACCAGTCTCACTTCAGTTCCTTTTGCATGAAGAGCTCAGA
ATCAAAAGAGGAAACCAACCCCTA
AGATGAGCTTTCCATGTAAATTTGTAGCCAGCTTCCTTCTGATTTTCAATGTTTCT
TCCAAAGGTGCAGTCTCCAAAGAG
ATTACGAATGCCTTGGAAACCTGGGGTGCCTTGGGTCAGGACATCAACTTGGACA
TTCCTAGTTTTCAAATGAGTGATGA
TATTGACGATATAAAATGGGAAAAAACTTCAGACAAGAAAAAGATTGCACAATTC
AGAAAAGAGAAAGAGACTTTCAAGG
AAAAAGATACATATAAGCTATTTAAAAATGGAACTCTGAAAATTAAGCATCTGAA
GACCGATGATCAGGATATCTACAAG
GTATCAATATATGATACAAAAGGAAAAAATGTGTTGGAAAAAATATTTGATTTGA
AGATTCAAGAGAGGGTCTCAAAACC
AAAGATCTCCTGGACTTGTATCAACACAACCCTGACCTGTGAGGTAATGAATGGA
ACTGACCCCGAATTAAACCTGTATC
AAGATGGGAAACATCTAAAACTTTCTCAGAGGGTCATCACACACAAGTGGACCAC
CAGCCTGAGTGCAAAATTCAAGTGC
ACAGCAGGGAACAAAGTCAGCAAGGAATCCAGTGTCGAGCCTGTCAGCTGTCCA
GAGAAAGGGATCCACAGGTGAGTAGG
GCCCGCTCCTTCTAGAGTCGAGCTCTCTTAAGGTAGCAAGGTTACAAGACAGGTT
TAAGGAGACCAATAGAAACTGGGCT
TGTCGAGACAGAGAAGACTCTTGCGTTTCTGATAGGCACCTATTGGTCTTACGCG
GCCGCGAATTCCAAGCTTGAGTATT
CTATCGTGTCACCTAAATAACTTGGCGTAATCATGGTCATATCTGTTTCCTGTGTG
AAATTGTTATCCGCTCACAATTCC
ACACAACATACGAGCCGGAAGCATAAAGTGTAAAGCCTGGGGTGCCTAATGAGT
GAGCTAACTCACATTAATTGCGTTGC
GCGATGCTTCCATTTTGTGAGGGTTAATGCTTCGAGAAGACATGATAAGATACAT
TGATGAGTTTGGACAAACCACAACAAGAATGCAGTGAAAAAAATGC-

FIG. 7A.

TTTATTTGTGAAATTTGTGATG
CTATTGCTTTATTTGTAACCATTATAAGCTGCAATAA
ACAAGTTAACAACAACAATTGCATTCATTTTATGTTTCAGGTTCAGGGGGAGATG
TGGGAGGTTTTTTAAAGCAAGTAAA
ACCTCTACAAATGTGGTAAAATCCGATAAGGATCGATTCCGGAGCCTGAATGGCG
AATGGACGCGCCCTGTAGCGGCGCA
TTAAGCGCGGCGGGTGTGGTGGTTACGCGCACGTGACCGCTACACTTGCCAGCGC
CCTAGCGCCCGCTCCTTTCGCTTTC
TTCCCTTCCTTTCTCGCCACGTTCGCCGGCTTTCCCCGTCAAGCTCTAAATCGGGG
GCTCCCTTTAGGGTTCCGATTTAG
TGCTTTACGGCACCTCGACCCCAAAAAACTTGATTAGGGTGATGGTTCACGTAGT
GGGCCATCGCCCTGATAGACGGTTT
TTCGCCCTTTGACGTTGGAGTCCACGTTCTTTAATAGTGGACTCTTGTTCCAAACT
GGAACAACACTCAACCCTATCTCG
GTCTATTCTTTTGATTTATAAGGGATTTTGCCGATTTCGGCCTATTGGTTAAAAAA
TGAGCTGATTTAACAAAAATTTAA
CGCGAATTTTAACAAAATATTAACGCTTACAATTTCGCCTGTGTACCTTCTGAGG
CGGAAAGAACCAGCTGTGGAATGTG
TGTCAGTTAGGGTGTGGAAAGTCCCCAGGCTCCCCAGCAGGCAGAAGTATGCAA
AGCATGCATCTCAATTAGTCAGCAAC
CAGGTGTGGAAAGTCCCCAGGCTCCCCAGCAGGCAGAAGTATGCAAAGCATGCA
TCTCAATTAGTCAGCAACCATAGTCC
CGCCCCTAACTCCGCCCATCCCGCCCCTAACTCCGCCCAGTTCCGCCCATTCTCC
GCCCCATGGCTGACTAATTTTTTTT
ATTTATGCATGAGGCCGAGGCCGCCTCGGCCTCTGAGCTATTCCAGAAGTAGTGAG
GAGGCTTTTTTGGAGGCCTAGGCTT
TTGCAAAAAGCTTGATTCTTCTGACACAACAGTCTCGAACTTAAGGCTAGAGCCA
CCATGATTGAACAAGATGGATTGCA
CGCAGGTTCTCCGGCCGCTTGGGTGGAGAGGCTATTCGGCTATGACTGGGCACAA
CAGACAATCGGCTGCTCTGATGCCG
CCGTGTTCCGGCTGTCAGCGCAGGGGCGCCCGGTTCTTTTTGTCAAGACCGACCT
GTCCGGTGCCCTGAATGAACTGCAG
GACGAGGCAGCGCGGCTATCGTGGCTGGCCACGACGGGCGTTCCTTGCGCAGCT
GTGCTCGACGTTGTCACTGAAGCGGG
AAGGGACTGGCTGCTATTGGGCGAAGTGCCGGGGCAGGATCTCCTGTCATCTCAC
CTTGCTCCTGCCGAGAAAGTATCCA
TCATGGCTGATGCAATGCGGCGGCTGCATACGCTTGATCCGGCTACCTGCCCATT
CGACCACCAAGCGAAACATCGCATC
GAGCGAGCACGTACTCGGATGGAAGCCGGTCTTGTCGATCAGGATGATCTGGAC
GAAGAGCATCAGGGGCTCGCGCCAGC
CGAACTGTTCGCCAGGCTCAAGGCGCGCATGCCCGACGGCGAGGATCTCGTCGT
GACCCATGGCGATGCCTGCTTGCCGA
ATATCATGGTGGAAAATGGCCGCTTTTCTGGATTCATCGATGTGGCCGGCTGGG
TGTGGCGGACCGCTATCAGGACATA
GCGTTGGCTACCCGTGATATTGCTGAAGAGCTTGGCGGCGAATGGGCTGACCGCT
TCCTCGTGCTTTACGGTATCGCCGC
TCCCGATTCGCAGCGCATCGCCTTCTATCGCCTTCTTGACGAGTTCTTCTGAGCC
GGACTCTGGGGTTCGAAATGACCGA
CCAAGCGACGCCCAACCTGCCATCACGATGGCCGCAATAAAATATCTTTATTTTC
ATTACATCTGTGTGTTGGTTTTTTGTGTGAAGATCCGCGTATGGTGCACTCTC-

FIG. 7B.

AGTACAATCTGCTCTGATGCCGCATAGTTAAGCCAGCCCCGACACCCGCCAA
CACCCGCTGACGCGCCCTGACGGGCTTGTCTGCTCCCGGCATCCGCTTACAGACA
AGCTGTGACCGTCTCCGGGAGCTGC
ATGTGTCAGAGGTTTTCACCGTCATCACCGAAACGCGCGAGACGAAAGGGCCTCG
TGATACGCCTATTTTTATAGGTTAA
TGTCATGATAATAATGGTTTCTTAGACGTCAGGTGGCACTTTTCGGGGAAATGTG
CGCGGAACCCCTATTTGTTTATTTT
TCTAAATACATTCAAATATGTATCCGCTCATGAGACAATAACCCTGATAAATGCT
TCAATAATATTGAAAAAGGAAGAGT
ATGAGTATTCAACATTTCCGTGTCGCCCTTATTCCCTTTTTTGCGGCATTTTGCCT
TCCTGTTTTTGCTCACCCAGAAAC
GCTGGTGAAAGTAAAAGATGCTGAAGATCAGTTGGGTGCACGAGTGGGTTACAT
CGAACTGGATCTCAACAGCGGTAAGA
TCCTTGAGAGTTTTCGCCCCGAAGAACGTTTTCCAATGATGAGCACTTTTAAAGT
TCTGCTATGTGGCGCGGTATTATCC
CGTATTGACGCCGGGCAAGAGCAACTCGGTCGCCGCATACACTATTCTCAGAATG
ACTTGGTTGAGTACTCACCAGTCAC
AGAAAGCATCTTACGGATGGCATGACAGTAAGAGAATTATGCAGTGCTGCCATA
ACCATGAGTGATAACACTGCGGCCA
ACTTACTTCTGACAACGATCGGAGGACCGAAGGAGCTAACCGCTTTTTTGCACAA
CATGGGGGATCATGTAACTCGCCTT
GATCGTTGGGAACCGGAGCTGAATGAAGCCATACCAAACGACGAGCGTGACACC
ACGATGCCTGTAGCAATGGCAACAAC
GTTGCGCAAACTATTAACTGGCGAACTACTTACTCTAGCTTCCCGGCAACAATTA
ATAGACTGGATGGAGGCGGATAAAG
TTGCAGGACCACTTCTGCGCTCGGCCCTTCCGGCTGGCTGGTTTATTGCTGATAA
ATCTGGAGCCGGTGAGCGTGGGTCT
CGCGGTATCATTGCAGCACTGGGGCCAGATGGTAAGCCCTCCCGTATCGTAGTTA
TCTACACGACGGGGAGTCAGGCAAC
TATGGATGAACGAAATAGACAGATCGCTGAGATAGGTGCCTCACTGATTAAGCAT
TGGTAACTGTCAGACCAAGTTTACT
CATATATACTTTAGATTGATTTAAAACTTCATTTTTAATTTAAAAGGATCTAGGTG
AAGATCCTTTTTGATAATCTCATG
ACCAAAATCCCTTAACGTGAGTTTTCGTTCCACTGAGCGTCAGACCCCGTAGAAA
AGATCAAAGGATCTTCTTGAGATCC
TTTTTTTCTGCGCGTAATCTGCTGCTTGCAAACAAAAAAACCACCGCTACCAGCG
GTGGTTTGTTTGCCGGATCAAGAGC
TACCAACTCTTTTTCCGAAGGTAACTGGCTTCAGCAGAGCGCAGATACCAAATAC
TGTCCTTCTAGTGTAGCCGTAGTTA
GGCCACCACTTCAAGAACTCTGTAGCACCGCCTACATACCTCGCTCTGCTAATCC
TGTTACCAGTGGCTGCTGCCAGTGG
CGATAAGTCGTGTCTTACCGGGTTGGACTCAAGACGATAGTTACCGGATAAGGCG
CAGCGGTCGGGCTGAACGGGGGGTT
CGTGCACACAGCCCAGCTTGGAGCGAACGACCTACACCGAACTGAGATACCTAC
AGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGACTTGAG
CGTCGATTTTTGTGATGCTCGTCAG
GGGGGCGGAGCCTATGGAAAAACGCCAGCAACGCGGCCTTTTTACGGTTCCTGG
CCTTTTGCTGGCCTTTTGCTCACATGGCTCGAC3'

FIG. 7C.

AGATCTTCAATATTGGCCATTAGCCATATTATTCATTGGTTATATAGCATAAATCAATATTGG
CTATTGGCCATTGCATACGTTGTATCTATATCATAATATGTACATTTATATTGGCTCATGTCCA
ATATGACCGCCATGTTGGCATTGATTATTGACTAGTTATTAATAGTAATCAATTACGGGGTCA
TTAGTTCATAGCCCATATATGGAGTTCCGCGTTACATAACTTACGGTAAATGGCCCGCCTGGC
TGACCGCCCAACGACCCCCGCCCATTGACGTCAATAATGACGTATGTTCCCATAGTAACGCCA
ATAGGGACTTTCCATTGACGTCAATGGGTGGAGTATTTACGGTAAACTGCCCACTTGGCAGTA
CATCAAGTGTATCATATGCCAAGTCCGCCCCCTATTGACGTCAATGACGGTAAATGGCCCGCC
TGGCATTATGCCCAGTACATGACCTTACGGGACTTTCCTACTTGGCAGTACATCTACGTATTA
GTCATCGCTATTACCATGGTGATGCGGTTTTGGCAGTACACCAATGGGCGTGGATAGCGGTTT
GACTCACGGGGATTTCCAAGTCTCCACCCCATTGACGTCAATGGGAGTTTGTTTTGGCACCAA
AATCAACGGGACTTTCCAAAATGTCGTAACAACTGCGATCGCCCGCCCCGTTGACGCAAATG
GGCGGTAGGCGTGTACGGTGGGAGGTCTATATAAGCAGAGCTCGTTTAGTGAACCGTCAGAT
CACTAGAAGCTTTATTGCGGTAGTTTATCACAGTTAAATTGCTAACGCAGTCAGTGCTTCTGA
CACAACAGTCTCGAACTTAAGCTGCAGTGACTCTCTTAAatccaccatggctacaggtgagtactcgGATCTA
GCGCTATATGCGTTGATGCAATTTCTATGCGCACCCGTTCTCGGAGCACTGTCCGACCGCTTT
GGCCGCCGCCCAGTCCTGCTCGCTTCGCTACTTGGAGCCACTATCGACTACGCGATCATGGCG
ACCACACCCGTCCTGTGGATCCTCTACGCCGGACGCATCGTGGCCGGCATCACCGGCGCCACA
GGTGCGGTTGCTGGCGCCTATATCGCCGACATCACCGATGGGGAAGATCGGGCTCGGCCACTTC
GGGCTCATGAGCGCTTGTTTCGGCTCTCTTAAGGTAGCAGATCCTTGCTAGAGTCGACCAATT
CTCATGTTTGACAGCTTATCATCGCAGATCCTGAGCTTGTATGGTGCACTCTCAGTACAATCT
GCTCTGCTGCCGCATAGTTAAGCCAGTATCTGCTCCCTGCTTGTGTGTTGGAGGTCGCTGAGT
AGTGCGCGAGCAAAATTTAAGCTACAACAAGGCAAGGCTTGACCGACAATTGCATGAAGAAT
CTGCTTAGGGTTAGGCGTTTTGCGCTGCTTCGCGATGTACGGGCCAGATATACGCGTATCTGA
GGGGACTAGGGTGTGTTTAGGCGCCCAGCGGGGCTTCGGTTGTACGCGGTTAGGAGTCCCCTC
AGGATATAGTAGTTTCGCTTTTGCATAGGGAGGGGGAAATGTAGTCTTATGCAATACACTTGT
AGTCTTGCAACATGGTAACGATGAGTTAGCAACATGCCTTACAAGGAGAGAAAAAGCACCGT
GCATGCCGATTGGTGGAAGTAAGGTGGTACGATCGTGCCTTATTAGGAAGGCAACAGACAGG
TCTGACATGGATTGGACGAACCACTGAATTCCGCATTGCAGAGATAATTGTATTTAAGTGCCT
AGCTCGATACAATAAACGCCATTTGACCATTCACCACATTGGTGTGCACCTCCAAGCTGGGTA
CCAGCTGCTAGCCTCGAGACGCGTGATTTCCTTCGAAGCTtgtcatggttggttcgctaaactgcatcgtcgctgtgtc
ccagaacatgggcatcggcaagaacggggacctgccctggccaccgctcaggaatgaattcagatatttccagagaatgaccacaacctcttcagtaga
aggtaaacagaatctggtgattatgggtaagaagacctggttctccattcctgagaagaatcgacctttaaagggtagaattaatttagttctcagcagagaa
ctcaaggaacctccacaaggagctcattttctttccagaagtctagatgatgccttaaaacttactgaacaaccagaattagcaaataaagtagacatggtct
ggatagttggtggcagttctgtttataaggaagccatgaatcacccaggccatcttaaactatttgtgacaaggatcatgcaagactttgaaagtgacacgttt
tttccagaaattgatttggagaaatataaacttctgccagaatacccaggtgttctctctgatgtccaggaggagaaaggcattaagtacaaatttgaagtata
tgagaagaatgattaatCGATCTTAAGTTTAATCTTTCCCGGGGGTACCGTCGACTGCGGCCGCGAATTC
CAAGCTTGAGTATTCTATCGTGTCACCTAAATAACTTGGCGTAATCATGGTCATATCTGTTTCC
TGTGTGAAATTGTTATCCGCTCACAATTCCACACAACATACGAGCCGGAAGCATAAAGTGTA
AAGCCTGGGGTGCCTAATGAGTGAGCTAACTCACATTAATTGCGTTGCGCGATGCTTCCATTT
TGTGAGGGTTAATGCTTCGAGAAGACATGATAAGATACATTGATGAGTTTGGACAAACCACA
ACAAGAATGCAGTGAAAAAAATGCTTTATTTGTGAAATTTGTGATGCTATTGCTTTATTTGTA
ACCATTATAAGCTGCAATAAACAAGTTAACAACAACAATTGCATTCATTTTATGTTTCAGGTT
CAGGGGGAGATGTGGGAGGTTTTTTAAAGCAAGTAAAACCTCTACAAATGTGGTAAAATCCG
ATAAGGATCGATTCCGGAGCCTGAATGGCGAATGGACGCGCCCTGTAGCGGCGCATTAAGCG
CGGCGGGTGTGGTGGTTACGCGCACGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAAATCGG
GGGCTCCCTTTAGGGTTCCGATTTAGTGCTTTACGGCACCTCGACCCCAAAAAACTTGATTAG
GGTGATGGTTCACGTAGTGGGCCATCGCCCTGATAGACGGTTTTTCGCCCTTTGACGTTGGAG
TCCACGTTCTTTAATAGTGGACTCTTGTTCCAAACTGGAACAACACTCAACCCTATCTCGGTC
TATTCTTTTGATTTATAAGGGATTTTGCCGATTTCGGCCTATTGGTTAAAAAATGAGCTGATTT
AACAAAAATTTAACGCGAATTTTAACAAAATATTAACGCTTACAATTTCGCCTGTGTACCTTC
TGAGGCGGAAAGAACCAGCTGTGGAATGTGTGTCAGTTAGGGTGTGGAAAGTCCCCAGGCTC
CCCAGCAGGCAGAAGTATGCAAAGCATGCATCTCAATTAGTCAGCAACCAGGTGTGGAAAGT
CCCCAGGCTCCCCAGCAGGCAGAAGTATGCAAAGCATGCATCTCAATTAGTCAGCAACCATA-

FIG. 14A.

GTCCCGCCCCTAACTCCGCCCATCCCGCCCCTAACTCCGCCCAGTTCCGCCCATTCTCCGCCCC
ATGGCTGACTAATTTTTTTTATTTATGCAGAGGCCGAGGCCGCCTCGGCCTCTGAGCTATTCC
AGAAGTAGTGAGGAGGCTTTTTTGGAGGCCTAGGCTTTTGCAAAAAGCTTGATTCTTCTGACA
CAACAGTCTCGAACTTAAGGCTAGAGCCACCATGATTGAACAAGATGGATTGCACGCAGGTT
CTCCGGCCGCTTGGGTGGAGAGGCTATTCGGCTATGACTGGGCACAACAGACAATCGGCTGC
TCTGATGCCGCCGTGTTCCGGCTGTCAGCGCAGGGGCGCCCGGTTCTTTTTGTCAAGACCGAC
CTGTCCGGTGCCCTGAATGAACTGCAGGACGAGGCAGCGCGGCTATCGTGGCTGGCCACGAC
GGGCGTTCCTTGCGCAGCTGTGCTCGACGTTGTCACTGAAGCGGGAAGGGACTGGCTGCTATT
GGGCGAAGTGCCGGGGCAGGATCTCCTGTCATCTCACCTTGCTCCTGCCGAGAAAGTATCCAT
CATGGCTGATGCAATGCGGCGGCTGCATACGCTTGATCCGGCTACCTGCCCATTCGACCACCA
AGCGAAACATCGCATCGAGCGAGCACGTACTCGGATGGAAGCCGGTCTTGTCGATCAGGATG
ATCTGGACGAAGAGCATCAGGGGCTCGCGCCAGCCGAACTGTTCGCCAGGCTCAAGGCGCGC
ATGCCCGACGGCGAGGATCTCGTCGTGACCCATGGCGATGCCTGCTTGCCGAATATCATGGTG
GAAAATGGCCGCTTTTCTGGATTCATCGACTGTGGCCGGCTGGGTGTGGCGGACCGCTATCAG
GACATAGCGTTGGCTACCCGTGATATTGCTGAAGAGCTTGGCGGCGAATGGGCTGACCGCTTC
CTCGTGCTTTACGGTATCGCCGCTCCCGATTCGCAGCGCATCGCCTTCTATCGCCTTCTTGACG
AGTTCTTCTGAGCGGGACTCTGGGGTTCGAAATGACCGACCAAGCGACGCCCAACCTGCCAT
CACGATGGCCGCAATAAAATATCTTTATTTTCATTACATCTGTGTGTTGGTTTTTTGTGTGAAG
ATCCGCGTATGGTGCCACTCTCAGTACAATCTGCTCTGATGCCGCATAGTTAAGCCAGCCCCGA
CACCCGCCAACACCCGCTGACGCGCCCTGACGGGCTTGTCTGCTCCCGGCATCCGCTTACAGA
CAAGCTGTGACCGTCTCCGGGAGCTGCATGTGTCAGAGGTTTTCACCGTCATCACCGAAACGC
GCGAGACGAAAGGGCCTCGTGATACGCCTATTTTTATAGGTTAATGTCATGATAATAATGGTT
TCTTAGACGTCAGGTGGCACTTTTCGGGGAAATGTGCGCGGAACCCCTATTTGTTTATTTTTCT
AAATACATTCAAATATGTATCCGCTCATGAGACAATAACCCTGATAAATGCTTCAATAATATT
GAAAAAGGAAGAGTATGAGTATTCAACATTTCCGTGTCGCCCTTATTCCCTTTTTTGCGGCAT
TTTGCCTTCCTGTTTTTGCTCACCCAGAAACGCTGGTGAAAGTAAAAGATGCTGAAGATCAGT
TGGGTGCACGAGTGGGTTACATCGAACTGGATCTCAACAGCGGTAAGATCCTTGAGAGTTTTC
GCCCCGAAGAACGTTTTCCAATGATGAGCACTTTTAAAGTTCTGCTATGTGGCGCGGTATTAT
CCCGTATTGACGCCGGGCAAGACCAACTCGGTCGCCGCATACACTATTCTCAGAATGACTTGG
TTGAGTACTCACCAGTCACAGAAAAGCATCTTACGGATGGCATGACAGTAAGAGAATTATGC
AGTGCTGCCATAACCATGAGTGATAACACTGCGGCCAACTTACTTCTGACAACGATCGGAGC
ACCGAAGGAGCTAACCGCTTTTTTGCACAACATGGGGGATCATGTAACTCGCCTTGATCGTTG
GGAACCGGAGCTGAATGAAGCCATACCAAACGACGAGCGTGACACCAGATGCCTGTAGCAA
TGGCAACAACGTTGCGCAAACTATTAACTGGCGAACTACTTACTCTAGCTTCCCGGCAACAAT
TAATAGACTGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCATTGCAGCA
CTGGGGCCAGATGGTAAGCCCTCCCGTATCGTAGTTATCTACACGACGGGGAGTCAGGCAAC
TATGGATGAACGAAATAGACAGATCGCTGAGATAGGTGCCTCACTGATTAAGCATTGGTAAC
TGTCAGACCAAGTTTACTCATATATACTTTAGATTGATTTAAAACTTCATTTTTAATTTAAAAG
GATCTAGGTGAAGATCCTTTTTGATAATCTCATGACCAAAATCCCTTAACGTGAGTTTTCGTT
CCACTGAGCGTCAGACCCCGTAGAAAAGATCAAAGGATCTTCTTGAGATCCTTTTTTTCTGCG
CGTAATCTGCTGCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATACCAAATACTGT
CCTTCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGGGTT
GGACTCAAGACGATAGTTACCGGATAAGGCGCAGCGGTCGGGCTGAACGGGGGGTTCGTGCA
CACAGCCCAGCTTGGAGCGAACGACCTACACCGAACTGAGATACCTACAGCGTGAGCTATGA
GAAAGCGCCACGCTTCCCGAAGGGAGAAAGGCGGACAGGTATCCGGTAAGCGGCAGGGTCG
GAACAGGAGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGGCGGAGCCTA
TGGAAAAACGCCAGCAACGCGGCCTTTTTACGGTTCCTGGCCTTTTGCTGGCCTTTTGCTCAC
ATGGCTCGAC

FIG. 14B.

GATCTTCAATATTGGCCATTAGCCATATTATTCATTGGTTATATAGCATAAATCAATATTGGCT
ATTGGCCATTGCATACGTTGTATCTATATCATAATATGTACATTTATATTGGCTCATGTCCAAT
ATGACCGCCATGTTGGCATTGATTATTGACTAGTTATTAATAGTAATCAATTACGGGGTCATT
AGTTCATAGCCCATATATGGAGTTCCGCGTTACATAACTTACGGTAAATGGCCCGCCTGGCTG
ACCGCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGTACA
TCAAGTGTATCATATGCCAAGTCCGCCCCCTATTGACGTCAATGACGGTAAATGGCCCGCCTG
GCATTATGCCCAGTACATGACCTTACGGGACTTTCCTACTTGGCAGTACATCTACGTATTAGT
CATCGTATTACCATGGTGATGCGGTTTTGGCAGTACACCAATGGGCGTGGATAGCGGTTTGA
CTCACGGGGATTTCCAAGTCTCCACCCCATTGACGTCAATGGGAGTTTGTTTTGGCACCAAAA
TCAACGGGACTTTCCAAAATGTCGTAACAACTGCGATCGCCCGCCCCGTTGACGCAAATGGG
CGGTAGGCGTGTACGGTGGGAGGTCTATATAAGCAGAGCTCGTTTAGTGAACCGTCAGATCA
CTGAATTCTGACGACCTACTGATTAACGGCCATAGAGGCCTCCTGCAGATCACTAGAAGCTTT
ATTGCGGTAGTTTATCACAGTTAAATTGCTAACGCAGTCAGTGCTTCTGACACAACAGTCTCG
AACTTAAGCTGCAGTGACTCTCTTAAatccaccatggctacagGTGAGTACTCGCTACCTTAAGAGAGG
CCTATCTGGCCAGTTAGCAGTCGAAGAAAGAAGTTTAAGAGAGCCGAAACAAGCGCTCATGA
GCCCGAAGTGGCGAGCCCGATCTTCCCCATCGGTGATGTCGGCGATATAGGCGCCAGCAACC
GCACCTGTGGCGCCGGTGATGCCGGCCACGATGCGTCCGGCGTAGAGGATCCACAGGACGGG
TGTGGTCGCCATGATCGCGTAGTCGATAGTGGCTCCAACTAGCGAAGCGAGCAGGACTGGGC
GGCGGCCAAAGCGGTCGGACAGTGCTCCGAGAACGGGTGCGCATAGAAATTGCATCAACGCA
TATAGCGCTAGATCCTTGCTAGAGTCGAGATCTGTCGAGCCATGTGAGCAAAAGGCCAGCAA
AAGGCCAGGAACCGTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCATAGCTCACGCTGTAGGTAT
CTCAGTTCGGTGTAGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAGACACGACTTATCG
CCACTGGCAGCAGCCACTGGTAACAGGATTAGCAGAGCGAGGTATGTAGGCGGTGCTACAGA
GTTCTTGAAGTGGTGGCCTAACTACGGCTACACTAGAAGGACAGTATTTGGTATCTGCGCTCT
GCTGAAGCCAGTTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAAAAGGATCTCAA
GAAGATCCTTTGATCTTTTCTACGGGGTCTGACGCTCAGTGGAACGAAAACTCACGTTAAGGG
ATTTTGGTCATGAGATTATCAAAAAGGATCTTCACCTAGATCCTTTTatcggtgtgaaataccgcacagatgc
gtaaggagaaaataccgcatcaggaaattgtaagcgttaataattcagaagaactcgtcaagaaggcgatagaaggcgatgcgctgcgaatcgggagc
ggcgataccgtaaagcacgaggaagcggtcagcccattcgccgccaagctcttcagcaatatcacgggtagccaacgctatgtcctgatagcggtccgc
cacacccagccggccacagtcgatgaatccagaaaagcggccattttccaccatgatattcggcaagcaggcatg\cgccatgggtcacgacgagatcctc
gccgtcgggcatgctcgccttgagcctggcgaacagttcggctggcgcgagcccctgatgctcttcgtccagatcatcctgatcgacaagaccggcttcca
tccgagtacgtgctcgctcgatgcgatgtttcgcttggtggtcgaatgggcaggtagccggatcaagcgtatgcagccgccgcattgcatcagccatgatg
gatactttctcggcaggagcaaggtgagatgacaggagatcctgccccggcacttcgcccaatagcagccagtcccttcccgcttcagtgacaacgtcga
gcacagctgcgcaaggaacgcccgtcgtggccagccacgatagccgcgctgcctcgtcttgcagttcattcagggcaccggacaggtcggtcttgacaa
aaagaaccgggcgcccctgcgctgacagccggaacacggcggcatcagagcagccgattgtctgttgtgcccagtcatagccgaatagcctctccaccc
aagcggccggagaacctgcgtgcaatccatcttgttcaatcatgcgaaacgatcctcatcctgtctcttgatcagagcttgatcccctgcgccatcagatcct
ggcggcgagaaagccatccagtttactttgcagggcttgtcaaccttaccagatAAAAGTGCTCATCATTGGAAAACGTTCAA
TTcTGAGGCGGAAAGAACCAGCTGTGGAATGTGTGTCAGTTAGGGTGTGGAAAGTCCCCAGG
CTCCCCAGCAGGCAGAAGTATGCAAAGCATGCATCTCAATTAGTCAGCAACCAGGTGTGGAA
AGTCCCCAGGCTCCCCAGCAGGCAGAAGTATGCAAAGCATGCATCTCAATTAGTCAGCAACC
ATAGTCCCGCCCCTAACTCCGCCCATCCCGCCCCTAACTCCGCCCAGTTCCGCCCATTCTCCG
CCCCATGGCTGACTAATTTTTTTTATTTATGCAGAGGCCGAGGCCGCCTCGGCCTCTGAGCTA
TTCCAGAAGTAGTGAGGAGGCTTTTTTGGAGGCCTAGGCTTTTGCAAAAAGCTTGATTCTTCT
GACACAACAGTCTCGAACTTAAGGCTAGAGCCACCATGATTGAACAAGATGGATTGCACGCA
GGTTCTCCGGCCGCTTGGGTGGAGAGGCTATTCGGCTATGACTGGGCACAACAGACAATCGG
CTGCTCTGATGCCGCCGTGTTCCGGCTGTCAGCGCAGGGGCGCCCGGTTCTTTTTGTCAAGAC
CGACCTGTCCGGTGCCCTGAATGAACTGCAGGACGAGGCAGCGCGGCTATCGTGGCTGGCCA
CGACGGGCGTTCCTTGCGCAGCTGTGCTCGACGTTGTCACTGAAGCGGGAAGGGACTGGCTG-

FIG. 15A

CTATTGGGCGAAGTGCCGGGGCAGGATCTCCTGTCATCTCACCTTGCTCCTGCCGAGAAAGTA
TCCATCATGGCTGATGCAATGCGGCGGCTGCATACGCTTGATCCGGCTACCTGCCCATTCGAC
CACCAAGCGAAACATCGCATCGAGCGAGCACGTACTCGGATGGAAGCCGGTCTTGTCGATCA
GGATGATCTGGACGAAGAGCATCAGGGGCTCGCGCCAGCCGAACTGTTCGCCAGGCTCAAGG
CGCGCATGCCCGACGGCGAGGATCTCGTCGTGACCCATGGCGATGCCTGCTTGCCGAATATCA
TGGTGGAAAATGGCCGCTTTTCTGGATTCATCGACTGTGGCCGGCTGGGTGTGGCGGACCGCT
ATCAGGACATAGCGTTGGCTACCCGTGATATTGCTGAAGAGCTTGGCGGCGAATGGGCTGAC
CGCTTCCTCGTGCTTTACGGTATCGCCGCTCCCGATTCGCAGCGCATCGCCTTCTATCGCCTTC
TTGACGAGccaTTCtgatggaggtagCGGCCGCTAACCTGGTTGCTGACTAATTGAGATGCATGCTTT
GCATACTTCTGCCTGCTGGGGAGCCTGGGGACTTTCCACACCCTAACTGACACACATTCCACA
GCTGGTTCTTTCCGCCTCAGAAGGTACACAGGCGAAATTGTAAGCGTTAATATTTTGTTAAAA
TTCGCGTTAAATTTTTGTTAAATCAGCTCATTTTTTAACCAATAGGCCGAAATCGGCAAAATC
CCTTATAAATCAAAAGAATAGACCGAGATAGGGTTGAGTGTTGTTCCAGTTTGGAACAAGAG
TCCACTATTAAAGAACGTGGACTCCAACGTCAAAGGGCGAAAAACCGTCTATCAGGGCGATG
GCCCAC

FIG. 15B.

GATCTTCAATATTGGCCATTAGCCATATTATTCATTGGTTATATAGCATAAATCAATATTGGCT
ATTGGCCATTGCATACGTTGTATCTATATCATAATATGTACATTTATATTGGCTCATGTCCAAT
ATGACCGCCATGTTGGCATTGATTATTGACTAGTTATTAATAGTAATCAATTACGGGGTCATT
AGTTCATAGCCCATATATGGAGTTCCGCGTTACATAACTTACGGTAAATGGCCCGCCTGGCTG
ACCGCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGTACA
TCAAGTGTATCATATGCCAAGTCCGCCCCCTATTGACGTCAATGACGGTAAATGGCCCGCCTG
GCATTATGCCCAGTACATGACCTTACGGGACTTTCCTACTTGGCAGTACATCTACGTATTAGT
CATCGCTATTACCATGGTGATGCGGTTTTGGCAGTACACCAATGGGCGTGGATAGCGGTTTGA
CTCACGGGGATTTCCAAGTCTCCACCCCATTGACGTCAATGGGAGTTTGTTTTGGCACCAAAA
TCAACGGGACTTTCCAAAATGTCGTAACAACTGCGATCGCCCGCCCCGTTGACGCAAATGGG
CGGTAGGCGTGTACGGTGGGAGGTCTATATAAGCAGAGCTcgtttagtgaaccgtCAGATCACTAGAA
GCTTTATTGCGGTAGTTTATCACAGTTAAATTGCTAACGCAGTCAGTGCTTCTGACACAACAG
TCTCGAACTTAAGCTGCAGTGACTCTCTTAAatccaccatggctacagGTGAGTACTCGCTACCTTAAG
AGAGGCCTATCTGGCCAGTTAGCAGTCGAAGAAAGAAGTTTAAGAGAGCCGAAACAAGCGCT
CATGAGCCCGAAGTGGCGAGCCCGATCTTCCCCATCGGTGATGTCGGCGATATAGGCGCCAG
CAACCGCACCTGTGGCGCCGGTGATGCCGGCCACGATGCGTCCGGCGTAGAGGATCCACAGG
ACGGGTGTGGTCGCCATGATCGCGTAGTCGATAGTGGCTCCAAGTAGCGAAGCGAGCAGGAC
TGGGCGGCGGCCAAAGCGGTCGGACAGTGCTCCGAGAACGGGTGCGCATAGAAATTGCATCA
ACGCATATAGCGCTAGATCCTTGCTAGAGTCGAGATCTGTCGAGCCATGTGAGCAAAAGGCC
AGCAAAAGGCCAGGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCACGAACCCCCCGTT
CAGCCCGACCGCTGCGCCTTATCCGGTAACTATCGTCTTGAGTCCAACCCGGTAAGACACGAC
TTATCGCCACTGGCAGCAGCCACTGGTAACAGGATTAGCAGAGCGAGTATGTAGGCGGTGC
TACAGAGTTCTTGAAGTGGTGGCCTAACTACGGCTACACTAGAAGGACACTATTTGGTATCTG
CGCTCTGCTGAAGCCAGTTACCTTCGGAAAAAGAGTTGGTAGCTCTTGATCCGGCAAACAAA
CCACCGCTGGTAGCGGTGGTTTTTTTGTTTGCAAGCAGCAGATTACGCGGAGAAAAAAAGGA
TCTCAAGAAGATCCTTTGATCTTTTCTACGGGGTCTGACGCTCAGTGGAACGAAAACTCACGT
TAAGGGATTTTGGTCATGAGATTATCAAAAAGGATCTTCACCTAGATCCTTTTatcggtgtgaaataccg
cacagatgcgtaaggagaaaataccgcatcaggaaattgtaagcgttaataattcagaagaactcgtcaagaaggcgatagaaggcgatgcgctgcgaa
tcgggagcggcgataccgtaaagcacgaggaagcggtcagcccattcgccgccaagctcttcagcaatatcacgggtagccaacgctatgtcctgatag
cggtccgccacacccagccggccacagtcgatgaatccagaaaagcggccattttccaccatgatattcggcaagcaggcatcgccatgggtcacgacg
agatcctcgccgtcgggcatgctcgccttgagcctggcgaacagttcggctggcgcgagcccctgatgctcttcgtccagatcatcctgatcgacaagacc
ggcttccatccgagtacgtgctcgctcgatgcgatgtttcgcttggtggtcgaatgggcaggtagccggatcaagcgtatgcagccgccgcattgcatcag
ccatgatggatactttctcggcaggagcaaggtgagatgacaggagatcctgccccggcacttcgcccaatagcagccagtcccttcccgcttcagtgaca
acgtcgagcacagctgcgcaaggaacgcccgtcgtggccagccacgatagccgcgctgcctcgtcttgcagttcattcagggcaccggacaggtcggtc
ttgacaaaaagaaccggcgcccctgcgctgacagccggaacacggcggcatcagagcagccgattgtctgttgtgcccagtcatagccgaatagcctc
tccacccaagcggccggagaacctgcgtgcaatccatcttgttcaatcatgcgaaacgatcctcatcctgtctcttgatcagagcttgatcccctgcgccatc
agatccttggcggcgagaaagccatccagtttactttgcagggcttgtcaaccttaccagatAAAAGTGCTCATCATTGGAAAACGT
TCAATTcTGAGGCGGAAAGAACCAGCTGTGGAATGTGTGTCAGTTAGGGTGTGGAAAGTCCCC
AGGCTCCCCAGCAGGCAGAAGTATGCAAAGCATGCATCTCAATTAGTCAGCAACCAGGTGTG
GAAAGTCCCCAGGCTCCCCAGCAGGCAGAAGTATGCAAAGCATGCATCTCAATTAGTCAGCA
ACCATAGTCCCGCCCCTAACTCCGCCCATCCCGCCCCTAACTCCGCCCAGTTCCGCCCATTCT
CCGCCCCATGGCTGACTAATTTTTTTTATTTATGCAGAGGCCGAGGCCTCGGCCTCTGAG
CTATTCCAGAAGTAGTGAGGAGGCTTTTTTGGAGGCCTAGGCTTTTGCAAAAAGCTTGATTCT
TCTGACACAACAGTCTCGAACTTAAGGCTAGAGCCACCATGATTGAACAAGATGGATTGCAC
GCAGGTTCTCCGGCCGCTTGGGTGGAGAGGCTATTCGGCTATGACTGGGCACAACAGACAAT
CGGCTGCTCTGATGCCGCCGTGTTCCGGCTGTCAGCGCAGGGGCGCCCGGTTCTTTTTGTCAA
GACCGACCTGTCCGGTGCCCTGAATGAACTGCAGGACGAGGCAGCGCGGCTATCGTGGCTGG
CCACGACGGGCGTTCCTTGCGCAGCTGTGCTCGACGTTGTCACTGAAGCGGGAAGGGACTGG
CTGCTATTGGGCGAAGTGCCGGGGCAGGATCTCCTGTCATCTCACCTTGCTCCTGCCGAGAAA-

FIG. 16A.

GTATCCATCATGGCTGATGCAATGCGGCGGCTGCATACGCTTGATCCGGCTACCTGCCCATTC
GACCACCAAGCGAAACATCGCATCGAGCGAGCACGTACTCGGATGGAAGCCGGTCTTGTCGA
TCAGGATGATCTGGACGAAGAGCATCAGGGGCTCGCGCCAGCCGAACTGTTCGCCAGGCTCA
AGGCGCGCATGCCCGACGGCGAGGATCTCGTCGTGACCCATGGCGATGCCTGCTTGCCGAAT
ATCATGGTGGAAAATGGCCGCTTTTCTGGATTCATCGACTGTGGCCGGCTGGGTGTGGCGGAC
CGCTATCAGGACATAGCGTTGGCTACCCGTGATATTGCTGAAGAGCTTGGCGGCGAATGGGC
TGACCGCTTCCTCGTGCTTTACGGTATCGCCGCTCCCGATTCGCAGCGCATCGCCTTCTATCGC
CTTCTTGACGAGccaTTCtgctggatggCTacAGGTcgcagccctggcgtcgtgattagtgatgatgaaccaggttatgaccttgattta
ttttgcatacctaatcattatgctgaggatttggaaagggtgtttattcctcatggactaattatggacaggactgaacgtcttgctcgagatgtgatgaaggag
atgggaggccatcacattgtagcccctctgtgtgctcaaggggggctataaattctttgctgacctgctggattacatcaaagcactgaatagaaatagtgata
gatccattcctatgactgtagattttatcagactgaagagctattgtaatgaccagtcaacaggggacataaaagtaattggtggagatgatctctcaacttta
actggaaagaatgtcttgattgtggaagatataaattgacactggcaaaacaatgcagactttgctttccttggtcaggcagtataatccaaagatggtcaagg
tcgcaagcttgctggtgaaaaggaccccacgaagtgttggatataagccagactttgttggatttgaaattccagacaagtttgttgtaggatatgcccttga
ctataatgaaf\tacttcagggatttgaatcatgtttgtgtcattagtgaaactggaaaagcaaaatacaaagcctaaGCGGCCGCTAACCTGGT
TGCTGACTAATTGAGATGCATGCTTTGCATACTTCTGCCTGCTGGGGAGCCTGGGGACTTTCC
ACACCCTAACTGACACACATTCCACAGCTGGTTCTTTCCGCCTCAGAAGGTACACAGGCGAAA
TTGTAAGCGTTAATATTTTGTTAAAATTCGCGTTAAATTTTTGTTAAATCATGCTCATTTTTTAA
CCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGG
CGAAAAACCGTCTATCAGGGCGATGGCCCAC

FIG. 16B.

FIG. 25A.
FIG. 25B.
FIG. 25C.
FIG. 25D.
DNA Binding Domain
S/D
DNA Binding Domain
S/D
Neo
Activation Domain
S/D
Activation Domain
S/D
Neo

CACCTAAATTGTAAGCGTTAATATTTTGTTAAAATTCGCGTTAAATTTTTGT
TAAATCAGCTCATTTTTTAACCAATAGGCCGAAATCGGCAAAATCCCTTAT
AAATCAAAAGAATAGACCGAGATAGGGTTGAGTGTTGTTCCAGTTTGGAA
CAAGAGTCCACTATTAAAGAACGTGGACTCCAACGTCAAAGGGCGAAAAA
CCGTCTATCAGGGCGATGGCCCACTACGTGAACCATCACCCTAATCAAGTT
TTTTGGGGTCGAGGTGCCGTAAAGCACTAAATCGGAACCCTAAAGGGAGC
CCCCGATTTAGAGCTTGACGGGGAAAGCCGGCGAACGTGGCGAGAAAGGA
AGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAG
GGCGCGTCCCATTCGCCATTCAGGCTGCGCAACTGTTGGGAAGGGCGATC
GGTGCGGGCCTCTTCGCTATTACGCCAGCTGGCGAAAGGGGGATGTGCTG
CAAGGCGATTAAGTTGGGTAACGCCAGGGTTTTCCCAGTCACGACGTTGTA
AAACGACGGCCAGTGAATTGTAATACGACTCACTATAGGGCGAATTGGGT
ACaattcaattcgtcgacctcgaaattctaccgggtaggggaggcgcttttcccaaggcagtctggagcatgcgctttag
cagccccgctgggcacttggcgctacacaagtggcctctggcctcgcacacattccacatccaccggtaggcgccaacc
ggctccgttctttggtggccccttcgcgccaccttctactcctcccctagtcaggaagttcccccccgccccgcanctcgcg
tcgtgcaggacgtgacaaatggaatagcacgtctcactagtctcgtgcagatggacaagcaccgctgagcaatggagc
gggtaggcctttggggcagcggccaatagcagctttgctccttcgctttctgggctcagaggctggnaaggggtgggtcc
gggggcgggctcaggggcgggctcaggggcggggcgggcgcccgaaggtcctccggaggcccggcattctgcacg
cttcaaaagcgcacgtctgccgcgctgttctcctcttcctcatctccgggcctttcgacctgcatccatctagatctcgagca
gctgaagcttaccatgaccgagtacaagcccacggtgcgcctcgccacccgcgacgacgtcccccgggccgtacgcac
cctcgccgccgcgttcgccgactaccccgccacgcgccacaccgtcgacccggaccgccacatcgagcgggtcaccga
gctgcaagaactcttcctcacgcgcgtcgggctcgacatcggcaaggtgtgggtcgcggacgacggcgccgcggtggc
ggtctggaccacgccggagagcgtcgaagcgggggcggtgttcgccgagatcggcccgcgcatggccgagttgagcg
gttcccggctggccgcgcagcaacagatggaaggcctcctggcgccgcaccgggcccaaggagcccgcgtggttcctt
ggcccaccgtcgggcgtcttcgcccgaccaccagggcaagggtctggcaagcgccgtcgtgctccccggagtggagg
cggccgagcgcgccggggtgcccgccttcctggagacctccgcgccccgcaacctccccttctacgagcggctcggctt
caccgtcaccgccgacgtcgaggtgcccgaaggaccgcgcacctggtgcatgaccgcaagcccggtgcctgacgcc
cgccccacgacccgcagcgcccgaccgaaaggagcgcacgaccccatgcatcgatggcactgggcaggtaagtatcc
aggttagcGATCTTCAATATTGGCCATTAGCCATATTATTCATTGGTTATATAGC
ATAAATCAATATTGGCTATTGGCCATTGCATACGTTGTATCTATATCATAAT
ATGTACATTTATATTGGCTCATGTCCAATATGACCGCCATGTTGGCATTGA
TTATTGACTAGTTATTAATAGTAATCAATTACGGGGTCATTAGTTCATAGC
CCATATATGGAGTTCCGCGTTACATAACTTACGGTAAATGGCCCGCCTGGC
TGACCGCCCAACGACCCCCGCCCATTGACGTCAATAATGACGTATGTTCCC
ATAGTAACGCCAATAGGGACTTTCCATTGACGTCAATGGGTGGAGTATTTA
CGGTAAACTGCCCACTTGGCAGTACATCAAGTGTATCATATGCCAAGTCCG
CCCCCTATTGACGTCAATGACGGTAAATGGCCCGCCTGGCATTATGCCCAG
TACATGACCTTACGGGACTTTCCTACTTGGCAGTACATCTACGTATTAGTC
ATCGCTATTACCATGGTGATGCGGTTTTGGCAGTACACCAATGGGCGTGGA
TAGCGGTTTGACTCACGGGGATTTCCAAGTCTCCACCCCATTGACGTCAAT
GGGAGTTTGTTTTGGCACCAAAATCAACGGGACTTTCCAAAATGTCGTAAC
AACTGCGATCGCCCGCCCCGTTGACGCAAATGGGCGGTAGGCGTGTACGG
TGGGAGGTCTATATAAGCAGAGCTCGTTTAGTGAACCGTCAGATCACTAGA
AGTTTATTGCGGTAGTTTATCACAGTTAAATTGCTAACGCAGTCAGTGCT
TCTGACACAACAGTCTCGAACTTAAGCTGCAGTGACTCTCTtaattaaccaccgctac
aggtgagtactcgGATCTGCTACCTTAAgagaggcctatctggccagttagcagtcgaagaaagaagtttaa
GAGAGCCGAAACAAGCGCTCATGAGCCCGAAGTGGCGAGCCCGATCTTCC
CCATCGGTGATGTCGGCGATATAGGCGCCAGCAACCGCACCTGTGGCGCC-

FIG. 29A.

GGTGATGCCGGCCACGATGCGTCCGGCGTAGAGGATCCACAGGACGGGTG
TGGTCGCCATGATCGCGTAGTCGATAGTGGCTCCAAGTAGCGAAGCGAGC
AGGACTGGGCGGCGGCCAAAGCGGTCGGACAGTGCTCCGAGAACGGGTGC
GCATAGAAATTGCATCAACGCATATAGCGCTAGATCCTTGCTAGAGTCGAG
GCCGCCACCGCGGTGGAGCTCCAGCTTTTGTTCCCTTTAGTGAGGGTTAAT
TTCGAGCTTGGCGTAATCATGGTCATAGCTGTTTCCTGTGGTGAAATTGTTA
TCCGCTCACAATTCCACAACATACGAGCCGGAAGCATAAAGTGTAAAG
CCTGGGGTGCCTAATGAGTGAGCTAACTCACATTAATTGCGTTGCGCTCAC
TGCCCGCTTTCCAGTCGGGAAACCTGTCGTGCCAGCTGCATTAATGAATCC
GCCAACGCGCGGGGAGAGGCGGTTTGCGTATTGGGCGCTCTTCCGCTTCCT
CGCTCACTGACTCGCTGCGCTCGGTCGTTCGGCTGCGGCGAGCGGTATCAG
CTCACTCAAAGGCGGTAATACGGTTATCCACAGAATCAGGGGATAACGCA
GGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTG
GCGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTGC
GCCTTATCCGGTAACTATCGTCTTGAGTCCAACCCGGTAAGACACGACTTA
TCGCCACTGGCAGCAGCCACTGGTAACAGGATTAGCAGAGCGAGGTATGT
AGGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAAA
AAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAACT
CACGTTAAGGGATTTTGGTCATGAGATTATCAAAAAGGATCTTCACCTAGA
TCCTTTTAAATTAAAAATGAAGTTTTAAATCAATCTAAAGTATATATGAGT
AAACTTGGTCTGACAGTTACCAATGCTTAATCAGTGAGGCACCTATCTCAG
CGATCTGTCTATTTCGTTCATCCATAGTTGCCTGACTCCCCGTCGTGTAGAT
AACTACGATACGGGAGGGCTTACCATCTGGCCCCAGTGCTGCAATGATACC
GCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATAG
TTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTAC
ATGATCCCCCATGTTGTGCAAAAAAGCGGTTAGCTCCTTCGGTCCTCCGAT
CGTTGTCAGAAGTAAGTTGGCCGCAGTGTTATCACTCATGGTTATGGCAGC
ACTGCATAATTCTCTTACTGTCATGCCATCCGTAAGATGCTTTTCTGTGACT
GGTGAGTACTCAACCAAGTCATTCTGAGAATAGTGTATGCGGCGACCGAG
TTGCTCTTGCCCGGCGTCAATACGGGATAATACCGCGCCACATAGCAGAAC
TTTAAAAGTGCTCATCATTGGAAAACGTTCTTCGGGGCGAAAACTCTCAAG
GATCTTACCGCTGTTGAGATCCAGTTCGATGTAACCCACTCGTGCACCCAA
CTGATCTTCAGCATCTTTTACTTTCACCAGCGTTTCTGGGTGAGCAAAAAC
AGGAAGGCAAAATGCCGCAAAAAAGGGAATAAGGGCGACACGGAAATGT
TGAATACTCATACTCTTCCTTTTTCAATATTATTGAAGCATTTATCAGGGTT
ATTGTCTCATGAGCGGATACATATTTGAATGTATTTAGAAAAATAAACAAA
TAGGGGTTCCGCGCACATTTCCCCGAAAAGTGC

FIG. 29B.

GATCTTCAATATTGGCCATTAGCCATATTATTCATTGGTTATATAGCATAAA
TCAATATTGGCTATTGGCCATTGCATACGTTGTATCTATATCATAATATGTA
CATTTATATTGGCTCATGTCCAATATGACCGCCATGTTGGCATTGATTATTG
ACTAGTTATTAATAGTAATCAATTACGGGGTCATTAGTTCATAGCCCATAT
ATGGAGTTCCGCGTTACATAACTTACGGTAAATGGCCCGCCTGGCTGACCG
CCCAACGACCCCCGCCCATTGACGTCAATAATGACGTATGTTCCCATAGTA
ACGCCAATAGGGACTTTCCATTGACGTCAATGGGTGGAGTATTTACGGTAA
ACTGCCCACTTGGCAGTACATCAAGTGTATCATATGCCAAGTCCGCCCCT
ATTGACGTCAATGACGGTAAATGGCCCGCCTGGCATTATGCCCAGTACATG
ACCTTACGGGACTTTCCTACTTGGCAGTACATCTACGTATTAGTCATCGCT
ATTACCATGGTGATGCGGTTTTGGCAGTACACCAATGGGCGTGGATAGCG
GTTTGACTCACGGGGATTTCCAAGTCTCCACCCCATTGACGTCAATGGGAG
TTTGTTTTGGCACCAAAATCAACGGGACTTTCCAAAATGTCGTAACAACTG
CGATCGCCCGCCCCGTTGACGCAAATGGGCGGTAGGCGTGTACGGTGGGA
GGTCTATATAAGCAGAGCTCGTTTAGTGAACCGTCAGATCACTGAATTCTG
ACGACCTACTGATTAACGGCCATAGAGGCCTCCTGCAGAACTGTCTTAGTG
ACAACTATCGATTTCCACACATTATACGAGCCGATGTTAATTGTCAACAGC
TCATGCATGACGTCCCGGGAGCAGACAAGCCCGACCATGGCTCGAGTAAT
ACGACTCACTATAGGGCGACAGGTGAGTACTCGCTACCTTAAggcctatctggccg
tttaaacagatgtgtataagagacagctcttaaGGTAGCCTGTCTCTTATACACATCTagatccttg
ctagagtcgaccaattctcatgtttgacagcttatcatcgcagatcctgagcttgtatggtgcactctcagtacaatctgctct
gctgccgcatagttaagccagtatctgctccctgcttgtgtgttggaggtcgctgagtagtgcgcgagcaaaatttaagcta
caacaaggcaaggcttgaccgacaattgcatgaagaatctgcttagggttaggcgttttgcgctgcttcgcgatgtacggg
ccagatatacgcgtatctgaggggactagggtgtgtttaggcgcccagcggggcttcggttgtacgcggttaggagtccc
ctcaggatatagtagtttcgcttttgcatagggagggggaaatgtagtcttatgcaatacacttgtagtcttgcaacatggtaa
cgatgagttagcaacatgccttacaaggagagaaaaagcaccgtgcatgccgattggtggaagtaaggtggtacgatcgt
gccttattaggaaggcaacagacaggtctgacatggattggacgaaccactgaattccgcattgcagagataattgtattta
agtgcctagctcgatacaataaacgccatttgaccattcaccacattggtgtgcacctccaagctgggtaccagctgctagc
ctcgagacgcgtgatttccttcgaagcttgtcatggttggttcgctaaactgcatcgtcgctgtgtcccagaacatgggcatc
ggcaagaacggggacctgccctggccaccgctcaggaatgaattcagatatttccagagaatgaccacaacctcttcagt
agaaggtaaacagaatctggtgattatgggtaagaagacctggttctccattcctgagaagaatcgacctttaaagggtaga
attaatttagttctcagcagagaactcaaggaacctccacaaggagctcattttctttccagaagtctagatgatgccttaaaa
cttactgaacaaccagaattagcaaataaagtagacatggtctggatagttggtggcagttctgtttataaggaagccatga
atcacccaggccatcttaaactatttgtgacaaggatcatgcaagactttgaaagtgacacgtttttccagaaattgatttgg
agaaatataaacttctgccagaatacccaggtgttctctctgatgtccaggaggagaaaggcattaagtacaaatttgaagt
atatgagaagaatgTTAATTAAgggcaccaataactgccttaaaaaattacgccccgccctgccactcatcgcagt
actgttgtaattcattaagcattctgccgacatggaagccatcacagacggcatgatgaacctgaatcgccagcggcatca
gcaccttgtcgccttgcgtataatatttgcccatggtgaaaacgggggcgaagaagttgtccatattggccacgtttaaatca
aaactggtgaaactcacccagggattggctgagacgaaaaacatattctcaataaaccctttagggaaataggccaggtttt
caccgtaacacgccacatcttgcgaatatatgtgtagaaactgccggaaatcgtcgtggtattcactccagagcgatgaaa
acgtttcagtttgctcatggaaaacggtgtaacaagggtgaacactatccagctcaccgtctttcattgccata
cggaattccggatgagcattcatcaggcgggcaagaatgtgaataaaggccggataaaacttgtgcttatttttctttacggt
ctttaaaaaggccgtaatatccagctgaacggtctggttataggtacattgagcaactgactgaaatgcctcaaaatgttcttt
acgatgccattgggatatatcaacggtggtatatccagtgatttttttctccattttagcttccttagctcctgaaaatctcgata
actcaaaaaatacgcccggtagtgatcttatttcattatggtgaaagttggaacctcttacgtgccgatcaacgtctcattttcg
ccaaaTTAATTAAGGCGCGCCgctctcctggctaggagtcacgtagaaaggactaccgacgaaggaactt
gggtcgccggtgtgttcgtatatggaggtagtaagacctccctttacaacctaaggcgagaactgcccttgctattccaca
atgtcgtcttacaccattgagtcgtctcccctttggaatggcccctggacccggcccacaacctggcccgctaaggggagtc
cattgtctgttatttcatggtcttttacaaactcatatatttgctgaggttttgaaggatgcgattaaggaccttgttatgacaa-

FIG. 30A.

agcccgctcctacctgcaatatcagggtgactgtgtgcagctttgacgatggagtagatttgcctccctggtttccacctatg
gtggaaggggctgccgcggagggtgatgacggagatgacggagatgaaggaggtgatggagatgagggtgaggaag
ggcaggagtgatgtaacttgttaggagacgccctcaatcgtattaaaagccgtgtattccccgcactaaagaataaatccc
cagtagacatcatgcgtgctgttggtgtatttctgggcccatctgtcttgtcaccattttcgtcctcccaacatggggcaattggg
catacccatgttgtcacgtcactcagctccgcgctcaacaccttctcgcgttggaaaacattagcgacatttacctggtgagc
aatcagacatgcgacggctttagcctggcctccttaaattcacctaagaatgggagcaaccagcatgcaggaaaggaca
agcagcgaaaattcacgcccccttgggaggtggcggcatatgcaaaggatagcactcccactctactactgggtatcatat
gctgactgtatatgcatgaggatagcatatgctacccggatacagattaggatagcatatactacccagatatagattaggat
agcatatgctacccagatatagattaggatagcctatgctacccagatataaattaggatagcatatactacccagatataga
ttaggatagcatatgctacccagatatagattaggatagcctatgctacccagatatagattaggatagcatatgctacccag
atatagattaggatagcatatgctatccagatatttgggtagtatatgctacccagatataaattaggatagcatatactaccct
aatctctattaggatagcatatgctacccggatacagattaggatagcatatactacccagatatagattaggatagcatatg
ctacccagatatagattaggatagcctatgctacccagatataaattaggatagcatatactacccagatatagattaggata
gcatatgctacccagatatagattaggatagcctatgctacccagatatagattaggatagcatatgctatccagatatttgg
gtagtatatgctacccatggcaacattagcccaccgtgctctcagcgacctcgtgaatatgaggaccaacaaccctgtgctt
ggcgctcaggcgcaagtgtgtgtaatttgtcctccagatcgcagcaatcgcgcccctatcttggcccgcccacctacttatg
caggtattccccggggtgccattagtggttttgtgggcaagtggtttgaccgcagtggttagcggggttacaatcagccaa
gttattacacccttattttacagtccaaaaccgcagggcggcgtgtgggggctgacgcgtgcccccactccacaatttcaaa
aaaaagagtggccacttgtctttgtttatgggccccattggcgtggagcccgtttaattttcgggggtgttagagacaacca
gtggagtccgctgctgtcggcgtccactctctttccccttgttacaaatagagtgtaacaacatggttcacctgtcttggtccc
tgcctgggacacatcttaataaccccagtatcatattgcactaggattatgtgttgcccatagccataaattcgtgtgagatgg
acatccagtctttacggcttgtccccaccccatggatttctattgttaaagatattcagaatgtttcattcctacactagtatttatt
gcccaaggggtttgtgagggttatattggtgtcatagcacaatgccaccactgaacccccgtccaaattttattctggggg
cgtcacctgaaaccttgttttcgagcacctcacatacaccttactgttcacaactcagcagttattctattagctaaacgaagg
agaatgaagaagcaggcgaagattcaggagagttcactgcccgctcctgatcttcagccactgcccttgtgactaaaatg
gttcactaccctcgtggaatcctgaccccatgtaaataaaaccgtgacagctcatggggtgggagatatcgctgttccttag
gaccttttactaaccctaattcgatagcatatgcttcccgttgggtaacatatgctattgaattagggttagtctggatagtat
atactactacccgggaagcatatgctacccgtttagggttaacaagggggccttataaacactattgctaatgccctcttgag
ggtccgcttatcggtagctacacaggcccctctgattgacgttggtgtagcctcccgtagtcttcctgggcccctgggaggt
acatgtcccccagcatggtgtaagagcttcagccaagagttacacataaaggcaatgttgtgttgcagtccacagactgca
aagtctgctccaggatgaaagccactcagtgttggcaaatgtgcacatccatttataaggatgtcaactacagtcagagaac
ccctttgtgtttggtcccccccgtgtcacatgtggaacagggcccagttggcaagttgtaccaaccaactgaagggattac
atgcactgccccgaatacaaaacaaaagcgctcctcgtaccagcgaagaaggggcagagatgccgtagtcaggtttagtt
cgtccggcggcggGCGGCCGCAAGGCGCGCCGGATCCACAGGACGGGTGTGGTC
GCCATGATCGCGTAGTCGATAGTGGCTCCAAGTAGCGAAGCGAGCAGGAC
TGGGCGGCGGCCAAAGCGGTCGGACAGTGCTCCGAGAACGGGTGCGCATA
GAAATTGCATCAACGCATATAGCGCTAGATCCTTGCTAGAGTCGAGATCTG
TCGAGCCATGTGAGCAAAAGGCCAGCAAAAGGCCAGGAACCGTAAAAAGG
CCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGA
TACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCT
TATCCGGTAACTATCGTCTTGAGTCCAACCCGGTAAGACACGACTTATCGC
CACTGGCAGCAGCCACTGGTAACAGGATTAGCAGAGCGAGGTATGTAGGC
GGTGCTACAGAGTTCTTGAAGTGGTGGCCTAACTACGGCTACACTAGAAG
GACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTT-

FIG. 30B.

TTTTTGTTTGCAAGCAGCAGATTACGCGCAGAAAAAAAGGATCTCAAGAA
GATCCTTTGATCTTTTCTACGGGGTCTGACGCTCAGTGGAACGAAAACTCA
CGTTAAGGGATTTTGGTCATGAGATTATCAAAAAGGATCTTCACCTAGATC
CTTTTATCGGTGTGAAATACCGCACAGATGCGTAAGGAGAAAATACCGCAT
CAGGAAATTGTAAGCGTTAATAATTCAGAAGAACTCGTCAAGAAGGCGAT
AGAAGGCGATGCGCTGCGAATCGGGAGCGGCGATACCGTAAAGCACGAGG
AAGCGGTCAGCCCATTCGCCGCCAAGCTCTTCAGCAATATCACGGGTAGCCC
AACGCTATGTCCTGATAGCGGTCCGCCACACCCAGCCGGCCACAGTCGATG
AATCCAGAAAAGCGGCCATTTTCCACCATGATATTCGGCAAGCAGGCATCG
CCATGGGTCACGACGAGATCCTCGCCGTCGGGCATGCTCGCCTTGAGCCTG
GCGAACAGTTCGGCTGGCGCGAGCCCCTGATGCTCTTCGTCCAGATCATCC
TGATCGACAAGACCGGCTTCCATCCGAGTACGTGCTCGCTCGATGCGATGT
TTCGCTTGGTGGTCGAATGGGCAGGTAGCCGGATCAAGCGTATGCAGCCG
CCGCATTGCATCAGCCATGATGGATACTTTCTCGGCAGGAGCAAGGTGAG
ATGACAGGAGATCCTGCCCCGGCACTTCGCCCAATAGCAGCCAGTCCCTTC
CCGCTTCAGTGACAACGTCGAGCACAGCTGCGCAAGGAACGCCCGTCGTG
GCCAGCCACGATAGCCGCGCTGCCTCGTCTTGCAGTTCATTCAGGGCACCG
GACAGGTCGGTCTTGACAAAAAGAACCGGGCGCCCCTGCGCTGACAGCCG
GAACACGGCGGCATCAGAGCAGCCGATTGTCTGTTGTGCCCAGTCATAGCC
GAATAGCCTCTCCACCCAAGCGGCCGGAGAACCTGCGTGCAATCCATCTTG
TTCAATCATGCGAAACGATCCTCATCCTGTCTCTTGATCAGAGCTTGATCC
CCTGCGCCATCAGATCCTTGGCGGCGAGAAAGCCATCCAGTTTACTTTGCA
GGGCTTGTCAACCTTACCAGATAAAAGTGCTCATCATTGGAAAAcattcaattcgt
cgacctcgaaattctaccgggtaggggaggcgcttttcccaaggcagtctggagcatgcgctttagcagccccgctgggc
acttggcgctacacaagtggcctctggcctcgcacacattccacatccaccggtaggcgccaaccggctccgttctttggt
ggccccttcgcgccaccttctactcctcccctagtcaggaagttcccccccgccccgcanctcgcgtcgtgcaggacgtg
acaaatggaaatagcacgtctcactagtctcgtgcagatggacaagcaccgctgagcaatggagcgggtaggcctttggg
gcagcggccaatagcagctttgctccttcgctttctgggctcagaggctggnaaggggtggggtccgggggcgggctcag
gggcgggctcaggggcggggcgggcgcccgaaggtcctccggaggcccggcattctgcacgcttcaaaagcgcacgt
ctgccgcgctgttctcctcttcctcatctccgggcctttcgacctgcatccatctagatctcgagcagctgaagcttaccatga
ccgagtacaagcccacggtgcgcctcgccacccgcgacgacgtcccccgggccgtacgcaccctcgccgccgcgttcg
ccgactaccccgccacgcgccacaccgtcgacccggaccgccacatcgagcgggtcaccgagctgcaagaactcttcct
cacgcgcgtcgggctcgacatcggcaaggtgtgggtcgcggacgacggcgccgcggtggcggtctggaccacgccg
gagagcgtcgaagcgggggcggtgttcgccgagatcggcccgcgcatggccgagttgagcggttcccggctggccgc
gcagcaacagatggaaggcctcctggcgccgcaccgggcccaaggagcccgcgtggttcctggcccaccgtcgggc
gtcttcgcccgaccaccagggcaagggtctggcaagcgccgtcgtgctcccggagtggaggcggccgagcgcgccg
gggtgcccgccttcctggagacctccgcgccccgcaacctccccttctacgagcggctcggcttcaccgtcaccgccgac
gtcgaggtgcccgaaggaccgcgcacctggtgcatgacccgcaagcccggtgcctgacgcccgccccacgacccgca
gcgcccgaccgaaaggagcgcacgaccccatgcatcgatggcactgggcaggtaagtatcaaggttagcGGCCGC
TAACCTGGTTGCTGACTAATTGAGATGCATGCTTTGCATACTTCTGCCTGCT
GGGGAGCCTGGGGACTTTCCACACCCTAACTGACACACATTCCACAGCTGG
TTCTTTCCGCCTCAGAAGGTACACAGGCGAAATTGTAAGCGTTAATATTTT
GTTAAAATTCGCGTTAAATTTTTGTTAAATCAGCTCATTTTTTAACCAATAG
GCCGAAATCGGCAAAATCCCTTATAAATCAAAAGAATAGACCGAGATAGG
GTTGAGTGTTGTTCCAGTTTGGAACAAGAGTCCACTATTAAAGAACGTGGA
CTCCAACGTCAAAGGGCGAAAAACCGTCTATCAGGGCGATGGCCCAC

FIG. 30C.

GATCTTCAATATTGGCCATTAGCCATATTATTCATTGGTTATATAGCATAAA
TCAAATATTGGCTATTGGCCATTGCATACGTTGTATCTATATCATAATATGTA
CATTTATATTGGCTCATGTCCAATATGACCGCCATGTTGGCATTGATTATTG
ACTAGTTATTAATAGTAATCAATTACGGGGTCATTAGTTCATAGCCCATAT
ATGGAGTTCCGCGTTACATAACTTACGGTAAATGGCCCGCCTGGCTGACCG
CCCAACGACCCCCGCCCATTGACGTCAATAATGACGTATGTTCCCATAGTA
ACGCCAATAGGGACTTTCCATTGACGTCAATGGGTGGAGTATTTACGGTAA
ACTGCCCACTTGGCAGTACATCAAGTGTATCATATGCCAAGTCCGCCCCCT
ATTGACGTCAATGACGGTAAATGGCCCGCCTGGCATTATGCCCAGTACATG
ACCTTACGGGACTTTCCTACTTGGCAGTACATCTACGTATTAGTCATCGCT
ATTACCATGGTGATGCGGTTTTGGCAGTACACCAATGGGCGTGGATAGCG
GTTTGACTCACGGGGATTTCCAAGTCTCCACCCCATTGACGTCAATGGGAG
TTTGTTTTGGCACCAAAATCAACGGGACTTTCCAAAATGTCGTAACAACTG
CGATCGCCCGCCCCGTTGACGCAAATGGGCGGTAGGCGTGTACGGTGGGA
GGTCTATATAAGCAGAGCTCGTTTAGTGAACCGTCAGATCACTGAATTCTG
ACGACCTACTGATTAACGGCCATAGAGGCCTCCTGCAGAACTGTCTTAGTG
ACAACTATCGATTTCCACACATTATACGAGCCGATGTTAATTGTCAACAGC
TCATGCATGACGTCCCGGGAGCAGACAAGCCCGACCATGGCTCGAGTAAT
ACGACTCACTATAGGGCGACAGGTGAGTACTCGCTACCTTAAggcctatctggccg
tttaaacagatgtgtataagagacagctctcttaaGGTAGCCTGTCTCTTATACACATCTagatccttg
ctagagtcgaccaattctcatgtttgacagcttatcatcgcagatcctgagcttgtatggtgcactctcagtacaatctgctct
gctgccgcatagttaagccagtatctgctccctgcttgtgtgttggaggtcgctgagtagtgcgcgagcaaaatttaagcta
caacaaggcaaggcttgaccgacaattgcatgaagaatctgcttagggttaggcgtttgcgctgcttcgcgatgtacggg
ccagatatacgcgtatctgaggggactagggtgtgtttaggcgcccagcggggcttcggttgtacgcggttaggagtccc
ctcaggatatagtagtttcgcttttgcatagggagggggaaatgtagtcttatgcaatacacttgtagtcttgcaacatggtaa
cgatgagttagcaacatgccttacaaggagagaaaaagcaccgtgcatgccgattggtggaagtaaggtggtacgatcgt
gccttattaggaaggcaacagacaggtctgacatggattggacgaaccactgaattccgcattgcagagataattgtattta
agtgcctagctcgatacaataaacgccatttgaccattcaccacattggtgtgcacctccaagctgggtaccagctgctagc
ctcgagacgcgtgatttccttcgaagcttgtcatggttggttcgctaaactgcatcgtcgctgtgtcccagaacatgggcatc
ggcaagaacggggacctgccctggccaccgctcaggaatgaattcagatatttccagagaatgaccacaacctcttcagt
agaaggtaaacagaatctggtgattatgggtaagaagacctggttctccattcctgagaagaatctgacctttaaagggtaga
attaatttagttctcagcagagaactcaaggaacctccacaaggagctcattttctttccagaagtctagatgatgccttaaa
cttactgaacaaccagaattagcaaataaagtagacatggtctggatagttggtggcagttctgtttataaggaagccatga
atcacccaggccatcttaaactatttgtgacaaggatcatgcaagactttgaaagtgacacgtttttttccagaaattgatttgg
agaaatataaacttctgccagaatacccaggtgttctctctgatgtccaggaggagaaaggcattaagtacaaatttgaagt
atatgagaagaatgTTAATTAAgggcaccaataactgccttaaaaaattacgccccgccctgccactcatcgcagt
actgttgtaattcattaagcattctgccgacatggaagccatcacagacggcatgatgaacctgaatcgccagcggcatca
gcaccttgtcgccttgcgtataatatttgcccatggtgaaaacgggggcgaagaagttgtccatattggccacgtttaaatca
aaactggtgaaactcacccagggattggctgagacgaaaaacatattctcaataaaccctttagggaaataggccaggtttt
caccgtaacacgccacatcttgcgaatatatgtgtagaaactgccggaaatcgtcgtggtattcactccagagcgatgaaa
acgtttcagtttgctcatggaaaacggtgtaacaagggtgaacactatcccatatcaccagctcaccgtctttcattgccata
cggaattccggatgagcattcatcaggcgggcaagaatgtgaataaaggccggataaaacttgtgcttatttttctttacggt
ctttaaaaaggccgtaatatccagctgaacggtctggttataggtacattgagcaactgactgaaatgcctcaaaatgttcttt
acgatgccattgggatatatcaacggtggtatatccagtgatttttttctccattttagcttccttagctcctgaaaatctcgata
actcaaaaaatacgcccggtagtgatcttatttcattatggtgaaagttggaacctcttacgtgccgatcaacgtctcattttcg
ccaaaTTAATTAAGGCGCGCCgctctcctggctaggagtcacgtagaaaggactaccgacgaaggaactt
gggtcgccggtgtgttcgtatatgggaggtagtaagacctccctttacaacctaaggcgaggaactgcccttgctattccaca
atgtcgtcttacaccattgagtcgtctcccctttggaatggcccctggacccggcccacaacctggcccgctaagggagtc
cattgtctgttatttcatggtctttttacaaactcatatatttgctgaggttttgaaggatgcgattaaggaccttgttatgacaa-

FIG. 31A.

agcccgctcctacctgcaatatcagggtgactgtgtgcagctttgacgatggagtagatttgcctccctggtttccacctatg
gtggaaggggctgccgcggagggtgatgacggagatgacggagatgaaggaggtgatggagatgagggtgaggaag
ggcaggagtgatgtaacttgttaggagacgccctcaatcgtattaaaagccgtgtattccccgcactaaagaataaatccc
cagtagacatcatgcgtgctgttggtgtatttctggccatctgtcttgtcaccattttcgtcctcccaacatggggcaattggg
catacccatgttgtcacgtcactcagctccgcgctcaacaccttctcgcgttggaaaacattagcgacatttacctggtgagc
aatcagacatgcgacggctttagcctggcctccttaaattcacctaagaatgggagcaaccagcatgcaggaaaaggaca
agcagcgaaaattcacgccccttgggaggtggcggcatatgcaaaggatagcactcccactctactactgggtatcatat
gctgactgtatatgcatgaggatagcatatgctacccggatacagattaggatagcatatactacccagatatagattaggat
agcatatgctacccagatatagattaggatagcctatgctacccagatataaattaggatagcatatactacccagatataga
ttaggatagcatatgctacccagatatagattaggatagcctatgctacccagatatagattaggatagcatatgctacccag
atatagattaggatagcatatgctatccagatatttgggtagtatatgctacccagatataaattaggatagcatatactaccct
aatctctattaggatagcatatgctacccggatacagattaggatagcatatactacccagatatagattaggatagcatatg
ctacccagatatagattaggatagcctatgctacccagatataaattaggatagcatatactacccagatatagattaggata
gcatatgctacccagatatagattaggatagcctatgctacccagatatagattaggatagcatatgctatccagatatttgg
gtagtatatgctacccatggcaacattagcccaccgtgctctcagcgacctcgtgaatatgaggaccaacaaccctgtgctt
ggcgctcaggcgcaagtgtgtgtaatttgtcctccagatcgcagcaatcgcgcccctatcttggcccgcccacctacttatg
caggtattccccggggtgccattagtggttttgtgggcaagtggtttgaccgcagtggttagcggggttacaatcagccaa
gttattacacccttatttacagtccaaaaccgcagggcggcgtgtgggggctgacgcgtgcccccactccacaatttcaaa
aaaaagagtggccacttgtctttgtttatgggccccattggcgtggagccccgtttaattttcgggggtgttagagacaacca
gtggagtccgctgctgtcggcgtccactctctttccccttgttacaaatagagtgtaacaacatggttcacctgtcttggtccc
tgcctgggacacatcttaataaccccagtatcatattgcactaggattatgtgttgcccatagccataaattcgtgtgagatgg
acatccagtctttacggcttgtccccaccccatggatttctattgttaaagatattcagaatgtttcattcctacactagtatttatt
gcccaaggggtttgtgagggttatattggtgtcatagcacaatgccaccactgaaccccccgtccaaattttattctggggg
cgtcacctgaaaccttgttttcgagcacctcacatacaccttactgttcacaactcagcagttattctattagctaaacgaagg
agaatgaagaagcaggcgaagattcaggagagttcactgcccgctccttgatcttcagccactgcccttgtgactaaaatg
gttcactaccctcgtggaatcctgaccccatgtaaataaaaccgtgacagctcatggggtgggagatatcgctgttccttag
gaccttttactaaccctaattcgatagcatatgcttcccgttgggtaacatatgctattgaattagggttagtctggatagtat
atactactacccgggaagcatatgctacccgtttagggttaacaagggggccttataaacactattgctaatgccctcttgag
ggtccgcttatcggtagctacacaggcccctctgattgacgttggtgtagcctcccgtagtcttcctgggcccctgggaggt
acatgtcccccagcattggtgtaagagcttcagccaagagttacacataaaggcaatgttgtgttgcagtccacagactgca
aagtctgctccaggatgaaagccactcagtgttggcaaatgtgcacatccatttataaggatgtcaactacagtcagagaac
ccctttgtgtttggtcccccccgtgtcacatgtggaacagggcccagttggcaagttgtaccaaccaactgaagggattac
atgcactgccccgaatacaaaacaaaagcgctcctcgtaccagcgaagaaggggcagagatgccgtagtcaggtttagtt
cgtccggcggcggGCGGCCGCAAGGCGCGCCGGATCCACAGGACGGGTGTGGTC
GCCATGATCGCGTAGTCGATAGTGGCTCCAAGTAGCGAAGCGAGCAGGAC
TGGGCGGCGGCCAAAGCGGTCGGACAGTGCTCCGAGAACGGGTGCGCATA
GAAATTGCATCAACGCATATAGCGCTAGATCCTTGCTAGAGTCGAGATCTG
TCGAGCCATGTGAGCAAAAGGCCAGCAAAAGGCCAGGAACCGTAAAAAGG
CCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGA
TACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCT
TATCCGGTAACTATCGTCTTGAGTCCAACCCGGTAAGACACGACTTATCGC
CACTGGCAGCAGCCACTGGTAACAGGATTAGCAGAGCGAGGTATGTAGGC
GGTGCTACAGAGTTCTTGAAGTGGTGGCCTAACTACGGCTACACTAGAAG
GACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTT-

FIG. 31B.

TTTTTGTTTGCAAGCAGCAGATTACGCGCAGAAAAAAAGGATCTCAAGAA
TATCCTTGATCTTTTCTACGGGGTCTGACGCTCAGTGGAACGAAAACTCA
CGTTAAGGGATTTTGGTCATGAGATTATCAAAAAGGATCTTCACCTAGATC
CTTTTATCGGTGTGAAATACCGCACAGATGCGTAAGGAGAAAATACCGCAT
CAGGAAATTGTAAGCGTTAATAATTCAGAAGAACTCGTCAAGAAGGCGAT
AGAAGGCGATGCGCTGCGAATCGGGAGCGGCGATACCGTAAAGCACGAGG
AAGCGGTCAGCCCATTCGCCGCCAAGCTCTTCAGCAATATCACGGGTAGCC
AACGCTATGTCCTGATAGCGGTCCGCCACACCCAGCCGGCCACAGTCGATG
AATCCAGAAAAGCGGCCATTTTCCACCATGATATTCGGCAAGCAGGCATCG
CCATGGGTCACGACGAGATCCTCGCCGTCGGGCATGCTCGCCTTGAGCCTG
GCGAACAGTTCGGCTGGCGCGAGCCCCTGATGCTCTTCGTCCAGATCATCC
TGATCGACAAGACCGGCTTCCATCCGAGTACGTGCTCGCTCGATGCGATGT
TTCGCTTGGTGGTCGAATGGGCAGGTAGCCGGATCAAGCGTATGCAGCCG
CCGCATGCATCAGCCATGATGGATACTTTCTCGGCAGGAGCAAGGTGAG
ATGACAGGAGATCCTGCCCCGGCACTTCGCCCAATAGCAGCCAGTCCCTTC
CCGCTTCAGTGACAACGTCGAGCACAGCTGCGCAAGGAACGCCCGTCGTG
GCCAGCCACGATAGCCGCGCTGCCTCGTCTTGCAGTTCATTCAGGGCACCG
GACAGGTCGGTCTTGACAAAAAGAACCGGGCGCCCCTGCGCTGACAGCCG
GAACACGGCGGCATCAGAGCAGCCGATTGTCTGTTGTGCCCAGTCATAGCC
GAATAGCCTCTCCACCCAAGCGGCCGGAGAACCTGCGTGCAATCCATCTTG
TTCAATCATGCGAAACGATCCTCATCCTGTCTCTTGATCAGAGCTTGATCC
CCTGCGCCATCAGATCCTTGGCGGCGAGAAAGCCATCCAGTTTACTTTGCA
GGGCTTGTCAACCTTACCAGATAAAAGTGCTCATCATTGGAAAAcattcaattcgt
cgacctcgaaattctaccgggtaggggaggcgcttttcccaaggcagtctggagcatgcgctttagcagccccgctgggc
acttggcgctacacaagtggcctctggcctcgcacacattccacatccaccggtaggcgccaaccggctccgttctttggt
ggccccttcgcgccaccttctactcctcccctagtcaggaagttcccccccgccccgcanctcgcgtcgtgcaggacgtg
acaaatggaaatagcacgtctcactagtctcgtgcagatggacaagcaccgctgagcaatggagcgggtaggcctttggg
gcagcggccaatagcagctttgctccttcgctttctgggctcagaggctggnaaggggtgggtccgggggcgggctcag
gggcgggctcaggggcggggcgggcgcccgaaggtcctccggaggcccggcattctgcacgcttcaaaagcgcacgt
ctgccgcgctgttctcctcttcctcatctccgggcctttcgacctgcatccatctagatctcgagcagctgaagcttaccatga
ccgagtacaagcccacggtgcgcctcgccacccgcgacgacgtccccgggccgtacgcaccctcgccgccgcgttcg
ccgactaccccgccacgcgccacacccgtcgacccggaccgccacatcgagcgggtcaccgagctgcaagaactcttcct
cacgcgcgtcgggctcgacatcggcaaggtgtgggtcgcggacgacggcgccgcggtggcggtctggaccacgccg
gagagcgtcgaagcgggggcggtgttcgccgagatcggcccgcgcatggccgagttgagcggttcccggctggccgc
gcagcaacagatggaaggcctcctggcgccgcaccgggcccaaggagcccgcgtggttccttggcccaccgtcgggc
gtcttcgcccgaccaccagggcaagggtctggcaagcgccgtcgtgctccccggagtggaggcggccgagcgcgccg
gggtgcccgccttcctggagacctccgcgccccgcaacctccccttctacgagcggctcggcttcaccgtcaccgccgac
gtcgaggtgcccgaaggaccgcgcacctggtgcatgacccgcaagcccggtgcctgacgcccgccccacgacccgca
gcgcccgaccgaaaggagcgcacgaccccatgcatcgatggcactgggcaggtaagtatcaaggttagcGGCCGC
TAACCTGGTTGCTGACTAATTGAGATGCATGCTTTGCATACTTCTGCCTGCT
GGGGAGCCTGGGGACTTTCCACACCCTAACTGACACACATTCCACAGCTGG
TTCTTTCCGCCTCAGAAGGTACACAGGCGAAATTGTAAGCGTTAATATTTT
GTTAAAATTCGCGTTAAATTTTTGTTAAATCAGCTCATTTTTTAACCAATAG
GCCGAAATCGGCAAAATCCCTTATAAATCAAAAGAATAGACCGAGATAGG
GTTGAGTGTTGTTCCAGTTTGGAACAAGAGTCCACTATTAAAGAACGTGGA
CTCCAACGTCAAAGGGCGAAAAACCGTCTATCAGGGCGATGGCCCAC

FIG. 31C.

GATCTTCAATATTGGCCATTAGCCATATTATTCATTGGTTATATAGCATAAA
TCAATATTGGCTATTGGCCATTGCATACGTTGTATCTATATCATAATATGTA
CATTTATATTGGCTCATGTCCAATATGACCGCCATGTTGGCATTGATTATTG
ACTAGTTATTAATAGTAATCAATTACGGGGTCATTAGTTCATAGCCCATAT
ATGGAGTTCCGCGTTACATAACTTACGGTAAATGGCCCGCCTGGCTGACCG
CCCAACGACCCCCGCCCATTGACGTCAATAATGACGTATGTTCCCATAGTA
ACGCCAATAGGGACTTTCCATTGACGTCAATGGGTGGAGTATTTACGGTAA
ACTGCCCACTTGGCAGTACATCAAGTGTATCATATGCCAAGTCCGCCCCCT
ATTGACGTCAATGACGGTAAATGGCCCGCCTGGCATTATGCCCAGTACATG
ACCTTACGGGACTTTCCTACTTGGCAGTACATCTACGTATTAGTCATCGCT
ATTACCATGGTGATGCGGTTTTGGCAGTACACCAATGGGCGTGGATAGCG
GTTTGACTCACGGGGATTTCCAAGTCTCCACCCCATTGACGTCAATGGGAG
TTTGTTTTGGCACCAAAATCAACGGGACTTTCCAAAATGTCGTAACAACTG
CGATCGCCCGCCCCGTTGACGCAAATGGGCGGTAGGCGTGTACGGTGGGA
GGTCTATATAAGCAGAGCTCGTTTAGTGAACCGTCAGATCACTGAATTCTG
ACGACCTACTGATTAACGGCCAGATCTAAGCTAGCGCCGCCACCATGGGCC
CTAAAAAGAAGCGTAAAGTCGCCCCCCCGACCGATGTCAGCCTGGGGGAC
GAGCTCCACTTAGACGGCGAGGACGTGGCGATGGCGCATGCCGACGCGCT
AGACGATTTCGATCTGGACATGTTGGGGGACGGGGATTCCCCGGGGCCGG
GATTTACCCCCCACGACTCCGCCCCCTACGGCGCTCTGGATATGGCCGACT
TCGAGTTTGAGCAGATGTTTACCGATGCCCTTGGAATTGACGAGTACGGTG
GGGAATTCAGGTGAGTACTCGCTACCTTAAggcctatctggccgtttaaacagatgtgtataag
agacagctctcttaaGGTAGCCTGTCTCTTATACACATCTagatccttgctagagtcgaccaattctc
atgtttgacagcttatcatcgcagatcctgagcttgtatggtgcactctcagtacaatctgctctgctgccgcatagttaagcc
agtatctgctccctgcttgtgtgttggaggtcgctgagtagtgcgcgagcaaaatttaagctacaacaaggcaaggcttgac
cgacaattgcatgaagaatctgcttagggttaggcgttttgcgctgcttcgcgatgtacgggccagatatacgcgtatctga
ggggactagggtgtgtttaggcgcccagcggggcttcggttgtacgcggttaggagtcccctcaggatatagtagtttcgc
ttttgcatagggagggggaaatgtagtcttatgcaatacacttgtagtcttgcaacatggtaacgatgagttagcaacatgcc
ttacaaggagagaaaaagcaccgtgcatgccgattggtggaagtaaggtggtacgatcgtgccttattaggaaggcaaca
gacaggtctgacatggattggacgaaccactgaattccgcattgcagagataattgtatttaagtgcctagctcgatacaata
aacgccatttgaccattcaccacattggtgtgcacctccaagctgggtaccagctgctagcctcgagacgcgtgatttcctt
cgaagcttgtcatggttggttcgctaaactgcatcgtcgctgtgtcccagaacatgggcatcggcaagaacggggacctgc
cctggccaccgctcaggaatgaattcagatatttccagagaatgaccacaacctcttcagtagaaggtaaacagaatctggt
gattatgggtaagaagacctggttctccattcctgagaagaatcgacctttaaagggtagaattaatttagttctcagcagag
aactcaaggaacctccacaaggagctcattttctttccagaagtctagatgatgccttaaaacttactgaacaaccagaatta
gcaaataaagtagacatggtctggatagttggtggcagttctgtttataaggaagccatgaatcacccaggccatcttaaac
tatttgtgacaaggatcatgcaagactttgaaagtgacacgtttttttccagaaattgatttggagaaatataaacttctgccag
aatacccaggtgttctctctgatgtccaggaggagaaaggcattaagtacaaatttgaagtatatgagaagaatgTTAA
TTAAgggcaccaataactgccttaaaaaattacgccccgccctgccactcatcgcagtactgttgtaattcattaagcat
tctgccgacatggaagccatcacagacggcatgatgaacctgaatcgccagcggcatcagcaccttgtcgcctgcgtata
atatttgcccatggtgaaaacgggggcgaagaagttgtccatattggccacgtttaaatcaaaactggtgaaactcacccag
ggattggctgagacgaaaaacatattctcaataaaccctttagggaaataggccaggttttcaccgtaacacgccacatctt
gcgaatatatgtgtagaaactgccggaaatcgtcgtggtattcactccagagcgatgaaaacgtttcagtttgctcatggaa
aacggtgtaacaagggtgaacactatcccatatcaccagctcaccgtctttcattgccatacggaattccggatgagcattc
atcaggcgggcaagaatgtgaataaaggccggataaaacttgtgcttatttttctttacggtctttaaaaaggccgtaatatcc
agctgaacggtctggttataggtacattgagcaactgactgaaatgcctcaaaatgttctttacgatgccattgggatatatca
acggtggtatatccagtgatttttttctccatttagcttccttagctcctgaaaatctcgataactcaaaaaatacgcccggtag
tgatcttatttcattatggtgaaagttggaacctcttacgtgccgatcaacgtctcattttcgccaaaTTAATTAAGG
CGCGCCgctctcctggctaggagtcacgtagaaaggactaccgacgaaggaacttgggtcgccggtgtgtcgtat-

FIG. 32A.

atggaggtagtaagacctccctttacaacctaaggcgaggaactgcccttgctattccacaatgtcgtcttacaccattgagt
cgtctcccctttggaatggcccctggacccggcccacaacctggcccgctaagggagtccattgtctgttatttcatggtctt
tttacaaactcatatatttgctgaggtttgaaggatgcgattaaggaccttgttatgacaaagcccgctcctacctgcaatatc
agggtgactgtgtgcagctttgacgatggagtagatttgcctccctggtttccacctatggtggaaggggctgccgcggag
ggtgatgacggagatgacggagatgaaggaggtgatggagatgagggtgaggaagggcaggagtgatgtaacttgtta
ggagaacgccctcaatcgtattaaaagccgtgtattcccccgcactaaagaataaatccccagtagacatcatgcgtgctgtt
ggtgtatttctggccatctgtcttgtcaccattttcgtcctcccaacatggggcaattgggcatacccatgttgtcacgtcactc
agctccgcgctcaacaccttctcgcgttggaaaacattagcgacatttacctggtgagcaatcagacatgcgacggctttag
cctggcctccttaaattcacctaagaatgggagcaaccagcatgcaggaaaaggacaagcagcgaaaattcacgcccccct
tgggaggtggcggcatatgcaaaggatagcactcccactctactactgggtatcatatgctgactgtatatgcatgaggata
gcatatgctacccggatacagattaggatagcatatactacccagatatagattaggatagcatatgctacccagatatagat
taggatagcctatgctacccagatataaattaggatagcatatactacccagatatagattaggatagcatatgctacccaga
tatagattaggatagcctatgctacccagatatagattaggatagcatatgctacccagatatagattaggatagcatatgcta
tccagatatttgggtagtatatgctacccagatataaattaggatagcatatactaccctaatctctattaggatagcatatgct
accggatacagattaggatagcatatactacccagatatagattaggatagcatatgctacccagatatagattaggatag
cctatgctacccagatataaattaggatagcatatactacccagatatagattaggatagcatatgctacccagatatagatta
ggatagcctatgctacccagatatagattaggatagcatatgctatccagatattgggtagtatatgctacccatggcaaca
ttagcccaccgtgctctcagcgacctcgtgaatatgaggaccaacaaccctgtgcttggcgctcaggcgcaagtgtgtgta
atttgtcctccagatcgcagcaatcgcgcccctatcttggcccgcccacctacttatgcaggtattcccggggtgccatta
gtggtttgtgggcaagtggtttgaccgcagtggttagcggggttacaatcagccaagttattacacccttattttacagtcca
aaaccgcagggcggcgtgtgggggctgacgcgtgcccccactccacaatttcaaaaaaaagagtggccacttgtctttgt
ttatgggccccattggcgtggagccccgtttaattttcgggggtgttagagacaaccagtggagtccgctgctgtcggcgt
ccactctctttccccttgttacaaatagagtgtaacaacatggttcacctgtcttggtccctgcctgggacacatcttaataacc
ccagtatcatattgcactaggattatgtgttgcccatagccataaattcgtgtgagatggacatccagtctttacggcttgtcc
ccaccccatgggatttctattgttaaagatattcagaatgtttcattcctacactagtatttattgcccaaggggtttgtgagggtt
atattggtgtcatagcacaatgccaccactgaacccccgtccaaattttattctgggggcgtcacctgaaaccttgttttcga
gcacctcacatacaccttactgttcacaactcagcagttattctattagctaaacgaaggagaatgaagaagcaggcgaag
attcaggagagttcactgcccgctccttgatcttcagccactgcccttgtgactaaaatggttcactaccctcgtggaatcctg
accccatgtaaataaaaccgtgacagctcatggggtgggagatatcgctgttccttaggacccttttactaaccctaattcga
tagcatatgcttcccgttgggtaacatatgctattgaattagggttagtctggatagtatatactactacccgggaagcatatg
ctacccgtttagggttaacaagggggccttataaacactattgctaatgccctcttgagggtccgcttatcggtagctacaca
ggcccctctgattgacgttggtgtagcctcccgtagtcttcctgggcccctgggaggtacatgtcccccagcattggtgtaa
gagcttcagccaagagttacacataaaggcaatgttgtgttgcagtccacagactgcaaagtctgctccaggatgaaagcc
actcagtggttggcaaatgtgcacatccatttataaggatgtcaactacagtcagagaacccctttgtgtttggtcccccccgt
gtcacatgtggaacagggcccagttggcaagttgtaccaaccaactgaagggattacatgcactgccccgaatacaaaac
aaaagcgctcctcgtaccagcgaagaagggggcagagatgccgtagtcaggtttagttcgtccggcggcggGCGGC
CGCAAGGCGCGCCGGATCCACAGGACGGGTGTGGTCGCCATGATCGCGTA
GTCGATAGTGGCTCCAAGTAGCGAAGCGCGAGCAGGACTGGGCGGCGGCCAA
AGCGGTCGGACAGTGCTCCGAGAACGGGTGCGCATAGAAATTGCATCAAC
GCATATAGCGCTAGATCCTTGCTAGAGTCGAGATCTGTCGAGCCATGTGAC
CAAAAGGCCAGCAAAAGGCCAGGAACCGTAAAAAGGCCGCGTTGCTGGCG
TTTTTCCATAGGCTCCGCCCCCCTGACGAGCATCACAAAAATCGACGCTCA
AGTCAGAGGTGGCGAAACCCGACAGGACTATAAAGATACCAGGCGTTTCC
CCCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTGT
GTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCC
ACTGGTAACAGGATTAGCAGAGCGAGGTATGTAGGCGGTGCTACAGAGT-

FIG. 32B.

TCTTGAAGTGGTGGCCTAACTACGGCTACACTAGAAGGACAGTATTTGGTA
TCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTT
CTACGGGGTCTGACGCTCAGTGGAACGAAAACTCACGTTAAGGGATTTTG
GTCATGAGATTATCAAAAAGGATCTTCACCTAGATCCTTTTATCGGTGTGA
AATACCGCACAGATGCGTAAGGAGAAAATACCGCATCAGGAAATTGTAAG
CGTTAATAATTCAGAAGAACTCGTCAAGAAGGCGATAGAAGGCGATGCGC
TGCGAATCGGGAGCGGCGATACCGTAAAGCACGAGGAAGCGGTCAGCCCA
TTCGCCGCCAAGCTCTTCAGCAATATCACGGGTAGCCAACGCTATGTCCTG
ATAGCGGTCCGCCACACCCAGCCGGCCACAGTCGATGAATCCAGAAAAGC
GGCCATTTTCCACCATGATATTCGGCAAGCAGGCATCGCCATGGGTCACGA
CGAGATCCTCGCCGTCGGGCATGCTCGCCTTGAGCCTGGCGAACAGTTCGG
CTGGCGCGAGCCCCTGATGCTCTTCGTCCAGATCATCCTGATCGACAAGAC
CGGCTTCCATCCGAGTACGTGCTCGCTCGATGCGATGTTTCGCTTGGTGGT
CGAATGGGCAGGTAGCCGGATCAAGCGTATGCAGCCGCCGCATTGCATCA
GCCATGATGGATACTTTCTCGGCAGGAGCAAGGTGAGATGACAGGAGATC
CTGCCCCGGCACTTCGCCCAATAGCAGCCAGTCCCTTCCCGCTTCAGTGAC
AACGTCGAGCACAGCTGCGCAAGGAACGCCCGTCGTGGCCAGCCACGATA
GCCGCGCTGCCTCGTCTTGCAGTTCATTCAGGGCACCGGACAGGTCGGTCT
TGACAAAAAGAACCGGGCGCCCCTGCGCTGACAGCCGGAACACGGCGGCA
TCAGAGCAGCCGATTGTCTGTTGTGCCCAGTCATAGCCGAATAGCCTCTCC
ACCCAAGCGGCCGGAGAACCTGCGTGCAATCCATCTTGTTCAATCATGCGA
AACGATCCTCATCCTGTCTCTTGATCAGAGCTTGATCCCCTGCGCCATCAG
ATCCTTGGCGGCGAGAAAGCCATCCAGTTTACTTTGCAGGGCTTGTCAACC
TTACCAGATAAAAGTGCTCATCATTGGAAAAcattcaattcgtcgacctcgaaattctaccggg
taggggaggcgcttttcccaaggcagtctggagcatgcgctttagcagccccgctgggcacttggcgctacacaagtggc
ctctggcctcgcacacattccacatccaccggtaggcgccaaccggctccgttctttggtggccccttcgcgccaccttcta
ctcctcccctagtcaggaagttcccccccgccccgcanctcgcgtcgtgcaggacgtgacaaatggaaatagcacgtctc
actagtctcgtgcagatggacaagcaccgctgagcaatggagcgggtaggcctttggggcagcggccaatagcagcttt
gctccttcgctttctgggctcagaggctggnaagggggtgggtccaaaaacgggctcaggggcgggctcaggggcggg
gcgggcgcccgaaggtcctccggaggcccggcattctgcacgcttcaaaagcgcacgtctgccgcgctgttctcctcttc
ctcatctccgggcctttcgacctgcatccatctagatctcgagcagctgaagcttaccatgaccgagtacaagcccacggt
gcgcctcgccacccgcgacgacgtcccccgggccgtacgcaccctcgccgccgcgttcgccgactaccccgccacgcg
ccacaccgtcgacccggaccgccacatcgagcgggtcaccgagctgcaagaactcttcctcacgcgcgtcgggctcgac
atcggcaaggtgtgggtcgcggacgacggcgccgcggtggcggtctggaccacgccggagagcgtcgaagcggggg
cggtgttcgccgagatcggcccgcgcatggccgagttgagcggttcccggctggccgcgcagcaacagatggaaggcc
tcctggcgccgcaccgggcccaaggagcccgcgtggttcctggcccaccgtcgggcgtcttcgcccgaccaccaggg
caagggtctggcaagcgccgtcgtgctccccggagtggaggcggccgagcgcgccggggtgcccgccttcctggaga
cctccgcgccccgcaacctccccttctacgagcggctcggcttcaccgtcaccgccgacgtcgaggtgcccgaaggacc
gcgcacctggtgcatgacccgcaagcccggtgcctgacgcccgccccacgacccgcagcgcccgaccgaaaggagcg
cacgaccccatgcatcgatggcactgggcaggtaagtatcaaggttagcGGCCGCTAACCTGGTTGCT
GACTAATTGAGATGCATGCTTTGCATACTTCTGCCTGCTGGGGAGCCTGGG
GACTTTCCACACCCTAACTGACACACATTCCACAGCTGGTTCTTTCCGCCTC
AGAAGGTACACAGGCGAAATTGTAAGCGTTAATATTTTGTTAAAATTCGCG
TTAAATTTTTGTTAAATCAGCTCATTTTTTAACCAATAGGCCGAAATCGGC
AAAATCCCTTATAAATCAAAAGAATAGACCGAGATAGGGTTGAGTGTTGT
CCAGTTTGGAACAAGAGTCCACTATTAAAGAACGTGGACTCCAACGTCAAA
GGGCGAAAAACCGTCTATCAGGGCGATGGCCCAC

FIG. 32C.

GATCTTCAATATTGGCCATTAGCCATATTATTCATTGGTTATATAGCATAAA
TCAATATTGGCTATTGGCCATTGCATACGTTGTATCTATATCATAATATGTA
CATTTATATTGGCTCATGTCCAATATGACCGCCATGTTGGCATTGATTATTG
ACTAGTTATTAATAGTAATCAATTACGGGGTCATTAGTTCATAGCCCATAT
ATGGAGTTCCGCGTTACATAACTTACGGTAAATGGCCCGCCTGGCTGACCG
CCCAACGACCCCCGCCCATTGACGTCAATAATGACGTATGTTCCCATAGTA
ACGCCAATAGGGACTTTCCATTGACGTCAATGGGTGGAGTATTTACGGTAA
ACTGCCCACTTGGCAGTACATCAAGTGTATCATATGCCAAGTCCGCCCCCT
ATTGACGTCAATGACGGTAAATGGCCCGCCTGGCATTATGCCCAGTACATG
ACCTTACGGGACTTTCCTACTTGGCAGTACATCTACGTATTAGTCATCGCT
ATTACCATGGTGATGCGGTTTTGGCAGTACACCAATGGGCGTGGATAGCG
GTTTGACTCACGGGGATTTCCAAGTCTCCACCCCATTGACGTCAATGGGAG
TTTGTTTTGGCACCAAAATCAACGGGACTTTCCAAAATGTCGTAACAACTG
CGATCGCCCGCCCCGTTGACGCAAATGGGCGGTAGGCGTGTACGGTGGGA
GGTCTATATAAGCAGAGCTCGTTTAGTGAACCGTCAGATCACTGAATTCTG
ACGACCTACTGATTAACGGCCAGATCTAAGCTAGCTTCCTGAAAGATGAAG
CTACTGTCTTCTATCGAACAAGCATGCGATATTTGCCGACTTAAAAAGCTC
AAGTGCTCCAAAGAAAAACCGAAGTGCGCCAAGTGTCTGAAGAACAACTG
GGAGTGTCGCTACTCTCCCAAAACCAAAAGGTCTCCGCTGACTAGGGCACA
TCTGACAGAAGTGGAATCAAGGCTAGAAAGACTGGAACAGCTATTTCTACT
GATTTTTCCTCGAGAAGACCTTGACATGATTTTGAAAATGGATTCTTTACA
GGATATAAAAGCATTGTTAACAGGATTATTTGTACAAGATAATGTGAATAA
AGATGCCGTCACAGATAGATTGGCTTCAGTGGAGACTGATATGCCTCTAAC
ATTGAGACAGCATAGAATAAGTGCGACATCATCATCGGAAGAGAGTAGTA
ACAAAGGTCAAAGACAGTTGACTGTATCGCCGGAATTCAGGTGAGTACTC
GCTACCTTAAggcctatctggccgtttaaacagatgtgtataagagacagctctcttaaGGTAGCCTGTC
TCTTATACACATCTagatccttgctagagtcgaccaattctcatgtttgacagcttatcatcgcagatcctgagct
tgtatggtgcactctcagtacaatctgctctgctgccgcatagttaagccagtatctgctccctgcttgtgtgttggaggtcgc
tgagtagtgcgcgagcaaaatttaagctacaacaaggcaaggcttgaccgacaattgcatgaagaatctgcttagggttag
gcgtttgcgctgcttcgcgatgtacgggccagatatacgcgtatctgaggggactagggtgtgtttaggcgcccagcgg
ggcttcggttgtacgcggttaggagtcccctcaggatatagtagtttcgcttttgcatagggagggggaaatgtagtcttatg
caatacacttgtagtcttgcaacatggtaacgatgagttagcaacatgccttacaaggagagaaaaagcaccgtgcatgcc
gattggtggaagtaaggtggtacgatcgtgccttattaggaaggcaacagacaggtctgacatggattggacgaaccact
gaattccgcattgcagagataattgtatttaagtgcctagctcgatacaataaacgccatttgaccattcaccacattggtgtg
cacctccaagctgggtaccagctgctagcctcgagacgcgtgatttccttcgaagcttgtcatggttggttcgctaactgc
atcgtcgctgtgtcccagaacatgggcatcggcaagaacggggacctgccctggccaccgctcaggaatgaattcagata
tttccagagaatgaccacaacctcttcagtagaaggtaaacagaatctggtgattatgggtaagaagacctggttctccattc
ctgagaagaatcgacctttaaagggtagaattaatttagttctcagcagagaactcaaggaacctccacaaggagctcatttt
ctttccagaagtctagatgatgccttaaaacttactgaacaaccagaattagcaaataaagtagacatggtctggatagttgg
tggcagttctgtttataaggaagccatgaatcacccaggccatcttaaactatttgtgacaaggatcatgcaagactttgaaa
gtgacacgtttttccagaaattgattggagaaatataaacttctgccagaatacccaggtgttctctctgatgtccaggagg
agaaaggcattaagtacaaatttgaagtatatgagaagaatgTTAATTAAgggcaccaattaactgccttaaaaaat
tacgccccgccctgccactcatcgcagtactgttgtaattcattaagcattctgccgacatggaagccatcacagacggcat
gatgaacctgaatcgccagcggcatcagcaccttgtcgccttgcgtataatatttgcccatggtgaaaacgggggcgaag
aagttgtccatattggccacgtttaaatcaaaactggtgaaactcacccagggattggctgagacgaaaaacatattctcaat
aaaccctttagggaaataggccaggttttcaccgtaacacgccacatcttgcgaatatatgtgtagaaactgccggaaatcg
tcgtggtattcactccagagcgatgaaaacgtttcagtttgctcatggaaaacggtgtaacaagggtgaacactatcccatat
caccagctcaccgtctttcattgccatacggaattccggatgagcattcatcaggcgggcaagaatgtgaataaaggccgg
ataaaacttgtgcttatttttctttacggtctttaaaaaggccgtaatatccagctgaacggtctggttataggtacattgagc-

FIG. 33A.

aactgactgaaatgcctcaaaatgttctttacgatgccattgggatatatcaacggtggtatatccagtgatttttttctccatttt
agcttccttagctcctgaaaatctcgataactcaaaaaatacgcccggtagtgatcttattcattatggtgaaagttggaacc
tcttacgtgccgatcaacgtctcattttcgccaaaTTAATTAAGGCGCGCCgctctcctggctaggagtcacg
tagaaaggactaccgacgaaggaacttgggtcgccggtgtgttcgtatatggaggtagtaagacctccctttacaacctaa
ggcgaggaactgcccttgctattccacaatgtcgtcttacaccattgagtcgtctcccctttggaatggcccctggacccgg
cccacaacctggcccgctaagggagtccattgtctgttatttcatggtcttttacaaactcatatatttgctgaggttttgaag
gatgcgattaaggaccttgttatgacaaagcccgctcctacctgcaatatcagggtgactgtgtgcagctttgacgatggag
tagatttgcctccctggtttccacctatggtggaaggggctgccgcggagggtgatgacggagatgacggagatgaagg
aggtgatggagatgagggtgaggaaggcaggagtgatgtaacttgttaggagacgccctcaatcgtattaaaagccgtg
tattcccccgcactaaagaataaatccccagtagacatcatgcgtgctgttggtgtatttctggccatctgtcttgtcaccattt
tcgtcctcccaacatggggcaattgggcatacccatgttgtcacgtcactcagctccgcgctcaacaccttctcgcgttgga
aaacattagcgacatttacctggtgagcaatcagacatgcgacggctttagcctggcctccttaaattcacctaagaatggg
agcaaccagcatgcaggaaaaggacaagcagcgaaaattcacgcccccttgggaggtggcggcatatgcaaaggatag
cactcccactctactactgggtatcatatgctgactgtatatgcatgaggatagcatatgctacccggatacagattaggata
gcatatactacccagatatagattaggatagcatatgctacccagatatagattaggatagcctatgctacccagatataaatt
aggatagcatatactacccagatatagattaggatagcatatgctacccagatatagattaggatagcctatgctacccagat
atagattaggatagcatatgctacccagatatagattaggatagcatatgctatccagatatttgggtagtatatgctacccag
atataaattaggatagcatatactaccctaatctctattaggatagcatatgctacccggatacagattaggatagcatatact
acccagatatagattaggatagcatatgctacccagatatagattaggatagcctatgctacccagatataaattaggatagc
atatactacccagatatagattaggatagcatatgctacccagatatagattaggatagcctatgctacccagatatagatta
ggatagcatatgctatccagatatttgggtagtatatgctacccatggcaacattagcccaccgtgctctcagcgacctcgtg
aatatgaggaccaacaaccctgtgcttggcgctcaggcgcaagtgtgtgtaatttgtcctccagatcgcagcaatcgcgcc
cctatcttggcccgcccacctacttatgcaggtattcccggggtgccattagtggttttgtgggcaagtggtttgaccgcag
tggttagcggggttacaatcagccaagttattacacccttattttacagtccaaaaccgcagggcggcgtgtgggggctga
cgcgtgcccccactccacaatttcaaaaaaaagagtggccacttgtctttgtttatgggccccattggcgtggagccccgttt
aatttcgggggtgttagagacaaccagtggagtccgctgctgtcggcgtccactctctttccccttgttacaaatagagtgt
aacaacatggttcacctgtcttggtccctgcctgggacacatcttaataaccccagtatcatattgcactaggattatgtgttg
cccatagccataaattcgtgtgagatggacatccagtctttacggcttgtccccaccccatggatttctattgttaaagatattc
agaatgtttcattcctacactagtatttattgcccaaggggtttgtgagggttatattggtgtcatagcacaatgccaccactga
acccccccgtccaaattttattctgggggcgtcacctgaaaccttgttttcgagcacctcacatacaccttactgttcacaactc
agcagttattctattagctaaacgaaggagaatgaagaagcaggcgaagattcaggagagttcactgcccgctccttgatc
ttcagccactgcccttgtgactaaaatggttcactaccctcgtggaatcctgaccccatgtaaataaaaccgtgacagctcat
ggggtgggagatatcgctgttccttaggacccttttactaaccctaattcgatagcatatgcttcccgttgggtaacatatgct
attgaattagggttagtctggatagtatatactactacccgggaagcatatgctacccgtttagggttaacaagggggcctta
taaacactattgctaatgccctcttgagggtccgcttatcggtagctacacaggcccctctgattgacgttggtgtagcctcc
cgtagtcttcctgggcccctgggaggtacatgtcccccagcattggtgtaagagcttcagccaagagttacacataaaggc
aatgttgtgttgcagtccacagactgcaaagtctgctccaggatgaaagccactcagtgttggcaaatgtgcacatccattta
taaggatgtcaactacagtcagagaacccctttgtgtttggtccccccccgtgtcacatgtggaacagggcccagttggca
agttgtaccaaccaactgaagggattacatgcactgccccgaatacaaaacaaaagcgctcctcgtaccagcgaagaagg
ggcagagatgccgtagtcaggttagttcgtccggcggcggGCGGCCGCAAGGCGCGCCGGATCC
ACAGGACGGGTGTGGTCGCCATGATCGCGTAGTCGATAGTGGCTCCAAGT
AGCGAAGCGAGCAGGACTGGGCGGCGGCCAAAGCGGTCGGACAGTGCTCC
GAGAACGGGTGCGCATAGAAATTGCATCAACGCATATAGCGCTAGATCCT
TGCTAGAGTCGAGATCTGTCGAGCCATGTGAGCAAAAGGCCAGCAAAAGG
CCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAAC
CCGACAGGACTATAAAGATACCAGGCGTTTCCCCCTGGAAGCTCCCTCGTG
CGCTCTCCTGTTCCGACCCTGCCGCTTACCGGATACCTGTCCGCCTTTCTCC
CTTCGGGAAGCGTGGCGCTTTCTCATAGCTCACGCTGTAGGTATCTCAGT-

FIG. 33B.

TCGGTGTAGGTCGTTCGCTCCAAGCTGGGCTGTGTGCACGAACCCCCCGTT
CAGCCCGACCGCTGCGCCTTATCCGGTAACTATCGTCTTGAGTCCAACCCG
GTAAGACACGACTTATCGCCACTGGCAGCAGCCACTGGTAACAGGATTAG
CAGAGCGAGGTATGTAGGCGGTGCTACAGAGTTCTTGAAGTGGTGGCCTA
ACTACGGCTACACTAGAAGGACAGTATTTGGTATCTGCGCTCTGCTGAAGC
CAGTTACCTTCGGAAAAAGAGTTGGTAGCTCTTGATCCGCCAAACAAACCA
CCGCTGGTAGCGGTGGTTTTTTTGTTTGCAAGCAGCAGATTACGCGCAGAA
AAAAAGGATCTCAAGAAGATCCTTTGATCTTTTCTACGGGGTCTGACGCTC
AGTGGAACGAAAACTCACGTTAAGGGATTTTGGTCATGAGATTATCAAAA
AGGATCTTCACCTAGATCCTTTTATCGGTGTGAAATACCGCACAGATGCGT
AAGGAGAAAATACCGCATCAGGAAATTGTAAGCGTTAATAATTCAGAAGA
ACTCGTCAAGAAGGCGATAGAAGGCGATGCGCTGCGAATCGGGAGCGGCG
ATACCGTAAAGCACGAGGAAGCGGTCAGCCCATTCGCCGCCAAGCTCTTCA
GCAATATCACGGGTAGCCAACGCTATGTCCTGATAGCGGTCCGCCACACCC
AGCCGGCCACAGTCGATGAATCCAGAAAAGCGGCCATTTTCCACCATGATA
TTCGGCAAGCAGGCATCGCCATGGGTCACGACGAGATCCTCGCCGTCGGG
CATGCTCGCCTTGAGCCTGGCGAACAGTTCGGCTGGCGCGAGCCCCTGATG
CTCTTCGTCCAGATCATCCTGATCGACAAGACCGGCTTCCATCCGAGTACG
TGCTCGCTCGATGCGATGTTTCGCTTGGTGGTCGAATGGGCAGGTAGCCGG
ATCAAGCGTATGCAGCCGCCGCATTGCATCAGCCATGATGGATACTTTCTC
GGCAGGAGCAAGGTGAGATGACAGGAGATCCTGCCCCGGCACTTCGCCCA
ATAGCAGCCAGTCCCTTCCCGCTTCAGTGACAACGTCGAGCACAGCTGCGC
AAGGAACGCCCGTCGTGGCCAGCCACGATAGCCGCGCTGCCTCGTCTTGCA
GTTCATTCAGGGCACCGGACAGGTCGGTCTTGACAAAAAGAACCGGGCGC
CCCTGCGCTGACAGCCGGAACACGGCGGCATCAGAGCAGCCGATTGTCTG
TTGTGCCCAGTCATAGCCGAATAGCCTCTCCACCCAAGCGGCCGGAGAACC
TGCGTGCAATCCATCTTGTTCAATCATGCGAAACGATCCTCATCCTGTCTCT
TGATCAGAGCTTGATCCCCTGCGCCATCAGATCCTTGGCGGCGAGAAAGCC
ATCCAGTTTACTTTGCAGGGCTTGTCAACCTTACCAGATAAAAGTGCTCAT
CATTGGAAAAcattcaattcgtcgacctcgaaattctaccgggtaggggaggcgcttttcccaaggcagtctgga
gcatgcgctttagcagccccgctgggcacttggcgctacacaagtggcctctggcctcgcacacattccacatccaccggt
aggcgccaaccggctccgttctttggtggccccttcgcgccaccttctactcctcccctagtcaggaagttcccccccgccc
cgcanctcgcgtcgtgcaggacgtgacaaatggaaatagcacgtctcactagtctcgtgcagatggacaagcaccgctga
gcaatggagcgggtaggcctttggggcagcggccaatagcagctttgctccttcgctttctgggctcagaggctggnaag
gggtgggtccgggggcgggctcaggggcgggctcaggggcggggcgggcgcccgaaggtcctccggaggcccgg
cattctgcacgcttcaaaagcgcacgtctgccgcgctgttctcctcttcctcatctccgggcctttcgacctgcatccatctag
atctcgagcagctgaagcttaccatgaccgagtacaagcccacggtgcgcctcgccacccgcgacgacgtccccgggc
cgtacgcaccctcgccgccgcgttcgccgactaccccgccacgcgccacaccgtcgacccggaccgccacatcgagcg
ggtcaccgagctgcaagaactcttcctcacgcgcgtcgggctcgacatcggcaaggtgtgggtcgcggacgacggcgc
cgcggtggcggtctggaccacgccggagagcgtcgaagcgggggcggtgttcgccgagatcggcccgcgcatggcc
gagttgagcggttcccggctggccgcgcagcaacagatggaaggcctcctggcagccgcaccgggcccaaggagcccg
cgtggttccttggcccaccgtcgggcgtcttcgcccgaccaccagggcaagggtctggcaagcgccgtcgtgctccccg
gagtggaggcggccgagcgcgccggggtgcccgccttcctggagacctccgcgcccgcaacctccccttctacgagc
ggctcggcttcaccgtcaccgccgacgtcgaggtgcccgaaggaccgcgcacctggtgcatgacccgcaagcccggtg
cctgacgcccgccccacgacccgcagcgcccgaccgaaaggagcgcacgaccccatgcatcgatggcactgggcagg
taagtatcaaggttagcGGCCGCTAACCTGGTTGCTGACTAATTGAGATGCATGCTTT
GCATACTTCTGCCTGCTGGGGAGCCTGGGGACTTTCCACACCCTAACTGAC
ACACATTCCACAGCTGGTTCTTTCCGCCTCAGAAGGTACACAGGCAGAAATT
GTAAGCGTTAATATTTTGTTAAAATTCGCGTTAAATTTTTGTTAAATCAGC-

FIG. 33C.

TCATTTTTTAACCAATAGGCCGAAATCGGCAAAATCCCTTATAAATCAAAA
GAATAGACCGAGATAGGGTTGAGTGTTGTTCCAGTTTGGAACAAGAGTCC
ACTATTAAAGAACGTGGACTCCAACGTCAAAGGGCGAAAAACCGTCTATC
AGGGCGATGGCCCAC

FIG. 33D.

tcaacgacaggagcacgatcatgcgcacccgtggccaggacccaacgctgcccgagatgcgccgcgtgcggctgctgg
agatggcggacgcgatggatatgttctgccaagggttggtttgcgcattcacagttctccgcaagaattgattggctccaatt
cttggagtggtgaatccgttagcgaggtgccgccggcttccattcaggtcgaggtggcccggctccatgcaccgcgacg
caacgcggggaggcagacaaggtatagggcggcgcctacaatccatgccaacccgttccatgtgctcgccgaggcggc
ataaatcgccgtgacgatcagcggtccagtgatcgaagttaggctggtaagagccgcgagcgatccttgaagctgtccct
gatggtcgtcatctacctgcctggacagcatggcctgcaacgcgggcatcccgatgccgccggaagcgagaagaatcat
aatggggaaggccatccagcctcgcgtcgcgaacgccagcaagacgtagcccagcgcgtcggccgccatgccggcga
taatggcctgcttctcgccgaaacgtttggtggcgggaccagtgacgaaggcttgagcgagggcgtgcaagattccgaat
accgcaagcgacaggccgatcatcgtcgcgctccagcgaaagcggtcctcgccgaaaatgacccagagcgctgccggc
acctgtcctacgagttgcatgataaagaagacagtcataagtgcggcgacgatagtcatgccccgcgcccaccggaagg
agctgactgggttgaaggctctcaagggcatcggtcgacgctctcccttatgcgactcctgcattaggaagcagcccagta
gtaggttgaggccgttgagcaccgccgccgcaaggaatggtgcatgcaaggagatggcgcccaacagtcccccggcca
cggggcctgccaccatacccacgccgaaacaagcgctcatgagcccgaagtggcgagcccgatcttccccatcggtgat
gtcggcgatataggcgccagcaaccgcacctgtggcgccggtgatgccggccacgatgcgtccggcgtagaggatcca
caggacgggtgtggtcgccatgatcgcgtagtcgatagtggctccaagtagcgaagcgagcaggactgggcggcggcc
aaagcggtcggacagtgctccgagaacgggtgcgcatagaaattgcatcaacgcatatagcgctagcagcacgccatag
tgactggcgatgctgtcggaatggacgatatcccgcaagaggcccggcagtaccggcataaccaagcctatgcctacag
catccagggtgacggtgccgaggatgacgatgagcgcattgttagatttcatacacggtgcctgactgcgttagcaattta
actgtgataaactaccgcattaaagcttatcgatttccacacattatacgagccgatgttaattgtcaacagctcatgcatgacg
tcccgggagcagacaagcccgtcagggcgcgtcagcgggtgttggcgggtgtcggggctggcttaactatgcggcatc
agagcagattgtactgagagtgcaccatatgcggtgtgaaataccgcacagatgcgtaaggagaaaataccgcatcaggc
gccattcgccattcaggctgcgcaactgttgggaagggcgatcggtgcgggcctcttcgctattacgccagctggcgaaa
gggggatgtgctgcaaggcgattaagttgggtaacgccagggttttcccagtcacgacgttgtaaaacgacggccagtga
attcGAGCTCaTACTTCGAATAGGGATAACAGGGTAATGCGATagcggccgcaatCG
CTCTCTTAAGGTAGCccgtgcTGGCAAACAGCTATTATGGGTATTATGGGTGG
GCCCTAGAAAGCTTggcgtaatcatggtcatagctgtttcctgtgtgaaattgttatccgctcacaattccacac
aacatacgagccggaagcataaagtgtaaagcctggggtgcctaatgagtgagctaactcacattaattgcgttgcgctca
ctgcccgcttccagtcgggaaacctgtcgtgccagctgcattaatgacccgcgaggtcgccgccccgtaacccctacc
gctgaaagttctgcaaagcctgatgggacataagtccatcagttcaacggaagtctacacgaaggtttttgcgctggatgtg
gctgcccggcaccgggtgcagtttgcgatgccggagtctgatgcggttgcgatgctgaaacaattatcctgagaataaatg
ccttggcctttatatggaaatgtggaactgagtggatatgctgtttttgtctgttaaacagagaagctggctgttatccactga
gaagcgaacgaaacagtcgggaaaatctcccattatcgtagagatccgcattattaatctcaggagcctgtgtagcgtttat
aggaagtagtgttctgtcatgatgcctgcaagcggtaacgaaaacgattgaatatgccttcaggaacaatagaaatcttcg
tgcggtgttacgttgaagtggagcggattatgtcagcaatggacagaacaacctaatgaacacagaaccatgatgtggtct
gtccttttacagccagtagtgctcgccgcagtcgagcgacagggcgaagccctcgagtgagcgaggaagcaccaggga
acagcacttatatattctgcttacacacgatgcctgaaaaacttcccttggggttatccacttatccacggggatatttttata
attatttttttatagtttttagatcttctttttagagcgccttgtaggcctttatccatgctggttctagagaaggtgttgtgacaa
attgccctttcagtgtgacaaatcaccctcaaatgacagtcctgtctgtgacaaattgcccttaaccctgtgacaaattgccct
cagaagaagctgtttttcacaaagttatccctgcttattgactctttttatttagtgtgacaatctaaaaacttgtcacacttcac
atggatctgtcatggcggaaacagcggttatcaatcacaagaaacgtaaaaatagcccgcgaatcgtccagtcaaacgac
ccactgaggcggcatatagtctctcccgggatcaaaaacgtatgctgtatctgttcgttgaccagatcagaaaatctgatg
gcaccctacaggaacatgacggtatctgcgagatccatgttgctaaatatgctgaaatattcggattgacctctgcggaagc
cagtaaggatatacggcaggcattgaagagtttcgcggggaaggaagtggtttttatcgccctgaagaggatgccggcg
atgaaaaaggctatgaatcttttccttggtttatcaaacgtgcgcacagtccatccagagggctttacagtgtacatatcaacc
catatctcattcccttctttatcgggttacagaaccggtttacgcagtttcggcttagtgaaacaaaagaaatcaccaatccgt
atgccatgcgtttatacgaatccctgtgtcagtatcgtaagccggatggctcaggcatcgtctctctgaaaatcgactggatc
atagagcgttaccagctgcctcaaagttaccagcgtatgcctgacttccgccgccgcttcctgcaggtctgtgttaatgaga
tcaacagcagaactccaatgcgcctctcatacatgagaaaaagaaaggccgccagacgactcatatcgtatttccttccg
cgatatcacttccatgacgacaggatagtctgagggttatctgtcacagatttgagggtggttcgtcacatttgttctgacct-

FIG. 34A.

actgagggtaatttgtcacagttttgctgtttccttcagcctgcatggattttctcatactttttgaactgtaatttttaaggaagc
caaatttgagggcagtttgtcacagttgatttccttctctttcccttcgtcatgtgacctgatatcgggggttagttcgtcatcat
tgatgagggttgattatcacagtttattactctgaattggctatccgcgtgtgtacctctacctggagtttttcccacggtggat
atttcttcttgcgctgagcgtaagagctatctgacagaacagttcttctttgcttcctcgccagttcgctcgctatgctcggtta
cacggctgcggcgagcgctagtgataataagtgactgaggtatgtgctcttcttatctcctttgtagtgttgctcttattttaaa
caactttgcggtttttgatgactttgcgattttgttgttgctttgcagtaaattgcaagatttaataaaaaaacgcaaagcaatg
attaaaggatgttcagaatgaaactcatggaaacacttaaccagtgcataaacgctggtcatgaaatgacgaaggctatcg
ccattgcacagtttaatgatgacagcccggaagcgaggaaaataacccggcgctggagaataggtgaagcagcggattt
agttggggtttcttctcaggctatcagagatgccgagaaagcagggcgactaccgcacccggatatggaaattcgaggac
gggttgagcaacgtgttggttatacaattgaacaaattaatcatatgcgtgatgtgtttggtacgcgattgcgacgtgctgaa
gacgtatttccaccggtgatcggggttgctgcccataaaggtggcgtttacaaaacctcagtttctgttcatcttgctcaggat
ctggctctgaaggggctacgtgttttgctcgtggaaggtaacgacccccagggaacagcctcaatgtatcacggatgggt
accagatcttcatattcatgcagaagacactctcctgcctttctatcttggggaaaaggacgatgtcacttatgcaataaagc
ccacttgctggccggggcttgacattattccttcctgtctggctctgcaccgtattgaaactgagttaatgggcaaatttgatg
aaggtaaactgcccaccgatccacacctgatgctccgactggccattgaaactgttgctcatgactatgatgtcatagttatt
gacagcgcgcctaacctgggtatcggcacgattaatgtcgtatgtgctgctgatgtgctgattgttcccacgcctgctgagtt
gtttgactacacctccgcactgcagtttttcgatatgcttcgtgatctgctcaagaacgttgatcttaaagggttcgagcctgat
gtacgtattttgcttaccaaatacagcaatagtaatggctctcagtccccgtggatggaggagcaaattcgggatgcctggg
gaagcatggttctaaaaaatgttgtacgtgaaacggatgaagttggtaaaggtcagatccggatgagaactgtttttgaaca
ggccattgatcaacgctcttcaactggtgcctggagaaatgctctttctatttgggaacctgtctgcaatgaaattttcgatcgt
ctgattaaaccacgctgggagattagataatgaagcgtgcgcctgttattccaaaacatacgctcaatactcaaccggttga
agatacttcgttatcgacaccagctgccccgatggtggattcgttaattgcgcgcgtaggagtaatggctcgcggtaatgcc
attactttgcctgtatgtggtcgggatgtgaagtttactcttgaagtgctccggggtgatagtgttgagaagacctctcgggt
atggtcaggtaatgaacgtgaccaggagctgcttactgaggacgcactggatgatctcatcccttcttttctactgactggtc
aacagacaccggcgttcggtcgaagagtatctggtgtcatagaaattgccgatgggagtcgccgtcgtaaagctgctgca
cttaccgaaagtgattatcgtgttctggttggcgagctggatgatgagcagatggctgcattatccagattgggtaacgatta
tcgcccaacaagtgcttatgaacgtggtcagcgttatgcaagccgattgcagaatgaatttgctggaaatatttctgcgctgg
ctgatgcggaaaatatttcacgtaagattattacccgctgtatcaacaccgccaaattgcctaaatcagttgttgctcttttttct
caccccggtgaactatctgcccggtcaggtgatgcacttcaaaaagcctttacagataaagaggaattacttaagcagcag
gcatctaaccttcatgagcagaaaaaagctggggtgatatttgaagctgaagaagttatcactcttttaacttctgtgcttaaa
acgtcatctgcatcaagaactagtttaagctcacgacatcagtttgctcctggagcgacagtattgtataagggcgataaaat
ggtgcttaacctggacaggtctcgtgttccaactgagtgtatagagaaaattgaggccattcttaaggaacttgaaaagcca
gcaccctgatgcgaccacgttttagtctacgtttatctgtctttacttaatgtcctttgttacaggccagaaagcataactggcc
tgaatattctctctgggccagaagcttggcccactgttccacttgtatcgtcggtctgataatcagactgggaccacggtccc
actcgtatcgtcggtctgattattagtctgggaccacggtcccactcgtatcgtcggtctgattattagtctgggaccacggt
cccactcgtatcgtcggtctgataatcagactgggaccacggtcccactcgtatcgtcggtctgattattagtctgggaccat
ggtcccactcgtatcgtcggtctgattattagtctgggaccacggtcccactcgtatcgtcggtctgattattagtctggaacc
acggtcccactcgtatcgtcggtctgattattagtctgggaccacggtcccactcgtatcgtcggtctgattattagtctggg
accacgatcccactcgtgttgtcggtctgattatcggtctgggaccacggtcccacttgtattgtcgatcagactatcagcgt
gagactacgattccatcaatgcctgtcaagggcaagtattgacatgtcgtcgtaacctgtagaacggagtaacctcggtgtg
cggttgtatgcctgctgtggattgctgctgtgtcctgcttatccacaacattttgcgcacggttatgtggacaaaatacctgC
GCTAGAgaaaagagtttgtagaaacgcaaaaaggccatccgtcaggatggccttctgcttaatttgatgcctggcagt
ttatggcgggcgtcctgcccgccaccctccgggccgttgcttcgcaacgttcaaatccgctcccggcggatttgtcctactc
aggagagcgttcaccgacaaacaacagataaaacgaaaggcccagtctttcgactgagcctttcgttttatttgatgcctgg
cagttccctactctcgcatggggagaccccacactaccatcggcgctacggcgtttcacttctgagttcggcatggggtca
ggtgggaccaccgcgctactgccgccaggcaaattctgttttatcagaccgcttctgcgttctgggccgc

FIG. 34B.

GATCTTCAATATTGGCCATTAGCCATATTATTCATTGGTTATATAGCATAAA
TCAATATTGGCTATTGGCCATTGCATACGTTGTATCTATATCATAATATGTA
CATTTATATTGGCTCATGTCCAATATGACCGCCATGTTGGCATTGATTATTG
ACTAGTTATTAATAGTAATCAATTACGGGGTCATTAGTTCATAGCCCATAT
ATGGAGTTCCGCGTTACATAACTTACGGTAAATGGCCCGCCTGGCTGACCG
CCCAACGACCCCCGCCCATTGACGTCAATAATGACGTATGTTCCCATAGTA
ACGCCAATAGGGACTTTCCATTGACGTCAATGGGTGGAGTATTTACGGTAA
ACTGCCCACTTGGCAGTACATCAAGTGTATCATATGCCAAGTCCGCCCCCT
ATTGACGTCAATGACGGTAAATGGCCCGCCTGGCATTATGCCCAGTACATG
ACCTTACGGGACTTTCCTACTTGGCAGTACATCTACGTATTAGTCATCGCT
ATTACCATGGTGATGCGGTTTTGGCAGTACACCAATGGGCGTGGATAGCG
CTTTGACTCACGGGGATTTCCAAGTCTCCACCCCATTGACGTCAATGGGAG
TTTGTTTTGGCACCAAAATCAACGGGACTTTCCAAAATGTCGTAACAACTG
CGATCGCCCGCCCCGTTGACGCAAATGGGCGGTAGGCGTGTACGGTGGGA
GGTCTATATAAGCAGAGCTcgtttagtgaaccgtcagatcactgaattctgacgacctactgattaacggc
catagaggcctcctgcagaactgtcttagtgacaactatCGATTTCCACACATTATACGAGCCGAT
GTTAATTGTCAACAGCTCATGCATGACGTCCCGGGAGCAGACAAGCCCCacc
atggctcgagTAATACGACTCACTATAGGGCGACAGGTGAGTACTCGCTACCTT
AAGAGAGGCCTATCTGGCCAGTTAGCAGTCGAAGAAAGAAGTTTAAGAGA
GCCGAAACAAGCGCTCATGAGCCCGAAGTGGCGAGCCCGATCTTCCCCAT
CGGTGATGTCGGCGATATAGGCGCCAGCAACCGCACCTGTGGCGCCGGTG
ATGCCGGCCACGATGCGTCCGGCGTAGAGGATCCACAGGACGGGTGTGGT
CGCCATGATCGCGTAGTCGATAGTGGCTCCAAGTAGCGAAGCGAGCAGGA
CTGGGCGGCGGCCAAAGCGGTCGGACAGTGCTCCGAGAACGGGTGCGCAT
AGAAATTGCATCAACGCATATAGCGCTAGATCCTTGCTAGAGTCGAGATCT
GTCGAGCCATGTGAGCAAAAGGCCAGCAAAAGGCCAGGAACCGTAAAAAG
GCCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGAC
CCTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTCG
CTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATC
GCCACTGGCAGCAGCCACTGGTAACAGGATTAGCAGAGCGAGGTATGTAG
GCGGTGCTACAGAGTTCTTGAAGTGGTGGCCTAACTACGGCTACACTAGAA
GGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTT
TTTTTGTTTGCAAGCAGCAGATTACGCGCAGAAAAAAAGGATCTCAAGAA
GATCCTTTGATCTTTTCTACGGGGTCTGACGCTCAGTGGAACGAAAACTCA
CGTTAAGGGATTTTGGTCATGAGATTATCAAAAAGGATCTTCACCTAGATC
CTTTTatcggtgtgaaataccgcagatgcgtaaggagaaaataccgcatcaggaaattgtaagcgttaataattcag
aagaactcgtcaagaaggcgatagaaggcgatgcgctgcgaatcgggagcggcgataccgtaaagcacgaggaagcg
gtcagcccattcgccgccaagctcttcagcaatatcacgggtagccaacgctatgtcctgatagcggtccgccacacccag
ccggccacagtcgatgaatccagaaaagcggccattttccaccatgatattcggcaagcaggcatcgccatgggtcacga
cgagatcctcgccgtcgggcatgctcgccttgagcctggcgaacagttcggctggcgcgagcccctgatgctcttcgtcc
agatcatcctgatcgacaagaccggcttccatccgagtacgtgctcgctcgatgcgatgtttcgcttggtggtcgaatgggc
aggtagccggatcaagcgtatgcagccgccgcattgcatcagccatgatggatactttctcggcaggagcaaggtgagat
gacaggagatcctgccccggcacttcgcccaatagcagccagtcccttcccgcttcagtgacaacgtcgagcacagctgc
gcaaggaacgcccgtcgtggccagccacgatagccgcgctgcctcgtcttgcagttcatcagggcaccggacaggtc-

FIG. 35A.

ggtcttgacaaaaagaaccgggcgcccctgcgctgacagccggaacacggcggcatcagagcagccgattgtctgttgt
gcccagtcatagccgaatagcctctccacccaagcggccggagaacctgcgtgcaatccatcttgttcaatcatgcgaaac
gatccctcatcctgtctcttgatcagagcttgatcccctgcgccatcagatccttggcggcgagaaagccatccagtttacttt
gcagggcttgtcaaccttaccagatAAAAGTGCTCATCATTGGAAAACGTTCAATTcTGAG
GCGGAAAGAACCAGCTGTGGAATGTGTGTCAGTTAGGGTGTGGAAAGTCC
CCAGGCTCCCCAGCAGGCAGAAGTATGCAAAGCATGCATCTCAATTAGTCA
GCAACCAGGTGTGGAAAGTCCCCAGGCTCCCCAGCAGGCAGAAGTATGCA
AAGCATGCATCTCAATTAGTCAGCAACCATAGTCCCGCCCCTAACTCCGCC
CATCCCGCCCCTAACTCCGCCCAGTTCCGCCCATTCTCCGCCCCATGGCTG
ACTAATTTTTTTTATTTATGCAGAGGCCGAGGCCGCCTCGGCCTCTGAGCT
ATTCCAGAAGTAGTGAGGAGGCTTTTTTGGAGGCCTAGGCTTTTGCAAAAA
GCTTGATTCTTCTGACACAACAGTCTCGAACTTAAGGCTAGAGCCACCATG
ATTGAACAAGATGGATTGCACGCAGGTTCTCCGGCCGCTTGGGTGGAGAG
GCTATTCGGCTATGACTGGGCACAACAGACAATCGGCTGCTCTGATGCCGC
CGTGTTCCGGCTGTCAGCGCAGGGGCGCCCGGTTCTTTTTGTCAAGACCGA
CCTGTCCGGTGCCCTGAATGAACTGCAGGACGAGGCAGCGCGGCTATCGT
GGCTGGCCACGACGGGCGTTCCTTGCGCAGCTGTGCTCGACGTTGTCACTG
AAGCGGGAAGGGACTGGCTGCTATTGGGCGAACTGCCGGGGCAGGATCTC
CTGTCATCTCACCTTGCTCCTGCCGAGAAAGTATCCATCATGGCTGATGCA
ATGCGGCGGCTGCATACGCTTGATCCGGCTACCTGCCCATTCGACCACCAA
GCGAAACATCGCATCGAGCGAGCACGTACTCGGATGGAAGCCGGTCTTGT
CGATCAGGATGATCTGGACGAAGAGCATCAGGGGCTCGCGCCAGCCGAAC
TGTTCGCCAGGCTCAAGGCGCGCATGCCCGACGGCGAGGATCTCGTCGTG
ACCCATGGCGATGCCTGCTTGCCGAATATCATGGTGGAAAATGGCCGCTTT
TCTGGATTCATCGACTGTGGCCGGCTGGGTGTGGCGGACCGCTATCAGGAC
ATAGCGTTGGCTACCCGTGATATTGCTGAAGAGCTTGGCGGCGAATGGGCT
GACCGCTTCCTCGTGCTTTACGGTATCGCCGCTCCCGATTCGCAGCGCATC
GCCTTCTATCGCCTTCTTGACGAGccaTTCtgctggcaggtaagtcgcagccctggcgtcgtgatt
agtgatgatgaaccaggttatgaccttgatttattttgcatacctaatcattatgctgaggatttggaaagggtgtttattcctca
tggactaattatggacaggactgaacgtcttgctcgagatgtgatgaaggagatgggaggccatcacattgtagccctctg
tgtgctcaaggggggctataaattctttgctgacctgctggattacatcaaagcactgaatagaaatagtgatagatccattc
ctatgactgtagattttatcagactgaagagctattgtaatgaccagtcaacaggggacataaaagtaattggtggagatgat
ctctcaactttaactggaaagaatgtcttgattgtggaagatataattgacactggcaaaacaatgcagacttgcttccttg
gtcaggcagtataatccaaagatggtcaaggtcgcaagcttgctggtgaaaggaccccacgaagtgttggatataagcc
agactttgttggatttgaaattccagacaagtttgttgtaggatatgcccttgactataatgaatacttcagggatttgaatcat
gtttgtgtcattagtgaaactggaaaagcaaaatacaaagcctaaGCGGCCGCTAACCTGGTTGCTGA
CTAATTGAGATGCATGCTTTGCATACTTCTGCCTGCTGGGGAGCCTGGGGA
CTTTCCACACCCTAACTGACACACATTCCACAGCTGGTTCTTTCCGCCTCAG
AAGGTACACAGGCGAAATTGTAAGCGTTAATATTTTGTTAAAATTCGCGTT
AAATTTTTGTTAAATCAGCTCATTTTTTAACCAATAGGCCGAAATCGGCAA
AATCCCTTATAAATCAAAAGAATAGACCGAGATAGGGTTGAGTGTTGTTCC
AGTTTGGAACAAGAGTCCACTATTAAAGAACGTGGACTCCAACGTCAAAG
GGCGAAAAACCGTCTATCAGGGCGATGGCCCAC

FIG. 35B.

GATCTTCAATATTGGCCATTAGCCATATTATTCATTGGTTATATAGCATAAA
TCAATATTGGCTATTGGCCATTGCATACGTTGTATCTATATCATAATATGTA
CATTTATATTGGCTCATGTCCAATATGACCGCCATGTTGGCATTGATTATTG
ACTAGTTATTAATAGTAATCAATTACGGGGTCATTAGTTCATAGCCCATAT
ATGGAGTTCCGCGTTACATAACTTACGGTAAATGGCCCGCCTGGCTGACCG
CCCAACGACCCCCGCCCATTGACGTCAATAATGACGTATGTTCCCATAGTA
ACGCCAATAGGGACTTTCCATTGACGTCAATGGGTGGAGTATTTACGGTAA
ACTGCCCACTTGGCAGTACATCAAGTGTATCATATGCCAAGTCCGCCCCCT
ATTGACGTCAATGACGGTAAATGGCCCGCCTGGCATTATGCCCACTACATG
ACCTTACGGGACTTTCCTACTTGGCAGTACATCTACGTATTAGTCATCGCT
ATTACCATGGTGATGCGGTTTTGGCAGTACACCAATGGGCGTGGATAGCG
GTTTGACTCACGGGGATTTCCAAGTCTCCACCCCATTGACGTCAATGGGAG
TTTGTTTTGGCACCAAAATCAACGGGACTTTCCAAAATGTCGTAACAACTG
CGATCGCCCGCCCCGTTGACGCAAATGGGCGGTAGGCGTGTACGGTGGGA
GGTCTATATAAGCAGAGCTCGTTTAGTGAACCGTCAGATCACTGAATTCTG
ACGACCTACTGATTAACGGCCATAGAGGCCTCCTGCAGAACTGTCTTAGTG
ACAACTATCGATTTCCACACATTATACGAGCCGATGTTAATTGTCAACAGC
TCATGCATGACGTCCCGGGAGCAGACAAGCCCGACCATGGCTCGAGTAAT
ACGACTCACTATAGGGCGACAGGTGAGTACTCGCTACCTTAAggcctatctggccg
tttaaacagatgtgtataagagacagctctcttaaGGTAGCCTGTCTCTTATACACATCTagatccttg
ctagagtcgaccaattctcatgtttgacagcttatcatcgcagatcctgagcttgtatggtgcactctcagtacaatctgctct
gctgccgcatagttaagccagtatctgctccctgcttgtgtgttggaggtcgctgagtagtgcgcgagcaaaatttaagcta
caacaaggcaaggcttgaccgacaattgcatgaagaatctgcttagggttaggcgttttgcgctgcttcgcgatgtacggg
ccagatatacgcgtatctgaggggactagggtgtgtttaggcgcccagcggggcttcggttgtacgcggttaggagtccc
ctcaggatatagtagtttcgcttttgcatagggagggggaaatgtagtcttatgcaatacacttgtagtcttgcaacatggtaa
cgatgagttagcaacatgccttacaaggagagaaaaagcaccgtgcatgccgattggtggaagtaaggtggtacgatcgt
gccttattaggaaggcaacagacaggtctgacatggattggacgaaccactgaattccgcattgcagagataattgtattta
agtgcctagctcgatacaataaacgccatttgaccattcaccacattggtgtgcacctccaagctgggtaccagctgctagc
ctcgagacgcgtgatttccttcgaagcttgtcatggttggttcgctaaactgcatcgtcgctgtgtcccagaacatgggcatc
ggcaagaacggggacctgccctggccaccgctcaggaatgaattcagatatttccagagaatgaccacaacctcttcagt
agaaggtaaacagaatctggtgattatgggtaagaagacctggttctccattcctgagaagaatcgacctttaaagggtaga
attaatttagttctcagcagagaactcaaggaacctccacaaggagctcattttctttccagaagtctagatgatccttaaaa
cttactgaacaaccagaattagcaaataaagtagacatggtctggatagttggtggcagttctgtttataaggaagccatga
atcacccaggccatcttaaactatttgtgacaaggatcatgcaagactttgaaagtgacacgtttttccagaaattgatttgg
agaaatataaacttctgccagaatacccaggtgttctctctgatgtccaggagaaaggcattaagtacaaatttgaagt
atatgagaagaatgTTAATTAAgggcaccaataactgccttaaaaaattacgccccgccctgccactcatcgcagt
actgttgtaattcattaagcattctgccgacatggaagccatcacagacggcatgatgaacctgaatcgccagcggcatca
gcaccttgtcgcctgcgtataatatttgcccatggtgaaaacgggggcgaagaagttgtccatattggccacgtttaaatca
aaactggtgaaactcacccagggattggctgagacgaaaaacatattctcaataaaccctttagggaaataggccaggtttt
caccgtaacacgccacatcttgcgaatatatgtgtagaaactgccggaaatcgtcgtggtattcactccagagcgatgaaa
acgtttcagtttgctcatggaaaacggtgtaacaagggtgaacactatcccatatcaccagctcaccgtctttcattgccata
cggaattccggatgagcattcatcaggcgggcaagaatgtgaataaaggccggataaaacttgtgcttatttttctttacggt
ctttaaaaaggccgtaatatccagctgaacggtctggttataggtacattgagcaactgactgaaatgcctcaaaatgttcttt
acgatgccattgggatatatcaacggtggtatatccagtgatttttttctccattttagcttccttagctcctgaaaatctcgata
actcaaaaaatacgcccggtagtgatcttatttcattatggtgaaagttggaacctcttacgtgccgatcaacgtctcattttcg
ccaaaTTAATTAAGGCGCGCCgctctcctggctaggagtcacgtagaaaggactaccgacgaaggaactt
gggtcgccggtgtgttcgtatatggaggtagtaagacctccctttacaacctaaggcgaggaactgcccttgctattccaca
atgtcgtcttacaccattgagtcgtctcccctttggaatggcccctggacccggcccacaacctggcccgctaagggagtc
cattgtctgttatttcatggtcttttacaaactcatatatttgctgaggttttgaaggatgcgattaaggaccttgttatgacaa-

FIG. 37A.

agcccgctcctacctgcaatatcagggtgactgtgtgcagctttgacgatggagtagatttgcctccctggtttccacctatg
gtggaaggggctgccgcggagggtgatgacggagatgacggagatgaaggaggtgatggagatgagggtgaggaag
ggcaggagtgatgtaacttgttaggagacgccctcaatcgtattaaaagccgtgtattccccgcactaaagaataaatccc
cagtagacatcatgcgtgctgttggtgtatttctggccatctgtcttgtcaccattttcgtcctcccaacatggggcaattggg
catacccatgttgtcacgtcactcagctccgcgctcaacaccttctcgcgttggaaaacattagcgacatttacctggtgagc
aatcagacatgcgacggctttagcctggcctccttaaattcacctaagaatgggagcaaccagcatgcaggaaaaggaca
agcagcgaaaattcacgccccttgggaggtggcggcatatgcaaaggatagcactcccactctactactgggtatcatat
gctgactgtatatgcatgaggatagcatatgctacccggatacagattaggatagcatatactacccagatatagattaggat
agcatatgctacccagatatagattaggatagcctatgctacccagatataaattaggatagcatatactacccagatataga
ttaggatagcatatgctacccagatatagattaggatagcctatgctacccagatatagatttaggatagcatatgctacccag
atatagattaggatagcatatgctatccagatatttgggtagtatatgctacccagatataaattaggatagcatatactaccct
aatctctattaggatagcatatgctacccggatacagattaggatagcatatactacccagatatagattaggatagcatatg
ctacccagatatagattaggatagcctatgctacccagatataaattaggatagcatatactacccagatatagattaggata
gcatatgctacccagatatagattaggatagcctatgctacccagatatagattaggatagcatatgctatccagatatttgg
gtagtatatgctacccatggcaacattagcccaccgtgctctcagcgacctcgtgaatatgaggaccaacaaccctgtgctt
ggcgctcaggcgcaagtgtgtgtaatttgtcctccagatcgcagcaatcgcgcccctatcttggcccgcccacctacttatg
caggtattccccggggtgccattagtggttttgtgggcaagtggtttgaccgcagtggttagcggggttacaatcagccaa
gttattacacccttattttacagtccaaaaccgcagggcggcgtgtgggggctgacgcgtgcccccactccacaatttcaaa
aaaaagagtggccacttgtctttgtttatgggccccattggcgtggagccccgtttaattttcgggggtgttagagacaacca
gtggagtccgctgctgtcggcgtccactctctttccccttgttacaaatagagtgtaacaacatggttcacctgtcttggtccc
tgcctgggacacatcttaataaccccagtatcatattgcactaggattatgtgttgcccatagccataaattcgtgtgagatgg
acatccagtctttacggcttgtccccaccccatggatttctattgttaaagatattcagaatgtttcattcctacactagtatttatt
gcccaaggggtttgtgagggttatattggtgtcatagcacaatgccaccactgaaccccccgtccaaattttattctggggg
cgtcacctgaaaccttgttttcgagcacctcacatacaccttactgttcacaactcagcagttattctattagctaaacgaagg
agaatgaagaagcaggcgaagattcaggagagttcactgcccgctccttgatcttcagccactgcccttgtgactaaaatg
gttcactaccctcgtggaatcctgaccccatgtaaataaaaccgtgacagctcatggggtgggagatatcgctgttccttag
gacccttttactaaccctaattcgatagcatatgcttcccgttgggtaacatatgctattgaattagggttagtctggatagtat
atactactacccgggaagcatatgctacccgtttagggttaacaagggggccttataaacactattgctaatgccctcttgag
ggtccgcttatcggtagctacacaggcccctctgattgacgttggtgtagcctcccgtagtcttcctgggcccctgggaggt
acatgtcccccagcattggtgtaagagcttcagccaagagttacacataaaggcaatgttgtgttgcagtccacagactgca
aagtctgctccaggatgaaagccactcagtgttggcaaatgtgcacatccatttataaggatgtcaactacagtcagagaac
ccctttgtgtttggtcccccccgtgtcacatgtggaacagggcccagttggcaagttgtaccaaccaactgaagggattac
atgcactgccccgaatacaaaacaaaagcgctcctcgtaccagcgaagaaggggcagagatgccgtagtcaggtttagtt
cgtccggcggcggGCGGCCGCAAGGCGCGCCGGATCCACAGGACGGGTGTGGTC
GCCATGATCGCGTAGTCGATAGTGGCTCCAAGTAGCGAAGCGAGCAGGAC
TGGGCGGCGGCCAAAGCGGTCGGACAGTGCTCCGAGAACGGGTGCGCATA
GAAATTGCATCAACGCATATAGCGCTAGATCCTTGCTAGAGTCGAGATCTG
TCGAGCCATGTGAGCAAAAGGCCAGCAAAAGGCCAGGAACCGTAAAAAGG
CCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGA
TACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCT
TATCCGGTAACTATCGTCTTGAGTCCAACCCGGTAAGACACGACTTATCGC
CACTGGCAGCAGCCACTGGTAACAGGATTAGCAGAGCGAGGTATGTAGGC
GGTGCTACAGAGTTCTTGAAGTGGTGGCCTAACTACGGCTACACTAGAAG
GACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTT-

FIG. 37B.

TTTTTGTTTGCAAGCAGCAGATTACGCGCAGAAAAAAAGGATCTCAAGAA
GATCCTTTGATCTTTTCTACGGGGTCTGACGCTCAGTGGAACGAAAACTCA
CGTTAAGGGATTTTGGTCATGAGATTATCAAAAAGGATCTTCACCTAGATC
CTTTTATCGGTGTGAAATACCGCACAGATGCGTAAGGAGAAAATACCGCAT
CAGGAAATTGTAAGCGTTAATAATTCAGAAGAACTCGTCAAGAAGGCGAT
AGAAGGCGATGCGCTGCGAATCGGGAGCGGCGATACCGTAAAGCACGAGG
AAGCGGTCAGCCCATTCGCCGCCAAGCTCTTCAGCAATATCACGGGTAGCC
AACGCTATGTCCTGATAGCGGTCCGCCACACCCAGCCGGCCACAGTCGATG
AATCCAGAAAAGCGGCCATTTTCCACCATGATATTCGGCAAGCAGGCATCG
CCATGGGTCACGACGAGATCCTCGCCGTCGGGCATGCTCGCCTTGAGCCTG
GCGAACAGTTCGGCTGGCGCGAGCCCCTGATGCTCTTCGTCCAGATCATCC
TGATGGACAAGACCGGCTTCCATCCGAGTACGTGCTCGCTCGATGCGATGT
TTCGCTTGGTGGTCGAATGGGCAGGTAGCCGGATCAAGCGTATGCAGCCG
CCGCATTGCATCAGCCATGATGGATACTTTCTCGGCAGGAGCAAGGTGAG
ATGACAGGAGATCCTGCCCCGGCACTTCGCCCAATAGCAGCCAGTCCCTTC
CCGCTTCAGTGACAACGTCGAGCACAGCTGCGCAAGGAACGCCCGTCGTG
GCCAGCCACGATAGCCGCGCTGCCTCGTCTTGCAGTTCATTCAGGGCACCG
GACAGGTCGGTCTTGACAAAAAGAACCGGGCGCCCCTGCGCTGACAGCCG
GAACACGGCGGCATCAGAGCAGCCGATTGTCTGTTGTGCCCAGTCATAGCC
GAATAGCCTCTCCACCCAAGCGGCCGGAGAACCTGCGTGCAATCCATCTTG
TTCAATCATGCGAAACGATCCTCATCCTGTCTCTTGATCAGAGCTTGATCC
CCTGCGCCATCAGATCCTTGGCGGCGAGAAAGCCATCCAGTTTACTTTGCA
GGGCTTGTCAACCTTACCAGATAAAAGTGCTCATCATTGGAAAAcattcaattcgt
cgacctcgaaattctaccgggtaggggaggcgcttttcccaaggcagtctggagcatgcgctttagcagccccgctgggc
acttggcgctacacaagtggcctctggcctcgcacacattccacatccaccggtaggcgccaaccggctccgttctttggt
ggccccttcgcgccaccttctactcctcccctagtcaggaagttcccccccgccccgcanctcgcgtcgtgcaggacgtg
acaaatggaaatagcacgtctcactagtctcgtgcagatggacaagcaccgctgagcaatggagcgggtaggcctttggg
gcagcggccaatagcagctttgctccttcgctttctgggctcagaggctggnaaggggtgggtccgggggcgggctcag
gggcgggctcaggggcggggcgggcgcccgaaggtcctccggaggcccggcattctgcacgcttcaaaagcgcacgt
ctgccgcgctgttctcctcttcctcatctccgggcctttcgacctgcatccatctagatctcgagcagctgaagcttaccatga
ccgagtacaagcccacggtgcgcctcgccacccgcgacgacgtccccgggccgtacgcaccctcgccgccgcgttcg
ccgactaccccgccacgcgccacaccgtcgacccggaccgccacatcgagcgggtcaccgagctgcaagaactcttcct
cacgcgcgtcgggctcgacatcggcaaggtgtgggtcgcggacgacggcgccgcggtggcggtctggaccacgccg
gagagcgtcgaagcgggggcggtgttcgccgagatcggcccgcgcatggccgagttgagcggttcccggctggccgc
gcagcaacagatggaaggcctcctggcgccgcaccgggcccaaggagcccgcgtggttccttggcccaccgtcgggc
gtcttcgcccgaccaccagggcaagggtctggcaagcgccgtcgtgctccccggagtggaggcggccgagcgcgccg
gggtgcccgccttcctggagacctccgcgccccgcaacctccccttctacgagcggctcggcttcaccgtcaccgccgac
gtcgaggtgcccgaaggaccgcgcacctggtgcatgacccgcaagcccggtgcctgacgcccgccccacgacccgca
gcgcccgaccgaaaggagcgcacgaccccatgcatcgatggcactgggcaggtaagtatcaaggttagcGGCCGC
TAACCTGGTTGCTGACTAATTGAGATGCATGCTTTGCATACTTCTGCCTGCT
GGGGAGCCTGGGGACTTTCCACACCCTAACTGACACACATTCCACAGCTGG
TTCTTTCCGCCTCAGAAGGTACACAGGCGAAATTGTAAGCGTTAATATTTT
GTTAAAATTCGCGTTAAATTTTTGTTAAATCAGCTCATTTTTTAACCAATAG
GCCGAAATCGGCAAAATCCCTTATAAATCAAAAGAATAGACCGAGATAGG
GTTGAGTGTTGTTCCAGTTTGGAACAAGAGTCCACTATTAAAGAACGTGGA
CTCCAACGTCAAAGGGCGAAAAACCGTCTATCAGGGCGATGGCCCAC

FIG. 37C.

SEQUENCE LISTING

```
<160> NUMBER OF SEQ ID NOS: 33

<210> SEQ ID NO 1
<211> LENGTH: 39
<212> TYPE: DNA
<213> ORGANISM: Homo sapiens

<400> SEQUENCE: 1

tccttcgaag cttgtcatgg ttggttcgct aaactgcat                          39


<210> SEQ ID NO 2
<211> LENGTH: 40
<212> TYPE: DNA
<213> ORGANISM: Homo sapiens

<400> SEQUENCE: 2

aaacttaaga tcgattaatc attcttctca tatacttcaa                         40


<210> SEQ ID NO 3
<211> LENGTH: 28
<212> TYPE: DNA
<213> ORGANISM: Homo sapiens

<400> SEQUENCE: 3

atccaccatg gctacaggtg agtactcg                                      28


<210> SEQ ID NO 4
<211> LENGTH: 36
<212> TYPE: DNA
<213> ORGANISM: Homo sapiens

<400> SEQUENCE: 4

gatccgagta ctcacctgta gccatggtgg atttaa                             36
```

-continued

<210> SEQ ID NO 5
<211> LENGTH: 33
<212> TYPE: DNA
<213> ORGANISM: Homo sapiens

<400> SEQUENCE: 5
ggcgagatct agcgctatat gcgttgatgc aat 33

<210> SEQ ID NO 6
<211> LENGTH: 51
<212> TYPE: DNA
<213> ORGANISM: Homo sapiens

<400> SEQUENCE: 6
ggccagatct gctaccttaa gagagccgaa acaagcgctc atgagcccga a 51

<210> SEQ ID NO 7
<211> LENGTH: 6084
<212> TYPE: DNA
<213> ORGANISM: Homo sapiens

<400> SEQUENCE: 7
agatcttcaa tattggccat tagccatatt attcattggt tatatagcat aaatcaatat 60
tggctattgg ccattgcata cgttgtatct atatcataat atgtacattt atattggctc 120
atgtccaata tgaccgccat gttggcattg attattgact agttattaat agtaatcaat 180
tacggggtca ttagttcata gcccatatat ggagttccgc gttacataac ttacggtaaa 240
tggcccgcct ggctgaccgc ccaacgaccc ccgcccattg acgtcaataa tgacgtatgt 300
tcccatagta acgccaatag ggactttcca ttgacgtcaa tgggtggagt atttacggta 360
aactgcccac ttggcagtac atcaagtgta tcatatgcca agtccgcccc ctattgacgt 420
caatgacggt aaatggcccg cctggcatta tgcccagtac atgaccttac gggactttcc 480
tacttggcag tacatctacg tattagtcat cgctattacc atggtgatgc ggttttggca 540
gtacaccaat gggcgtggat agcggtttga ctcacgggga tttccaagtc tccaccccat 600
tgacgtcaat gggagtttgt tttggcacca aaatcaacgg gactttccaa aatgtcgtaa 660
caactgcgat cgcccgcccc gttgacgcaa atgggcggta ggcgtgtacg gtgggaggtc 720
tatataagca gagctcgttt agtgaaccgt cagatcacta gaagctttat tgcggtagtt 780
tatcacagtt aaattgctaa cgcagtcagt gcttctgaca caacagtctc gaacttaagc 840
tgcagtgact ctcttaatta actccaccag tctcacttca gttccttttg cctccaccag 900
tctcacttca gttccttttg catgaagagc tcagaatcaa aagaggaaac caacccctaa 960
gatgagcttt ccatgtaaat ttgtagccag cttccttctg attttcaatg tttcttccaa 1020
aggtgcagtc tccaaagaga ttacgaatgc cttggaaacc tggggtgcct tgggtcagga 1080
catcaacttg gacattccta gttttcaaat gagtgatgat attgacgata taaaatggga 1140
aaaaacttca gacaagaaaa agattgcaca attcagaaaa gagaaagaga ctttcaagga 1200
aaaagataca tataagctat ttaaaaatgg aactctgaaa attaagcatc tgaagaccga 1260
tgatcaggat atctacaagg tatcaatata tgatacaaaa ggaaaaaatg tgttggaaaa 1320
aatatttgat ttgaagattc aagagagggt ctcaaaacca aagatctcct ggacttgtat 1380
caacacaacc ctgacctgtg aggtaatgaa tggaactgac cccgaattaa acctgtatca 1440
agatgggaaa catctaaaac tttctcagag ggtcatcaca cacaagtgga ccaccagcct 1500
gagtgcaaaa ttcaagtgca cagcagggaa caaagtcagc aaggaatcca gtgtcgagcc 1560

-continued

```
tgtcagctgt ccagagaaag ggatccaggt gagtagggcc cgatccttct agagtcgagc   1620
tctcttaagg tagcaaggtt acaagacagg tttaaggaga ccaatagaaa ctgggcttgt   1680
cgagacagag aagactcttg cgtttctgat aggcacctat tggtcttacg cggccgcgaa   1740
ttccaagctt gagtattcta tcgtgtcacc taaataactt ggcgtaatca tggtcatatc   1800
tgtttcctgt gtgaaattgt tatccgctca caattccaca caacatacga gccggaagca   1860
taaagtgtaa agcctggggt gcctaatgag tgagctaact cacattaatt gcgttgcgcg   1920
atgcttccat tttgtgaggg ttaatgcttc gagaagacat gataagatac attgatgagt   1980
ttggacaaac cacaacaaga atgcagtgaa aaaaatgctt tatttgtgaa atttgtgatg   2040
ctattgcttt atttgtaacc attataagct gcaataaaca agttaacaac aacaattgca   2100
ttcattttat gtttcaggtt cagggggaga tgtgggaggt tttttaaagc aagtaaaacc   2160
tctacaaatg tggtaaaatc cgataaggat cgattccgga gcctgaatgg cgaatggacg   2220
cgccctgtag cggcgcatta agcgcggcgg gtgtggtggt tacgcgcacg tgaccgctac   2280
acttgccagc gccctagcgc ccgctccttt cgctttcttc ccttcctttc tcgccacgtt   2340
cgccggcttt ccccgtcaag ctctaaatcg ggggctccct ttagggttcc gatttagtgc   2400
tttacggcac ctcgacccca aaaaacttga ttagggtgat ggttcacgta gtgggccatc   2460
gccctgatag acggtttttc gccctttgac gttggagtcc acgttcttta atagtggact   2520
cttgttccaa actggaacaa cactcaaccc tatctcggtc tattcttttg atttataagg   2580
gattttgccg atttcggcct attggttaaa aaatgagctg atttaacaaa aatttaacgc   2640
gaattttaac aaaatattaa cgcttacaat ttcgcctgtg taccttctga ggcggaaaga   2700
accagctgtg gaatgtgtgt cagttagggt gtggaaagtc cccaggctcc ccagcaggca   2760
gaagtatgca aagcatgcat ctcaattagt cagcaaccag gtgtggaaag tccccaggct   2820
ccccagcagg cagaagtatg caaagcatgc atctcaatta gtcagcaacc atagtcccgc   2880
ccctaactcc gcccatcccg cccctaactc cgcccagttc cgcccattct ccgccccatg   2940
gctgactaat tttttttatt tatgcagagg ccgaggccgc ctcggcctct gagctattcc   3000
agaagtagtg aggaggcttt tttggaggcc taggcttttg caaaaagctt gattcttctg   3060
acacaacagt ctcgaactta aggctagagc caccatgatt gaacaagatg gattgcacgc   3120
aggttctccg gccgcttggg tggagaggct attcggctat gactgggcac aacagacaat   3180
cggctgctct gatgccgccg tgttccggct gtcagcgcag gggcgcccgg ttctttttgt   3240
caagaccgac ctgtccggtg ccctgaatga actgcaggac gaggcagcgc ggctatcgtg   3300
gctggccacg acgggcgttc cttgcgcagc tgtgctcgac gttgtcactg aagcgggaag   3360
ggactggctg ctattgggcg aagtgccggg gcaggatctc ctgtcatctc accttgctcc   3420
tgccgagaaa gtatccatca tggctgatgc aatgcggcgg ctgcatacgc ttgatccggc   3480
tacctgccca ttcgaccacc aagcgaaaca tcgcatcgag cgagcacgta ctcggatgga   3540
agccggtctt gtcgatcagg atgatctgga cgaagagcat caggggctcg cgccagccga   3600
actgttcgcc aggctcaagg cgcgcatgcc cgacggcgag gatctcgtcg tgacccatgg   3660
cgatgcctgc ttgccgaata tcatggtgga aaatggccgc ttttctggat tcatcgactg   3720
tggccggctg ggtgtggcgg accgctatca ggacatagcg ttggctaccc gtgatattgc   3780
tgaagagctt ggcggcgaat gggctgaccg cttcctcgtg ctttacggta tcgccgctcc   3840
cgattcgcag cgcatcgcct tctatcgcct tcttgacgag ttcttctgag cgggactctg   3900
```

-continued

```
gggttcgaaa tgaccgacca agcgacgccc aacctgccat cacgatggcc gcaataaaat   3960
atctttattt tcattacatc tgtgtgttgg ttttttgtgt gaagatccgc gtatggtgca   4020
ctctcagtac aatctgctct gatgccgcat agttaagcca gccccgacac ccgccaacac   4080
ccgctgacgc gccctgacgg gcttgtctgc tcccggcatc cgcttacaga caagctgtga   4140
ccgtctccgg gagctgcatg tgtcagaggt tttcaccgtc atcaccgaaa cgcgcgagac   4200
gaaagggcct cgtgatacgc ctatttttat aggttaatgt catgataata atggtttctt   4260
agacgtcagg tggcactttt cggggaaatg tgcgcggaac ccctatttgt ttatttttct   4320
aaatacattc aaatatgtat ccgctcatga gacaataacc ctgataaatg cttcaataat   4380
attgaaaaag gaagagtatg agtattcaac atttccgtgt cgcccttatt cccttttttg   4440
cggcattttg ccttcctgtt tttgctcacc cagaaacgct ggtgaaagta aaagatgctg   4500
aagatcagtt gggtgcacga gtgggttaca tcgaactgga tctcaacagc ggtaagatcc   4560
ttgagagttt tcgccccgaa gaacgttttc caatgatgag cacttttaaa gttctgctat   4620
gtggcgcggt attatcccgt attgacgccg ggcaagagca actcggtcgc cgcatacact   4680
attctcagaa tgacttggtt gagtactcac cagtcacaga aaagcatctt acggatggca   4740
tgacagtaag agaattatgc agtgctgcca taaccatgag tgataacact gcggccaact   4800
tacttctgac aacgatcgga ggaccgaagg agctaaccgc ttttttgcac aacatggggg   4860
atcatgtaac tcgccttgat cgttgggaac cggagctgaa tgaagccata ccaaacgacg   4920
agcgtgacac cacgatgcct gtagcaatgg caacaacgtt gcgcaaacta ttaactggcg   4980
aactacttac tctagcttcc cggcaacaat taatagactg gatggaggcg gataaagttg   5040
caggaccact tctgcgctcg gcccttccgg ctggctggtt tattgctgat aaatctggag   5100
ccggtgagcg tgggtctcgc ggtatcattg cagcactggg gccagatggt aagccctccc   5160
gtatcgtagt tatctacacg acggggagtc aggcaactat ggatgaacga aatagacaga   5220
tcgctgagat aggtgcctca ctgattaagc attggtaact gtcagaccaa gtttactcat   5280
atatacttta gattgattta aaacttcatt tttaatttaa aaggatctag gtgaagatcc   5340
tttttgataa tctcatgacc aaaatccctt aacgtgagtt ttcgttccac tgagcgtcag   5400
accccgtaga aaagatcaaa ggatcttctt gagatccttt ttttctgcgc gtaatctgct   5460
gcttgcaaac aaaaaaacca ccgctaccag cggtggtttg tttgccggat caagagctac   5520
caactctttt tccgaaggta actggcttca gcagagcgca gataccaaat actgtccttc   5580
tagtgtagcc gtagttaggc caccacttca agaactctgt agcaccgcct acatacctcg   5640
ctctgctaat cctgttacca gtggctgctg ccagtggcga taagtcgtgt cttaccgggt   5700
tggactcaag acgatagtta ccggataagg cgcagcggtc gggctgaacg gggggttcgt   5760
gcacacagcc cagcttggag cgaacgacct acaccgaact gagataccta cagcgtgagc   5820
tatgagaaag cgccacgctt cccgaaggga gaaaggcgga caggtatccg gtaagcggca   5880
gggtcggaac aggagagcgc acgagggagc ttccaggggg aaacgcctgg tatctttata   5940
gtcctgtcgg gtttcgccac ctctgacttg agcgtcgatt tttgtgatgc tcgtcagggg   6000
ggcggagcct atggaaaaac gccagcaacg cggccttttt acggttcctg gccttttgct   6060
ggccttttgc tcacatggct cgac                                          6084
```

<210> SEQ ID NO 8
<211> LENGTH: 6085
<212> TYPE: DNA
<213> ORGANISM: Homo sapiens -continued

<400> SEQUENCE: 8
agatcttcaa tattggccat tagccatatt attcattggt tatatagcat aaatcaatat 60
tggctattgg ccattgcata cgttgtatct atatcataat atgtacattt atattggctc 120
atgtccaata tgaccgccat gttggcattg attattgact agttattaat agtaatcaat 180
tacggggtca ttagttcata gcccatatat ggagttccgc gttacataac ttacggtaaa 240
tggcccgcct ggctgaccgc ccaacgaccc ccgcccattg acgtcaataa tgacgtatgt 300
tcccatagta acgccaatag ggactttcca ttgacgtcaa tgggtggagt atttacggta 360
aactgcccac ttggcagtac atcaagtgta tcatatgcca agtccgcccc ctattgacgt 420
caatgacggt aaatggcccg cctggcatta tgcccagtac atgaccttac gggactttcc 480
tacttggcag tacatctacg tattagtcat cgctattacc atggtgatgc ggttttggca 540
gtacaccaat gggcgtggat agcggtttga ctcacgggga tttccaagtc tccaccccat 600
tgacgtcaat gggagtttgt tttggcacca aaatcaacgg gactttccaa aatgtcgtaa 660
caactgcgat cgcccgcccc gttgacgcaa atgggcggta ggcgtgtacg gtgggaggtc 720
tatataagca gagctcgttt agtgaaccgt cagatcacta gaagctttat tgcggtagtt 780
tatcacagtt aaattgctaa cgcagtcagt gcttctgaca caacagtctc gaacttaagc 840
tgcagtgact ctcttaatta actccaccag tctcacttca gttccttttg cctccaccag 900
tctcacttca gttccttttg catgaagagc tcagaatcaa aagaggaaac caacccctaa 960
gatgagcttt ccatgtaaat ttgtagccag cttccttctg attttcaatg tttcttccaa 1020
aggtgcagtc tccaaagaga ttacgaatgc cttggaaacc tggggtgcct tgggtcagga 1080
catcaacttg gacattccta gttttcaaat gagtgatgat attgacgata taaaatggga 1140
aaaaacttca gacaagaaaa agattgcaca attcagaaaa gagaaagaga ctttcaagga 1200
aaaagataca tataagctat ttaaaaatgg aactctgaaa attaagcatc tgaagaccga 1260
tgatcaggat atctacaagg tatcaatata tgatacaaaa ggaaaaaatg tgttggaaaa 1320
aatatttgat ttgaagattc aagagagggt ctcaaaacca aagatctcct ggacttgtat 1380
caacacaacc ctgacctgtg aggtaatgaa tggaactgac cccgaattaa acctgtatca 1440
agatgggaaa catctaaaac tttctcagag ggtcatcaca cacaagtgga ccaccagcct 1500
gagtgcaaaa ttcaagtgca cagcagggaa caaagtcagc aaggaatcca gtgtcgagcc 1560
tgtcagctgt ccagagaaag ggatcccagg tgagtagggc ccgatccttc tagagtcgag 1620
ctctcttaag gtagcaaggt tacaagacag gtttaaggag accaatagaa actgggcttg 1680
tcgagacaga gaagactctt gcgtttctga taggcaccta ttggtcttac gcggccgcga 1740
attccaagct tgagtattct atcgtgtcac ctaaataact tggcgtaatc atggtcatat 1800
ctgtttcctg tgtgaaattg ttatccgctc acaattccac acaacatacg agccggaagc 1860
ataaagtgta aagcctgggg tgcctaatga gtgagctaac tcacattaat tgcgttgcgc 1920
gatgcttcca ttttgtgagg gttaatgctt cgagaagaca tgataagata cattgatgag 1980
tttggacaaa ccacaacaag aatgcagtga aaaaaatgct ttatttgtga aatttgtgat 2040
gctattgctt tatttgtaac cattataagc tgcaataaac aagttaacaa caacaattgc 2100
attcatttta tgtttcaggt tcagggggag atgtgggagg ttttttaaag caagtaaaac 2160
ctctacaaat gtggtaaaat ccgataagga tcgattccgg agcctgaatg gcgaatggac 2220
gcgccctgta gcggcgcatt aagcgcggcg ggtgtggtgg ttacgcgcac gtgaccgcta 2280

-continued

```
cacttgccag cgccctagcg cccgctcctt tcgctttctt cccttccttt ctcgccacgt   2340
tcgccggctt tccccgtcaa gctctaaatc gggggctccc tttagggttc cgatttagtg   2400
ctttacggca cctcgacccc aaaaaacttg attagggtga tggttcacgt agtgggccat   2460
cgccctgata gacggttttt cgccctttga cgttggagtc cacgttcttt aatagtggac   2520
tcttgttcca aactggaaca acactcaacc ctatctcggt ctattctttt gatttataag   2580
ggattttgcc gatttcggcc tattggttaa aaaatgagct gatttaacaa aaatttaacg   2640
cgaattttaa caaaatatta acgcttacaa tttcgcctgt gtaccttctg aggcggaaag   2700
aaccagctgt ggaatgtgtg tcagttaggg tgtggaaagt ccccaggctc cccagcaggc   2760
agaagtatgc aaagcatgca tctcaattag tcagcaacca ggtgtggaaa gtccccaggc   2820
tccccagcag gcagaagtat gcaaagcatg catctcaatt agtcagcaac catagtcccg   2880
cccctaactc cgcccatccc gcccctaact ccgcccagtt ccgcccattc tccgccccat   2940
ggctgactaa ttttttttat ttatgcagag gccgaggccg cctcggcctc tgagctattc   3000
cagaagtagt gaggaggctt ttttggaggc ctaggctttt gcaaaaagct tgattcttct   3060
gacacaacag tctcgaactt aaggctagag ccaccatgat tgaacaagat ggattgcacg   3120
caggttctcc ggccgcttgg gtggagaggc tattcggcta tgactgggca caacagacaa   3180
tcggctgctc tgatgccgcc gtgttccggc tgtcagcgca ggggcgcccg gttctttttg   3240
tcaagaccga cctgtccggt gccctgaatg aactgcagga cgaggcagcg cggctatcgt   3300
ggctggccac gacgggcgtt ccttgcgcag ctgtgctcga cgttgtcact gaagcgggaa   3360
gggactggct gctattgggc gaagtgccgg ggcaggatct cctgtcatct caccttgctc   3420
ctgccgagaa agtatccatc atggctgatg caatgcggcg gctgcatacg cttgatccgg   3480
ctacctgccc attcgaccac caagcgaaac atcgcatcga gcgagcacgt actcggatgg   3540
aagccggtct tgtcgatcag gatgatctgg acgaagagca tcaggggctc gcgccagccg   3600
aactgttcgc caggctcaag gcgcgcatgc ccgacggcga ggatctcgtc gtgacccatg   3660
gcgatgcctg cttgccgaat atcatggtgg aaaatggccg cttttctgga ttcatcgact   3720
gtggccggct gggtgtggcg gaccgctatc aggacatagc gttggctacc cgtgatattg   3780
ctgaagagct tggcggcgaa tgggctgacc gcttcctcgt gctttacggt atcgccgctc   3840
ccgattcgca gcgcatcgcc ttctatcgcc ttcttgacga gttcttctga gcgggactct   3900
ggggttcgaa atgaccgacc aagcgacgcc caacctgcca tcacgatggc cgcaataaaa   3960
tatctttatt ttcattacat ctgtgtgttg gttttttgtg tgaagatccg cgtatggtgc   4020
actctcagta caatctgctc tgatgccgca tagttaagcc agccccgaca cccgccaaca   4080
cccgctgacg cgccctgacg ggcttgtctg ctcccggcat ccgcttacag acaagctgtg   4140
accgtctccg ggagctgcat gtgtcagagg ttttcaccgt catcaccgaa acgcgcgaga   4200
cgaaagggcc tcgtgatacg cctattttta taggttaatg tcatgataat aatggtttct   4260
tagacgtcag gtggcacttt tcggggaaat gtgcgcggaa cccctatttg tttatttttc   4320
taaatacatt caaatatgta tccgctcatg agacaataac cctgataaat gcttcaataa   4380
tattgaaaaa ggaagagtat gagtattcaa catttccgtg tcgcccttat tccctttttt   4440
gcggcatttt gccttcctgt ttttgctcac ccagaaacgc tggtgaaagt aaaagatgct   4500
gaagatcagt tgggtgcacg agtgggttac atcgaactgg atctcaacag cggtaagatc   4560
cttgagagtt ttcgccccga agaacgtttt ccaatgatga gcacttttaa agttctgcta   4620
tgtggcgcgg tattatcccg tattgacgcc gggcaagagc aactcggtcg ccgcatacac   4680
```

-continued tattctcaga atgacttggt tgagtactca ccagtcacag aaaagcatct tacggatggc 4740
atgacagtaa gagaattatg cagtgctgcc ataaccatga gtgataacac tgcggccaac 4800
ttacttctga caacgatcgg aggaccgaag gagctaaccg cttttttgca caacatgggg 4860
gatcatgtaa ctcgccttga tcgttgggaa ccggagctga atgaagccat accaaacgac 4920
gagcgtgaca ccacgatgcc tgtagcaatg gcaacaacgt tgcgcaaact attaactggc 4980
gaactactta ctctagcttc ccggcaacaa ttaatagact ggatggaggc ggataaagtt 5040
gcaggaccac ttctgcgctc ggcccttccg gctggctggt ttattgctga taaatctgga 5100
gccggtgagc gtgggtctcg cggtatcatt gcagcactgg ggccagatgg taagccctcc 5160
cgtatcgtag ttatctacac gacggggagt caggcaacta tggatgaacg aaatagacag 5220
atcgctgaga taggtgcctc actgattaag cattggtaac tgtcagacca agtttactca 5280
tatatacttt agattgattt aaaacttcat ttttaattta aaaggatcta ggtgaagatc 5340
ctttttgata atctcatgac caaaatccct taacgtgagt tttcgttcca ctgagcgtca 5400
gaccccgtag aaaagatcaa aggatcttct tgagatcctt tttttctgcg cgtaatctgc 5460
tgcttgcaaa caaaaaaacc accgctacca gcggtggttt gtttgccgga tcaagagcta 5520
ccaactcttt ttccgaaggt aactggcttc agcagagcgc agataccaaa tactgtcctt 5580
ctagtgtagc cgtagttagg ccaccacttc aagaactctg tagcaccgcc tacatacctc 5640
gctctgctaa tcctgttacc agtggctgct gccagtggcg ataagtcgtg tcttaccggg 5700
ttggactcaa gacgatagtt accggataag gcgcagcggt cgggctgaac ggggggttcg 5760
tgcacacagc ccagcttgga gcgaacgacc tacaccgaac tgagatacct acagcgtgag 5820
ctatgagaaa gcgccacgct tcccgaaggg agaaaggcgg acaggtatcc ggtaagcggc 5880
agggtcggaa caggagagcg cacgagggag cttccagggg gaaacgcctg gtatctttat 5940
agtcctgtcg ggtttcgcca cctctgactt gagcgtcgat ttttgtgatg ctcgtcaggg 6000
gggcggagcc tatggaaaaa cgccagcaac gcggcctttt tacggttcct ggccttttgc 6060
tggccttttg ctcacatggc tcgac 6085

<210> SEQ ID NO 9
<211> LENGTH: 6086
<212> TYPE: DNA
<213> ORGANISM: Homo sapiens

<400> SEQUENCE: 9
agatcttcaa tattggccat tagccatatt attcattggt tatatagcat aaatcaatat 60
tggctattgg ccattgcata cgttgtatct atatcataat atgtacattt atattggctc 120
atgtccaata tgaccgccat gttggcattg attattgact agttattaat agtaatcaat 180
tacggggtca ttagttcata gcccatatat ggagttccgc gttacataac ttacggtaaa 240
tggcccgcct ggctgaccgc ccaacgaccc ccgcccattg acgtcaataa tgacgtatgt 300
tcccatagta acgccaatag ggactttcca ttgacgtcaa tgggtggagt atttacggta 360
aactgcccac ttggcagtac atcaagtgta tcatatgcca agtccgcccc ctattgacgt 420
caatgacggt aaatggcccg cctggcatta tgcccagtac atgaccttac gggactttcc 480
tacttggcag tacatctacg tattagtcat cgctattacc atggtgatgc ggttttggca 540
gtacaccaat gggcgtggat agcggtttga ctcacgggga tttccaagtc tccaccccat 600
tgacgtcaat gggagtttgt tttggcacca aaatcaacgg gactttccaa aatgtcgtaa 660

-continued

```
caactgcgat cgcccgcccc gttgacgcaa atgggcggta ggcgtgtacg gtgggaggtc    720
tatataagca gagctcgttt agtgaaccgt cagatcacta gaagctttat tgcggtagtt    780
tatcacagtt aaattgctaa cgcagtcagt gcttctgaca caacagtctc gaacttaagc    840
tgcagtgact ctcttaatta actccaccag tctcacttca gttccttttg cctccaccag    900
tctcacttca gttccttttg catgaagagc tcagaatcaa aagaggaaac caacccctaa    960
gatgagcttt ccatgtaaat ttgtagccag cttccttctg attttcaatg tttcttccaa   1020
aggtgcagtc tccaaagaga ttacgaatgc cttggaaacc tggggtgcct tgggtcagga   1080
catcaacttg gacattccta gttttcaaat gagtgatgat attgacgata taaaatggga   1140
aaaaacttca gacaagaaaa agattgcaca attcagaaaa gagaaagaga ctttcaagga   1200
aaaagataca tataagctat ttaaaaatgg aactctgaaa attaagcatc tgaagaccga   1260
tgatcaggat atctacaagg tatcaatata tgatacaaaa ggaaaaaatg tgttggaaaa   1320
aatatttgat ttgaagattc aagagagggt ctcaaaacca aagatctcct ggacttgtat   1380
caacacaacc ctgacctgtg aggtaatgaa tggaactgac cccgaattaa acctgtatca   1440
agatgggaaa catctaaaac tttctcagag ggtcatcaca cacaagtgga ccaccagcct   1500
gagtgcaaaa ttcaagtgca cagcagggaa caaagtcagc aaggaatcca gtgtcgagcc   1560
tgtcagctgt ccagagaaag ggatccacag gtgagtaggg cccgatcctt ctagagtcga   1620
gctctcttaa ggtagcaagg ttacaagaca ggtttaagga gaccaataga aactgggctt   1680
gtcgagacag agaagactct tgcgtttctg ataggcacct attggtctta cgcggccgcg   1740
aattccaagc ttgagtattc tatcgtgtca cctaaataac ttggcgtaat catggtcata   1800
tctgtttcct gtgtgaaatt gttatccgct cacaattcca cacaacatac gagccggaag   1860
cataaagtgt aaagcctggg gtgcctaatg agtgagctaa ctcacattaa ttgcgttgcg   1920
cgatgcttcc attttgtgag ggttaatgct tcgagaagac atgataagat acattgatga   1980
gtttggacaa accacaacaa gaatgcagtg aaaaaaatgc tttatttgtg aaatttgtga   2040
tgctattgct ttatttgtaa ccattataag ctgcaataaa caagttaaca acaacaattg   2100
cattcatttt atgtttcagg ttcaggggga gatgtgggag gtttttttaaa gcaagtaaaa   2160
cctctacaaa tgtggtaaaa tccgataagg atcgattccg gagcctgaat ggcgaatgga   2220
cgcgccctgt agcggcgcat taagcgcggc gggtgtggtg gttacgcgca cgtgaccgct   2280
acacttgcca gcgccctagc gcccgctcct ttcgctttct tcccttcctt tctcgccacg   2340
ttcgccggct ttccccgtca agctctaaat cgggggctcc ctttagggtt ccgatttagt   2400
gctttacggc acctcgaccc caaaaaactt gattagggtg atggttcacg tagtgggcca   2460
tcgccctgat agacggtttt tcgccctttg acgttggagt ccacgttctt taatagtgga   2520
ctcttgttcc aaactggaac aacactcaac cctatctcgg tctattcttt tgatttataa   2580
gggattttgc cgatttcggc ctattggtta aaaaatgagc tgatttaaca aaaatttaac   2640
gcgaatttta acaaaatatt aacgcttaca atttcgcctg tgtaccttct gaggcggaaa   2700
gaaccagctg tggaatgtgt gtcagttagg gtgtggaaag tccccaggct ccccagcagg   2760
cagaagtatg caaagcatgc atctcaatta gtcagcaacc aggtgtggaa agtccccagg   2820
ctccccagca ggcagaagta tgcaaagcat gcatctcaat tagtcagcaa ccatagtccc   2880
gcccctaact ccgcccatcc cgcccctaac tccgcccagt tccgcccatt ctccgcccca   2940
tggctgacta attttttta tttatgcaga ggccgaggcc gcctcggcct ctgagctatt   3000
ccagaagtag tgaggaggct tttttggagg cctaggcttt tgcaaaaagc ttgattcttc   3060
```

-continued

```
tgacacaaca gtctcgaact taaggctaga gccaccatga ttgaacaaga tggattgcac   3120

gcaggttctc cggccgcttg ggtggagagg ctattcggct atgactgggc acaacagaca   3180

atcggctgct ctgatgccgc cgtgttccgg ctgtcagcgc aggggcgccc ggttcttttt   3240

gtcaagaccg acctgtccgg tgccctgaat gaactgcagg acgaggcagc gcggctatcg   3300

tggctggcca cgacgggcgt tccttgcgca gctgtgctcg acgttgtcac tgaagcggga   3360

agggactggc tgctattggg cgaagtgccg gggcaggatc tcctgtcatc tcaccttgct   3420

cctgccgaga aagtatccat catggctgat gcaatgcggc ggctgcatac gcttgatccg   3480

gctacctgcc cattcgacca ccaagcgaaa catcgcatcg agcgagcacg tactcggatg   3540

gaagccggtc ttgtcgatca ggatgatctg gacgaagagc atcaggggct cgcgccagcc   3600

gaactgttcg ccaggctcaa ggcgcgcatg cccgacggcg aggatctcgt cgtgacccat   3660

ggcgatgcct gcttgccgaa tatcatggtg gaaaatggcc gcttttctgg attcatcgac   3720

tgtggccggc tgggtgtggc ggaccgctat caggacatag cgttggctac ccgtgatatt   3780

gctgaagagc ttggcggcga atgggctgac cgcttcctcg tgctttacgg tatcgccgct   3840

cccgattcgc agcgcatcgc cttctatcgc cttcttgacg agttcttctg agcgggactc   3900

tggggttcga aatgaccgac caagcgacgc ccaacctgcc atcacgatgg ccgcaataaa   3960

atatctttat tttcattaca tctgtgtgtt ggttttttgt gtgaagatcc gcgtatggtg   4020

cactctcagt acaatctgct ctgatgccgc atagttaagc cagccccgac acccgccaac   4080

acccgctgac gcgccctgac gggcttgtct gctcccggca tccgcttaca gacaagctgt   4140

gaccgtctcc gggagctgca tgtgtcagag gttttcaccg tcatcaccga aacgcgcgag   4200

acgaaagggc ctcgtgatac gcctattttt ataggttaat gtcatgataa taatggtttc   4260

ttagacgtca ggtggcactt ttcggggaaa tgtgcgcgga acccctattt gtttattttt   4320

ctaaatacat tcaaatatgt atccgctcat gagacaataa ccctgataaa tgcttcaata   4380

atattgaaaa aggaagagta tgagtattca acatttccgt gtcgccctta ttcccttttt   4440

tgcggcattt tgccttcctg tttttgctca cccagaaacg ctggtgaaag taaaagatgc   4500

tgaagatcag ttgggtgcac gagtgggtta catcgaactg gatctcaaca gcggtaagat   4560

ccttgagagt tttcgccccg aagaacgttt tccaatgatg agcactttta aagttctgct   4620

atgtggcgcg gtattatccc gtattgacgc cgggcaagag caactcggtc gccgcataca   4680

ctattctcag aatgacttgg ttgagtactc accagtcaca gaaaagcatc ttacggatgg   4740

catgacagta agagaattat gcagtgctgc cataaccatg agtgataaca ctgcggccaa   4800

cttacttctg acaacgatcg gaggaccgaa ggagctaacc gcttttttgc acaacatggg   4860

ggatcatgta actcgccttg atcgttggga accggagctg aatgaagcca taccaaacga   4920

cgagcgtgac accacgatgc ctgtagcaat ggcaacaacg ttgcgcaaac tattaactgg   4980

cgaactactt actctagctt cccggcaaca attaatagac tggatggagg cggataaagt   5040

tgcaggacca cttctgcgct cggcccttcc ggctggctgg tttattgctg ataaatctgg   5100

agccggtgag cgtgggtctc gcggtatcat tgcagcactg gggccagatg gtaagccctc   5160

ccgtatcgta gttatctaca cgacggggag tcaggcaact atggatgaac gaaatagaca   5220

gatcgctgag ataggtgcct cactgattaa gcattggtaa ctgtcagacc aagtttactc   5280

atatatactt tagattgatt taaaacttca tttttaattt aaaaggatct aggtgaagat   5340

cctttttgat aatctcatga ccaaaatccc ttaacgtgag ttttcgttcc actgagcgtc   5400
```

-continued

```
agaccccgta gaaaagatca aaggatcttc ttgagatcct ttttttctgc gcgtaatctg   5460

ctgcttgcaa acaaaaaaac caccgctacc agcggtggtt tgtttgccgg atcaagagct   5520

accaactctt tttccgaagg taactggctt cagcagagcg cagataccaa atactgtcct   5580

tctagtgtag ccgtagttag gccaccactt caagaactct gtagcaccgc ctacatacct   5640

cgctctgcta atcctgttac cagtggctgc tgccagtggc gataagtcgt gtcttaccgg   5700

gttggactca agacgatagt taccggataa ggcgcagcgg tcgggctgaa cggggggttc   5760

gtgcacacag cccagcttgg agcgaacgac ctacaccgaa ctgagatacc tacagcgtga   5820

gctatgagaa agcgccacgc ttcccgaagg gagaaaggcg gacaggtatc cggtaagcgg   5880

cagggtcgga acaggagagc gcacgaggga gcttccaggg ggaaacgcct ggtatcttta   5940

tagtcctgtc gggtttcgcc acctctgact tgagcgtcga tttttgtgat gctcgtcagg   6000

gggggcggagc ctatggaaaa acgccagcaa cgcggccttt ttacggttcc tggccttttg   6060

ctggcctttt gctcacatgg ctcgac                                         6086
```

<210> SEQ ID NO 10
<211> LENGTH: 38
<212> TYPE: DNA
<213> ORGANISM: Artificial Sequence
<220> FEATURE:
<221> NAME/KEY: modified_base
<222> LOCATION: (29)..(32)
<223> OTHER INFORMATION: a, c, t, g, other or unknown
<223> OTHER INFORMATION: Description of Artificial Sequence: Synthetic oligonucleotide

<400> SEQUENCE: 10

```
tttttttttt ttcgtcagcg gccgcatcnn nntttatt                            38
```

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11

```
cagatcacta gaagctttat tgcgg                                          25
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12

```
ttttcgtcag cggccgcatc                                                20
```

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13

```
actcataggc catagaggcc tatcacagtt aaattgctaa cgcag                    45
```

-continued

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
ctcgtttagt gcggccgctc agatcactga attctgacga cct 43

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
ctcgtttagt ggcgcgccag atcactgaat tctgacgacc t 41

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
gacctactga ttaacggcca ta 22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
tcgtcagaat tcagtgatct 20

<210> SEQ ID NO 18
<211> LENGTH: 6836
<212> TYPE: DNA
<213> ORGANISM: Homo sapiens

<400> SEQUENCE: 18
agatcttcaa tattggccat tagccatatt attcattggt tatatagcat aaatcaatat 60
tggctattgg ccattgcata cgttgtatct atatcataat atgtacattt atattggctc 120
atgtccaata tgaccgccat gttggcattg attattgact agttattaat agtaatcaat 180
tacggggtca ttagttcata gcccatatat ggagttccgc gttacataac ttacggtaaa 240
tggcccgcct ggctgaccgc ccaacgaccc ccgcccattg acgtcaataa tgacgtatgt 300
tcccatagta acgccaatag ggactttcca ttgacgtcaa tgggtggagt atttacggta 360
aactgcccac ttggcagtac atcaagtgta tcatatgcca agtccgcccc ctattgacgt 420
caatgacggt aaatggcccg cctggcatta tgcccagtac atgaccttac gggactttcc 480
tacttggcag tacatctacg tattagtcat cgctattacc atggtgatgc ggttttggca 540
gtacaccaat gggcgtggat agcggtttga ctcacgggga tttccaagtc tccaccccat 600

-continued

```
tgacgtcaat gggagtttgt tttggcacca aaatcaacgg gactttccaa aatgtcgtaa    660
caactgcgat cgcccgcccc gttgacgcaa atgggcggta ggcgtgtacg gtgggaggtc    720
tatataagca gagctcgttt agtgaaccgt cagatcacta gaagctttat tgcggtagtt    780
tatcacagtt aaattgctaa cgcagtcagt gcttctgaca caacagtctc gaacttaagc    840
tgcagtgact ctcttaaatc caccatggct acaggtgagt actcggatct agcgctatat    900
gcgttgatgc aatttctatg cgcacccgtt ctcggagcac tgtccgaccg ctttggccgc    960
cgcccagtcc tgctcgcttc gctacttgga gccactatcg actacgcgat catggcgacc   1020
acacccgtcc tgtggatcct ctacgccgga cgcatcgtgg ccggcatcac cggcgccaca   1080
ggtgcggttg ctggcgccta tatcgccgac atcaccgatg gggaagatcg ggctcgccac   1140
ttcgggctca tgagcgcttg tttcggctct cttaaggtag cagatccttg ctagagtcga   1200
ccaattctca tgtttgacag cttatcatcg cagatcctga gcttgtatgg tgcactctca   1260
gtacaatctg ctctgctgcc gcatagttaa gccagtatct gctccctgct tgtgtgttgg   1320
aggtcgctga gtagtgcgcg agcaaaattt aagctacaac aaggcaaggc ttgaccgaca   1380
attgcatgaa gaatctgctt agggttaggc gttttgcgct gcttcgcgat gtacgggcca   1440
gatatacgcg tatctgaggg gactagggtg tgtttaggcg cccagcgggg cttcggttgt   1500
acgcggttag gagtcccctc aggatatagt agtttcgctt ttgcataggg agggggaaat   1560
gtagtcttat gcaatacact tgtagtcttg caacatggta acgatgagtt agcaacatgc   1620
cttacaagga gagaaaaagc accgtgcatg ccgattggtg gaagtaaggt ggtacgatcg   1680
tgccttatta ggaaggcaac agacaggtct gacatggatt ggacgaacca ctgaattccg   1740
cattgcagag ataattgtat ttaagtgcct agctcgatac aataaacgcc atttgaccat   1800
tcaccacatt ggtgtgcacc tccaagctgg gtaccagctg ctagcctcga gacgcgtgat   1860
ttccttcgaa gcttgtcatg gttggttcgc taaactgcat cgtcgctgtg tcccagaaca   1920
tgggcatcgg caagaacggg gacctgccct ggccaccgct caggaatgaa ttcagatatt   1980
tccagagaat gaccacaacc tcttcagtag aaggtaaaca gaatctggtg attatgggta   2040
agaagacctg gttctccatt cctgagaaga atcgaccttt aaagggtaga attaatttag   2100
ttctcagcag agaactcaag gaacctccac aaggagctca ttttctttcc agaagtctag   2160
atgatgcctt aaaacttact gaacaaccag aattagcaaa taaagtagac atggtctgga   2220
tagttggtgg cagttctgtt tataaggaag ccatgaatca cccaggccat cttaaactat   2280
ttgtgacaag gatcatgcaa gactttgaaa gtgacacgtt ttttccagaa attgatttgg   2340
agaaatataa acttctgcca gaatacccag gtgttctctc tgatgtccag gaggagaaag   2400
gcattaagta caaatttgaa gtatatgaga agaatgatta atcgatctta agtttaatct   2460
ttcccggggg taccgtcgac tgcggccgcg aattccaagc ttgagtattc tatcgtgtca   2520
cctaaataac ttggcgtaat catggtcata tctgtttcct gtgtgaaatt gttatccgct   2580
cacaattcca cacaacatac gagccggaag cataaagtgt aaagcctggg gtgcctaatg   2640
agtgagctaa ctcacattaa ttgcgttgcg cgatgcttcc attttgtgag ggttaatgct   2700
tcgagaagac atgataagat acattgatga gtttggacaa accacaacaa gaatgcagtg   2760
aaaaaaatgc tttatttgtg aaatttgtga tgctattgct ttatttgtaa ccattataag   2820
ctgcaataaa caagttaaca acaacaattg cattcatttt atgtttcagg ttcaggggga   2880
gatgtgggag gtttttttaaa gcaagtaaaa cctctacaaa tgtggtaaaa tccgataagg   2940
```

-continued

```
atcgattccg gagcctgaat ggcgaatgga cgcgccctgt agcggcgcat taagcgcggc   3000
gggtgtggtg gttacgcgca cgtgaccgct acacttgcca gcgccctagc gcccgctcct   3060
ttcgctttct tcccttcctt tctcgccacg ttcgccggct ttccccgtca agctctaaat   3120
cgggggctcc ctttagggtt ccgatttagt gctttacggc acctcgaccc caaaaaactt   3180
gattagggtg atggttcacg tagtgggcca tcgccctgat agacggtttt tcgccctttg   3240
acgttggagt ccacgttctt taatagtgga ctcttgttcc aaactggaac aacactcaac   3300
cctatctcgg tctattcttt tgatttataa gggattttgc cgatttcggc ctattggtta   3360
aaaaatgagc tgatttaaca aaaatttaac gcgaatttta acaaaatatt aacgcttaca   3420
atttcgcctg tgtaccttct gaggcggaaa gaaccagctg tggaatgtgt gtcagttagg   3480
gtgtggaaag tccccaggct ccccagcagg cagaagtatg caaagcatgc atctcaatta   3540
gtcagcaacc aggtgtggaa agtccccagg ctccccagca ggcagaagta tgcaaagcat   3600
gcatctcaat tagtcagcaa ccatagtccc gcccctaact ccgcccatcc cgcccctaac   3660
tccgcccagt tccgcccatt ctccgcccca tggctgacta atttttttta tttatgcaga   3720
ggccgaggcc gcctcggcct ctgagctatt ccagaagtag tgaggaggct tttttggagg   3780
cctaggcttt tgcaaaaagc ttgattcttc tgacacaaca gtctcgaact taaggctaga   3840
gccaccatga ttgaacaaga tggattgcac gcaggttctc cggccgcttg ggtggagagg   3900
ctattcggct atgactgggc acaacagaca atcggctgct ctgatgccgc cgtgttccgg   3960
ctgtcagcgc aggggcgccc ggttcttttt gtcaagaccg acctgtccgg tgccctgaat   4020
gaactgcagg acgaggcagc gcggctatcg tggctggcca cgacgggcgt tccttgcgca   4080
gctgtgctcg acgttgtcac tgaagcggga agggactggc tgctattggg cgaagtgccg   4140
gggcaggatc tcctgtcatc tcaccttgct cctgccgaga aagtatccat catggctgat   4200
gcaatgcggc ggctgcatac gcttgatccg gctacctgcc cattcgacca ccaagcgaaa   4260
catcgcatcg agcgagcacg tactcggatg gaagccggtc ttgtcgatca ggatgatctg   4320
gacgaagagc atcaggggct cgcgccagcc gaactgttcg ccaggctcaa ggcgcgcatg   4380
cccgacggcg aggatctcgt cgtgacccat ggcgatgcct gcttgccgaa tatcatggtg   4440
gaaaatggcc gcttttctgg attcatcgac tgtggccggc tgggtgtggc ggaccgctat   4500
caggacatag cgttggctac ccgtgatatt gctgaagagc ttggcggcga atgggctgac   4560
cgcttcctcg tgctttacgg tatcgccgct cccgattcgc agcgcatcgc cttctatcgc   4620
cttcttgacg agttcttctg agcgggactc tggggttcga aatgaccgac caagcgacgc   4680
ccaacctgcc atcacgatgg ccgcaataaa atatctttat tttcattaca tctgtgtgtt   4740
ggttttttgt gtgaagatcc gcgtatggtg cactctcagt acaatctgct ctgatgccgc   4800
atagttaagc cagccccgac acccgccaac acccgctgac gcgccctgac gggcttgtct   4860
gctcccggca tccgcttaca gacaagctgt gaccgtctcc gggagctgca tgtgtcagag   4920
gttttcaccg tcatcaccga aacgcgcgag acgaaagggc ctcgtgatac gcctattttt   4980
ataggttaat gtcatgataa taatggtttc ttagacgtca ggtggcactt ttcggggaaa   5040
tgtgcgcgga acccctattt gtttattttt ctaaatacat tcaaatatgt atccgctcat   5100
gagacaataa ccctgataaa tgcttcaata atattgaaaa aggaagagta tgagtattca   5160
acatttccgt gtcgccctta ttcccttttt tgcggcattt tgccttcctg tttttgctca   5220
cccagaaacg ctggtgaaag taaaagatgc tgaagatcag ttgggtgcac gagtgggtta   5280
catcgaactg gatctcaaca gcggtaagat ccttgagagt tttcgccccg aagaacgttt   5340
```

-continued

```
tccaatgatg agcactttta aagttctgct atgtggcgcg gtattatccc gtattgacgc   5400
cgggcaagag caactcggtc gccgcataca ctattctcag aatgacttgg ttgagtactc   5460
accagtcaca gaaaagcatc ttacggatgg catgacagta agagaattat gcagtgctgc   5520
cataaccatg agtgataaca ctgcggccaa cttacttctg acaacgatcg gaggaccgaa   5580
ggagctaacc gcttttttgc acaacatggg ggatcatgta actcgccttg atcgttggga   5640
accggagctg aatgaagcca taccaaacga cgagcgtgac accacgatgc ctgtagcaat   5700
ggcaacaacg ttgcgcaaac tattaactgg cgaactactt actctagctt cccggcaaca   5760
attaatagac tggatggagg cggataaagt tgcaggacca cttctgcgct cggcccttcc   5820
ggctggctgg tttattgctg ataaatctgg agccggtgag cgtgggtctc gcggtatcat   5880
tgcagcactg gggccagatg gtaagccctc ccgtatcgta gttatctaca cgacggggag   5940
tcaggcaact atggatgaac gaaatagaca gatcgctgag ataggtgcct cactgattaa   6000
gcattggtaa ctgtcagacc aagtttactc atatatactt tagattgatt taaaacttca   6060
tttttaattt aaaaggatct aggtgaagat cctttttgat aatctcatga ccaaaatccc   6120
ttaacgtgag ttttcgttcc actgagcgtc agaccccgta gaaaagatca aaggatcttc   6180
ttgagatcct ttttttctgc gcgtaatctg ctgcttgcaa acaaaaaaac caccgctacc   6240
agcggtggtt tgtttgccgg atcaagagct accaactctt tttccgaagg taactggctt   6300
cagcagagcg cagataccaa atactgtcct tctagtgtag ccgtagttag gccaccactt   6360
caagaactct gtagcaccgc ctacatacct cgctctgcta atcctgttac cagtggctgc   6420
tgccagtggc gataagtcgt gtcttaccgg gttggactca agacgatagt taccggataa   6480
ggcgcagcgg tcgggctgaa cggggggttc gtgcacacag cccagcttgg agcgaacgac   6540
ctacaccgaa ctgagatacc tacagcgtga gctatgagaa agcgccacgc ttcccgaagg   6600
gagaaaggcg gacaggtatc cggtaagcgg cagggtcgga acaggagagc gcacgaggga   6660
gcttccaggg ggaaacgcct ggtatcttta tagtcctgtc gggtttcgcc acctctgact   6720
tgagcgtcga tttttgtgat gctcgtcagg ggggcggagc ctatggaaaa acgccagcaa   6780
cgcggccttt ttacggttcc tggccttttg ctggcctttt gctcacatgg ctcgac       6836
```

<210> SEQ ID NO 19
<211> LENGTH: 4644
<212> TYPE: DNA
<213> ORGANISM: Homo sapiens

<400> SEQUENCE: 19

```
gatcttcaat attggccatt agccatatta ttcattggtt atatagcata aatcaatatt     60
ggctattggc cattgcatac gttgtatcta tatcataata tgtacattta tattggctca    120
tgtccaatat gaccgccatg ttggcattga ttattgacta gttattaata gtaatcaatt    180
acggggtcat tagttcatag cccatatatg gagttccgcg ttacataact tacggtaaat    240
ggcccgcctg gctgaccgcc caacgacccc cgcccattga cgtcaataat gacgtatgtt    300
cccatagtaa cgccaatagg gactttccat tgacgtcaat gggtggagta tttacggtaa    360
actgcccact tggcagtaca tcaagtgtat catatgccaa gtccgccccc tattgacgtc    420
aatgacggta aatggcccgc ctggcattat gcccagtaca tgaccttacg ggactttcct    480
acttggcagt acatctacgt attagtcatc gctattacca tggtgatgcg gttttggcag    540
tacaccaatg ggcgtggata gcggtttgac tcacggggat ttccaagtct ccaccccatt    600
```

-continued

```
gacgtcaatg ggagtttgtt ttggcaccaa aatcaacggg actttccaaa atgtcgtaac    660
aactgcgatc gcccgccccg ttgacgcaaa tgggcggtag gcgtgtacgg tgggaggtct    720
atataagcag agctcgttta gtgaaccgtc agatcactga attctgacga cctactgatt    780
aacggccata gaggcctcct gcagatcact agaagcttta ttgcggtagt ttatcacagt    840
taaattgcta acgcagtcag tgcttctgac acaacagtct cgaacttaag ctgcagtgac    900
tctcttaaat ccaccatggc tacaggtgag tactcgctac cttaagagag gcctatctgg    960
cagttagca gtcgaagaaa gaagtttaag agagccgaaa caagcgctca tgagcccgaa    1020
tggcgagcc cgatcttccc catcggtgat gtcggcgata taggcgccag caaccgcacc    1080
gtggcgccg gtgatgccgg ccacgatgcg tccggcgtag aggatccaca ggacgggtgt    1140
gtcgccatg atcgcgtagt cgatagtggc tccaagtagc gaagcgagca ggactgggcg    1200
cggccaaag cggtcggaca gtgctccgag aacgggtgcg catagaaatt gcatcaacgc    1260
tatagcgct agatccttgc tagagtcgag atctgtcgag ccatgtgagc aaaaggccag    1320
aaaaggcca ggaaccgtaa aaaggccgcg ttgctggcgt ttttccatag gctccgcccc    1380
ctgacgagc atcacaaaaa tcgacgctca agtcagaggt ggcgaaaccc gacaggacta    1440
aaagatacc aggcgtttcc ccctggaagc tccctcgtgc gctctcctgt tccgaccctg    1500
cgcttaccg gatacctgtc cgcctttctc ccttcgggaa gcgtggcgct ttctcatagc    1560
cacgctgta ggtatctcag ttcggtgtag gtcgttcgct ccaagctggg ctgtgtgcac    1620
aacccccg ttcagcccga ccgctgcgcc ttatccggta actatcgtct tgagtccaac    1680
cggtaagac acgacttatc gccactggca gcagccactg gtaacaggat tagcagagcg    1740
ggtatgtag gcggtgctac agagttcttg aagtggtggc ctaactacgg ctacactaga    1800
ggacagtat ttggtatctg cgctctgctg aagccagtta ccttcggaaa aagagttggt    1860
gctcttgat ccggcaaaca aaccaccgct ggtagcggtg gtttttttgt ttgcaagcag    1920
agattacgc gcagaaaaaa aggatctcaa gaagatcctt tgatcttttc tacggggtct    1980
acgctcagt ggaacgaaaa ctcacgttaa gggattttgg tcatgagatt atcaaaaagg    2040
tcttcacct agatcctttt atcggtgtga aataccgcac agatgcgtaa ggagaaaata    2100
cgcatcagg aaattgtaag cgttaataat tcagaagaac tcgtcaagaa ggcgatagaa    2160
gcgatgcgc tgcgaatcgg gagcggcgat accgtaaagc acgaggaagc ggtcagccca    2220
tcgccgcca agctcttcag caatatcacg ggtagccaac gctatgtcct gatagcggtc    2280
gccacaccc agccggccac agtcgatgaa tccagaaaag cggccatttt ccaccatgat    2340
ttcggcaag caggcatcgc catgggtcac gacgagatcc tcgccgtcgg gcatgctcgc    2400
ttgagcctg gcgaacagtt cggctggcgc gagcccctga tgctcttcgt ccagatcatc    2460
tgatcgaca agaccggctt ccatccgagt acgtgctcgc tcgatgcgat gtttcgcttg    2520
tggtcgaat gggcaggtag ccggatcaag cgtatgcagc cgccgcattg catcagccat    2580
atggatact ttctcggcag gagcaaggtg agatgacagg agatcctgcc ccggcacttc    2640
cccaatagc agccagtccc ttcccgcttc agtgacaacg tcgagcacag ctgcgcaagg    2700
acgcccgtc gtggccagcc acgatagccg cgctgcctcg tcttgcagtt cattcagggc    2760
ccggacagg tcggtcttga caaaaagaac cgggcgcccc tgcgctgaca gccggaacac    2820
gcggcatca gagcagccga ttgtctgttg tgcccagtca tagccgaata gcctctccac    2880
caagcggcc ggagaacctg cgtgcaatcc atcttgttca atcatgcgaa acgatcctca    2940
cctgtctct tgatcagagc ttgatcccct gcgccatcag atccttggcg gcgagaaagc    3000
```

-continued atccagttt actttgcagg gcttgtcaac cttaccagat aaaagtgctc atcattggaa 3060 acgttcaat tctgaggcgg aaagaaccag ctgtggaatg tgtgtcagtt agggtgtgga 3120 agtccccag gctccccagc aggcagaagt atgcaaagca tgcatctcaa ttagtcagca 3180 ccaggtgtg gaaagtcccc aggctcccca gcaggcagaa gtatgcaaag catgcatctc 3240 attagtcag caaccatagt cccgccccta actccgccca tcccgcccct aactccgccc 3300 gttccgccc attctccgcc ccatggctga ctaatttttt ttatttatgc agaggccgag 3360 ccgcctcgg cctctgagct attccagaag tagtgaggag gcttttttgg aggcctaggc 3420 tttgcaaaa agcttgattc ttctgacaca acagtctcga acttaaggct agagccacca 3480 gattgaaca agatggattg cacgcaggtt ctccggccgc ttgggtggag aggctattcg 3540 ctatgactg ggcacaacag acaatcggct gctctgatgc cgccgtgttc cggctgtcag 3600 gcaggggcg cccggttctt tttgtcaaga ccgacctgtc cggtgccctg aatgaactgc 3660 ggacgaggc agcgcggcta tcgtggctgg ccacgacggg cgttccttgc gcagctgtgc 3720 cgacgttgt cactgaagcg ggaagggact ggctgctatt gggcgaagtg ccggggcagg 3780 tctcctgtc atctcacctt gctcctgccg agaaagtatc catcatggct gatgcaatgc 3840 gcggctgca tacgcttgat ccggctacct gcccattcga ccaccaagcg aaacatcgca 3900 cgagcgagc acgtactcgg atggaagccg gtcttgtcga tcaggatgat ctggacgaag 3960 gcatcaggg gctcgcgcca gccgaactgt tcgccaggct caaggcgcgc atgcccgacg 4020 cgaggatct cgtcgtgacc catggcgatg cctgcttgcc gaatatcatg gtggaaaatg 4080 ccgcttttc tggattcatc gactgtggcc ggctgggtgt ggcggaccgc tatcaggaca 4140 agcgttggc tacccgtgat attgctgaag agcttggcgg cgaatgggct gaccgcttcc 4200 cgtgcttta cggtatcgcc gctcccgatt cgcagcgcat cgccttctat cgccttcttg 4260 cgagccatt ctgatggagg tagcggccgc taacctggtt gctgactaat tgagatgcat 4320 ctttgcata cttctgcctg ctggggagcc tggggacttt ccacacccta actgacacac 4380 ttccacagc tggttctttc cgcctcagaa ggtacacagg cgaaattgta agcgttaata 4440 tttgttaaa attcgcgtta aatttttgtt aaatcagctc attttttaac caataggccg 4500 aatcggcaa aatcccttat aaatcaaaag aatagaccga gatagggttg agtgttgttc 4560 agtttggaa caagagtcca ctattaaaga acgtggactc caacgtcaaa gggcgaaaaa 4620 cgtctatca gggcgatggc ccac 4644

<210> SEQ ID NO 20
<211> LENGTH: 5247
<212> TYPE: DNA
<213> ORGANISM: Homo sapiens

<400> SEQUENCE: 20
gatcttcaat attggccatt agccatatta ttcattggtt atatagcata aatcaatatt 60
ggctattggc cattgcatac gttgtatcta tatcataata tgtacattta tattggctca 120
tgtccaatat gaccgccatg ttggcattga ttattgacta gttattaata gtaatcaatt 180
acggggtcat tagttcatag cccatatatg gagttccgcg ttacataact tacggtaaat 240
ggcccgcctg gctgaccgcc caacgacccc cgcccattga cgtcaataat gacgtatgtt 300
cccatagtaa cgccaatagg gactttccat tgacgtcaat gggtggagta tttacggtaa 360
actgcccact tggcagtaca tcaagtgtat catatgccaa gtccgccccc tattgacgtc 420

-continued

```
aatgacggta aatggcccgc ctggcattat gcccagtaca tgaccttacg ggactttcct    480
acttggcagt acatctacgt attagtcatc gctattacca tggtgatgcg gttttggcag    540
tacaccaatg ggcgtggata gcggtttgac tcacggggat ttccaagtct ccaccccatt    600
gacgtcaatg ggagtttgtt ttggcaccaa aatcaacggg actttccaaa atgtcgtaac    660
aactgcgatc gcccgccccg ttgacgcaaa tgggcggtag gcgtgtacgg tgggaggtct    720
atataagcag agctcgttta gtgaaccgtc agatcactag aagctttatt gcggtagttt    780
atcacagtta aattgctaac gcagtcagtg cttctgacac aacagtctcg aacttaagct    840
gcagtgactc tcttaaatcc accatggcta caggtgagta ctcgctacct taagagaggc    900
ctatctggcc agttagcagt cgaagaaaga agtttaagag agccgaaaca agcgctcatg    960
agcccgaagt ggcgagcccg atcttcccca tcggtgatgt cggcgatata ggcgccagca   1020
accgcacctg tggcgccggt gatgccggcc acgatgcgtc cggcgtagag gatccacagg   1080
acgggtgtgg tcgccatgat cgcgtagtcg atagtggctc caagtagcga agcgagcagg   1140
actgggcggc ggccaaagcg gtcggacagt gctccgagaa cgggtgcgca tagaaattgc   1200
atcaacgcat atagcgctag atccttgcta gagtcgagat ctgtcgagcc atgtgagcaa   1260
aaggccagca aaaggccagg aaccgtaaaa aggccgcgtt gctggcgttt ttccataggc   1320
tccgcccccc tgacgagcat cacaaaaatc gacgctcaag tcagaggtgg cgaaacccga   1380
caggactata aagataccag gcgtttcccc ctggaagctc cctcgtgcgc tctcctgttc   1440
cgaccctgcc gcttaccgga tacctgtccg cctttctccc ttcgggaagc gtggcgcttt   1500
ctcatagctc acgctgtagg tatctcagtt cggtgtaggt cgttcgctcc aagctgggct   1560
gtgtgcacga accccccgtt cagcccgacc gctgcgcctt atccggtaac tatcgtcttg   1620
agtccaaccc ggtaagacac gacttatcgc cactggcagc agccactggt aacaggatta   1680
gcagagcgag gtatgtaggc ggtgctacag agttcttgaa gtggtggcct aactacggct   1740
acactagaag gacagtattt ggtatctgcg ctctgctgaa gccagttacc ttcggaaaaa   1800
gagttggtag ctcttgatcc ggcaaacaaa ccaccgctgg tagcggtggt ttttttgttt   1860
gcaagcagca gattacgcgc agaaaaaaag gatctcaaga agatcctttg atcttttcta   1920
cggggtctga cgctcagtgg aacgaaaact cacgttaagg gattttggtc atgagattat   1980
caaaaaggat cttcacctag atccttttat cggtgtgaaa taccgcacag atgcgtaagg   2040
agaaaatacc gcatcaggaa attgtaagcg ttaataattc agaagaactc gtcaagaagg   2100
cgatagaagg cgatgcgctg cgaatcggga gcggcgatac cgtaaagcac gaggaagcgg   2160
tcagcccatt cgccgccaag ctcttcagca atatcacggg tagccaacgc tatgtcctga   2220
tagcggtccg ccacacccag ccggccacag tcgatgaatc cagaaaagcg gccattttcc   2280
accatgatat tcggcaagca ggcatcgcca tgggtcacga cgagatcctc gccgtcgggc   2340
atgctcgcct tgagcctggc gaacagttcg gctggcgcga gcccctgatg ctcttcgtcc   2400
agatcatcct gatcgacaag accggcttcc atccgagtac gtgctcgctc gatgcgatgt   2460
ttcgcttggt ggtcgaatgg gcaggtagcc ggatcaagcg tatgcagccg ccgcattgca   2520
tcagccatga tggatacttt ctcggcagga gcaaggtgag atgacaggag atcctgcccc   2580
ggcacttcgc ccaatagcag ccagtccctt cccgcttcag tgacaacgtc gagcacagct   2640
gcgcaaggaa cgcccgtcgt ggccagccac gatagccgcg ctgcctcgtc ttgcagttca   2700
ttcagggcac cggacaggtc ggtcttgaca aaaagaaccg ggcgcccctg cgctgacagc   2760
cggaacacgg cggcatcaga gcagccgatt gtctgttgtg cccagtcata gccgaatagc   2820
```

-continued

```
ctctccaccc aagcggccgg agaacctgcg tgcaatccat cttgttcaat catgcgaaac   2880
gatcctcatc ctgtctcttg atcagagctt gatcccctgc gccatcagat ccttggcggc   2940
gagaaagcca tccagtttac tttgcagggc ttgtcaacct taccagataa aagtgctcat   3000
cattggaaaa cgttcaattc tgaggcggaa agaaccagct gtggaatgtg tgtcagttag   3060
ggtgtggaaa gtccccaggc tccccagcag gcagaagtat gcaaagcatg catctcaatt   3120
agtcagcaac caggtgtgga aagtccccag gctccccagc aggcagaagt atgcaaagca   3180
tgcatctcaa ttagtcagca accatagtcc cgcccctaac tccgcccatc ccgcccctaa   3240
ctccgcccag ttccgcccat tctccgcccc atggctgact aatttttttt atttatgcag   3300
aggccgaggc cgcctcggcc tctgagctat tccagaagta gtgaggaggc ttttttggag   3360
gcctaggctt ttgcaaaaag cttgattctt ctgacacaac agtctcgaac ttaaggctag   3420
agccaccatg attgaacaag atggattgca cgcaggttct ccggccgctt gggtggagag   3480
gctattcggc tatgactggg cacaacagac aatcggctgc tctgatgccg ccgtgttccg   3540
gctgtcagcg caggggcgcc cggttctttt tgtcaagacc gacctgtccg gtgccctgaa   3600
tgaactgcag gacgaggcag cgcggctatc gtggctggcc acgacgggcg ttccttgcgc   3660
agctgtgctc gacgttgtca ctgaagcggg aagggactgg ctgctattgg gcgaagtgcc   3720
ggggcaggat ctcctgtcat ctcaccttgc tcctgccgag aaagtatcca tcatggctga   3780
tgcaatgcgg cggctgcata cgcttgatcc ggctacctgc ccattcgacc accaagcgaa   3840
acatcgcatc gagcgagcac gtactcggat ggaagccggt cttgtcgatc aggatgatct   3900
ggacgaagag catcaggggc tcgcgccagc cgaactgttc gccaggctca aggcgcgcat   3960
gcccgacggc gaggatctcg tcgtgaccca tggcgatgcc tgcttgccga atatcatggt   4020
ggaaaatggc cgcttttctg gattcatcga ctgtggccgg ctgggtgtgg cggaccgcta   4080
tcaggacata gcgttggcta cccgtgatat tgctgaagag cttggcggcg aatgggctga   4140
ccgcttcctc gtgctttacg gtatcgccgc tcccgattcg cagcgcatcg ccttctatcg   4200
ccttcttgac gagccattct gctggatggc tacaggtcgc agccctggcg tcgtgattag   4260
tgatgatgaa ccaggttatg accttgattt attttgcata cctaatcatt atgctgagga   4320
tttggaaagg gtgtttattc ctcatggact aattatggac aggactgaac gtcttgctcg   4380
agatgtgatg aaggagatgg gaggccatca cattgtagcc ctctgtgtgc tcaagggggg   4440
ctataaattc tttgctgacc tgctggatta catcaaagca ctgaatagaa atagtgatag   4500
atccattcct atgactgtag attttatcag actgaagagc tattgtaatg accagtcaac   4560
aggggacata aaagtaattg gtggagatga tctctcaact ttaactggaa agaatgtctt   4620
gattgtggaa gatataattg acactggcaa aacaatgcag actttgcttt ccttggtcag   4680
gcagtataat ccaaagatgg tcaaggtcgc aagcttgctg gtgaaaagga ccccacgaag   4740
tgttggatat aagccagact ttgttggatt tgaaattcca gacaagtttg ttgtaggata   4800
tgcccttgac tataatgaat acttcaggga tttgaatcat gtttgtgtca ttagtgaaac   4860
tggaaaagca aaatacaaag cctaagcggc cgctaacctg gttgctgact aattgagatg   4920
catgctttgc atacttctgc ctgctgggga gcctggggac tttccacacc ctaactgaca   4980
cacattccac agctggttct ttccgcctca gaaggtacac aggcgaaatt gtaagcgtta   5040
atattttgtt aaaattcgcg ttaaattttt gttaaatcag ctcatttttt aaccaatagg   5100
ccgaaatcgg caaaatccct tataaatcaa aagaatagac cgagataggg ttgagtgttg   5160
```

-continued

```
ttccagtttg gaacaagagt ccactattaa agaacgtgga ctccaacgtc aaagggcgaa   5220

aaaccgtcta tcagggcgat ggcccac                                       5247
```

<210> SEQ ID NO 21
<211> LENGTH: 5382
<212> TYPE: DNA
<213> ORGANISM: Homo sapiens
<220> FEATURE:
<221> NAME/KEY: modified_base
<222> LOCATION: (890)
<223> OTHER INFORMATION: a, c, t, g, other or unknown
<221> NAME/KEY: modified_base
<222> LOCATION: (1042)
<223> OTHER INFORMATION: a, c, t, g, other or unknown

<400> SEQUENCE: 21

```
cacctaaatt gtaagcgtta atattttgtt aaaattcgcg ttaaattttt gttaaatcag     60

ctcatttttt aaccaatagg ccgaaatcgg caaaatccct tataaatcaa aagaatagac    120

cgagataggg ttgagtgttg ttccagtttg gaacaagagt ccactattaa agaacgtgga    180

ctccaacgtc aaagggcgaa aaaccgtcta tcagggcgat ggcccactac gtgaaccatc    240

accctaatca agttttttgg ggtcgaggtg ccgtaaagca ctaaatcgga accctaaagg    300

gagcccccga tttagagctt gacggggaaa gccggcgaac gtggcgagaa aggaagggaa    360

gaaagcgaaa ggagcgggcg ctagggcgct ggcaagtgta gcggtcacgc tgcgcgtaac    420

caccacaccc gccgcgctta atgcgccgct acagggcgcg tcccattcgc cattcaggct    480

gcgcaactgt tgggaagggc gatcggtgcg ggcctcttcg ctattacgcc agctggcgaa    540

agggggatgt gctgcaaggc gattaagttg ggtaacgcca gggttttccc agtcacgacg    600

ttgtaaaacg acggccagtg aattgtaata cgactcacta tagggcgaat tgggtacaat    660

tcaattcgtc gacctcgaaa ttctaccggg taggggaggc gcttttccca aggcagtctg    720

gagcatgcgc tttagcagcc ccgctgggca cttggcgcta cacaagtggc ctctggcctc    780

gcacacattc cacatccacc ggtaggcgcc aaccggctcc gttctttggt ggccccttcg    840

cgccaccttc tactcctccc ctagtcagga agttcccccc cgccccgcan ctcgcgtcgt    900

gcaggacgtg acaaatggaa atagcacgtc tcactagtct cgtgcagatg gacaagcacc    960

gctgagcaat ggagcgggta ggcctttggg gcagcggcca atagcagctt tgctccttcg   1020

ctttctgggc tcagaggctg gnaaggggtg ggtccggggg cgggctcagg ggcgggctca   1080

ggggcggggc gggcgcccga aggtcctccg gaggcccggc attctgcacg cttcaaaagc   1140

gcacgtctgc cgcgctgttc tcctcttcct catctccggg cctttcgacc tgcatccatc   1200

tagatctcga gcagctgaag cttaccatga ccgagtacaa gcccacggtg cgcctcgcca   1260

cccgcgacga cgtcccccgg gccgtacgca ccctcgccgc cgcgttcgcc gactaccccg   1320

ccacgcgcca caccgtcgac ccggaccgcc acatcgagcg ggtcaccgag ctgcaagaac   1380

tcttcctcac gcgcgtcggg ctcgacatcg gcaaggtgtg ggtcgcggac gacggcgccg   1440

cggtggcggt ctggaccacg ccggagagcg tcgaagcggg ggcggtgttc gccgagatcg   1500

gcccgcgcat ggccgagttg agcggttccc ggctggccgc gcagcaacag atggaaggcc   1560

tcctggcgcc gcaccggccc caaggagccc gcgtggttcc ttggcccacc gtcgggcgtc   1620

ttcgcccgac caccagggca agggtctggc aagcgccgtc gtgctccccg gagtggaggc   1680

ggccgagcgc gccggggtgc ccgccttcct ggagacctcc gcgccccgca acctcccctt   1740

ctacgagcgg ctcggcttca ccgtcaccgc cgacgtcgag gtgcccgaag gaccgcgcac   1800
```

-continued

```
ctggtgcatg acccgcaagc ccggtgcctg acgcccgccc cacgacccgc agcgcccgac   1860
cgaaaggagc gcacgacccc atgcatcgat ggcactgggc aggtaagtat caaggttagc   1920
gatcttcaat attggccatt agccatatta ttcattggtt atatagcata aatcaatatt   1980
ggctattggc cattgcatac gttgtatcta tatcataata tgtacattta tattggctca   2040
tgtccaatat gaccgccatg ttggcattga ttattgacta gttattaata gtaatcaatt   2100
acggggtcat tagttcatag cccatatatg gagttccgcg ttacataact tacggtaaat   2160
ggcccgcctg gctgaccgcc caacgacccc cgcccattga cgtcaataat gacgtatgtt   2220
cccatagtaa cgccaatagg gactttccat tgacgtcaat gggtggagta tttacggtaa   2280
actgcccact tggcagtaca tcaagtgtat catatgccaa gtccgccccc tattgacgtc   2340
aatgacggta aatggcccgc ctggcattat gcccagtaca tgaccttacg ggactttcct   2400
acttggcagt acatctacgt attagtcatc gctattacca tggtgatgcg gttttggcag   2460
tacaccaatg ggcgtggata gcggtttgac tcacggggat ttccaagtct ccaccccatt   2520
gacgtcaatg ggagtttgtt ttggcaccaa aatcaacggg actttccaaa atgtcgtaac   2580
aactgcgatc gcccgccccg ttgacgcaaa tgggcggtag gcgtgtacgg tgggaggtct   2640
atataagcag agctcgttta gtgaaccgtc agatcactag aagctttatt gcggtagttt   2700
atcacagtta aattgctaac gcagtcagtg cttctgacac aacagtctcg aacttaagct   2760
gcagtgactc tcttaattaa ccaccgctac aggtgagtac tcggatctgc taccttaaga   2820
gaggcctatc tggccagtta gcagtcgaag aaagaagttt aagagagccg aaacaagcgc   2880
tcatgagccc gaagtggcga gcccgatctt ccccatcggt gatgtcggcg atataggcgc   2940
cagcaaccgc acctgtggcg ccggtgatgc cggccacgat gcgtccggcg tagaggatcc   3000
acaggacggg tgtggtcgcc atgatcgcgt agtcgatagt ggctccaagt agcgaagcga   3060
gcaggactgg gcggcggcca aagcggtcgg acagtgctcc gagaacgggt gcgcatagaa   3120
attgcatcaa cgcatatagc gctagatcct tgctagagtc gaggccgcca ccgcggtgga   3180
gctccagctt ttgttccctt tagtgagggt taatttcgag cttggcgtaa tcatggtcat   3240
agctgtttcc tgtgtgaaat tgttatccgc tcacaattcc acacaacata cgagccggaa   3300
gcataaagtg taaagcctgg ggtgcctaat gagtgagcta actcacatta attgcgttgc   3360
gctcactgcc cgctttccag tcgggaaacc tgtcgtgcca gctgcattaa tgaatcggcc   3420
aacgcgcggg gagaggcggt ttgcgtattg ggcgctcttc cgcttcctcg ctcactgact   3480
cgctgcgctc ggtcgttcgg ctgcggcgag cggtatcagc tcactcaaag gcggtaatac   3540
ggttatccac agaatcaggg gataacgcag gaaagaacat gtgagcaaaa ggccagcaaa   3600
aggccaggaa ccgtaaaaag gccgcgttgc tggcgttttt ccataggctc cgcccccctg   3660
acgagcatca caaaaatcga cgctcaagtc agaggtggcg aaacccgaca ggactataaa   3720
gataccaggc gtttccccct ggaagctccc tcgtgcgctc tcctgttccg accctgccgc   3780
ttaccggata cctgtccgcc tttctccctt cgggaagcgt ggcgctttct catagctcac   3840
gctgtaggta tctcagttcg gtgtaggtcg ttcgctccaa gctgggctgt gtgcacgaac   3900
cccccgttca gcccgaccgc tgcgccttat ccggtaacta tcgtcttgag tccaacccgg   3960
taagacacga cttatcgcca ctggcagcag ccactggtaa caggattagc agagcgaggt   4020
atgtaggcgg tgctacagag ttcttgaagt ggtggcctaa ctacggctac actagaagga   4080
cagtatttgg tatctgcgct ctgctgaagc cagttacctt cggaaaaaga gttggtagct   4140
cttgatccgg caaacaaacc accgctggta gcggtggttt ttttgtttgc aagcagcaga   4200
```

-continued ttacgcgcag aaaaaaagga tctcaagaag atcctttgat cttttctacg gggtctgacg 4260
ctcagtggaa cgaaaactca cgttaaggga ttttggtcat gagattatca aaaaggatct 4320
tcacctagat ccttttaaat taaaaatgaa gttttaaatc aatctaaagt atatatgagt 4380
aaacttggtc tgacagttac caatgcttaa tcagtgaggc acctatctca gcgatctgtc 4440
tatttcgttc atccatagtt gcctgactcc ccgtcgtgta gataactacg atacgggagg 4500
gcttaccatc tggccccagt gctgcaatga taccgcgaga cccacgctca ccggctccag 4560
atttatcagc aataaaccag ccagccggaa gggccgagcg cagaagtggt cctgcaactt 4620
tatccgcctc catccagtct attaattgtt gccgggaagc tagagtaagt agttcgccag 4680
ttaatagttt gcgcaacgtt gttgccattg ctacaggcat cgtggtgtca cgctcgtcgt 4740
ttggtatggc ttcattcagc tccggttccc aacgatcaag gcgagttaca tgatccccca 4800
tgttgtgcaa aaaagcggtt agctccttcg gtcctccgat cgttgtcaga agtaagttgg 4860
ccgcagtgtt atcactcatg gttatggcag cactgcataa ttctcttact gtcatgccat 4920
ccgtaagatg cttttctgtg actggtgagt actcaaccaa gtcattctga gaatagtgta 4980
tgcggcgacc gagttgctct tgcccggcgt caatacggga taataccgcg ccacatagca 5040
gaactttaaa agtgctcatc attggaaaac gttcttcggg gcgaaaactc tcaaggatct 5100
taccgctgtt gagatccagt tcgatgtaac ccactcgtgc acccaactga tcttcagcat 5160
cttttacttt caccagcgtt tctgggtgag caaaaacagg aaggcaaaat gccgcaaaaa 5220
agggaataag ggcgacacgg aaatgttgaa tactcatact cttccttttt caatattatt 5280
gaagcattta tcagggttat tgtctcatga gcggatacat atttgaatgt atttagaaaa 5340
ataaacaaat aggggttccg cgcacatttc cccgaaaagt gc 5382

<210> SEQ ID NO 22
<211> LENGTH: 9737
<212> TYPE: DNA
<213> ORGANISM: Homo sapiens
<220> FEATURE:
<221> NAME/KEY: modified_base
<222> LOCATION: (8347)
<223> OTHER INFORMATION: a, c, t, g, other or unknown
<221> NAME/KEY: modified_base
<222> LOCATION: (8499)
<223> OTHER INFORMATION: a, c, t, g, other or unknown

<400> SEQUENCE: 22
gatcttcaat attggccatt agccatatta ttcattggtt atatagcata aatcaatatt 60
ggctattggc cattgcatac gttgtatcta tatcataata tgtacattta tattggctca 120
tgtccaatat gaccgccatg ttggcattga ttattgacta gttattaata gtaatcaatt 180
acggggtcat tagttcatag cccatatatg gagttccgcg ttacataact tacggtaaat 240
ggcccgcctg gctgaccgcc caacgacccc cgcccattga cgtcaataat gacgtatgtt 300
cccatagtaa cgccaatagg gactttccat tgacgtcaat gggtggagta tttacggtaa 360
actgcccact tggcagtaca tcaagtgtat catatgccaa gtccgccccc tattgacgtc 420
aatgacggta aatggcccgc ctggcattat gcccagtaca tgaccttacg ggactttcct 480
acttggcagt acatctacgt attagtcatc gctattacca tggtgatgcg gttttggcag 540
tacaccaatg ggcgtggata gcggtttgac tcacggggat ttccaagtct ccaccccatt 600
gacgtcaatg ggagtttgtt ttggcaccaa aatcaacggg actttccaaa atgtcgtaac 660
aactgcgatc gcccgccccg ttgacgcaaa tgggcggtag gcgtgtacgg tgggaggtct 720

-continued

```
atataagcag agctcgttta gtgaaccgtc agatcactga attctgacga cctactgatt    780
aacggccata gaggcctcct gcagaactgt cttagtgaca actatcgatt tccacacatt    840
atacgagccg atgttaattg tcaacagctc atgcatgacg tcccgggagc agacaagccc    900
gaccatggct cgagtaatac gactcactat agggcgacag gtgagtactc gctaccttaa    960
ggcctatctg gccgtttaaa cagatgtgta taagagacag ctctcttaag gtagcctgtc   1020
tcttatacac atctagatcc ttgctagagt cgaccaattc tcatgtttga cagcttatca   1080
tcgcagatcc tgagcttgta tggtgcactc tcagtacaat ctgctctgct gccgcatagt   1140
taagccagta tctgctccct gcttgtgtgt tggaggtcgc tgagtagtgc gcgagcaaaa   1200
tttaagctac aacaaggcaa ggcttgaccg acaattgcat gaagaatctg cttagggtta   1260
ggcgttttgc gctgcttcgc gatgtacggg ccagatatac gcgtatctga ggggactagg   1320
gtgtgtttag gcgcccagcg gggcttcggt tgtacgcggt taggagtccc ctcaggatat   1380
agtagtttcg cttttgcata gggaggggga aatgtagtct tatgcaatac acttgtagtc   1440
ttgcaacatg gtaacgatga gttagcaaca tgccttacaa ggagagaaaa agcaccgtgc   1500
atgccgattg gtggaagtaa ggtggtacga tcgtgcctta ttaggaaggc aacagacagg   1560
tctgacatgg attggacgaa ccactgaatt ccgcattgca gagataattg tatttaagtg   1620
cctagctcga tacaataaac gccatttgac cattcaccac attggtgtgc acctccaagc   1680
tgggtaccag ctgctagcct cgagacgcgt gatttccttc gaagcttgtc atggttggtt   1740
cgctaaactg catcgtcgct gtgtcccaga acatgggcat cggcaagaac ggggacctgc   1800
cctggccacc gctcaggaat gaattcagat atttccagag aatgaccaca acctcttcag   1860
tagaaggtaa acagaatctg gtgattatgg gtaagaagac ctggttctcc attcctgaga   1920
agaatcgacc tttaaagggt agaattaatt tagttctcag cagagaactc aaggaacctc   1980
cacaaggagc tcattttctt tccagaagtc tagatgatgc cttaaaactt actgaacaac   2040
cagaattagc aaataaagta gacatggtct ggatagttgg tggcagttct gtttataagg   2100
aagccatgaa tcacccaggc catcttaaac tatttgtgac aaggatcatg caagactttg   2160
aaagtgacac gttttttcca gaaattgatt tggagaaata taaacttctg ccagaatacc   2220
caggtgttct ctctgatgtc caggaggaga aaggcattaa gtacaaattt gaagtatatg   2280
agaagaatgt taattaaggg caccaataac tgccttaaaa aaattacgcc ccgccctgcc   2340
actcatcgca gtactgttgt aattcattaa gcattctgcc gacatggaag ccatcacaga   2400
cggcatgatg aacctgaatc gccagcggca tcagcacctt gtcgccttgc gtataatatt   2460
tgcccatggt gaaaacgggg gcgaagaagt tgtccatatt ggccacgttt aaatcaaaac   2520
tggtgaaact cacccaggga ttggctgaga cgaaaaacat attctcaata aaccctttag   2580
ggaaataggc caggttttca ccgtaacacg ccacatcttg cgaatatatg tgtagaaact   2640
gccggaaatc gtcgtggtat tcactccaga gcgatgaaaa cgtttcagtt tgctcatgga   2700
aaacggtgta acaagggtga acactatccc atatcaccag ctcaccgtct ttcattgcca   2760
tacggaattc cggatgagca ttcatcaggc gggcaagaat gtgaataaag gccggataaa   2820
acttgtgctt attttctttt acggtctttt aaaaggccgt aatatccagc tgaacggtct   2880
ggttataggt acattgagca actgactgaa atgcctcaaa atgttcttta cgatgccatt   2940
gggatatatc aacggtggta tatccagtga ttttttctc cattttagct tccttagctc   3000
ctgaaaatct cgataactca aaaaatacgc ccggtagtga tcttatttca ttatggtgaa   3060
```

-continued

```
agttggaacc tcttacgtgc cgatcaacgt ctcattttcg ccaaattaat taaggcgcgc   3120
cgctctcctg gctaggagtc acgtagaaag gactaccgac gaaggaactt gggtcgccgg   3180
tgtgttcgta tatggaggta gtaagacctc cctttacaac ctaaggcgag gaactgccct   3240
tgctattcca caatgtcgtc ttacaccatt gagtcgtctc ccctttggaa tggcccctgg   3300
acccggccca caacctggcc cgctaaggga gtccattgtc tgttatttca tggtcttttt   3360
acaaactcat atatttgctg aggttttgaa ggatgcgatt aaggaccttg ttatgacaaa   3420
gcccgctcct acctgcaata tcagggtgac tgtgtgcagc tttgacgatg gagtagattt   3480
gcctccctgg tttccaccta tggtggaagg ggctgccgcg gagggtgatg acggagatga   3540
cggagatgaa ggaggtgatg gagatgaggg tgaggaaggg caggagtgat gtaacttgtt   3600
aggagacgcc ctcaatcgta ttaaaagccg tgtattcccc cgcactaaag aataaatccc   3660
cagtagacat catgcgtgct gttggtgtat ttctggccat ctgtcttgtc accattttcg   3720
tcctcccaac atggggcaat tgggcatacc catgttgtca cgtcactcag ctccgcgctc   3780
aacaccttct cgcgttggaa aacattagcg acatttacct ggtgagcaat cagacatgcg   3840
acggctttag cctggcctcc ttaaattcac ctaagaatgg gagcaaccag catgcaggaa   3900
aaggacaagc agcgaaaatt cacgccccct tgggaggtgg cggcatatgc aaaggatagc   3960
actcccactc tactactggg tatcatatgc tgactgtata tgcatgagga tagcatatgc   4020
tacccggata cagattagga tagcatatac tacccagata tagattagga tagcatatgc   4080
tacccagata tagattagga tagcctatgc tacccagata taaattagga tagcatatac   4140
tacccagata tagattagga tagcatatgc tacccagata tagattagga tagcctatgc   4200
tacccagata tagattagga tagcatatgc tacccagata tagattagga tagcatatgc   4260
tatccagata tttgggtagt atatgctacc cagatataaa ttaggatagc atatactacc   4320
ctaatctcta ttaggatagc atatgctacc cggatacaga ttaggatagc atatactacc   4380
cagatataga ttaggatagc atatgctacc cagatataga ttaggatagc ctatgctacc   4440
cagatataaa ttaggatagc atatactacc cagatataga ttaggatagc atatgctacc   4500
cagatataga ttaggatagc ctatgctacc cagatataga ttaggatagc atatgctatc   4560
cagatatttg ggtagtatat gctacccatg gcaacattag cccaccgtgc tctcagcgac   4620
ctcgtgaata tgaggaccaa caaccctgtg cttggcgctc aggcgcaagt gtgtgtaatt   4680
tgtcctccag atcgcagcaa tcgcgcccct atcttggccc gcccacctac ttatgcaggt   4740
attccccggg gtgccattag tggttttgtg ggcaagtggt ttgaccgcag tggttagcgg   4800
ggttacaatc agccaagtta ttacaccctt attttacagt ccaaaaccgc agggcggcgt   4860
gtgggggctg acgcgtgccc ccactccaca atttcaaaaa aaagagtggc cacttgtctt   4920
tgtttatggg ccccattggc gtggagcccc gtttaatttt cgggggtgtt agagacaacc   4980
agtggagtcc gctgctgtcg gcgtccactc tctttcccct tgttacaaat agagtgtaac   5040
aacatggttc acctgtcttg gtccctgcct gggacacatc ttaataaccc cagtatcata   5100
ttgcactagg attatgtgtt gcccatagcc ataaattcgt gtgagatgga catccagtct   5160
ttacggcttg tccccacccc atggatttct attgttaaag atattcagaa tgtttcattc   5220
ctacactagt atttattgcc caaggggttt gtgagggtta tattggtgtc atagcacaat   5280
gccaccactg aaccccccgt ccaaatttta ttctgggggc gtcacctgaa accttgtttt   5340
cgagcacctc acatacacct tactgttcac aactcagcag ttattctatt agctaaacga   5400
aggagaatga agaagcaggc gaagattcag gagagttcac tgcccgctcc ttgatcttca   5460
```

-continued

```
gccactgccc ttgtgactaa aatggttcac taccctcgtg gaatcctgac cccatgtaaa   5520
taaaaccgtg acagctcatg gggtgggaga tatcgctgtt ccttaggacc cttttactaa   5580
ccctaattcg atagcatatg cttcccgttg ggtaacatat gctattgaat tagggttagt   5640
ctggatagta tatactacta cccgggaagc atatgctacc cgtttagggt taacaagggg   5700
gccttataaa cactattgct aatgccctct tgagggtccg cttatcggta gctacacagg   5760
cccctctgat tgacgttggt gtagcctccc gtagtcttcc tgggcccctg ggaggtacat   5820
gtcccccagc attggtgtaa gagcttcagc caagagttac acataaaggc aatgttgtgt   5880
tgcagtccac agactgcaaa gtctgctcca ggatgaaagc cactcagtgt tggcaaatgt   5940
gcacatccat ttataaggat gtcaactaca gtcagagaac ccctttgtgt ttggtccccc   6000
cccgtgtcac atgtggaaca gggcccagtt ggcaagttgt accaaccaac tgaagggatt   6060
acatgcactg ccccgaatac aaaacaaaag cgctcctcgt accagcgaag aaggggcaga   6120
gatgccgtag tcaggtttag ttcgtccggc ggcgggcggc cgcaaggcgc gccggatcca   6180
caggacgggt gtggtcgcca tgatcgcgta gtcgatagtg gctccaagta gcgaagcgag   6240
caggactggg cggcggccaa agcggtcgga cagtgctccg agaacgggtg cgcatagaaa   6300
ttgcatcaac gcatatagcg ctagatcctt gctagagtcg agatctgtcg agccatgtga   6360
gcaaaaggcc agcaaaaggc caggaaccgt aaaaaggccg cgttgctggc gtttttccat   6420
aggctccgcc cccctgacga gcatcacaaa aatcgacgct caagtcagag gtggcgaaac   6480
ccgacaggac tataaagata ccaggcgttt ccccctggaa gctccctcgt gcgctctcct   6540
gttccgaccc tgccgcttac cggatacctg tccgcctttc tcccttcggg aagcgtggcg   6600
ctttctcata gctcacgctg taggtatctc agttcggtgt aggtcgttcg ctccaagctg   6660
ggctgtgtgc acgaaccccc cgttcagccc gaccgctgcg ccttatccgg taactatcgt   6720
cttgagtcca acccggtaag acacgactta tcgccactgg cagcagccac tggtaacagg   6780
attagcagag cgaggtatgt aggcggtgct acagagttct tgaagtggtg gcctaactac   6840
ggctacacta gaaggacagt atttggtatc tgcgctctgc tgaagccagt taccttcgga   6900
aaaagagttg gtagctcttg atccggcaaa caaaccaccg ctggtagcgg tggttttttt   6960
gtttgcaagc agcagattac gcgcagaaaa aaaggatctc aagaagatcc tttgatcttt   7020
tctacggggt ctgacgctca gtggaacgaa aactcacgtt aagggatttt ggtcatgaga   7080
ttatcaaaaa ggatcttcac ctagatcctt ttatcggtgt gaaataccgc acagatgcgt   7140
aaggagaaaa taccgcatca ggaaattgta agcgttaata attcagaaga actcgtcaag   7200
aaggcgatag aaggcgatgc gctgcgaatc gggagcggcg ataccgtaaa gcacgaggaa   7260
gcggtcagcc cattcgccgc caagctcttc agcaatatca cgggtagcca acgctatgtc   7320
ctgatagcgg tccgccacac ccagccggcc acagtcgatg aatccagaaa agcggccatt   7380
ttccaccatg atattcggca agcaggcatc gccatgggtc acgacgagat cctcgccgtc   7440
gggcatgctc gccttgagcc tggcgaacag ttcggctggc gcgagcccct gatgctcttc   7500
gtccagatca tcctgatcga caagaccggc ttccatccga gtacgtgctc gctcgatgcg   7560
atgtttcgct tggtggtcga atgggcaggt agccggatca agcgtatgca gccgccgcat   7620
tgcatcagcc atgatggata ctttctcggc aggagcaagg tgagatgaca ggagatcctg   7680
ccccggcact tcgcccaata gcagccagtc ccttcccgct tcagtgacaa cgtcgagcac   7740
agctgcgcaa ggaacgcccg tcgtggccag ccacgatagc cgcgctgcct cgtcttgcag   7800
```

-continued

```
ttcattcagg gcaccggaca ggtcggtctt gacaaaaaga accgggcgcc cctgcgctga   7860

cagccggaac acggcggcat cagagcagcc gattgtctgt tgtgcccagt catagccgaa   7920

tagcctctcc acccaagcgg ccggagaacc tgcgtgcaat ccatcttgtt caatcatgcg   7980

aaacgatcct catcctgtct cttgatcaga gcttgatccc ctgcgccatc agatccttgg   8040

cggcgagaaa gccatccagt ttactttgca gggcttgtca accttaccag ataaaagtgc   8100

tcatcattgg aaaacattca attcgtcgac ctcgaaattc taccgggtag gggaggcgct   8160

tttcccaagg cagtctggag catgcgcttt agcagccccg ctgggcactt ggcgctacac   8220

aagtggcctc tggcctcgca cacattccac atccaccggt aggcgccaac cggctccgtt   8280

ctttggtggc cccttcgcgc caccttctac tcctccccta gtcaggaagt tcccccccgc   8340

cccgcanctc gcgtcgtgca ggacgtgaca aatggaaata gcacgtctca ctagtctcgt   8400

gcagatggac aagcaccgct gagcaatgga gcgggtaggc ctttggggca gcggccaata   8460

gcagctttgc tccttcgctt tctgggctca gaggctggna aggggtgggt ccgggggcgg   8520

gctcaggggc gggctcaggg gcggggcggg cgcccgaagg tcctccggag gcccggcatt   8580

ctgcacgctt caaaagcgca cgtctgccgc gctgttctcc tcttcctcat ctccgggcct   8640

ttcgacctgc atccatctag atctcgagca gctgaagctt accatgaccg agtacaagcc   8700

cacggtgcgc ctcgccaccc gcgacgacgt cccccgggcc gtacgcaccc tcgccgccgc   8760

gttcgccgac taccccgcca cgcgccacac cgtcgacccg gaccgccaca tcgagcgggt   8820

caccgagctg caagaactct tcctcacgcg cgtcgggctc gacatcggca aggtgtgggt   8880

cgcggacgac ggcgccgcgg tggcggtctg gaccacgccg gagagcgtcg aagcgggggc   8940

ggtgttcgcc gagatcggcc cgcgcatggc cgagttgagc ggttcccggc tggccgcgca   9000

gcaacagatg gaaggcctcc tggcgccgca ccgggcccaa ggagcccgcg tggttccttg   9060

gcccaccgtc gggcgtcttc gcccgaccac cagggcaagg gtctggcaag cgccgtcgtg   9120

ctccccggag tggaggcggc cgagcgcgcc ggggtgcccg ccttcctgga gacctccgcg   9180

ccccgcaacc tccccttcta cgagcggctc ggcttcaccg tcaccgccga cgtcgaggtg   9240

cccgaaggac cgcgcacctg gtgcatgacc cgcaagcccg gtgcctgacg cccgccccac   9300

gacccgcagc gcccgaccga aaggagcgca cgaccccatg catcgatggc actgggcagg   9360

taagtatcaa ggttagcggc cgctaacctg gttgctgact aattgagatg catgctttgc   9420

atacttctgc ctgctgggga gcctggggac tttccacacc ctaactgaca cacattccac   9480

agctggttct ttccgcctca gaaggtacac aggcgaaatt gtaagcgtta atattttgtt   9540

aaaattcgcg ttaaattttt gttaaatcag ctcatttttt aaccaatagg ccgaaatcgg   9600

caaaatccct tataaatcaa aagaatagac cgagataggg ttgagtgttg ttccagtttg   9660

gaacaagagt ccactattaa agaacgtgga ctccaacgtc aaagggcgaa aaaccgtcta   9720

tcagggcgat ggcccac                                                  9737
```

<210> SEQ ID NO 23
<211> LENGTH: 9737
<212> TYPE: DNA
<213> ORGANISM: Homo sapiens
<220> FEATURE:
<221> NAME/KEY: modified_base
<222> LOCATION: (8347)
<223> OTHER INFORMATION: a, c, t, g, other or unknown
<221> NAME/KEY: modified_base
<222> LOCATION: (8499)
<223> OTHER INFORMATION: a, c, t, g, other or unknown -continued

<400> SEQUENCE: 23

```
gatcttcaat attggccatt agccatatta ttcattggtt atatagcata aatcaatatt      60
ggctattggc cattgcatac gttgtatcta tatcataata tgtacattta tattggctca     120
tgtccaatat gaccgccatg ttggcattga ttattgacta gttattaata gtaatcaatt     180
acggggtcat tagttcatag cccatatatg gagttccgcg ttacataact tacggtaaat     240
ggcccgcctg gctgaccgcc caacgacccc cgcccattga cgtcaataat gacgtatgtt     300
cccatagtaa cgccaatagg gactttccat tgacgtcaat gggtggagta tttacggtaa     360
actgcccact tggcagtaca tcaagtgtat catatgccaa gtccgccccc tattgacgtc     420
aatgacggta aatggcccgc ctggcattat gcccagtaca tgaccttacg ggactttcct     480
acttggcagt acatctacgt attagtcatc gctattacca tggtgatgcg gttttggcag     540
tacaccaatg ggcgtggata gcggtttgac tcacggggat ttccaagtct ccaccccatt     600
gacgtcaatg ggagtttgtt ttggcaccaa aatcaacggg actttccaaa atgtcgtaac     660
aactgcgatc gcccgccccg ttgacgcaaa tgggcggtag gcgtgtacgg tgggaggtct     720
atataagcag agctcgttta gtgaaccgtc agatcactga attctgacga cctactgatt     780
aacggccata gaggcctcct gcagaactgt cttagtgaca actatcgatt tccacacatt     840
atacgagccg atgttaattg tcaacagctc atgcatgacg tcccgggagc agacaagccc     900
gaccatggct cgagtaatac gactcactat agggcgacag gtgagtactc gctaccttaa     960
ggcctatctg gccgtttaaa cagatgtgta taagagacag ctctcttaag gtagcctgtc    1020
tcttatacac atctagatcc ttgctagagt cgaccaattc tcatgtttga cagcttatca    1080
tcgcagatcc tgagcttgta tggtgcactc tcagtacaat ctgctctgct gccgcatagt    1140
taagccagta tctgctccct gcttgtgtgt tggaggtcgc tgagtagtgc gcgagcaaaa    1200
tttaagctac aacaaggcaa ggcttgaccg acaattgcat gaagaatctg cttagggtta    1260
ggcgttttgc gctgcttcgc gatgtacggg ccagatatac gcgtatctga ggggactagg    1320
gtgtgtttag gcgcccagcg ggcttcggt tgtacgcggt taggagtccc ctcaggatat    1380
agtagtttcg cttttgcata gggaggggga aatgtagtct tatgcaatac acttgtagtc    1440
ttgcaacatg gtaacgatga gttagcaaca tgccttacaa ggagagaaaa agcaccgtgc    1500
atgccgattg gtggaagtaa ggtggtacga tcgtgcctta ttaggaaggc aacagacagg    1560
tctgacatgg attggacgaa ccactgaatt ccgcattgca gagataattg tatttaagtg    1620
cctagctcga tacaataaac gccatttgac cattcaccac attggtgtgc acctccaagc    1680
tgggtaccag ctgctagcct cgagacgcgt gatttccttc gaagcttgtc atggttggtt    1740
cgctaaactg catcgtcgct gtgtcccaga acatgggcat cggcaagaac ggggacctgc    1800
cctggccacc gctcaggaat gaattcagat atttccagag aatgaccaca acctcttcag    1860
tagaaggtaa acagaatctg gtgattatgg gtaagaagac ctggttctcc attcctgaga    1920
agaatcgacc tttaaagggt agaattaatt tagttctcag cagagaactc aaggaacctc    1980
cacaaggagc tcattttctt tccagaagtc tagatgatgc cttaaaactt actgaacaac    2040
cagaattagc aaataaagta gacatggtct ggatagttgg tggcagttct gtttataagg    2100
aagccatgaa tcacccaggc catcttaaac tatttgtgac aaggatcatg caagactttg    2160
aaagtgacac gttttttcca gaaattgatt tggagaaata taaacttctg ccagaatacc    2220
caggtgttct ctctgatgtc caggaggaga aaggcattaa gtacaaattt gaagtatatg    2280
agaagaatgt taattaaggg caccaataac tgccttaaaa aaattacgcc ccgccctgcc    2340
```

-continued

```
actcatcgca gtactgttgt aattcattaa gcattctgcc gacatggaag ccatcacaga   2400
cggcatgatg aacctgaatc gccagcggca tcagcacctt gtcgccttgc gtataatatt   2460
tgcccatggt gaaaacgggg gcgaagaagt tgtccatatt ggccacgttt aaatcaaaac   2520
tggtgaaact cacccaggga ttggctgaga cgaaaaacat attctcaata aaccctttag   2580
ggaaataggc caggttttca ccgtaacacg ccacatcttg cgaatatatg tgtagaaact   2640
gccggaaatc gtcgtggtat tcactccaga gcgatgaaaa cgtttcagtt tgctcatgga   2700
aaacggtgta acaagggtga acactatccc atatcaccag ctcaccgtct ttcattgcca   2760
tacggaattc cggatgagca ttcatcaggc gggcaagaat gtgaataaag gccggataaa   2820
acttgtgctt atttttcttt acggtcttta aaaaggccgt aatatccagc tgaacggtct   2880
ggttataggt acattgagca actgactgaa atgcctcaaa atgttcttta cgatgccatt   2940
gggatatatc aacggtggta tatccagtga tttttttctc cattttagct tccttagctc   3000
ctgaaaatct cgataactca aaaaatacgc ccggtagtga tcttatttca ttatggtgaa   3060
agttggaacc tcttacgtgc cgatcaacgt ctcattttcg ccaaattaat taaggcgcgc   3120
cgctctcctg gctaggagtc acgtagaaag gactaccgac gaaggaactt gggtcgccgg   3180
tgtgttcgta tatggaggta gtaagacctc cctttacaac ctaaggcgag gaactgccct   3240
tgctattcca caatgtcgtc ttacaccatt gagtcgtctc ccctttggaa tggcccctgg   3300
acccggccca caacctggcc cgctaaggga gtccattgtc tgttatttca tggtcttttt   3360
acaaactcat atatttgctg aggttttgaa ggatgcgatt aaggaccttg ttatgacaaa   3420
gcccgctcct acctgcaata tcagggtgac tgtgtgcagc tttgacgatg gagtagattt   3480
gcctccctgg tttccaccta tggtggaagg ggctgccgcg gagggtgatg acggagatga   3540
cggagatgaa ggaggtgatg gagatgaggg tgaggaaggg caggagtgat gtaacttgtt   3600
aggagacgcc ctcaatcgta ttaaaagccg tgtattcccc cgcactaaag aataaatccc   3660
cagtagacat catgcgtgct gttggtgtat ttctggccat ctgtcttgtc accattttcg   3720
tcctcccaac atggggcaat tgggcatacc catgttgtca cgtcactcag ctccgcgctc   3780
aacaccttct cgcgttggaa aacattagcg acatttacct ggtgagcaat cagacatgcg   3840
acggctttag cctggcctcc ttaaattcac ctaagaatgg gagcaaccag catgcaggaa   3900
aaggacaagc agcgaaaatt cacgccccct tgggaggtgg cggcatatgc aaaggatagc   3960
actcccactc tactactggg tatcatatgc tgactgtata tgcatgagga tagcatatgc   4020
tacccggata cagattagga tagcatatac tacccagata tagattagga tagcatatgc   4080
tacccagata tagattagga tagcctatgc tacccagata taaattagga tagcatatac   4140
tacccagata tagattagga tagcatatgc tacccagata tagattagga tagcctatgc   4200
tacccagata tagattagga tagcatatgc tacccagata tagattagga tagcatatgc   4260
tatccagata tttgggtagt atatgctacc cagatataaa ttaggatagc atatactacc   4320
ctaatctcta ttaggatagc atatgctacc cggatacaga ttaggatagc atatactacc   4380
cagatataga ttaggatagc atatgctacc cagatataga ttaggatagc ctatgctacc   4440
cagatataaa ttaggatagc atatactacc cagatataga ttaggatagc atatgctacc   4500
cagatataga ttaggatagc ctatgctacc cagatataga ttaggatagc atatgctatc   4560
cagatatttg ggtagtatat gctacccatg gcaacattag cccaccgtgc tctcagcgac   4620
ctcgtgaata tgaggaccaa caaccctgtg cttggcgctc aggcgcaagt gtgtgtaatt   4680
```

-continued

```
tgtcctccag atcgcagcaa tcgcgcccct atcttggccc gcccacctac ttatgcaggt   4740
attccccggg gtgccattag tggttttgtg ggcaagtggt ttgaccgcag tggttagcgg   4800
ggttacaatc agccaagtta ttacaccctt attttacagt ccaaaaccgc agggcggcgt   4860
gtgggggctg acgcgtgccc ccactccaca atttcaaaaa aaagagtggc cacttgtctt   4920
tgtttatggg ccccattggc gtggagcccc gtttaatttt cgggggtgtt agagacaacc   4980
agtggagtcc gctgctgtcg gcgtccactc tctttcccct tgttacaaat agagtgtaac   5040
aacatggttc acctgtcttg gtccctgcct gggacacatc ttaataaccc cagtatcata   5100
ttgcactagg attatgtgtt gcccatagcc ataaattcgt gtgagatgga catccagtct   5160
ttacggcttg tccccacccc atggatttct attgttaaag atattcagaa tgtttcattc   5220
ctacactagt atttattgcc caaggggttt gtgagggtta tattggtgtc atagcacaat   5280
gccaccactg aacccccgt ccaaatttta ttctgggggc gtcacctgaa accttgtttt   5340
cgagcacctc acatacacct tactgttcac aactcagcag ttattctatt agctaaacga   5400
aggagaatga agaagcaggc gaagattcag gagagttcac tgcccgctcc ttgatcttca   5460
gccactgccc ttgtgactaa aatggttcac taccctcgtg gaatcctgac cccatgtaaa   5520
taaaaccgtg acagctcatg gggtgggaga tatcgctgtt ccttaggacc cttttactaa   5580
ccctaattcg atagcatatg cttcccgttg ggtaacatat gctattgaat tagggttagt   5640
ctggatagta tatactacta cccgggaagc atatgctacc cgtttagggt taacaagggg   5700
gccttataaa cactattgct aatgccctct tgagggtccg cttatcggta gctacacagg   5760
cccctctgat tgacgttggt gtagcctccc gtagtcttcc tgggcccctg ggaggtacat   5820
gtcccccagc attggtgtaa gagcttcagc caagagttac acataaaggc aatgttgtgt   5880
tgcagtccac agactgcaaa gtctgctcca ggatgaaagc cactcagtgt tggcaaatgt   5940
gcacatccat ttataaggat gtcaactaca gtcagagaac ccctttgtgt ttggtccccc   6000
cccgtgtcac atgtggaaca gggcccagtt ggcaagttgt accaaccaac tgaagggatt   6060
acatgcactg ccccgaatac aaaacaaaag cgctcctcgt accagcgaag aaggggcaga   6120
gatgccgtag tcaggtttag ttcgtccggc ggcgggcggc cgcaaggcgc gccggatcca   6180
caggacgggt gtggtcgcca tgatcgcgta gtcgatagtg gctccaagta gcgaagcgag   6240
caggactggg cggcggccaa agcggtcgga cagtgctccg agaacgggtg cgcatagaaa   6300
ttgcatcaac gcatatagcg ctagatcctt gctagagtcg agatctgtcg agccatgtga   6360
gcaaaaggcc agcaaaaggc caggaaccgt aaaaaggccg cgttgctggc gtttttccat   6420
aggctccgcc cccctgacga gcatcacaaa aatcgacgct caagtcagag gtggcgaaac   6480
ccgacaggac tataaagata ccaggcgttt ccccctggaa gctccctcgt gcgctctcct   6540
gttccgaccc tgccgcttac cggatacctg tccgcctttc tcccttcggg aagcgtggcg   6600
ctttctcata gctcacgctg taggtatctc agttcggtgt aggtcgttcg ctccaagctg   6660
ggctgtgtgc acgaaccccc cgttcagccc gaccgctgcg ccttatccgg taactatcgt   6720
cttgagtcca acccggtaag acacgactta tcgccactgg cagcagccac tggtaacagg   6780
attagcagag cgaggtatgt aggcggtgct acagagttct tgaagtggtg gcctaactac   6840
ggctacacta gaaggacagt atttggtatc tgcgctctgc tgaagccagt taccttcgga   6900
aaaagagttg gtagctcttg atccggcaaa caaaccaccg ctggtagcgg tggttttttt   6960
gtttgcaagc agcagattac gcgcagaaaa aaaggatctc aagaagatcc tttgatcttt   7020
tctacggggt ctgacgctca gtggaacgaa aactcacgtt aagggatttt ggtcatgaga   7080
```

-continued

```
ttatcaaaaa ggatcttcac ctagatcctt ttatcggtgt gaaataccgc acagatgcgt   7140
aaggagaaaa taccgcatca ggaaattgta agcgttaata attcagaaga actcgtcaag   7200
aaggcgatag aaggcgatgc gctgcgaatc gggagcggcg ataccgtaaa gcacgaggaa   7260
gcggtcagcc cattcgccgc caagctcttc agcaatatca cgggtagcca acgctatgtc   7320
ctgatagcgg tccgccacac ccagccggcc acagtcgatg aatccagaaa agcggccatt   7380
ttccaccatg atattcggca agcaggcatc gccatgggtc acgacgagat cctcgccgtc   7440
gggcatgctc gccttgagcc tggcgaacag ttcggctggc gcgagcccct gatgctcttc   7500
gtccagatca tcctgatcga caagaccggc ttccatccga gtacgtgctc gctcgatgcg   7560
atgtttcgct tggtggtcga atgggcaggt agccggatca agcgtatgca gccgccgcat   7620
tgcatcagcc atgatggata ctttctcggc aggagcaagg tgagatgaca ggagatcctg   7680
ccccggcact tcgcccaata gcagccagtc ccttcccgct tcagtgacaa cgtcgagcac   7740
agctgcgcaa ggaacgcccg tcgtggccag ccacgatagc cgcgctgcct cgtcttgcag   7800
ttcattcagg gcaccggaca ggtcggtctt gacaaaaaga accgggcgcc cctgcgctga   7860
cagccggaac acggcggcat cagagcagcc gattgtctgt tgtgcccagt catagccgaa   7920
tagcctctcc acccaagcgg ccggagaacc tgcgtgcaat ccatcttgtt caatcatgcg   7980
aaacgatcct catcctgtct cttgatcaga gcttgatccc ctgcgccatc agatccttgg   8040
cggcgagaaa gccatccagt ttactttgca gggcttgtca accttaccag ataaaagtgc   8100
tcatcattgg aaaacattca attcgtcgac ctcgaaattc taccgggtag gggaggcgct   8160
tttcccaagg cagtctggag catgcgcttt agcagccccg ctgggcactt ggcgctacac   8220
aagtggcctc tggcctcgca cacattccac atccaccggt aggcgccaac cggctccgtt   8280
ctttggtggc cccttcgcgc caccttctac tcctccccta gtcaggaagt tcccccccgc   8340
cccgcanctc gcgtcgtgca ggacgtgaca aatggaaata gcacgtctca ctagtctcgt   8400
gcagatggac aagcaccgct gagcaatgga gcgggtaggc ctttggggca gcggccaata   8460
gcagctttgc tccttcgctt tctgggctca gaggctggna aggggtgggt ccgggggcgg   8520
gctcagggc gggctcaggg gcggggcggg cgcccgaagg tcctccggag gcccggcatt   8580
ctgcacgctt caaaagcgca cgtctgccgc gctgttctcc tcttcctcat ctccgggcct   8640
ttcgacctgc atccatctag atctcgagca gctgaagctt accatgaccg agtacaagcc   8700
cacggtgcgc ctcgccaccc gcgacgacgt cccccgggcc gtacgcaccc tcgccgccgc   8760
gttcgccgac taccccgcca cgcgccacac cgtcgacccg gaccgccaca tcgagcgggt   8820
caccgagctg caagaactct tcctcacgcg cgtcgggctc gacatcggca aggtgtgggt   8880
cgcggacgac ggcgccgcgg tggcggtctg gaccacgccg gagagcgtcg aagcgggggc   8940
ggtgttcgcc gagatcggcc cgcgcatggc cgagttgagc ggttcccggc tggccgcgca   9000
gcaacagatg gaaggcctcc tggcgccgca ccgggcccaa ggagcccgcg tggttccttg   9060
gcccaccgtc gggcgtcttc gcccgaccac cagggcaagg gtctggcaag cgccgtcgtg   9120
ctccccggag tggaggcggc cgagcgcgcc ggggtgcccg ccttcctgga gacctccgcg   9180
ccccgcaacc tccccttcta cgagcggctc ggcttcaccg tcaccgccga cgtcgaggtg   9240
cccgaaggac cgcgcacctg gtgcatgacc cgcaagcccg gtgcctgacg cccgccccac   9300
gacccgcagc gcccgaccga aaggagcgca cgaccccatg catcgatggc actgggcagg   9360
taagtatcaa ggttagcggc cgctaacctg gttgctgact aattgagatg catgctttgc   9420
```

-continued

```
atacttctgc ctgctgggga gcctggggac tttccacacc ctaactgaca cacattccac   9480

agctggttct ttccgcctca gaaggtacac aggcgaaatt gtaagcgtta atattttgtt   9540

aaaattcgcg ttaaattttt gttaaatcag ctcatttttt aaccaatagg ccgaaatcgg   9600

caaaatccct tataaatcaa aagaatagac cgagataggg ttgagtgttg ttccagtttg   9660

gaacaagagt ccactattaa agaacgtgga ctccaacgtc aaagggcgaa aaaccgtcta   9720

tcagggcgat ggcccac                                                  9737
```

<210> SEQ ID NO 24
<211> LENGTH: 9871
<212> TYPE: DNA
<213> ORGANISM: Homo sapiens
<220> FEATURE:
<221> NAME/KEY: modified_base
<222> LOCATION: (8481)
<223> OTHER INFORMATION: a, c, t, g, other or unknown
<221> NAME/KEY: modified_base
<222> LOCATION: (8633)
<223> OTHER INFORMATION: a, c, t, g, other or unknown

<400> SEQUENCE: 24

```
gatcttcaat attggccatt agccatatta ttcattggtt atatagcata aatcaatatt     60

ggctattggc cattgcatac gttgtatcta tatcataata tgtacattta tattggctca    120

tgtccaatat gaccgccatg ttggcattga ttattgacta gttattaata gtaatcaatt    180

acggggtcat tagttcatag cccatatatg gagttccgcg ttacataact tacggtaaat    240

ggcccgcctg gctgaccgcc caacgacccc cgcccattga cgtcaataat gacgtatgtt    300

cccatagtaa cgccaatagg gactttccat tgacgtcaat gggtggagta tttacggtaa    360

actgcccact tggcagtaca tcaagtgtat catatgccaa gtccgccccc tattgacgtc    420

aatgacggta aatggcccgc ctggcattat gcccagtaca tgaccttacg ggactttcct    480

acttggcagt acatctacgt attagtcatc gctattacca tggtgatgcg gttttggcag    540

tacaccaatg ggcgtggata gcggtttgac tcacggggat ttccaagtct ccaccccatt    600

gacgtcaatg ggagtttgtt ttggcaccaa aatcaacggg actttccaaa atgtcgtaac    660

aactgcgatc gcccgccccg ttgacgcaaa tgggcggtag gcgtgtacgg tgggaggtct    720

atataagcag agctcgttta gtgaaccgtc agatcactga attctgacga cctactgatt    780

aaagatctaa gctagcgccg ccaccatggg ccctaaaaag aagcgtaaag tcgccccccc    840

gaccgatgtc agcctggggg acgagctcca cttagacggc gaggacgtgg cgatggcgca    900

tgccgacgcg ctagacgatt tcgatctgga catgttgggg gacggggatt ccccggggcc    960

gggatttacc ccccacgact ccgcccccta cggcgctctg gatatggccg acttcgagtt   1020

tgagcagatg tttaccgatg cccttggaat tgacgagtac ggtggggaat tcaggtgagt   1080

actcgctacc ttaaggccta tctggccgtt taaacagatg tgtataagag acagctctct   1140

taaggtagcc tgtctcttat acacatctag atccttgcta gagtcgacca attctcatgt   1200

ttgacagctt atcatcgcag atcctgagct tgtatggtgc actctcagta caatctgctc   1260

tgctgccgca tagttaagcc agtatctgct ccctgcttgt gtgttggagg tcgctgagta   1320

gtgcgcgagc aaaatttaag ctacaacaag gcaaggcttg accgacaatt gcatgaagaa   1380

tctgcttagg gttaggcgtt ttgcgctgct tcgcgatgta cgggccagat atacgcgtat   1440

ctgaggggac tagggtgtgt ttaggcgccc agcggggctt cggttgtacg cggttaggag   1500

tcccctcagg atatagtagt ttcgcttttg catagggagg gggaaatgta gtcttatgca   1560
```

-continued

```
atacacttgt agtcttgcaa catggtaacg atgagttagc aacatgcctt acaaggagag   1620

aaaaagcacc gtgcatgccg attggtggaa gtaaggtggt acgatcgtgc cttattagga   1680

aggcaacaga caggtctgac atggattgga cgaaccactg aattccgcat tgcagagata   1740

attgtattta agtgcctagc tcgatacaat aaacgccatt tgaccattca ccacattggt   1800

gtgcacctcc aagctgggta ccagctgcta gcctcgagac gcgtgatttc cttcgaagct   1860

tgtcatggtt ggttcgctaa actgcatcgt cgctgtgtcc cagaacatgg gcatcggcaa   1920

gaacggggac ctgccctggc caccgctcag gaatgaattc agatatttcc agagaatgac   1980

cacaacctct tcagtagaag gtaaacagaa tctggtgatt atgggtaaga agacctggtt   2040

ctccattcct gagaagaatc gacctttaaa gggtagaatt aatttagttc tcagcagaga   2100

actcaaggaa cctccacaag gagctcattt tctttccaga agtctagatg atgccttaaa   2160

acttactgaa caaccagaat tagcaaataa agtagacatg gtctggatag ttggtggcag   2220

ttctgtttat aaggaagcca tgaatcaccc aggccatctt aaactatttg tgacaaggat   2280

catgcaagac tttgaaagtg acacgttttt tccagaaatt gatttggaga aatataaact   2340

tctgccagaa tacccaggtg ttctctctga tgtccaggag gagaaaggca ttaagtacaa   2400

atttgaagta tatgagaaga atgttaatta agggcaccaa taactgcctt aaaaaaatta   2460

cgccccgccc tgccactcat cgcagtactg ttgtaattca ttaagcattc tgccgacatg   2520

gaagccatca cagacggcat gatgaacctg aatcgccagc ggcatcagca ccttgtcgcc   2580

ttgcgtataa tatttgccca tggtgaaaac gggggcgaag aagttgtcca tattggccac   2640

gtttaaatca aaactggtga aactcaccca gggattggct gagacgaaaa acatattctc   2700

aataaaccct ttagggaaat aggccaggtt ttcaccgtaa cacgccacat cttgcgaata   2760

tatgtgtaga aactgccgga aatcgtcgtg gtattcactc cagagcgatg aaaacgtttc   2820

agtttgctca tggaaaacgg tgtaacaagg gtgaacacta tcccatatca ccagctcacc   2880

gtctttcatt gccatacgga attccggatg agcattcatc aggcgggcaa gaatgtgaat   2940

aaaggccgga taaaacttgt gcttattttt ctttacggtc tttaaaaagg ccgtaatatc   3000

cagctgaacg gtctggttat aggtacattg agcaactgac tgaaatgcct caaaatgttc   3060

tttacgatgc cattgggata tatcaacggt ggtatatcca gtgatttttt tctccatttt   3120

agcttcctta gctcctgaaa atctcgataa ctcaaaaaat acgcccggta gtgatcttat   3180

ttcattatgg tgaaagttgg aacctcttac gtgccgatca acgtctcatt ttcgccaaat   3240

taattaaggc gcgccgctct cctggctagg agtcacgtag aaaggactac cgacgaagga   3300

acttgggtcg ccggtgtgtt cgtatatgga ggtagtaaga cctcccttta caacctaagg   3360

cgaggaactg cccttgctat tccacaatgt cgtcttacac cattgagtcg tctccccttt   3420

ggaatggccc ctggacccgg cccacaacct ggcccgctaa gggagtccat tgtctgttat   3480

ttcatggtct tttacaaac tcatatattt gctgaggttt tgaaggatgc gattaaggac   3540

cttgttatga caaagcccgc tcctacctgc aatatcaggg tgactgtgtg cagctttgac   3600

gatggagtag atttgcctcc ctggtttcca cctatggtgg aaggggctgc cgcggagggt   3660

gatgacggag atgacggaga tgaaggaggt gatggagatg agggtgagga agggcaggag   3720

tgatgtaact tgttaggaga cgccctcaat cgtattaaaa gccgtgtatt cccccgcact   3780

aaagaataaa tccccagtag acatcatgcg tgctgttggt gtatttctgg ccatctgtct   3840

tgtcaccatt ttcgtcctcc caacatgggg caattgggca tacccatgtt gtcacgtcac   3900

tcagctccgc gctcaacacc ttctcgcgtt ggaaaacatt agcgacattt acctggtgag   3960
```

-continued

```
caatcagaca tgcgacggct ttagcctggc ctccttaaat tcacctaaga atgggagcaa   4020
ccagcatgca ggaaaaggac aagcagcgaa aattcacgcc cccttgggag gtggcggcat   4080
atgcaaagga tagcactccc actctactac tgggtatcat atgctgactg tatatgcatg   4140
aggatagcat atgctacccg gatacagatt aggatagcat atactaccca gatatagatt   4200
aggatagcat atgctaccca gatatagatt aggatagcct atgctaccca gatataaatt   4260
aggatagcat atactaccca gatatagatt aggatagcat atgctaccca gatatagatt   4320
aggatagcct atgctaccca gatatagatt aggatagcat atgctaccca gatatagatt   4380
aggatagcat atgctatcca gatatttggg tagtatatgc tacccagata taaattagga   4440
tagcatatac taccctaatc tctattagga tagcatatgc tacccggata cagattagga   4500
tagcatatac tacccagata tagattagga tagcatatgc tacccagata tagattagga   4560
tagcctatgc tacccagata taaattagga tagcatatac tacccagata tagattagga   4620
tagcatatgc tacccagata tagattagga tagcctatgc tacccagata tagattagga   4680
tagcatatgc tatccagata tttgggtagt atatgctacc catggcaaca ttagcccacc   4740
gtgctctcag cgacctcgtg aatatgagga ccaacaaccc tgtgcttggc gctcaggcgc   4800
aagtgtgtgt aatttgtcct ccagatcgca gcaatcgcgc ccctatcttg gcccgcccac   4860
ctacttatgc aggtattccc cggggtgcca ttagtggttt tgtgggcaag tggtttgacc   4920
gcagtggtta gcggggttac aatcagccaa gttattacac ccttatttta cagtccaaaa   4980
ccgcagggcg gcgtgtgggg gctgacgcgt gcccccactc cacaatttca aaaaaaagag   5040
tggccacttg tctttgttta tgggccccat tggcgtggag ccccgtttaa ttttcggggg   5100
tgttagagac aaccagtgga gtccgctgct gtcggcgtcc actctctttc cccttgttac   5160
aaatagagtg taacaacatg gttcacctgt cttggtccct gcctgggaca catcttaata   5220
accccagtat catattgcac taggattatg tgttgcccat agccataaat tcgtgtgaga   5280
tggacatcca gtctttacgg cttgtcccca ccccatggat ttctattgtt aaagatattc   5340
agaatgtttc attcctacac tagtatttat tgcccaaggg gtttgtgagg gttatattgg   5400
tgtcatagca caatgccacc actgaacccc ccgtccaaat tttattctgg gggcgtcacc   5460
tgaaaccttg ttttcgagca cctcacatac accttactgt tcacaactca gcagttattc   5520
tattagctaa acgaaggaga atgaagaagc aggcgaagat tcaggagagt tcactgcccg   5580
ctccttgatc ttcagccact gcccttgtga ctaaaatggt tcactaccct cgtggaatcc   5640
tgaccccatg taaataaaac cgtgacagct catggggtgg gagatatcgc tgttccttag   5700
gaccctttta ctaaccctaa ttcgatagca tatgcttccc gttgggtaac atatgctatt   5760
gaattagggt tagtctggat agtatatact actacccggg aagcatatgc tacccgttta   5820
gggttaacaa gggggcctta taaacactat tgctaatgcc ctcttgaggg tccgcttatc   5880
ggtagctaca caggcccctc tgattgacgt tggtgtagcc tcccgtagtc ttcctgggcc   5940
cctgggaggt acatgtcccc cagcattggt gtaagagctt cagccaagag ttacacataa   6000
aggcaatgtt gtgttgcagt ccacagactg caaagtctgc tccaggatga aagccactca   6060
gtgttggcaa atgtgcacat ccatttataa ggatgtcaac tacagtcaga gaaccccttt   6120
gtgtttggtc cccccccgtg tcacatgtgg aacagggccc agttggcaag ttgtaccaac   6180
caactgaagg gattacatgc actgccccga atacaaaaca aaagcgctcc tcgtaccagc   6240
gaagaagggg cagagatgcc gtagtcaggt ttagttcgtc cggcggcggg cggccgcaag   6300
```

-continued

```
gcgcgccgga tccacaggac gggtgtggtc gccatgatcg cgtagtcgat agtggctcca   6360
agtagcgaag cgagcaggac tgggcggcgg ccaaagcggt cggacagtgc tccgagaacg   6420
ggtgcgcata gaaattgcat caacgcatat agcgctagat ccttgctaga gtcgagatct   6480
gtcgagccat gtgagcaaaa ggccagcaaa aggccaggaa ccgtaaaaag gccgcgttgc   6540
tggcgttttt ccataggctc cgcccccctg acgagcatca caaaaatcga cgctcaagtc   6600
agaggtggcg aaacccgaca ggactataaa gataccaggc gtttccccct ggaagctccc   6660
tcgtgcgctc tcctgttccg accctgccgc ttaccggata cctgtccgcc tttctccctt   6720
cgggaagcgt ggcgctttct catagctcac gctgtaggta tctcagttcg gtgtaggtcg   6780
ttcgctccaa gctgggctgt gtgcacgaac cccccgttca gcccgaccgc tgcgccttat   6840
ccggtaacta tcgtcttgag tccaacccgg taagacacga cttatcgcca ctggcagcag   6900
ccactggtaa caggattagc agagcgaggt atgtaggcgg tgctacagag ttcttgaagt   6960
ggtggcctaa ctacggctac actagaagga cagtatttgg tatctgcgct ctgctgaagc   7020
cagttacctt cggaaaaaga gttggtagct cttgatccgg caaacaaacc accgctggta   7080
gcggtggttt ttttgtttgc aagcagcaga ttacgcgcag aaaaaaagga tctcaagaag   7140
atcctttgat cttttctacg gggtctgacg ctcagtggaa cgaaaactca cgttaaggga   7200
ttttggtcat gagattatca aaaaggatct tcacctagat ccttttatcg gtgtgaaata   7260
ccgcacagat gcgtaaggag aaaataccgc atcaggaaat tgtaagcgtt aataattcag   7320
aagaactcgt caagaaggcg atagaaggcg atgcgctgcg aatcgggagc ggcgataccg   7380
taaagcacga ggaagcggtc agcccattcg ccgccaagct cttcagcaat atcacgggta   7440
gccaacgcta tgtcctgata gcggtccgcc acacccagcc ggccacagtc gatgaatcca   7500
gaaaagcggc cattttccac catgatattc ggcaagcagg catcgccatg ggtcacgacg   7560
agatcctcgc cgtcgggcat gctcgccttg agcctggcga acagttcggc tggcgcgagc   7620
ccctgatgct cttcgtccag atcatcctga tcgacaagac cggcttccat ccgagtacgt   7680
gctcgctcga tgcgatgttt cgcttggtgg tcgaatgggc aggtagccgg atcaagcgta   7740
tgcagccgcc gcattgcatc agccatgatg gatactttct cggcaggagc aaggtgagat   7800
gacaggagat cctgccccgg cacttcgccc aatagcagcc agtcccttcc cgcttcagtg   7860
acaacgtcga gcacagctgc gcaaggaacg cccgtcgtgg ccagccacga tagccgcgct   7920
gcctcgtctt gcagttcatt cagggcaccg gacaggtcgg tcttgacaaa aagaaccggg   7980
cgcccctgcg ctgacagccg gaacacggcg gcatcagagc agccgattgt ctgttgtgcc   8040
cagtcatagc cgaatagcct ctccacccaa gcggccggag aacctgcgtg caatccatct   8100
tgttcaatca tgcgaaacga tcctcatcct gtctcttgat cagagcttga tcccctgcgc   8160
catcagatcc ttggcggcga gaaagccatc cagtttactt tgcagggctt gtcaacctta   8220
ccagataaaa gtgctcatca ttggaaaaca ttcaattcgt cgacctcgaa attctaccgg   8280
gtaggggagg cgcttttccc aaggcagtct ggagcatgcg ctttagcagc cccgctgggc   8340
acttggcgct acacaagtgg cctctggcct cgcacacatt ccacatccac cggtaggcgc   8400
caaccggctc cgttctttgg tggccccttc gcgccacctt ctactcctcc cctagtcagg   8460
aagttccccc ccgccccgca nctcgcgtcg tgcaggacgt gacaaatgga aatagcacgt   8520
ctcactagtc tcgtgcagat ggacaagcac cgctgagcaa tggagcgggt aggcctttgg   8580
ggcagcggcc aatagcagct ttgctccttc gctttctggg ctcagaggct ggnaaggggt   8640
gggtccgggg gcgggctcag ggcgggctc aggggcgggg cgggcgcccg aaggtcctcc   8700
```

```
ggaggcccgg cattctgcac gcttcaaaag cgcacgtctg ccgcgctgtt ctcctcttcc   8760

tcatctccgg gcctttcgac ctgcatccat ctagatctcg agcagctgaa gcttaccatg   8820

accgagtaca agcccacggt gcgcctcgcc acccgcgacg acgtccccccg ggccgtacgc   8880

accctcgccg ccgcgttcgc cgactacccc gccacgcgcc acaccgtcga cccggaccgc   8940

cacatcgagc gggtcaccga gctgcaagaa ctcttcctca cgcgcgtcgg gctcgacatc   9000

ggcaaggtgt gggtcgcgga cgacggcgcc gcggtggcgg tctggaccac gccggagagc   9060

gtcgaagcgg gggcggtgtt cgccgagatc ggcccgcgca tggccgagtt gagcggttcc   9120

cggctggccg cgcagcaaca gatggaaggc ctcctggcgc cgcaccgggc ccaaggagcc   9180

cgcgtggttc cttggcccac cgtcgggcgt cttcgcccga ccaccagggc aagggtctgg   9240

caagcgccgt cgtgctcccc ggagtggagg cggccgagcg cgccggggtg cccgccttcc   9300

tggagacctc cgcgccccgc aacctcccct tctacgagcg gctcggcttc accgtcaccg   9360

ccgacgtcga ggtgcccgaa ggaccgcgca cctggtgcat gacccgcaag cccggtgcct   9420

gacgcccgcc ccacgacccg cagcgcccga ccgaaaggag cgcacgaccc catgcatcga   9480

tggcactggg caggtaagta tcaaggttag cggccgctaa cctggttgct gactaattga   9540

gatgcatgct ttgcatactt ctgcctgctg gggagcctgg ggactttcca caccctaact   9600

gacacacatt ccacagctgg ttctttccgc ctcagaaggt acacaggcga aattgtaagc   9660

gttaatattt tgttaaaatt cgcgttaaat ttttgttaaa tcagctcatt ttttaaccaa   9720

taggccgaaa tcggcaaaat cccttataaa tcaaaagaat agaccgagat agggttgagt   9780

gttgttccag tttggaacaa gagtccacta ttaaagaacg tggactccaa cgtcaaaggg   9840

cgaaaaaccg tctatcaggg cgatggccca c                                  9871
```

<210> SEQ ID NO 25
<211> LENGTH: 10060
<212> TYPE: DNA
<213> ORGANISM: Homo sapiens
<220> FEATURE:
<221> NAME/KEY: modified_base
<222> LOCATION: (8670)
<223> OTHER INFORMATION: a, c, t, g, other or unknown
<221> NAME/KEY: modified_base
<222> LOCATION: (8822)
<223> OTHER INFORMATION: a, c, t, g, other or unknown

<400> SEQUENCE: 25

```
gatcttcaat attggccatt agccatatta ttcattggtt atatagcata aatcaatatt     60

ggctattggc cattgcatac gttgtatcta tatcataata tgtacattta tattggctca    120

tgtccaatat gaccgccatg ttggcattga ttattgacta gttattaata gtaatcaatt    180

acggggtcat tagttcatag cccatatatg gagttccgcg ttacataact tacggtaaat    240

ggcccgcctg gctgaccgcc caacgacccc cgcccattga cgtcaataat gacgtatgtt    300

cccatagtaa cgccaatagg gactttccat tgacgtcaat gggtggagta tttacggtaa    360

actgcccact tggcagtaca tcaagtgtat catatgccaa gtccgccccc tattgacgtc    420

aatgacggta aatggcccgc ctggcattat gcccagtaca tgaccttacg ggactttcct    480

acttggcagt acatctacgt attagtcatc gctattacca tggtgatgcg gttttggcag    540

tacaccaatg ggcgtggata gcggtttgac tcacggggat ttccaagtct ccaccccatt    600

gacgtcaatg ggagtttgtt ttggcaccaa aatcaacggg actttccaaa atgtcgtaac    660

aactgcgatc gcccgccccg ttgacgcaaa tgggcggtag gcgtgtacgg tgggaggtct    720
```

-continued

```
atataagcag agctcgttta gtgaaccgtc agatcactga attctgacga cctactgatt    780
aacggccaga tctaagctag cttcctgaaa gatgaagcta ctgtcttcta tcgaacaagc    840
atgcgatatt tgccgactta aaaagctcaa gtgctccaaa gaaaaaccga agtgcgccaa    900
gtgtctgaag aacaactggg agtgtcgcta ctctcccaaa accaaaaggt ctccgctgac    960
tagggcacat ctgacagaag tggaatcaag gctagaaaga ctggaacagc tatttctact   1020
gatttttcct cgagaagacc ttgacatgat tttgaaaatg gattctttac aggatataaa   1080
agcattgtta acaggattat ttgtacaaga taatgtgaat aaagatgccg tcacagatag   1140
attggcttca gtggagactg atatgcctct aacattgaga cagcatagaa taagtgcgac   1200
atcatcatcg gaagagagta gtaacaaagg tcaaagacag ttgactgtat cgccggaatt   1260
caggtgagta ctcgctacct taaggcctat ctggccgttt aaacagatgt gtataagaga   1320
cagctctctt aaggtagcct gtctcttata cacatctaga tccttgctag agtcgaccaa   1380
ttctcatgtt tgacagctta tcatcgcaga tcctgagctt gtatggtgca ctctcagtac   1440
aatctgctct gctgccgcat agttaagcca gtatctgctc cctgcttgtg tgttggaggt   1500
cgctgagtag tgcgcgagca aaatttaagc tacaacaagg caaggcttga ccgacaattg   1560
catgaagaat ctgcttaggg ttaggcgttt tgcgctgctt cgcgatgtac gggccagata   1620
tacgcgtatc tgaggggact agggtgtgtt taggcgccca gcggggcttc ggttgtacgc   1680
ggttaggagt cccctcagga tatagtagtt tcgcttttgc atagggaggg ggaaatgtag   1740
tcttatgcaa tacacttgta gtcttgcaac atggtaacga tgagttagca acatgcctta   1800
caaggagaga aaaagcaccg tgcatgccga ttggtggaag taaggtggta cgatcgtgcc   1860
ttattaggaa ggcaacagac aggtctgaca tggattggac gaaccactga attccgcatt   1920
gcagagataa ttgtatttaa gtgcctagct cgatacaata aacgccattt gaccattcac   1980
cacattggtg tgcacctcca agctgggtac cagctgctag cctcgagacg cgtgatttcc   2040
ttcgaagctt gtcatggttg gttcgctaaa ctgcatcgtc gctgtgtccc agaacatggg   2100
catcggcaag aacggggacc tgccctggcc accgctcagg aatgaattca gatatttcca   2160
gagaatgacc acaacctctt cagtagaagg taaacagaat ctggtgatta tgggtaagaa   2220
gacctggttc tccattcctg agaagaatcg acctttaaag ggtagaatta atttagttct   2280
cagcagagaa ctcaaggaac ctccacaagg agctcatttt ctttccagaa gtctagatga   2340
tgccttaaaa cttactgaac aaccagaatt agcaaataaa gtagacatgg tctggatagt   2400
tggtggcagt tctgtttata aggaagccat gaatcaccca ggccatctta aactatttgt   2460
gacaaggatc atgcaagact ttgaaagtga cacgtttttt ccagaaattg atttggagaa   2520
atataaactt ctgccagaat acccaggtgt tctctctgat gtccaggagg agaaaggcat   2580
taagtacaaa tttgaagtat atgagaagaa tgttaattaa gggcaccaat aactgcctta   2640
aaaaaattac gccccgccct gccactcatc gcagtactgt tgtaattcat taagcattct   2700
gccgacatgg aagccatcac agacggcatg atgaacctga atcgccagcg gcatcagcac   2760
cttgtcgcct tgcgtataat atttgcccat ggtgaaaacg ggggcgaaga agttgtccat   2820
attggccacg tttaaatcaa aactggtgaa actcacccag ggattggctg agacgaaaaa   2880
catattctca ataaaccctt tagggaaata ggccaggttt tcaccgtaac acgccacatc   2940
ttgcgaatat atgtgtagaa actgccggaa atcgtcgtgg tattcactcc agagcgatga   3000
aaacgtttca gtttgctcat ggaaaacggt gtaacaaggg tgaacactat cccatatcac   3060
```

-continued

```
cagctcaccg tctttcattg ccatacggaa ttccggatga gcattcatca ggcgggcaag   3120
aatgtgaata aaggccggat aaaacttgtg cttatttttc tttacggtct ttaaaaaggc   3180
cgtaatatcc agctgaacgg tctggttata ggtacattga gcaactgact gaaatgcctc   3240
aaaatgttct ttacgatgcc attgggatat atcaacggtg gtatatccag tgattttttt   3300
ctccatttta gcttccttag ctcctgaaaa tctcgataac tcaaaaaata cgcccggtag   3360
tgatcttatt tcattatggt gaaagttgga acctcttacg tgccgatcaa cgtctcattt   3420
tcgccaaatt aattaaggcg cgccgctctc ctggctagga gtcacgtaga aaggactacc   3480
gacgaaggaa cttgggtcgc cggtgtgttc gtatatggag gtagtaagac ctccctttac   3540
aacctaaggc gaggaactgc ccttgctatt ccacaatgtc gtcttacacc attgagtcgt   3600
ctcccctttg gaatggcccc tggacccggc ccacaacctg gcccgctaag ggagtccatt   3660
gtctgttatt tcatggtctt tttacaaact catatatttg ctgaggtttt gaaggatgcg   3720
attaaggacc ttgttatgac aaagcccgct cctacctgca atatcagggt gactgtgtgc   3780
agctttgacg atggagtaga tttgcctccc tggtttccac ctatggtgga aggggctgcc   3840
gcggagggtg atgacggaga tgacggagat gaaggaggtg atggagatga gggtgaggaa   3900
gggcaggagt gatgtaactt gttaggagac gccctcaatc gtattaaaag ccgtgtattc   3960
ccccgcacta aagaataaat ccccagtaga catcatgcgt gctgttggtg tatttctggc   4020
catctgtctt gtcaccattt tcgtcctccc aacatggggc aattgggcat acccatgttg   4080
tcacgtcact cagctccgcg ctcaacacct tctcgcgttg gaaaacatta gcgacattta   4140
cctggtgagc aatcagacat gcgacggctt tagcctggcc tccttaaatt cacctaagaa   4200
tgggagcaac cagcatgcag gaaaaggaca agcagcgaaa attcacgccc ccttgggagg   4260
tggcggcata tgcaaaggat agcactccca ctctactact gggtatcata tgctgactgt   4320
atatgcatga ggatagcata tgctacccgg atacagatta ggatagcata tactacccag   4380
atatagatta ggatagcata tgctacccag atatagatta ggatagccta tgctacccag   4440
atataaatta ggatagcata tactacccag atatagatta ggatagcata tgctacccag   4500
atatagatta ggatagccta tgctacccag atatagatta ggatagcata tgctacccag   4560
atatagatta ggatagcata tgctatccag atatttgggt agtatatgct acccagatat   4620
aaattaggat agcatatact accctaatct ctattaggat agcatatgct acccggatac   4680
agattaggat agcatatact acccagatat agattaggat agcatatgct acccagatat   4740
agattaggat agcctatgct acccagatat aaattaggat agcatatact acccagatat   4800
agattaggat agcatatgct acccagatat agattaggat agcctatgct acccagatat   4860
agattaggat agcatatgct atccagatat ttgggtagta tatgctaccc atggcaacat   4920
tagcccaccg tgctctcagc gacctcgtga atatgaggac caacaaccct gtgcttggcg   4980
ctcaggcgca agtgtgtgta atttgtcctc cagatcgcag caatcgcgcc cctatcttgg   5040
cccgcccacc tacttatgca ggtattcccc ggggtgccat tagtggtttt gtgggcaagt   5100
ggtttgaccg cagtggttag cggggttaca atcagccaag ttattacacc cttattttac   5160
agtccaaaac cgcagggcgg cgtgtggggg ctgacgcgtg cccccactcc acaatttcaa   5220
aaaaaagagt ggccacttgt ctttgtttat gggccccatt ggcgtggagc cccgtttaat   5280
tttcgggggt gttagagaca accagtggag tccgctgctg tcggcgtcca ctctctttcc   5340
ccttgttaca aatagagtgt aacaacatgg ttcacctgtc ttggtccctg cctgggacac   5400
atcttaataa ccccagtatc atattgcact aggattatgt gttgcccata gccataaatt   5460
```

-continued

```
cgtgtgagat ggacatccag tctttacggc ttgtccccac cccatggatt tctattgtta   5520
aagatattca gaatgtttca ttcctacact agtatttatt gcccaagggg tttgtgaggg   5580
ttatattggt gtcatagcac aatgccacca ctgaaccccc cgtccaaatt ttattctggg   5640
ggcgtcacct gaaaccttgt tttcgagcac ctcacataca ccttactgtt cacaactcag   5700
cagttattct attagctaaa cgaaggagaa tgaagaagca ggcgaagatt caggagagtt   5760
cactgcccgc tccttgatct tcagccactg cccttgtgac taaaatggtt cactaccctc   5820
gtggaatcct gaccccatgt aaataaaacc gtgacagctc atggggtggg agatatcgct   5880
gttccttagg accctttac taaccctaat tcgatagcat atgcttcccg ttgggtaaca   5940
tatgctattg aattagggtt agtctggata gtatatacta ctacccggga agcatatgct   6000
acccgtttag ggttaacaag gggccttat aaacactatt gctaatgccc tcttgagggt   6060
ccgcttatcg gtagctacac aggcccctct gattgacgtt ggtgtagcct cccgtagtct   6120
tcctgggccc ctgggaggta catgtccccc agcattggtg taagagcttc agccaagagt   6180
tacacataaa ggcaatgttg tgttgcagtc cacagactgc aaagtctgct ccaggatgaa   6240
agccactcag tgttggcaaa tgtgcacatc catttataag gatgtcaact acagtcagag   6300
aacccctttg tgtttggtcc ccccccgtgt cacatgtgga acagggccca gttggcaagt   6360
tgtaccaacc aactgaaggg attacatgca ctgccccgaa tacaaaacaa aagcgctcct   6420
cgtaccagcg aagaaggggc agagatgccg tagtcaggtt tagttcgtcc ggcggcgggc   6480
ggccgcaagg cgcgccggat ccacaggacg ggtgtggtcg ccatgatcgc gtagtcgata   6540
gtggctccaa gtagcgaagc gagcaggact gggcggcggc caaagcggtc ggacagtgct   6600
ccgagaacgg gtgcgcatag aaattgcatc aacgcatata gcgctagatc cttgctagag   6660
tcgagatctg tcgagccatg tgagcaaaag gccagcaaaa ggccaggaac cgtaaaaagg   6720
ccgcgttgct ggcgtttttc cataggctcc gcccccctga cgagcatcac aaaaatcgac   6780
gctcaagtca gaggtggcga aacccgacag gactataaag ataccaggcg tttccccctg   6840
gaagctccct cgtgcgctct cctgttccga ccctgccgct taccggatac ctgtccgcct   6900
ttctcccttc gggaagcgtg gcgctttctc atagctcacg ctgtaggtat ctcagttcgg   6960
tgtaggtcgt tcgctccaag ctgggctgtg tgcacgaacc ccccgttcag cccgaccgct   7020
gcgccttatc cggtaactat cgtcttgagt ccaacccggt aagacacgac ttatcgccac   7080
tggcagcagc cactggtaac aggattagca gagcgaggta tgtaggcggt gctacagagt   7140
tcttgaagtg gtggcctaac tacggctaca ctagaaggac agtatttggt atctgcgctc   7200
tgctgaagcc agttaccttc ggaaaaagag ttggtagctc ttgatccggc aaacaaacca   7260
ccgctggtag cggtggtttt tttgtttgca agcagcagat tacgcgcaga aaaaaaggat   7320
ctcaagaaga tcctttgatc ttttctacgg ggtctgacgc tcagtggaac gaaaactcac   7380
gttaagggat tttggtcatg agattatcaa aaaggatctt cacctagatc cttttatcgg   7440
tgtgaaatac cgcacagatg cgtaaggaga aaataccgca tcaggaaatt gtaagcgtta   7500
ataattcaga agaactcgtc aagaaggcga tagaaggcga tgcgctgcga atcgggagcg   7560
gcgataccgt aaagcacgag gaagcggtca gcccattcgc cgccaagctc ttcagcaata   7620
tcacgggtag ccaacgctat gtcctgatag cggtccgcca cacccagccg gccacagtcg   7680
atgaatccag aaaagcggcc attttccacc atgatattcg gcaagcaggc atcgccatgg   7740
gtcacgacga gatcctcgcc gtcgggcatg ctcgccttga gcctggcgaa cagttcggct   7800
```

-continued

```
ggcgcgagcc cctgatgctc ttcgtccaga tcatcctgat cgacaagacc ggcttccatc   7860
cgagtacgtg ctcgctcgat gcgatgtttc gcttggtggt cgaatgggca ggtagccgga   7920
tcaagcgtat gcagccgccg cattgcatca gccatgatgg atactttctc ggcaggagca   7980
aggtgagatg acaggagatc ctgccccggc acttcgccca atagcagcca gtcccttccc   8040
gcttcagtga caacgtcgag cacagctgcg caaggaacgc ccgtcgtggc cagccacgat   8100
agccgcgctg cctcgtcttg cagttcattc agggcaccgg acaggtcggt cttgacaaaa   8160
agaaccgggc gcccctgcgc tgacagccgg aacacggcgg catcagagca gccgattgtc   8220
tgttgtgccc agtcatagcc gaatagcctc tccacccaag cggccggaga acctgcgtgc   8280
aatccatctt gttcaatcat gcgaaacgat cctcatcctg tctcttgatc agagcttgat   8340
cccctgcgcc atcagatcct tggcggcgag aaagccatcc agtttacttt gcagggcttg   8400
tcaaccttac cagataaaag tgctcatcat tggaaaacat tcaattcgtc gacctcgaaa   8460
ttctaccggg taggggaggc gcttttccca aggcagtctg gagcatgcgc tttagcagcc   8520
ccgctgggca cttggcgcta cacaagtggc ctctggcctc gcacacattc cacatccacc   8580
ggtaggcgcc aaccggctcc gttctttggt ggccccttcg cgccaccttc tactcctccc   8640
ctagtcagga agttcccccc cgccccgcan ctcgcgtcgt gcaggacgtg acaaatggaa   8700
atagcacgtc tcactagtct cgtgcagatg gacaagcacc gctgagcaat ggagcgggta   8760
ggcctttggg gcagcggcca atagcagctt tgctccttcg ctttctgggc tcagaggctg   8820
gnaaggggtg ggtccggggg cgggctcagg ggcgggctca ggggcggggc gggcgcccga   8880
aggtcctccg gaggcccggc attctgcacg cttcaaaagc gcacgtctgc cgcgctgttc   8940
tcctcttcct catctccggg cctttcgacc tgcatccatc tagatctcga gcagctgaag   9000
cttaccatga ccgagtacaa gcccacggtg cgcctcgcca cccgcgacga cgtccccggg   9060
gccgtacgca ccctcgccgc cgcgttcgcc gactaccccg ccacgcgcca caccgtcgac   9120
ccggaccgcc acatcgagcg ggtcaccgag ctgcaagaac tcttcctcac gcgcgtcggg   9180
ctcgacatcg gcaaggtgtg ggtcgcggac gacggcgccg cggtggcggt ctggaccacg   9240
ccggagagcg tcgaagcggg ggcggtgttc gccgagatcg gcccgcgcat ggccgagttg   9300
agcggttccc ggctggccgc gcagcaacag atggaaggcc tcctggcgcc gcaccgggcc   9360
caaggagccc gcgtggttcc ttggcccacc gtcgggcgtc ttcgcccgac caccagggca   9420
agggtctggc aagcgccgtc gtgctccccg gagtggaggc ggccgagcgc gccggggtgc   9480
ccgccttcct ggagacctcc gcgccccgca acctcccctt ctacgagcgg ctcggcttca   9540
ccgtcaccgc cgacgtcgag gtgcccgaag gaccgcgcac ctggtgcatg acccgcaagc   9600
ccggtgcctg acgcccgccc cacgacccgc agcgcccgac cgaaaggagc gcacgacccc   9660
atgcatcgat ggcactgggc aggtaagtat caaggttagc ggccgctaac ctggttgctg   9720
actaattgag atgcatgctt tgcatacttc tgcctgctgg ggagcctggg gactttccac   9780
accctaactg acacacattc cacagctggt tctttccgcc tcagaaggta cacaggcgaa   9840
attgtaagcg ttaatatttt gttaaaattc gcgttaaatt tttgttaaat cagctcattt   9900
tttaaccaat aggccgaaat cggcaaaatc ccttataaat caaaagaata gaccgagata   9960
gggttgagtg ttgttccagt ttggaacaag agtccactat taaagaacgt ggactccaac  10020
gtcaaagggc gaaaaaccgt ctatcagggc gatggcccac                        10060
```

<210> SEQ ID NO 26
<211> LENGTH: 7714

-continued

<212> TYPE: DNA
<213> ORGANISM: Homo sapiens

<400> SEQUENCE: 26
tcaacgacag gagcacgatc atgcgcaccc gtggccagga cccaacgctg cccgagatgc 60
gccgcgtgcg gctgctggag atggcggacg cgatggatat gttctgccaa gggttggttt 120
gcgcattcac agttctccgc aagaattgat tggctccaat tcttggagtg gtgaatccgt 180
tagcgaggtg ccgccggctt ccattcaggt cgaggtggcc cggctccatg caccgcgacg 240
caacgcgggg aggcagacaa ggtatagggc ggcgcctaca atccatgcca acccgttcca 300
tgtgctcgcc gaggcggcat aaatcgccgt gacgatcagc ggtccagtga tcgaagttag 360
gctggtaaga gccgcgagcg atccttgaag ctgtccctga tggtcgtcat ctacctgcct 420
ggacagcatg gcctgcaacg cgggcatccc gatgccgccg gaagcgagaa gaatcataat 480
ggggaaggcc atccagcctc gcgtcgcgaa cgccagcaag acgtagccca gcgcgtcggc 540
cgccatgccg gcgataatgg cctgcttctc gccgaaacgt ttggtggcgg gaccagtgac 600
gaaggcttga gcgagggcgt gcaagattcc gaataccgca agcgacaggc cgatcatcgt 660
cgcgctccag cgaaagcggt cctcgccgaa aatgacccag agcgctgccg gcacctgtcc 720
tacgagttgc atgataaaga agacagtcat aagtgcggcg acgatagtca tgccccgcgc 780
ccaccggaag gagctgactg ggttgaaggc tctcaagggc atcggtcgac gctctccctt 840
atgcgactcc tgcattagga agcagcccag tagtaggttg aggccgttga gcaccgccgc 900
cgcaaggaat ggtgcatgca aggagatggc gcccaacagt cccccggcca cggggcctgc 960
caccataccc acgccgaaac aagcgctcat gagcccgaag tggcgagccc gatcttcccc 1020
atcggtgatg tcggcgatat aggcgccagc aaccgcacct gtggcgccgg tgatgccggc 1080
cacgatgcgt ccggcgtaga ggatccacag gacgggtgtg gtcgccatga tcgcgtagtc 1140
gatagtggct ccaagtagcg aagcgagcag gactgggcgg cggccaaagc ggtcggacag 1200
tgctccgaga acgggtgcgc atagaaattg catcaacgca tatagcgcta gcagcacgcc 1260
atagtgactg gcgatgctgt cggaatggac gatatcccgc aagaggcccg gcagtaccgg 1320
cataaccaag cctatgccta cagcatccag ggtgacggtg ccgaggatga cgatgagcgc 1380
attgttagat ttcatacacg gtgcctgact gcgttagcaa tttaactgtg ataaactacc 1440
gcattaaagc ttatcgattt ccacacatta tacgagccga tgttaattgt caacagctca 1500
tgcatgacgt cccgggagca gacaagcccg tcagggcgcg tcagcgggtg ttggcgggtg 1560
tcggggctgg cttaactatg cggcatcaga gcagattgta ctgagagtgc accatatgcg 1620
gtgtgaaata ccgcacagat gcgtaaggag aaaataccgc atcaggcgcc attcgccatt 1680
caggctgcgc aactgttggg aagggcgatc ggtgcgggcc tcttcgctat tacgccagct 1740
ggcgaaaggg ggatgtgctg caaggcgatt aagttgggta acgccagggt tttcccagtc 1800
acgacgttgt aaaacgacgg ccagtgaatt cgagctcata cttcgaatag ggataacagg 1860
gtaatgcgat agcggccgca atcgctctct taaggtagcc cgtgctggca aacagctatt 1920
atgggtatta tgggtgggcc ctagaaagct tggcgtaatc atggtcatag ctgtttcctg 1980
tgtgaaattg ttatccgctc acaattccac acaacatacg agccggaagc ataaagtgta 2040
aagcctgggg tgcctaatga gtgagctaac tcacattaat tgcgttgcgc tcactgcccg 2100
ctttccagtc gggaaacctg tcgtgccagc tgcattaatg acccgcgagg tcgccgcccc 2160 gtaacccccct accgctgaaa gttctgcaaa gcctgatggg acataagtcc atcagttcaa 2220

-continued

```
cggaagtcta cacgaaggtt tttgcgctgg atgtggctgc ccggcaccgg gtgcagtttg   2280
cgatgccgga gtctgatgcg gttgcgatgc tgaaacaatt atcctgagaa taaatgcctt   2340
ggcctttata tggaaatgtg gaactgagtg gatatgctgt ttttgtctgt taaacagaga   2400
agctggctgt tatccactga gaagcgaacg aaacagtcgg gaaaatctcc cattatcgta   2460
gagatccgca ttattaatct caggagcctg tgtagcgttt ataggaagta gtgttctgtc   2520
atgatgcctg caagcggtaa cgaaaacgat ttgaatatgc cttcaggaac aatagaaatc   2580
ttcgtgcggt gttacgttga agtggagcgg attatgtcag caatggacag aacaacctaa   2640
tgaacacaga accatgatgt ggtctgtcct tttacagcca gtagtgctcg ccgcagtcga   2700
gcgacagggc gaagccctcg agtgagcgag gaagcaccag ggaacagcac ttatatattc   2760
tgcttacaca cgatgcctga aaaaacttcc cttggggtta tccacttatc cacggggata   2820
tttttataat tatttttttt atagttttta gatcttcttt tttagagcgc cttgtaggcc   2880
tttatccatg ctggttctag agaaggtgtt gtgacaaatt gccctttcag tgtgacaaat   2940
caccctcaaa tgacagtcct gtctgtgaca aattgccctt aaccctgtga caaattgccc   3000
tcagaagaag ctgttttttc acaaagttat ccctgcttat tgactctttt ttatttagtg   3060
tgacaatcta aaaacttgtc acacttcaca tggatctgtc atggcggaaa cagcggttat   3120
caatcacaag aaacgtaaaa atagcccgcg aatcgtccag tcaaacgacc tcactgaggc   3180
ggcatatagt ctctcccggg atcaaaaacg tatgctgtat ctgttcgttg accagatcag   3240
aaaatctgat ggcaccctac aggaacatga cggtatctgc gagatccatg ttgctaaata   3300
tgctgaaata ttcggattga cctctgcgga agccagtaag gatatacggc aggcattgaa   3360
gagtttcgcg gggaaggaag tggtttttta tcgccctgaa gaggatgccg gcgatgaaaa   3420
aggctatgaa tcttttcctt ggtttatcaa acgtgcgcac agtccatcca gagggcttta   3480
cagtgtacat atcaacccat atctcattcc cttctttatc gggttacaga accggtttac   3540
gcagtttcgg cttagtgaaa caaaagaaat caccaatccg tatgccatgc gtttatacga   3600
atccctgtgt cagtatcgta agccggatgg ctcaggcatc gtctctctga aaatcgactg   3660
gatcatagag cgttaccagc tgcctcaaag ttaccagcgt atgcctgact tccgccgccg   3720
cttcctgcag gtctgtgtta atgagatcaa cagcagaact ccaatgcgcc tctcatacat   3780
tgagaaaaag aaaggccgcc agacgactca tatcgtattt tccttccgcg atatcacttc   3840
catgacgaca ggatagtctg agggttatct gtcacagatt tgagggtggt tcgtcacatt   3900
tgttctgacc tactgagggt aatttgtcac agttttgctg tttccttcag cctgcatgga   3960
ttttctcata ctttttgaac tgtaattttt aaggaagcca aatttgaggg cagtttgtca   4020
cagttgattt ccttctcttt cccttcgtca tgtgacctga tatcgggggt tagttcgtca   4080
tcattgatga gggttgatta tcacagttta ttactctgaa ttggctatcc gcgtgtgtac   4140
ctctacctgg agtttttccc acggtggata tttcttcttg cgctgagcgt aagagctatc   4200
tgacagaaca gttcttcttt gcttcctcgc cagttcgctc gctatgctcg gttacacggc   4260
tgcggcgagc gctagtgata ataagtgact gaggtatgtg ctcttcttat ctccttttgt   4320
agtgttgctc ttattttaaa caactttgcg gtttttgat gactttgcga ttttgttgtt   4380
gctttgcagt aaattgcaag atttaataaa aaaacgcaaa gcaatgatta aaggatgttc   4440
agaatgaaac tcatggaaac acttaaccag tgcataaacg ctggtcatga aatgacgaag   4500
gctatcgcca ttgcacagtt taatgatgac agcccggaag cgaggaaaat aacccggcgc   4560
tggagaatag gtgaagcagc ggatttagtt ggggtttctt ctcaggctat cagagatgcc   4620
```

-continued

```
gagaaagcag ggcgactacc gcacccggat atggaaattc gaggacgggt tgagcaacgt   4680
gttggttata caattgaaca aattaatcat atgcgtgatg tgtttggtac gcgattgcga   4740
cgtgctgaag acgtatttcc accggtgatc ggggttgctg cccataaagg tggcgtttac   4800
aaaacctcag tttctgttca tcttgctcag gatctggctc tgaaggggct acgtgttttg   4860
ctcgtggaag gtaacgaccc ccagggaaca gcctcaatgt atcacggatg ggtaccagat   4920
cttcatattc atgcagaaga cactctcctg cctttctatc ttggggaaaa ggacgatgtc   4980
acttatgcaa taaagcccac ttgctggccg ggcttgaca ttattccttc ctgtctggct   5040
ctgcaccgta ttgaaactga gttaatgggc aaatttgatg aaggtaaact gcccaccgat   5100
ccacacctga tgctccgact ggccattgaa actgttgctc atgactatga tgtcatagtt   5160
attgacagcg cgcctaacct gggtatcggc acgattaatg tcgtatgtgc tgctgatgtg   5220
ctgattgttc ccacgcctgc tgagttgttt gactacacct ccgcactgca gtttttcgat   5280
atgcttcgtg atctgctcaa gaacgttgat cttaaagggt tcgagcctga tgtacgtatt   5340
ttgcttacca aatacagcaa tagtaatggc tctcagtccc cgtggatgga ggagcaaatt   5400
cgggatgcct ggggaagcat ggttctaaaa aatgttgtac gtgaaacgga tgaagttggt   5460
aaaggtcaga tccggatgag aactgttttt gaacaggcca ttgatcaacg ctcttcaact   5520
ggtgcctgga gaaatgctct ttctatttgg gaacctgtct gcaatgaaat tttcgatcgt   5580
ctgattaaac cacgctggga gattagataa tgaagcgtgc gcctgttatt ccaaaacata   5640
cgctcaatac tcaaccggtt gaagatactt cgttatcgac accagctgcc ccgatggtgg   5700
attcgttaat tgcgcgcgta ggagtaatgg ctcgcggtaa tgccattact ttgcctgtat   5760
gtggtcggga tgtgaagttt actcttgaag tgctccgggg tgatagtgtt gagaagacct   5820
ctcgggtatg gtcaggtaat gaacgtgacc aggagctgct tactgaggac gcactggatg   5880
atctcatccc ttcttttcta ctgactggtc aacagacacc ggcgttcggt cgaagagtat   5940
ctggtgtcat agaaattgcc gatgggagtc gccgtcgtaa agctgctgca cttaccgaaa   6000
gtgattatcg tgttctggtt ggcgagctgg atgatgagca gatggctgca ttatccagat   6060
tgggtaacga ttatcgccca acaagtgctt atgaacgtgg tcagcgttat gcaagccgat   6120
tgcagaatga atttgctgga aatatttctg cgctggctga tgcggaaaat atttcacgta   6180
agattattac ccgctgtatc aacaccgcca aattgcctaa atcagttgtt gctcttttt    6240
ctcaccccgg tgaactatct gcccggtcag gtgatgcact tcaaaaagcc tttacagata   6300
aagaggaatt acttaagcag caggcatcta accttcatga gcagaaaaaa gctggggtga   6360
tatttgaagc tgaagaagtt atcactcttt taacttctgt gcttaaaacg tcatctgcat   6420
caagaactag tttaagctca cgacatcagt ttgctcctgg agcgacagta ttgtataagg   6480
gcgataaaat ggtgcttaac ctggacaggt ctcgtgttcc aactgagtgt atagagaaaa   6540
ttgaggccat tcttaaggaa cttgaaaagc cagcaccctg atgcgaccac gttttagtct   6600
acgtttatct gtctttactt aatgtccttt gttacaggcc agaaagcata actggcctga   6660
atattctctc tgggccagaa gcttggccca ctgttccact tgtatcgtcg gtctgataat   6720
cagactggga ccacggtccc actcgtatcg tcggtctgat tattagtctg ggaccacggt   6780
cccactcgta tcgtcggtct gattattagt ctgggaccac ggtcccactc gtatcgtcgg   6840
tctgataatc agactgggac cacggtccca ctcgtatcgt cggtctgatt attagtctgg   6900
gaccatggtc ccactcgtat cgtcggtctg attattagtc tgggaccacg gtcccactcg   6960
```

-continued

```
tatcgtcggt ctgattatta gtctggaacc acggtcccac tcgtatcgtc ggtctgatta   7020

ttagtctggg accacggtcc cactcgtatc gtcggtctga ttattagtct gggaccacga   7080

tcccactcgt gttgtcggtc tgattatcgg tctgggacca cggtcccact tgtattgtcg   7140

atcagactat cagcgtgaga ctacgattcc atcaatgcct gtcaagggca agtattgaca   7200

tgtcgtcgta acctgtagaa cggagtaacc tcggtgtgcg gttgtatgcc tgctgtggat   7260

tgctgctgtg tcctgcttat ccacaacatt ttgcgcacgg ttatgtggac aaaatacctg   7320

cgctagagaa aagagtttgt agaaacgcaa aaaggccatc cgtcaggatg gccttctgct   7380

taatttgatg cctggcagtt tatggcgggc gtcctgcccg ccaccctccg ggccgttgct   7440

tcgcaacgtt caaatccgct cccggcggat ttgtcctact caggagagcg ttcaccgaca   7500

aacaacagat aaaacgaaag gcccagtctt tcgactgagc ctttcgtttt atttgatgcc   7560

tggcagttcc ctactctcgc atggggagac cccacactac catcggcgct acggcgtttc   7620

acttctgagt tcggcatggg gtcaggtggg accaccgcgc tactgccgcc aggcaaattc   7680

tgttttatca gaccgcttct gcgttctggg ccgc                                7714
```

<210> SEQ ID NO 27
<211> LENGTH: 5314
<212> TYPE: DNA
<213> ORGANISM: Homo sapiens

<400> SEQUENCE: 27

```
gatcttcaat attggccatt agccatatta ttcattggtt atatagcata aatcaatatt     60

ggctattggc cattgcatac gttgtatcta tatcataata tgtacattta tattggctca    120

tgtccaatat gaccgccatg ttggcattga ttattgacta gttattaata gtaatcaatt    180

acggggtcat tagttcatag cccatatatg gagttccgcg ttacataact tacggtaaat    240

ggcccgcctg gctgaccgcc caacgacccc cgcccattga cgtcaataat gacgtatgtt    300

cccatagtaa cgccaatagg gactttccat tgacgtcaat gggtggagta tttacggtaa    360

actgcccact tggcagtaca tcaagtgtat catatgccaa gtccgccccc tattgacgtc    420

aatgacggta aatggcccgc ctggcattat gcccagtaca tgaccttacg ggactttcct    480

acttggcagt acatctacgt attagtcatc gctattacca tggtgatgcg gttttggcag    540

tacaccaatg ggcgtggata gcggtttgac tcacggggat ttccaagtct ccaccccatt    600

gacgtcaatg ggagtttgtt ttggcaccaa aatcaacggg actttccaaa atgtcgtaac    660

aactgcgatc gcccgccccg ttgacgcaaa tgggcggtag gcgtgtacgg tgggaggtct    720

atataagcag agctcgttta gtgaaccgtc agatcactga attctgacga cctactgatt    780

aacggccata gaggcctcct gcagaactgt cttagtgaca actatcgatt tccacacatt    840

atacgagccg atgttaattg tcaacagctc atgcatgacg tcccgggagc agacaagccc    900

gaccatggct cgagtaatac gactcactat agggcgacag gtgagtactc gctaccttaa    960

gagaggccta tctggccagt tagcagtcga agaaagaagt ttaagagagc cgaaacaagc   1020

gctcatgagc ccgaagtggc gagcccgatc ttccccatcg gtgatgtcgg cgatataggc   1080

gccagcaacc gcacctgtgg cgccggtgat gccggccacg atgcgtccgg cgtagaggat   1140

ccacaggacg ggtgtggtcg ccatgatcgc gtagtcgata gtggctccaa gtagcgaagc   1200

gagcaggact gggcggcggc caaagcggtc ggacagtgct ccgagaacgg gtgcgcatag   1260

aaattgcatc aacgcatata gcgctagatc cttgctagag tcgagatctg tcgagccatg   1320

tgagcaaaag gccagcaaaa ggccaggaac cgtaaaaagg ccgcgttgct ggcgtttttc   1380
```

-continued

```
cataggctcc gccccctga cgagcatcac aaaaatcgac gctcaagtca gaggtggcga   1440
aacccgacag gactataaag ataccaggcg tttccccctg gaagctccct cgtgcgctct   1500
cctgttccga ccctgccgct taccggatac ctgtccgcct ttctcccttc gggaagcgtg   1560
gcgctttctc atagctcacg ctgtaggtat ctcagttcgg tgtaggtcgt tcgctccaag   1620
ctgggctgtg tgcacgaacc ccccgttcag cccgaccgct gcgccttatc cggtaactat   1680
cgtcttgagt ccaacccggt aagacacgac ttatcgccac tggcagcagc cactggtaac   1740
aggattagca gagcgaggta tgtaggcggt gctacagagt tcttgaagtg gtggcctaac   1800
tacggctaca ctagaaggac agtatttggt atctgcgctc tgctgaagcc agttaccttc   1860
ggaaaaagag ttggtagctc ttgatccggc aaacaaacca ccgctggtag cggtggtttt   1920
tttgtttgca agcagcagat tacgcgcaga aaaaaaggat ctcaagaaga tcctttgatc   1980
ttttctacgg ggtctgacgc tcagtggaac gaaaactcac gttaagggat tttggtcatg   2040
agattatcaa aaaggatctt cacctagatc cttttatcgg tgtgaaatac cgcacagatg   2100
cgtaaggaga aaataccgca tcaggaaatt gtaagcgtta ataattcaga agaactcgtc   2160
aagaaggcga tagaaggcga tgcgctgcga atcgggagcg gcgataccgt aaagcacgag   2220
gaagcggtca gcccattcgc cgccaagctc ttcagcaata tcacgggtag ccaacgctat   2280
gtcctgatag cggtccgcca cacccagccg gccacagtcg atgaatccag aaaagcggcc   2340
attttccacc atgatattcg gcaagcaggc atcgccatgg gtcacgacga gatcctcgcc   2400
gtcgggcatg ctcgccttga gcctggcgaa cagttcggct ggcgcgagcc cctgatgctc   2460
ttcgtccaga tcatcctgat cgacaagacc ggcttccatc cgagtacgtg ctcgctcgat   2520
gcgatgtttc gcttggtggt cgaatgggca ggtagccgga tcaagcgtat gcagccgccg   2580
cattgcatca gccatgatgg atactttctc ggcaggagca aggtgagatg acaggagatc   2640
ctgccccggc acttcgccca atagcagcca gtcccttccc gcttcagtga caacgtcgag   2700
cacagctgcg caaggaacgc ccgtcgtggc cagccacgat agccgcgctg cctcgtcttg   2760
cagttcattc agggcaccgg acaggtcggt cttgacaaaa agaaccgggc gcccctgcgc   2820
tgacagccgg aacacggcgg catcagagca gccgattgtc tgttgtgccc agtcatagcc   2880
gaatagcctc tccacccaag cggccggaga acctgcgtgc aatccatctt gttcaatcat   2940
gcgaaacgat cctcatcctg tctcttgatc agagcttgat cccctgcgcc atcagatcct   3000
tggcggcgag aaagccatcc agtttacttt gcagggcttg tcaaccttac cagataaaag   3060
tgctcatcat tggaaaacgt tcaattctga ggcggaaaga accagctgtg gaatgtgtgt   3120
cagttagggt gtggaaagtc cccaggctcc ccagcaggca gaagtatgca aagcatgcat   3180
ctcaattagt cagcaaccag gtgtggaaag tccccaggct ccccagcagg cagaagtatg   3240
caaagcatgc atctcaatta gtcagcaacc atagtcccgc ccctaactcc gcccatcccg   3300
cccctaactc cgcccagttc cgcccattct ccgccccatg gctgactaat tttttttatt   3360
tatgcagagg ccgaggccgc ctcggcctct gagctattcc agaagtagtg aggaggcttt   3420
tttggaggcc taggcttttg caaaaagctt gattcttctg acacaacagt ctcgaactta   3480
aggctagagc caccatgatt gaacaagatg gattgcacgc aggttctccg gccgcttggg   3540
tggagaggct attcggctat gactgggcac aacagacaat cggctgctct gatgccgccg   3600
tgttccggct gtcagcgcag gggcgcccgg ttctttttgt caagaccgac ctgtccggtg   3660
ccctgaatga actgcaggac gaggcagcgc ggctatcgtg gctggccacg acgggcgttc   3720
```

-continued

```
cttgcgcagc tgtgctcgac gttgtcactg aagcgggaag ggactggctg ctattgggcg   3780

aagtgccggg gcaggatctc ctgtcatctc accttgctcc tgccgagaaa gtatccatca   3840

tggctgatgc aatgcggcgg ctgcatacgc ttgatccggc tacctgccca ttcgaccacc   3900

aagcgaaaca tcgcatcgag cgagcacgta ctcggatgga agccggtctt gtcgatcagg   3960

atgatctgga cgaagagcat caggggctcg cgccagccga actgttcgcc aggctcaagg   4020

cgcgcatgcc cgacggcgag gatctcgtcg tgacccatgg cgatgcctgc ttgccgaata   4080

tcatggtgga aaatggccgc ttttctggat tcatcgactg tggccggctg ggtgtggcgg   4140

accgctatca ggacatagcg ttggctaccc gtgatattgc tgaagagctt ggcggcgaat   4200

gggctgaccg cttcctcgtg ctttacggta tcgccgctcc cgattcgcag cgcatcgcct   4260

tctatcgcct tcttgacgag ccattctgct ggatggctac aggtcgcagc cctggcgtcg   4320

tgattagtga tgatgaacca ggttatgacc ttgatttatt ttgcatacct aatcattatg   4380

ctgaggattt ggaaagggtg tttattcctc atggactaat tatggacagg actgaacgtc   4440

ttgctcgaga tgtgatgaag gagatgggag gccatcacat tgtagccctc tgtgtgctca   4500

agggggggcta taaattcttt gctgacctgc tggattacat caaagcactg aatagaaata   4560

gtgatagatc cattcctatg actgtagatt ttatcagact gaagagctat tgtaatgacc   4620

agtcaacagg ggacataaaa gtaattggtg gagatgatct ctcaacttta actggaaaga   4680

atgtcttgat tgtggaagat ataattgaca ctggcaaaac aatgcagact ttgctttcct   4740

tggtcaggca gtataatcca aagatggtca aggtcgcaag cttgctggtg aaaaggaccc   4800

cacgaagtgt tggatataag ccagactttg ttggatttga aattccagac aagtttgttg   4860

taggatatgc ccttgactat aatgaatact tcagggattt gaatcatgtt tgtgtcatta   4920

gtgaaactgg aaaagcaaaa tacaaagcct aagcggccgc taacctggtt gctgactaat   4980

tgagatgcat gctttgcata cttctgcctg ctggggagcc tggggacttt ccacacccta   5040

actgacacac attccacagc tggttctttc cgcctcagaa ggtacacagg cgaaattgta   5100

agcgttaata ttttgttaaa attcgcgtta aatttttgtt aaatcagctc atttttttaac   5160

caataggccg aaatcggcaa aatcccttat aaatcaaaag aatagaccga gatagggttg   5220

agtgttgttc cagtttggaa caagagtcca ctattaaaga acgtggactc caacgtcaaa   5280

gggcgaaaaa ccgtctatca gggcgatggc ccac                                 5314
```

<210> SEQ ID NO 28
<211> LENGTH: 9737
<212> TYPE: DNA
<213> ORGANISM: Homo sapiens
<220> FEATURE:
<221> NAME/KEY: modified_base
<222> LOCATION: (8347)
<223> OTHER INFORMATION: a, c, t, g, other or unknown
<221> NAME/KEY: modified_base
<222> LOCATION: (8499)
<223> OTHER INFORMATION: a, c, t, g, other or unknown

<400> SEQUENCE: 28

```
gatcttcaat attggccatt agccatatta ttcattggtt atatagcata aatcaatatt     60

ggctattggc cattgcatac gttgtatcta tatcataata tgtacattta tattggctca    120

tgtccaatat gaccgccatg ttggcattga ttattgacta gttattaata gtaatcaatt    180

acggggtcat tagttcatag cccatatatg gagttccgcg ttacataact tacggtaaat    240

ggcccgcctg gctgaccgcc caacgacccc cgcccattga cgtcaataat gacgtatgtt    300
```

-continued

```
cccatagtaa cgccaatagg gactttccat tgacgtcaat gggtggagta tttacggtaa    360
actgcccact tggcagtaca tcaagtgtat catatgccaa gtccgccccc tattgacgtc    420
aatgacggta aatggcccgc ctggcattat gcccagtaca tgaccttacg ggactttcct    480
acttggcagt acatctacgt attagtcatc gctattacca tggtgatgcg gttttggcag    540
tacaccaatg ggcgtggata gcggtttgac tcacggggat ttccaagtct ccaccccatt    600
gacgtcaatg ggagtttgtt ttggcaccaa aatcaacggg actttccaaa atgtcgtaac    660
aactgcgatc gcccgccccg ttgacgcaaa tgggcggtag gcgtgtacgg tgggaggtct    720
atataagcag agctcgttta gtgaaccgtc agatcactga attctgacga cctactgatt    780
aacggccata gaggcctcct gcagaactgt cttagtgaca actatcgatt tccacacatt    840
atacgagccg atgttaattg tcaacagctc atgcatgacg tcccgggagc agacaagccc    900
gaccatggct cgagtaatac gactcactat agggcgacag gtgagtactc gctaccttaa    960
ggcctatctg gccgtttaaa cagatgtgta taagagacag ctctcttaag gtagcctgtc   1020
tcttatacac atctagatcc ttgctagagt cgaccaattc tcatgtttga cagcttatca   1080
tcgcagatcc tgagcttgta tggtgcactc tcagtacaat ctgctctgct gccgcatagt   1140
taagccagta tctgctccct gcttgtgtgt tggaggtcgc tgagtagtgc gcgagcaaaa   1200
tttaagctac aacaaggcaa ggcttgaccg acaattgcat gaagaatctg cttagggtta   1260
ggcgttttgc gctgcttcgc gatgtacggg ccagatatac gcgtatctga ggggactagg   1320
gtgtgtttag gcgcccagcg ggcttcggt tgtacgcggt taggagtccc ctcaggatat   1380
agtagtttcg cttttgcata gggagggga aatgtagtct tatgcaatac acttgtagtc   1440
ttgcaacatg gtaacgatga gttagcaaca tgccttacaa ggagagaaaa agcaccgtgc   1500
atgccgattg gtggaagtaa ggtggtacga tcgtgcctta ttaggaaggc aacagacagg   1560
tctgacatgg attggacgaa ccactgaatt ccgcattgca gagataattg tatttaagtg   1620
cctagctcga tacaataaac gccatttgac cattcaccac attggtgtgc acctccaagc   1680
tgggtaccag ctgctagcct cgagacgcgt gatttccttc gaagcttgtc atggttggtt   1740
cgctaaactg catcgtcgct gtgtcccaga acatgggcat cggcaagaac ggggacctgc   1800
cctggccacc gctcaggaat gaattcagat atttccagag aatgaccaca acctcttcag   1860
tagaaggtaa acagaatctg gtgattatgg gtaagaagac ctggttctcc attcctgaga   1920
agaatcgacc tttaaagggt agaattaatt tagttctcag cagagaactc aaggaacctc   1980
cacaaggagc tcattttctt tccagaagtc tagatgatgc cttaaaactt actgaacaac   2040
cagaattagc aaataaagta gacatggtct ggatagttgg tggcagttct gtttataagg   2100
aagccatgaa tcacccaggc catcttaaac tatttgtgac aaggatcatg caagactttg   2160
aaagtgacac gtttttttcca gaaattgatt tggagaaata taaacttctg ccagaatacc   2220
caggtgttct ctctgatgtc caggaggaga aaggcattaa gtacaaattt gaagtatatg   2280
agaagaatgt taattaaggg caccaataac tgccttaaaa aaattacgcc ccgccctgcc   2340
actcatcgca gtactgttgt aattcattaa gcattctgcc gacatggaag ccatcacaga   2400
cggcatgatg aacctgaatc gccagcggca tcagcacctt gtcgccttgc gtataatatt   2460
tgcccatggt gaaaacgggg gcgaagaagt tgtccatatt ggccacgttt aaatcaaaac   2520
tggtgaaact cacccaggga ttggctgaga cgaaaaacat attctcaata aaccctttag   2580
ggaaataggc caggttttca ccgtaacacg ccacatcttg cgaatatatg tgtagaaact   2640
gccggaaatc gtcgtggtat tcactccaga gcgatgaaaa cgtttcagtt tgctcatgga   2700
```

-continued

```
aaacggtgta acaagggtga acactatccc atatcaccag ctcaccgtct ttcattgcca   2760
tacggaattc cggatgagca ttcatcaggc gggcaagaat gtgaataaag gccggataaa   2820
acttgtgctt atttttcttt acggtcttta aaaaggccgt aatatccagc tgaacggtct   2880
ggttataggt acattgagca actgactgaa atgcctcaaa atgttcttta cgatgccatt   2940
gggatatatc aacggtggta tatccagtga tttttttctc catttagct tccttagctc    3000
ctgaaaatct cgataactca aaaaatacgc ccggtagtga tcttatttca ttatggtgaa   3060
agttggaacc tcttacgtgc cgatcaacgt ctcattttcg ccaaattaat taaggcgcgc   3120
cgctctcctg gctaggagtc acgtagaaag gactaccgac gaaggaactt gggtcgccgg   3180
tgtgttcgta tatggaggta gtaagacctc cctttacaac ctaaggcgag gaactgccct   3240
tgctattcca caatgtcgtc ttacaccatt gagtcgtctc ccctttggaa tggcccctgg   3300
acccggccca caacctggcc cgctaaggga gtccattgtc tgttatttca tggtcttttt   3360
acaaactcat atatttgctg aggttttgaa ggatgcgatt aaggaccttg ttatgacaaa   3420
gcccgctcct acctgcaata tcagggtgac tgtgtgcagc tttgacgatg gagtagattt   3480
gcctccctgg tttccaccta tggtggaagg ggctgccgcg gagggtgatg acggagatga   3540
cggagatgaa ggaggtgatg gagatgaggg tgaggaaggg caggagtgat gtaacttgtt   3600
aggagacgcc ctcaatcgta ttaaaagccg tgtattcccc cgcactaaag aataaatccc   3660
cagtagacat catgcgtgct gttggtgtat ttctggccat ctgtcttgtc accattttcg   3720
tcctcccaac atggggcaat tggcatacc catgttgtca cgtcactcag ctccgcgctc   3780
aacaccttct cgcgttggaa aacattagcg acatttacct ggtgagcaat cagacatgcg   3840
acggctttag cctggcctcc ttaaattcac ctaagaatgg gagcaaccag catgcaggaa   3900
aaggacaagc agcgaaaatt cacgcccccct tgggaggtgg cggcatatgc aaaggatagc   3960
actcccactc tactactggg tatcatatgc tgactgtata tgcatgagga tagcatatgc   4020
tacccggata cagattagga tagcatatac tacccagata tagattagga tagcatatgc   4080
tacccagata tagattagga tagcctatgc tacccagata taaattagga tagcatatac   4140
tacccagata tagattagga tagcatatgc tacccagata tagattagga tagcctatgc   4200
tacccagata tagattagga tagcatatgc tacccagata tagattagga tagcatatgc   4260
tatccagata tttgggtagt atatgctacc cagatataaa ttaggatagc atatactacc   4320
ctaatctcta ttaggatagc atatgctacc cggatacaga ttaggatagc atatactacc   4380
cagatataga ttaggatagc atatgctacc cagatataga ttaggatagc ctatgctacc   4440
cagatataaa ttaggatagc atatactacc cagatataga ttaggatagc atatgctacc   4500
cagatataga ttaggatagc ctatgctacc cagatataga ttaggatagc atatgctatc   4560
cagatatttg ggtagtatat gctacccatg gcaacattag cccaccgtgc tctcagcgac   4620
ctcgtgaata tgaggaccaa caaccctgtg cttggcgctc aggcgcaagt gtgtgtaatt   4680
tgtcctccag atcgcagcaa tcgcgcccct atcttggccc gcccacctac ttatgcaggt   4740
attccccggg gtgccattag tggttttgtg ggcaagtggt ttgaccgcag tggttagcgg   4800
ggttacaatc agccaagtta ttacaccctt attttacagt ccaaaaccgc agggcggcgt   4860
gtgggggctg acgcgtgccc ccactccaca atttcaaaaa aaagagtggc cacttgtctt   4920
tgtttatggg ccccattggc gtggagcccc gtttaatttt cgggggtgtt agagacaacc   4980
agtggagtcc gctgctgtcg gcgtccactc tctttcccct tgttacaaat agagtgtaac   5040
```

-continued

```
aacatggttc acctgtcttg gtccctgcct gggacacatc ttaataaccc cagtatcata   5100
ttgcactagg attatgtgtt gcccatagcc ataaattcgt gtgagatgga catccagtct   5160
ttacggcttg tccccacccc atggatttct attgttaaag atattcagaa tgtttcattc   5220
ctacactagt atttattgcc caaggggttt gtgagggtta tattggtgtc atagcacaat   5280
gccaccactg aaccccccgt ccaaatttta ttctgggggc gtcacctgaa accttgtttt   5340
cgagcacctc acatacacct tactgttcac aactcagcag ttattctatt agctaaacga   5400
aggagaatga agaagcaggc gaagattcag gagagttcac tgcccgctcc ttgatcttca   5460
gccactgccc ttgtgactaa aatggttcac taccctcgtg gaatcctgac cccatgtaaa   5520
taaaaccgtg acagctcatg ggtgggaga tatcgctgtt ccttaggacc cttttactaa   5580
ccctaattcg atagcatatg cttcccgttg ggtaacatat gctattgaat tagggttagt   5640
ctggatagta tatactacta cccgggaagc atatgctacc cgtttagggt taacaagggg   5700
gccttataaa cactattgct aatgccctct tgagggtccg cttatcggta gctacacagg   5760
cccctctgat tgacgttggt gtagcctccc gtagtcttcc tgggcccctg ggaggtacat   5820
gtcccccagc attggtgtaa gagcttcagc caagagttac acataaaggc aatgttgtgt   5880
tgcagtccac agactgcaaa gtctgctcca ggatgaaagc cactcagtgt tggcaaatgt   5940
gcacatccat ttataaggat gtcaactaca gtcagagaac ccctttgtgt ttggtccccc   6000
cccgtgtcac atgtggaaca gggcccagtt ggcaagttgt accaaccaac tgaagggatt   6060
acatgcactg ccccgaatac aaaacaaaag cgctcctcgt accagcgaag aaggggcaga   6120
gatgccgtag tcaggtttag ttcgtccggc ggcgggcggc cgcaaggcgc gccggatcca   6180
caggacgggt gtggtcgcca tgatcgcgta gtcgatagtg gctccaagta gcgaagcgag   6240
caggactggg cggcggccaa agcggtcgga cagtgctccg agaacgggtg cgcatagaaa   6300
ttgcatcaac gcatatagcg ctagatcctt gctagagtcg agatctgtcg agccatgtga   6360
gcaaaaggcc agcaaaaggc caggaaccgt aaaaaggccg cgttgctggc gtttttccat   6420
aggctccgcc cccctgacga gcatcacaaa aatcgacgct caagtcagag gtggcgaaac   6480
ccgacaggac tataaagata ccaggcgttt ccccctggaa gctccctcgt gcgctctcct   6540
gttccgaccc tgccgcttac cggatacctg tccgcctttc tcccttcggg aagcgtggcg   6600
ctttctcata gctcacgctg taggtatctc agttcggtgt aggtcgttcg ctccaagctg   6660
ggctgtgtgc acgaaccccc cgttcagccc gaccgctgcg ccttatccgg taactatcgt   6720
cttgagtcca acccggtaag acacgactta tcgccactgg cagcagccac tggtaacagg   6780
attagcagag cgaggtatgt aggcggtgct acagagttct tgaagtggtg gcctaactac   6840
ggctacacta gaaggacagt atttggtatc tgcgctctgc tgaagccagt taccttcgga   6900
aaaagagttg gtagctcttg atccggcaaa caaaccaccg ctggtagcgg tggttttttt   6960
gtttgcaagc agcagattac gcgcagaaaa aaaggatctc aagaagatcc tttgatcttt   7020
tctacggggt ctgacgctca gtggaacgaa aactcacgtt aagggatttt ggtcatgaga   7080
ttatcaaaaa ggatcttcac ctagatcctt ttatcggtgt gaaataccgc acagatgcgt   7140
aaggagaaaa taccgcatca ggaaattgta agcgttaata attcagaaga actcgtcaag   7200
aaggcgatag aaggcgatgc gctgcgaatc gggagcggcg ataccgtaaa gcacgaggaa   7260
gcggtcagcc cattcgccgc caagctcttc agcaatatca cgggtagcca acgctatgtc   7320
ctgatagcgg tccgccacac ccagccggcc acagtcgatg aatccagaaa agcggccatt   7380
ttccaccatg atattcggca agcaggcatc gccatgggtc acgacgagat cctcgccgtc   7440
```

-continued gggcatgctc gccttgagcc tggcgaacag ttcggctggc gcgagcccct gatgctcttc 7500
gtccagatca tcctgatcga caagaccggc ttccatccga gtacgtgctc gctcgatgcg 7560
atgtttcgct tggtggtcga atgggcaggt agccggatca agcgtatgca gccgccgcat 7620
tgcatcagcc atgatggata ctttctcggc aggagcaagg tgagatgaca ggagatcctg 7680
ccccggcact tcgcccaata gcagccagtc ccttcccgct tcagtgacaa cgtcgagcac 7740
agctgcgcaa ggaacgcccg tcgtggccag ccacgatagc cgcgctgcct cgtcttgcag 7800
ttcattcagg gcaccggaca ggtcggtctt gacaaaaaga accgggcgcc cctgcgctga 7860
cagccggaac acggcggcat cagagcagcc gattgtctgt tgtgcccagt catagccgaa 7920
tagcctctcc acccaagcgg ccggagaacc tgcgtgcaat ccatcttgtt caatcatgcg 7980
aaacgatcct catcctgtct cttgatcaga gcttgatccc ctgcgccatc agatccttgg 8040
cggcgagaaa gccatccagt ttactttgca gggcttgtca accttaccag ataaaagtgc 8100
tcatcattgg aaaacattca attcgtcgac ctcgaaattc taccgggtag ggaggcgct 8160
tttcccaagg cagtctggag catgcgcttt agcagccccg ctgggcactt ggcgctacac 8220
aagtggcctc tggcctcgca cacattccac atccaccggt aggcgccaac cggctccgtt 8280
ctttggtggc cccttcgcgc caccttctac tcctccccta gtcaggaagt tcccccccgc 8340
cccgcanctc gcgtcgtgca ggacgtgaca aatggaaata gcacgtctca ctagtctcgt 8400
gcagatggac aagcaccgct gagcaatgga gcgggtaggc ctttggggca gcggccaata 8460
gcagctttgc tccttcgctt tctgggctca gaggctggna aggggtgggt ccgggggcgg 8520
gctcaggggc gggctcaggg gcggggcggg cgcccgaagg tcctccggag gcccggcatt 8580
ctgcacgctt caaaagcgca cgtctgccgc gctgttctcc tcttcctcat ctccgggcct 8640
ttcgacctgc atccatctag atctcgagca gctgaagctt accatgaccg agtacaagcc 8700
cacggtgcgc ctcgccaccc gcgacgacgt cccccgggcc gtacgcaccc tcgccgccgc 8760
gttcgccgac taccccgcca cgcgccacac cgtcgacccg gaccgccaca tcgagcgggt 8820
caccgagctg caagaactct tcctcacgcg cgtcgggctc gacatcggca aggtgtgggt 8880
cgcggacgac ggcgccgcgg tggcggtctg gaccacgccg gagagcgtcg aagcgggggc 8940
ggtgttcgcc gagatcggcc cgcgcatggc cgagttgagc ggttcccggc tggccgcgca 9000
gcaacagatg gaaggcctcc tggcgccgca ccgggcccaa ggagcccgcg tggttccttg 9060
gcccaccgtc gggcgtcttc gcccgaccac cagggcaagg gtctggcaag cgccgtcgtg 9120
ctccccggag tggaggcggc cgagcgcgcc ggggtgcccg ccttcctgga gacctccgcg 9180
ccccgcaacc tccccttcta cgagcggctc ggcttcaccg tcaccgccga cgtcgaggtg 9240
cccgaaggac cgcgcacctg gtgcatgacc cgcaagcccg gtgcctgacg cccgccccac 9300
gacccgcagc gcccgaccga aaggagcgca cgaccccatg catcgatggc actgggcagg 9360
taagtatcaa ggttagcggc cgctaacctg gttgctgact aattgagatg catgctttgc 9420
atacttctgc ctgctgggga gcctggggac tttccacacc ctaactgaca cacattccac 9480
agctggttct ttccgcctca gaaggtacac aggcgaaatt gtaagcgtta atattttgtt 9540
aaaattcgcg ttaaattttt gttaaatcag ctcatttttt aaccaatagg ccgaaatcgg 9600
caaaatccct tataaatcaa aagaatagac cgagataggg ttgagtgttg ttccagtttg 9660
gaacaagagt ccactattaa agaacgtgga ctccaacgtc aaagggcgaa aaaccgtcta 9720
tcagggcgat ggcccac 9737

-continued

```
<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Vector
      Promoter

<400> SEQUENCE: 29

acccaggtga tg                                                       12


<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Vector
      Promoter

<400> SEQUENCE: 30

accatgcagg tgatg                                                    15


<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Vector
      Promoter

<400> SEQUENCE: 31

accatggcag gtgatg                                                   16


<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Vector
      Promoter

<400> SEQUENCE: 32

accatgggca ggtgatg                                                  17


<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Vector
<223> OTHER INFORMATION: polyA tail

<400> SEQUENCE: 33

aaaaaaaaaa                                                          10
```

COMPOSITIONS AND METHODS FOR NON-TARGETED ACTIVATION OF ENDOGENOUS GENES

CROSS REFERENCE TO RELATED APPLICATIONS

This application is a divisional application of U.S. application Ser. No. 09/276,820, filed Mar. 26, 1999, entitled "COMPOSITIONS AND METHODS FOR NON-TARGETED ACTIVATION OF ENDOGENOUS GENES" which is a divisional application Ser. No. 09/263,814, filed Mar. 8, 1999, which is a continuation-in-part of U.S. application Ser. No. 09/253,022, filed Feb. 19, 1999, abandoned, which is a continuation-in-part of U.S. application Ser. No. 09/159,643, filed Sep. 24, 1998, abandoned, which is a continuation-in-part of U.S. application Ser. No. 08/941,223, filed Sep. 26, 1997, abandoned, the disclosures of all of which are incorporated herein by reference in their entireties.

BACKGROUND OF THE INVENTION

1. Field of the Invention

The present invention is in the fields of molecular biology and cellular biology. The invention is directed generally to activation of gene expression or causing over-expression of a gene by recombination methods in situ. More specifically, the invention is directed to activation of endogenous genes by non-targeted integration of specialized activation vectors, which are provided by the invention, into the genome of a host cell. The invention also is directed to methods for the identification, activation, and isolation of genes that were heretofore undiscoverable, and to host cells and vectors comprising such isolated genes. The invention also is directed to isolated genes, gene products, nucleic acid molecules, and compositions comprising such genes, gene products and nucleic acid molecules, that may be used in a variety of therapeutic and diagnostic applications. Thus, by the present invention, endogenous genes, including those associated with human disease and development, may be identified, activated, and isolated without prior knowledge of the sequence, structure, function, or expression profile of the genes.

2. Related Art

Identification and over-expression of novel genes associated with human disease is an important step towards developing new therapeutic drugs. Current approaches to creating libraries of cells for protein over-expression are based on the production and cloning of cDNA. Thus, in order to identify a new gene using this approach, the gene must be expressed in the cells that were used to make the library. The gene also must be expressed at sufficient levels to be adequately represented in the library. This is problematic because many genes are expressed only in very low quantities, in a rare population of cells, or during short developmental periods.

Furthermore, because of the large size of some mRNAs, it is difficult or impossible to produce full length cDNA molecules capable of expressing the biologically active protein. Lack of full-length cDNA molecules has also been observed for small mRNAs and is thought to be related to sequences in the message that are difficult to produce by reverse transcription or that are unstable during propagation in bacteria. As a result, even the most complete cDNA libraries express only a fraction of the entire set of possible genes.

Finally, many cDNA libraries are produced in bacterial vectors. Use of these vectors to express biologically active mammalian proteins is severely limited since most mammalian proteins do not fold correctly and/or are improperly glycosylated in bacteria.

Therefore, a method for creating a more representative library for protein expression, capable of facilitating faithful expression of biologically active proteins, would be extremely valuable.

Current methods for over-expressing proteins involve cloning the gene of interest and placing it, in a construct, next to a suitable promoter/enhancer, polyadenylation signal, and splice site, and introducing the construct into an appropriate host cell.

An alternative approach involves the use of homologous recombination to activate gene expression by targeting a strong promoter or other regulatory sequence to a previously identified gene.

WO 90/14092 describes in situ modification of genes, in mammalian cells, encoding proteins of interest. This application describes single-stranded oligonucleotides for site-directed modification of genes encoding proteins of interest. A marker may also be included. However, the methods are limited to providing an oligonucleotide sequence substantially homologous to a target site. Thus, the method requires knowledge of the site required for activation by site-directed modification and homologous recombination. Novel genes are not discoverable by such methods.

WO 91/06667 describes methods for expressing a mammalian gene in situ. With this method, an amplifiable gene is introduced next to a target gene by homologous recombination. When the cell is then grown in the appropriate medium, both the amplifiable gene and the target gene are amplified and there is enhanced expression of the target gene. As above, methods of introducing the amplifiable gene are limited to homologous recombination, and are not useful for activating novel genes whose sequence (or existence) is unknown.

WO 91/01140 describes the inactivation of endogenous genes by modification of cells by homologous recombination. By these methods, homologous recombination is used to modify and inactivate genes and to produce cells which can serve as donors in gene therapy.

WO 92/20808 describes methods for modifying genomic target sites in situ. The modifications are described as being small, for example, changing single bases in DNA. The method relies upon genomic modification using homologous DNA for targeting.

WO 92/19255 describes a method for enhancing the expression of a target gene, achieved by homologous recombination in which a DNA sequence is integrated into the genome or large genomic fragment. This modified sequence can then be transferred to a secondary host for expression. An amplifiable gene can be integrated next to the target gene so that the target region can be amplified for enhanced expression. Homologous recombination is necessary to this targeted approach.

WO 93/09222 describes methods of making proteins by activating an endogenous gene encoding a desired product. A regulatory region is targeted by homologous recombination and replacing or disabling the region normally associated with the gene whose expression is desired. This disabling or replacement causes the gene to be expressed at levels higher than normal.

WO 94/12650 describes a method for activating expression of and amplifying an endogenous gene in situ in a cell, which gene is not expressed or is not expressed at desired levels in the cell. The cell is transfected with exogenous DNA sequences which repair, alter, delete, or replace a sequence present in the cell or which are regulatory sequences not normally functionally linked to the endogenous gene in the cell. In order to do this, DNA sequences homologous to genomic DNA sequences at a preselected site are used to target the endogenous gene. In addition, amplifiable DNA encoding a selectable marker can be included. By culturing the homologously recombinant cells under conditions that select for amplification, both the endogenous gene and the amplifiable marker are co-amplified and expression of the gene increased.

WO 95/31560 describes DNA constructs for homologous recombination. The constructs include a targeting sequence, a regulatory sequence, an exon, and an unpaired splice donor site. The targeting is achieved by homologous recombination of the construct with genomic sequences in the cell and allows the production of a protein in vitro or in vivo.

WO 96/29411 describes methods using an exogenous regulatory sequence, an exogenous exon, either coding or non-coding, and a splice donor site introduced into a preselected site in the genome by homologous recombination. In this application, the introduced DNA is positioned so that the transcripts under control of the exogenous regulatory region include both the exogenous exon and endogenous exons present in either the thrombopoietin, DNase I, or β-interferon genes, resulting in transcripts in which the exogenous and exogenous exons are operably linked. The novel transcription units are produced by homologous recombination.

U.S. Pat. No. 5,272,071 describes the transcriptional activation of transcriptionally silent genes in a cell by inserting a DNA regulatory element capable of promoting the expression of a gene normally expressed in that cell. The regulatory element is inserted so that it is operably linked to the normally silent gene. The insertion is accomplished by means of homologous recombination by creating a DNA construct with a segment of the normally silent gene (the target DNA) and the DNA regulatory element used to induce the desired transcription.

U.S. Pat. No. 5,578,461 discusses activating expression of mammalian target genes by homologous recombination. A DNA sequence is integrated into the genome or a large genomic fragment to enhance the expression of the target gene. The modified construct can then be transferred to a secondary host. An amplifiable gene can be integrated adjacent to the target gene so that the target region is amplified for enhanced expression.

Both of the above approaches (construction of an over-expressing construct by cloning or by homologous recombination in vivo) require the gene to be cloned and sequenced before it can be over-expressed. Furthermore, using homologous recombination, the genomic sequence and structure must also be known.

Unfortunately, many genes have not yet been identified and/or sequenced. Thus, a method for over-expressing a gene of interest, whether or not it has been previously cloned, and whether or not its sequence and structure are known, would be useful.

BRIEF SUMMARY OF THE INVENTION

The invention is, therefore, generally directed to methods for over-expressing an endogenous gene in a cell, comprising introducing a vector containing a transcriptional regulatory sequence into the cell, allowing the vector to integrate into the genome of the cell by non-homologous recombination, and allowing over-expression of the endogenous gene in the cell. The method does not require previous knowledge of the sequence of the endogenous gene or even of the existence of the gene. Hence, the invention is directed to non-targeted gene activation, which as used herein means the activation of endogenous genes by non-targeted or non-homologous (as opposed to targeted or homologous) integration of specialized activation vectors into the genome of a host cell.

The invention also encompasses novel vector constructs for activating gene expression or over-expressing a gene through non-homologous recombination. The novel construct lacks homologous targeting sequences. That is, it does not contain nucleotide sequences that target host cell DNA and promote homologous recombination at the target site, causing over-expressing of a cellular gene via the introduced transcriptional regulatory sequence.

Novel vector constructs include a vector containing a transcriptional regulatory sequence operably linked to an unpaired splice donor sequence and further contains one or more amplifiable markers.

Novel vector constructs include constructs with a transcriptional regulatory sequence operably linked to a translational start codon, a signal secretion sequence, and an unpaired splice donor site; constructs with a transcriptional regulatory sequence, operably linked to a translation start codon, an epitope tag, and an unpaired splice donor site; constructs containing a transcriptional regulatory sequence operably linked to a translational start codon, a signal sequence and an epitope tag, and an unpaired splice donor site; constructs containing a transcriptional regulatory sequence operably linked to a translation start codon, a signal secretion sequence, an epitope tag, and a sequence-specific protease site, and an unpaired splice donor site.

The vector construct can contain one or more selectable markers for recombinant host cell selection. Alternatively, selection can be effected by phenotypic selection for a trait provided by the activated endogenous gene product.

These vectors, and indeed any of the vectors disclosed herein, and variants of the vectors that will be readily recognized by one of ordinary skill in the art, can be used in any of the methods described herein to form any of the compositions producible by these methods.

The transcriptional regulatory sequence used in the vector constructs of the invention includes, but is not limited to, a promoter. In preferred embodiments, the promoter is a viral promoter. In highly preferred embodiments, the viral promoter is the cytomegalovirus immediate early promoter. In alternative embodiments, the promoter is a cellular, non-viral promoter or inducible promoter.

The transcriptional regulatory sequence used in the vector construct of the invention may also include, but is not limited to, an enhancer. In preferred embodiments, the enhancer is a viral enhancer. In highly preferred embodiments, the viral enhancer is the cytomegalovirus immediate early enhancer. In alternative embodiments, the enhancer is a cellular non-viral enhancer.

In preferred embodiments of the methods described herein, the vector construct be, or may contain, linear RNA or DNA.

The cell containing the vector may be screened for expression of the gene.

The cell over-expressing the gene can be cultured in vitro under conditions favoring the production, by the cell, of desired amounts of the gene product (also referred to interchangeably herein as the "expression product") of the endogenous gene that has been activated or whose expression has been increased. The expression product can then be isolated and purified to use, for example, in protein therapy or drug discovery.

Alternatively, the cell expressing the desired gene product can be allowed to express the gene product in vivo. In certain such aspects of the invention, the cell containing a vector construct of the invention integrated into its genome may be introduced into a eukaryote (such as a vertebrate, particularly a mammal, more particularly a human) under conditions favoring the overexpression or activation of the gene by the cell in vivo in the eukaryote. In related such aspects of the invention, the cell may be isolated and cloned prior to being introduced into the eukaryote.

The invention is also directed to methods for over-expressing an endogenous gene in a cell, comprising introducing a vector containing a transcriptional regulatory sequence and one or more amplifiable markers into the cell, allowing the vector to integrate into the genome of the cell by non-homologous recombination, and allowing over-expression of the endogenous gene in the cell.

The cell containing the vector may be screened for over-expression of the gene.

The cell over-expressing the gene is cultured such that amplification of the endogenous gene is obtained. The cell can then be cultured in vitro so as to produce desired amounts of the gene product of the amplified endogenous gene that has been activated or whose expression has been increased. The gene product can then be isolated and purified.

Alternatively, following amplification, the cell can be allowed to express the endogenous gene and produce desired amounts of the gene product in vivo.

It is to be understood, however, that any vector used in the methods described herein can include one or more amplifiable markers. Thereby, amplification of both the vector and the DNA of interest (i.e., containing the over-expressed gene) occurs in the cell, and further enhanced expression of the endogenous gene is obtained. Accordingly, methods can include a step in which the endogenous gene is amplified.

The invention is also directed to methods for over-expressing an endogenous gene in a cell comprising introducing a vector containing a transcriptional regulatory sequence and an unpaired splice donor sequence into the cell, allowing the vector to integrate into the genome of the cell by non-homologous recombination, and allowing over-expression of the endogenous gene in the cell.

The cell containing the vector may be screened for expression of the gene.

The cell over-expressing the gene can be cultured in vitro so as to produce desirable amounts of the gene product of the endogenous gene whose expression has been activated or increased. The gene product can then be isolated and purified.

Alternatively, the cell can be allowed to express the desired gene product in vivo.

The vector construct can consist essentially of the transcriptional regulatory sequence.

The vector construct can consist essentially of the transcriptional regulatory sequence and one or more amplifiable markers.

The vector construct can consist essentially of the transcriptional regulatory sequence and the splice donor sequence.

Any of the vector constructs of the invention can also include a secretion signal sequence. The secretion signal sequence is arranged in the construct so that it will be operably linked to the activated endogenous protein. Thereby, secretion of the protein of interest occurs in the cell, and purification of that protein is facilitated. Accordingly, methods can include a step in which the protein expression product is secreted from the cell.

The invention also encompasses cells made by any of the above methods. The invention encompasses cells containing the vector constructs, cells in which the vector constructs have integrated into the cellular genome, and cells which are over-expressing desired gene products from an endogenous gene, over-expression being driven by the introduced transcriptional regulatory sequence.

The cells can be isolated and cloned.

The methods can be carried out in any cell of eukaryotic origin, such as fungal, plant or animal. In preferred embodiments, the methods of the invention may be carried out in vertebrate cells, and particularly mammalian cells including but not limited to rat, mouse, bovine, porcine, sheep, goat and human cells, and more particularly in human cells.

A single cell made by the methods described above can over-express a single gene or more than one gene. More than one gene in a cell can be activated by the integration of a single type of construct into multiple locations in the genome. Similarly, more than one gene in a cell can be activated by the integration of multiple constructs (i.e., more than one type of construct) into multiple locations in the genome. Therefore, a cell can contain only one type of vector construct or different types of constructs, each capable of activating an endogenous gene.

The invention is also directed to methods for making the cells described above by one or more of the following: introducing one or more of the vector constructs of the invention into a cell; allowing the introduced construct(s) to integrate into the genome of the cell by non-homologous recombination; allowing over-expression of one or more endogenous genes in the cell; and isolating and cloning the cell. The invention is also directed to cells produced by such methods, which may be isolated cells.

The invention also encompasses methods for using the cells described above to over-express a gene, such as an endogenous cellular gene, that has been characterized (for example, sequenced), uncharacterized (for example, a gene whose function is known but which has not been cloned or sequenced), or a gene whose existence was, prior to over-expression, unknown. The cells can be used to produce desired amounts of an expression product in vitro or in vivo. If desired, this expression product can then be isolated and purified, for example by cell lysis or by isolation from the growth medium (as when the vector contains a secretion signal sequence).

The invention also encompasses libraries of cells made by the above described methods. A library can encompass all of the clones from a single transfection experiment or a subset of clones from a single transfection experiment. The subset can over-express the same gene or more than one gene, for example, a class of genes. The transfection can have been done with a single construct or with more than one construct.

A library can also be formed by combining all of the recombinant cells from two or more transfection experiments, by combining one or more subsets of cells from a single transfection experiment or by combining subsets of cells from separate transfection experiments. The resulting library can express the same gene, or more than one gene, for example, a class of genes. Again, in each of these individual transfections, a unique construct or more than one construct can be used.

Libraries can be formed from the same cell type or different cell types.

The invention is also directed to methods for making libraries by selecting various subsets of cells from the same or different transfection experiments.

The invention is also directed to methods of using the above-described cells or libraries of cells to over-express or activate endogenous genes, or to obtain the gene expression products of such over-expressed or activated genes. According to this aspect of the invention, the cell or library may be screened for the expression of the gene and cells that express the desired gene product may be selected. The cell can then be used to isolate or purify the gene product for subsequent use. Expression in the cell can occur by culturing the cell in vitro, under conditions favoring the production of the expression product of the endogenous gene by the cell, or by allowing the cell to express the gene in vivo.

In preferred embodiments of the invention, the methods include a process wherein the expression product is isolated or purified. In highly preferred embodiments, the cells expressing the endogenous gene product are cultured under conditions favoring production of sufficient amounts of gene product for commercial application, and especially for diagnostic, therapeutic and drug discovery uses.

Any of the methods can further comprise introducing double-strand breaks into the genomic DNA in the cell prior to or simultaneously with vector integration.

The invention also is directed to vector constructs that are useful for activating expression of endogenous genes and for isolating the mRNA and cDNA corresponding to the activated genes.

In one such embodiment, the vector construct may comprise (a) a first transcriptional regulatory sequence operably linked to a first unpaired splice donor sequence, (b) a second transcriptional regulatory sequence operably linked to a second unpaired splice donor sequence; and (c) a linearization site, which may be located between the first and second transcriptional regulatory sequences. According to the invention, when the vector construct is transformed into a host cell and then integrates into the genome of the host cell, the first transcriptional regulatory sequence is preferably in an inverted orientation relative to the orientation of the second transcriptional regulatory sequence. In certain preferred such embodiments, the vector may be rendered linear by cleavage at the linearization site.

In another embodiment, the invention provides a linear vector construct having a 3' end and a 5' end, comprising a transcriptional regulatory sequence operably linked to an unpaired spliced donor site, wherein the transcriptional regulatory sequence is oriented in the linear vector construct in an orientation that directs transcription towards the 3' end or the 5' end of the linear vector construct.

In another embodiment, the invention provides a vector construct comprising, in sequential order, (a) a transcriptional regulatory sequence, (b) an unpaired splice donor site, (c) a rare cutting restriction site, and (d) a linearization site.

In another embodiment, the invention provides a vector construct comprising (a) a first transcriptional regulatory sequence operably linked to a selectable marker lacking a polyadenylation signal; and (b) a second transcriptional regulatory sequence operably linked to an exon-splice donor site complex, wherein the first transcriptional regulatory sequence is in the same orientation in the vector construct as is the second transcriptional regulatory sequence, and wherein the first transcriptional regulatory sequence is upstream of the second transcriptional regulatory sequence in the vector construct.

In additional embodiments, the invention provides vector constructs comprising a transcriptional regulatory sequence operably linked to a selectable marker lacking a polyadenylation signal, and further comprising an unpaired splice donor site.

In another embodiment, the invention provides vector constructs comprising a first transcriptional regulatory sequence operably linked to a selectable marker lacking a polyadenylation signal, and further comprising a second transcriptional regulatory sequence operably linked to an unpaired splice donor site.

According to the invention, the transcriptional regulatory sequence (or first or second transcriptional regulatory sequence, in vector constructs having more than one transcriptional regulatory sequence) may be a promoter, an enhancer, or a repressor, and is preferably a promoter, including an animal cell promoter, a plant cell promoter, or a fungal cell promoter, most preferably a promoter selected from the group consisting of a CMV immediate early gene promoter, an SV40 T antigen promoter, and a β-actin promoter. Other promoters of animal, plant, or fungal cell origin that may be used in accordance with the invention are known in the art and will be familiar to one of ordinary skill in view of the teachings herein.

The selectable marker used in the vector constructs of the invention may be any marker or marker gene that, upon integration of a vector containing the selectable marker into the host cell genome, permits the selection of a cell containing or expressing the marker gene. Suitable such selectable markers include, but are not limited to, a neomycin gene, a hypoxanthine phosphribosyl transferase gene, a puromycin gene, a dihydrooratase gene, a glutamine synthetase gene, a histidine D gene, a carbamyl phosphate synthase gene, a dihydrofolate reductase gene, a multidrug resistance 1 gene, an aspartate transcarbamylase gene, a xanthine-guanine phosphoribosyl transferase gene, an adenosine deaminase gene, and a thymidine kinase gene.

In related embodiments, the invention provides vector constructs comprising a positive selectable marker, a negative selectable marker, and an unpaired splice donor site, wherein the positive and negative selectable markers and the splice donor site are oriented in the vector construct in an orientation that results in expression of the positive selectable marker in active form, and either non-expression of said negative selectable marker or expression of the negative selectable marker in inactive form, when the vector construct is integrated into the genome of a eukaryotic host cell and activates an endogenous gene in the genome. In certain preferred such embodiments, either the positive selection marker, the negative selection marker, or both, may lack a polyadenylation signal. The positive selection marker used in these aspects of the invention may be any selection marker that, upon expression, produces a protein capable of facilitating the isolation of cells expressing the marker, including but not limited to a neomycin gene, a hypoxanthine phosphribosyl transferase gene, a puromycin gene, a dihydrooratase gene, a glutamine synthetase gene, a histidine D gene, a carbamyl phosphate synthase gene, a dihydrofolate reductase gene, a multidrug resistance 1 gene, an aspartate transcarbamylase gene, a xanthine-guanine phosphoribosyl transferase gene, or an adenosine deaminase gene. Analogously, the negative selection marker used in these aspects of the invention may be any selection marker that, upon expression, produces a protein capable of facilitating removal of cells expressing the marker, including but not limited to a hypoxanthine phosphribosyl transferase gene, a thymidine kinase gene, or a diphtheria toxin gene.

The invention also is directed to eukaryotic host cells, which may be isolated host cells, comprising one or more of the vector constructs of the invention. Preferred such eukaryotic host cells include, but are not limited to, animal cells (including, but not limited to, mammalian (particularly human) cells, insect cells, avian cells, annelid cells, amphibian cells, reptilian cells, and fish cells), plant cells, and fungal (particularly yeast) cells. In certain such host cells, the vector construct may be integrated into the genome of the host cell.

The invention also is directed to primer molecules comprising a PCR-amplifiable sequence and a degenerate 3' terminus. Primer molecules according to this aspect of the invention preferably have the general structure:

$$5'\text{-}(dT)_a\text{-X-}N_b\text{-TTTATT-3'},$$

wherein a is a whole number from 1 to 100 (preferably from 10 to 30), X is a PCR-amplifiable sequence consisting of a nucleic acid sequence of about 10–20 nucleotides in length, N is any nucleotide, and b is a whole number from 0 to 6. One preferred such primer has the nucleotide sequence 5'-TTTTTTTTTTTTCGTCAGCGGCCGCATCNNNTTT ATT-3' (SEQ ID NO:10). In related embodiments, the primer molecules according to this aspect of the invention may be biotinylated.

The invention also is directed to methods for first strand cDNA synthesis comprising (a) annealing a first primer of the invention (such as the primer described above) to an RNA template molecule to form an first primer-RNA complex, and (b) treating this first primer-RNA complex with reverse transcriptase and one or more deoxynucleoside triphosphate molecules under conditions favoring the reverse transcription of the first primer-RNA complex to synthesize a first strand cDNA.

The invention also is directed to methods for isolating activated genes, particularly from a host cell genome. These methods of the invention exploit the structure of the mRNA molecules produced using the non-targeted gene activation vectors of the invention. One such method of the invention comprises, for example, (a) introducing a vector construct comprising a transcriptional regulatory sequence and an unpaired splice donor site into a host cell (preferably one of the eukaryotic host cells described above), (b) allowing the vector construct to integrate into the genome of the host cell by non-homologous recombination, under conditions such that the vector activates an endogenous gene comprising an exon in the genome, (c) isolating RNA from the host cell, (d) synthesizing first strand cDNA according to the method of the invention described above, (e) annealing a second primer specific for the vector-encoded exon to the first strand cDNA to create a second primer-first strand cDNA complex, and (f) contacting the second primer-first strand cDNA complex with a DNA polymerase under conditions favoring the production of a second strand cDNA substantially complementary to the first strand cDNA. Methods according to this aspect of the invention may comprise one or more additional steps, such as treating the second strand cDNA with a restriction enzyme that cleaves at a restriction site located on the vector downstream of the unpaired splice donor site, or amplifying the second strand cDNA using a third primer specific for the vector-encoded exon and a fourth primer specific for the second primer. The invention also is directed to isolated genes produced according to these methods, and to vectors (which may be expression vectors) and host cells comprising these isolated genes. The invention also is directed to methods of producing a polypeptide, comprising cultivating a host cell comprising the isolated gene (or a vector, particularly an expression vector, comprising the isolated gene), and culturing the host cell under conditions favoring the expression by the host cell of a polypeptide encoded by the isolated gene. The invention also provides additional methods of producing a polypeptide, comprising introducing into a host cell a vector comprising a transcriptional regulatory sequence operably linked to an exonic region followed by an unpaired splice donor site, and culturing the host cell under conditions favoring the expression by said host cell of a polypeptide encoded by the exonic region, wherein the exon contains a translational start site positioned at any of the open reading frame positions relative to the 5'-most base of the unpaired splice donor site (e.g., the "A" in the ATG start codon may be at position −3 or at an increment of 3 bases upstream therefrom (e.g., −6, −9, −12, −15, −18, etc.), at position −2 or at an increment of 3 bases upstream therefrom (e.g., −5, −8, −11, −14, −17, −20, etc.), or at position −1 or at an increment of 3 bases upstream therefrom (e.g., −4, −7, −10, −13, −16, −19, etc.), relative to the 5'-most base of the splice donor site). In related embodiments, the methods of the invention may further comprise isolating the polypeptide. The invention also is directed to polypeptides, which may or may not be isolated polypeptides, produced according to these methods.

Other preferred embodiments of the present invention will be apparent to one of ordinary skill in light of the following drawings and description of the invention, and of the claims.

BRIEF DESCRIPTION OF THE DRAWINGS

FIGS. 5A–5D. Nucleotide sequence of pRIG8R1-CD2 (SEQ ID NO:7).

FIGS. 6A–6C. Nucleotide sequence of pRIG8R2-CD2 (SEQ ID NO:8).

FIGS. 7A–7C. Nucleotide sequence of pRIG8R3-CD2 (SEQ ID NO:9).

In FIG. 11B, a polyadenylation signal (pA) is located downstream of the selectable marker. In FIG. 11C, polyadenylation signals are omitted from the vector.

FIGS. 14A–14B. Nucleotide sequence of pRIG1 (SEQ ID NO:18).

FIGS. 15A–15B. Nucleotide sequence of pRIG21b (SEQ ID NO:19).

FIGS. 16A–16B. Nucleotide sequence of pRIG22b (SEQ ID NO:20).

FIG. 20A illustrates the transcripts produced upon vector integration near a multi-exon gene. FIG. 20B illustrates the transcripts produced upon vector integration near a single exon gene. Each horizontal line represents a DNA molecule. Vertical lines running through the DNA strand mark the upstream and downstream vector/cellular genome boundaries. The arrows denote promoter sequences located on the DNA molecule, and face in the direction of transcription. Transcribed regions include all sequences located downstream of each promoter Boxes indicate exons. Hatched boxes indicate untranslated regions. The endogenous exons are numbered using roman numerals. The following designations were used: splice donor site (S/D), hygromycin resistance gene (Hyg), neomycin resistance gene (Neo), vector promoter #1 (VP#1 ), vector promoter #2 (VP#2), endogenous promoter (EP), and polyadenylation signal (pA). Following integration, vector promoter #1 expresses a chimeric transcript containing the Hyg gene linked to the genomic sequences downstream of the integration site, including the processed (spliced) exons from the endogenous gene. Since transcript #1 contains a poly (A) signal from the endogenous gene, the Hyg gene product will be efficiently produced, thereby conferring drug resistance on the cell. In addition to transcript #1, the integrated vector will generate a second transcript, designated transcript #2, originating from vector promoter #2. In FIG. 20A, the neo gene is removed from transcript #2 upon splicing from the vector encoded splice donor site, and the first endogenous splice acceptor located downstream of the vector integration site (i.e. exon II in this example). Since multi-exon genes contain splice acceptor sites at the 5' end of each exon (except exon I), the neo gene will be removed from transcript #2 in cells in which the vector has integrated near, and transcriptionally activated, a multi-exon gene. As a result, cells having activated multi-exon genes may be eliminated by selecting with G418 and hygromycin. In FIG. 20B, the neo gene is not removed from transcript #2 by splicing, since single exon genes do not contain any splice acceptor sequences. Thus, cells containing a vector integrated near single exon genes will survive double selection with G418 and hygromycin. These cells can be used to efficiently isolate the activated single exon genes using methods described herein.

Figure 21:
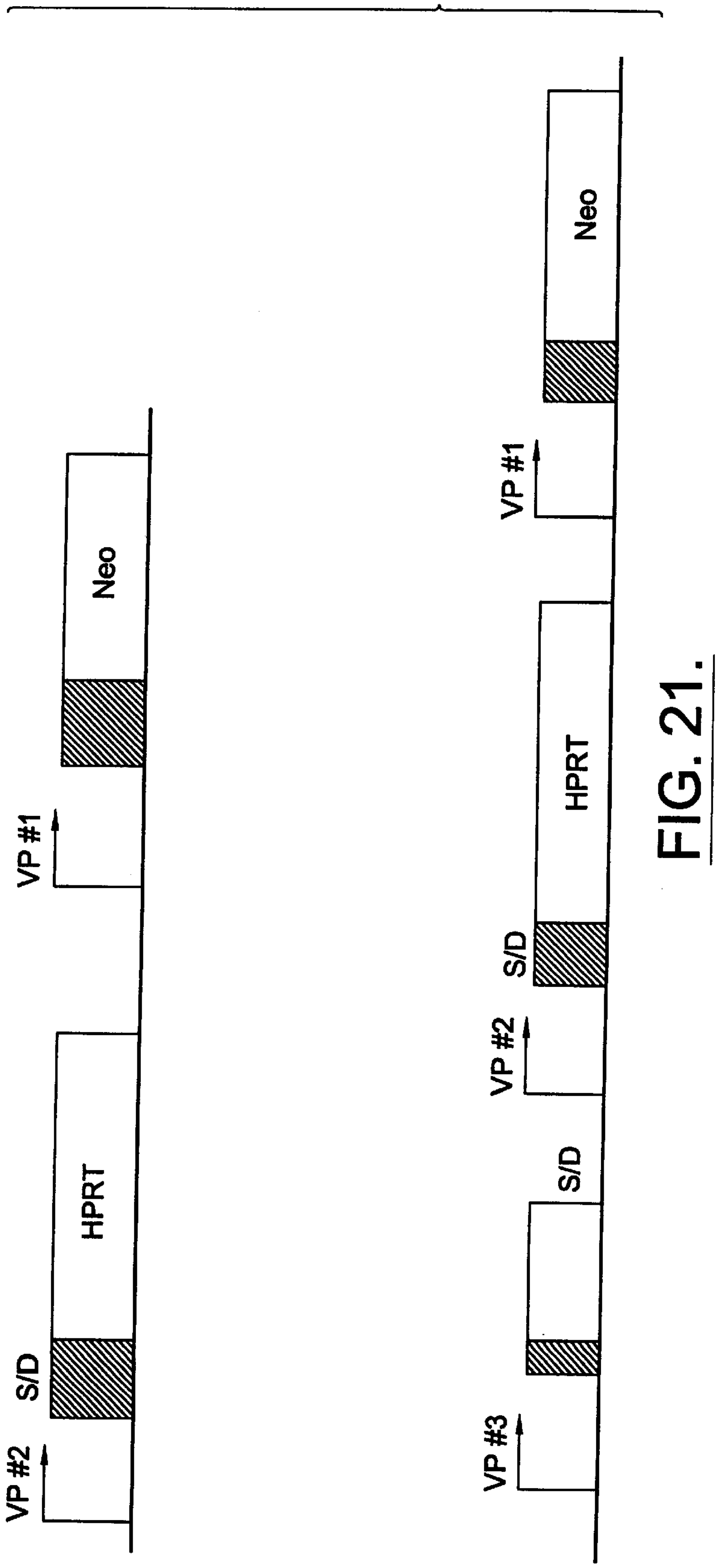
FIG. 21. Examples of dual trap vectors containing a positive and a negative selectable marker. Each vector is illustrated schematically in its linearized form. Each horizontal line represents a DNA molecule. The arrows denote promoter sequences located on the DNA molecule, and face in the direction of transcription. Transcribed regions include all sequences located downstream of a promoter. Boxes indicate exons. Hatched boxes indicate untranslated regions. The following designations were used: splice donor site (S/D), hypoxanthine phosphoribosyl transferase (HPRT), neomycin resistance gene (Neo), vector promoter #1 (VP #1), vector promoter #2 (VP#2), and vector promoter #3

(VP#3). In the vectors shown in FIG. 21, Neo represents the positive selectable marker and HPRT represents the negative selectable marker. In re 21B a third promoter is located upstream of the selectable markers. This upstream promoter is operably linked to an exon and unpaired splice donor site. FIG., The region designated exon contains a translation start codon in this example. As described herein, the exon may encode a methionine residue, a partial signal sequence, a full signal secretion sequence, a portion of a protein, or an epitope tag. In addition, the codons may be present in any reading frame relative to the splice donor site. In other vector examples not shown, the region designated exon lacks a translation start codon.

Figure 22:
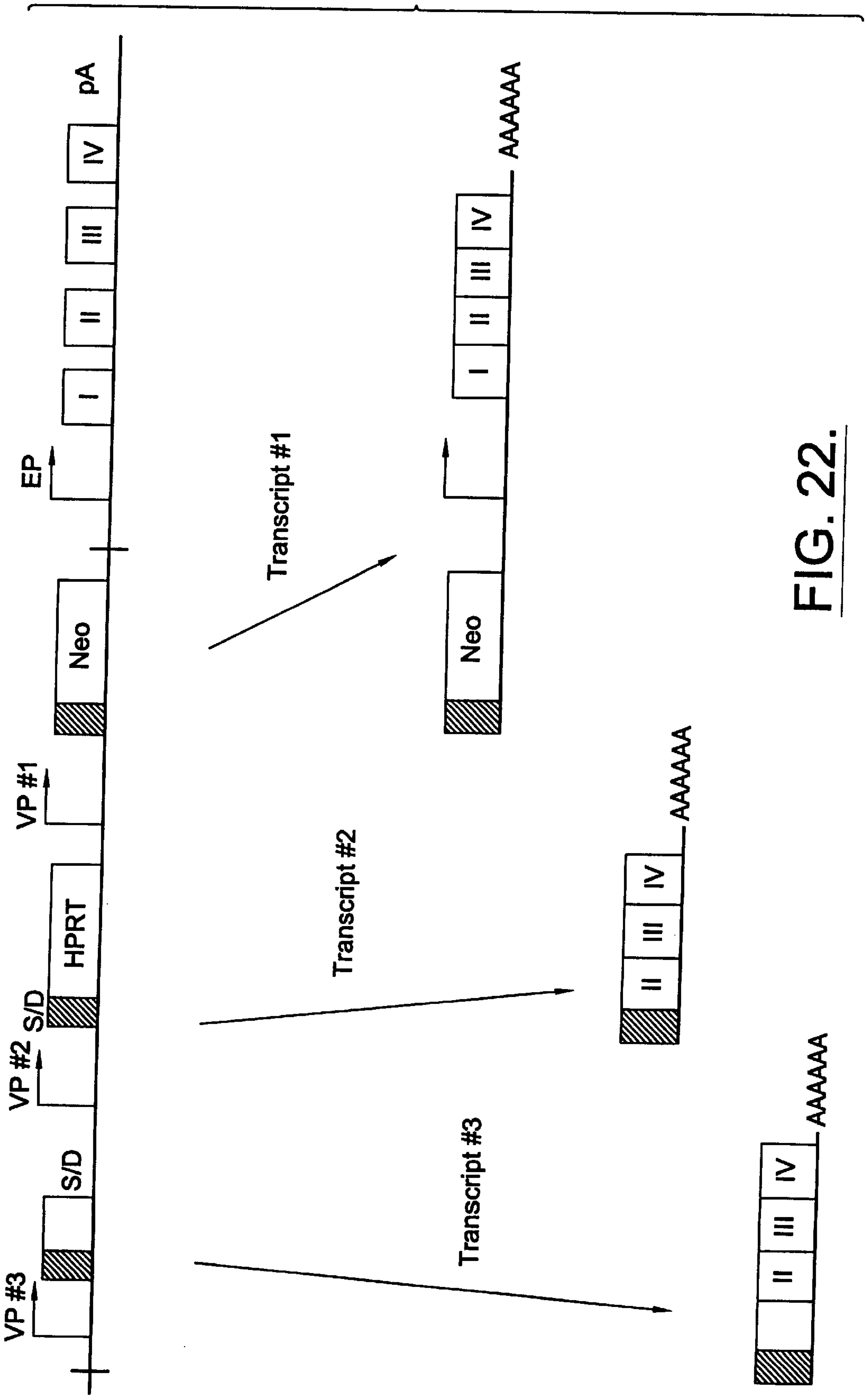
Figures 23A, 23B, 23C, 23D:
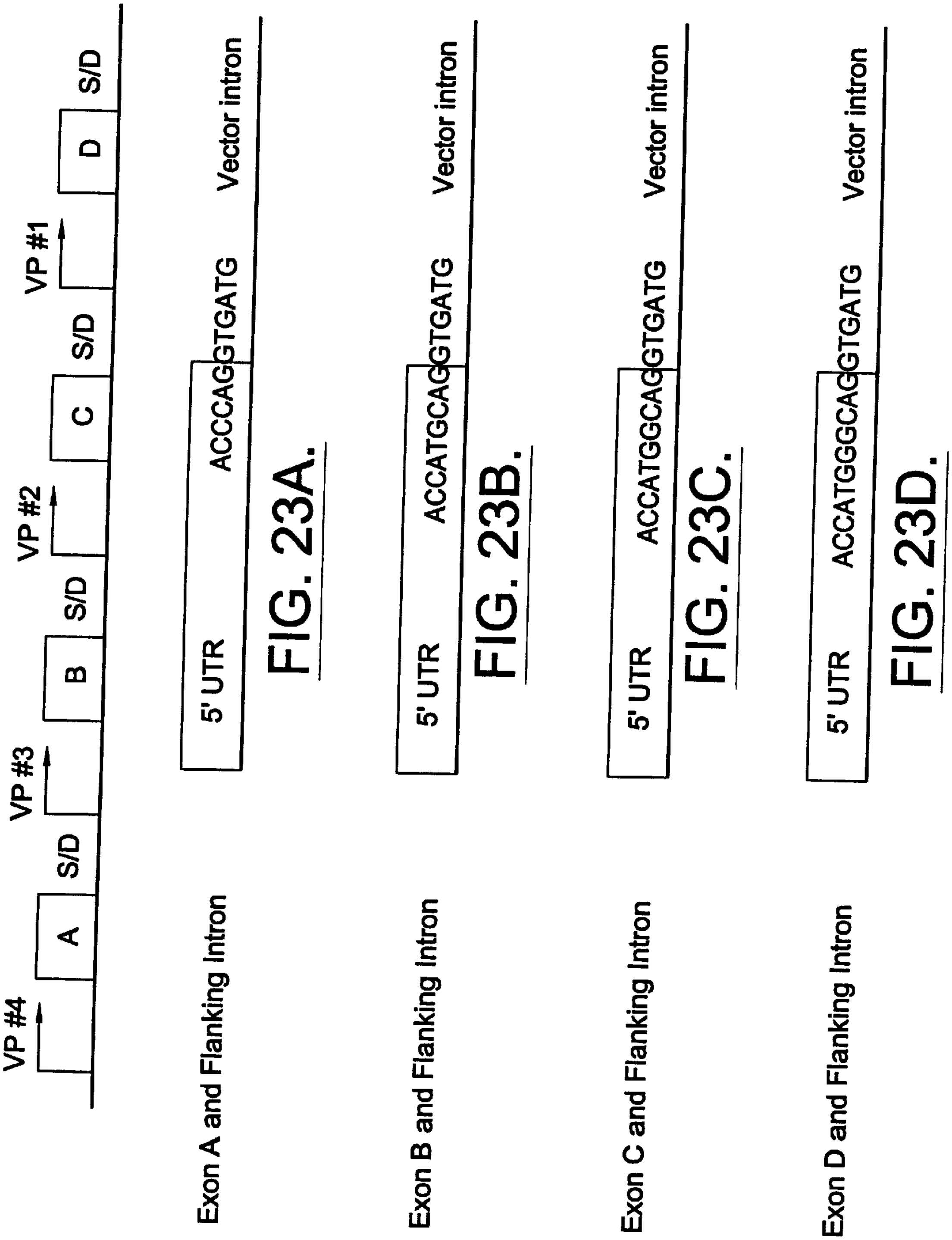

FIG. 22. Examples of transcripts produced by a dual positive/negative selectable marker vector integrated into a host cell genome upstream of a multi-exon endogenous gene. Each horizontal line represents a DNA molecule. Vertical lines running through the DNA strand mark the upstream and downstream vector/cellular genome boundaries. The arrows denote promoter sequences located on the DNA molecule, and face in the direction of transcription. Transcribed regions include all sequences located downstream of each promoter. Boxes indicate exons. Hatched boxes indicate untranslated regions. The endogenous exons are numbered using roman numerals. The following designations were used: splice donor site (S/D), neomycin resistance gene (Neo), vector promoter #1 (VP#1), vector promoter #2 (VP#2), vector promoter #3 (VP#3), polyadenylation signal (pA), and endogenous promoter (EP). Following integration, vector promoter #1 expresses a chimeric transcript containing the Neo gene linked to the genomic sequences downstream of the integration site, including the processed (spliced) exons from the endogenous gene. Since transcript #1 contains a poly (A) signal from the endogenous gene, the Neo gene product will be efficiently produced, thereby conferring drug resistance on the cell. In addition to transcript #1, the integrated vector will generate a second transcript, designated transcript #2, originating from vector promoter #2. In this example, the vector has integrated upstream of a multi-exon gene. Since multi exon genes contain splice acceptor sites at the 5' end of each exon, the HPRT gene will be removed from transcript #2 in cells in which the vector has integrated near, and transcriptionally activated, a multi-exon gene. As a result, cells containing activated multi-exon genes may be isolated by selecting with G418 and 8-Azaguanine 6-Thioguanine (AgThg). Thus, cells containing a vector integrated near single exon genes will survive double selection with G418 and AgThg. These cells can be used to efficiently isolate the activated multi-exon genes using methods described herein. In addition to transcripts #1 and #2, a third transcript, designated transcript #3 is produced from the integrated vector. Transcript #3, originating from vector promoter #3, contains an exonic sequence suitable for directing protein expression from the endogenous gene. This occurs following splicing from the first splice donor site downstream of promoter #3 to the first downstream splice acceptor site from the endogenous gene. In addition to directing protein expression, transcript #3, and/or transcripts #1 and/or #2, can be isolated for gene discovery purposes using the methods described herein.

FIGS. 23A–23D. Example of a multi-Promoter/Activation Exon Vector. Each vector is illustrated schematically in its linearized form. Each horizontal line represents a DNA molecule. The arrows denote promoter sequences. Boxes indicate exons. Hatched boxes indicate untranslated regions. It is understood that the exons on these vectors may be untranslated, or may contain a start codon and additional codons as described herein The following designations were used: splice donor site (S/D), vector promoter #1 (VP #1), vector promoter #2 (VP#2), vector promoter #3 (VP #3), and vector promoter #4 (VP#4). Individual vector activation exons are designated A, B, C, and D. Each activation exon may contain a different structure. The structure of each activation exon and its flanking intron are shown below. It is understood, however, that any activation exon described herein, may be used on these vectors, in any combination and/or order, including exons that encode signal sequences, partial signal sequences, epitope tags, proteins, portions of proteins, and protein motifs. Any of the exons may lack a start codon. In addition, while not illustrated in these examples, these vectors may contain a selectable marker and/or an amplifiable marker. The selectable marker may contain a poly (A) signal or a splice donor site. When present, the splice donor site may be located upstream or downstream of the selectable marker. Alternatively, the selectable marker may not be operably linked to a poly (A) signal and/or a splice donor site.

Figure 24:
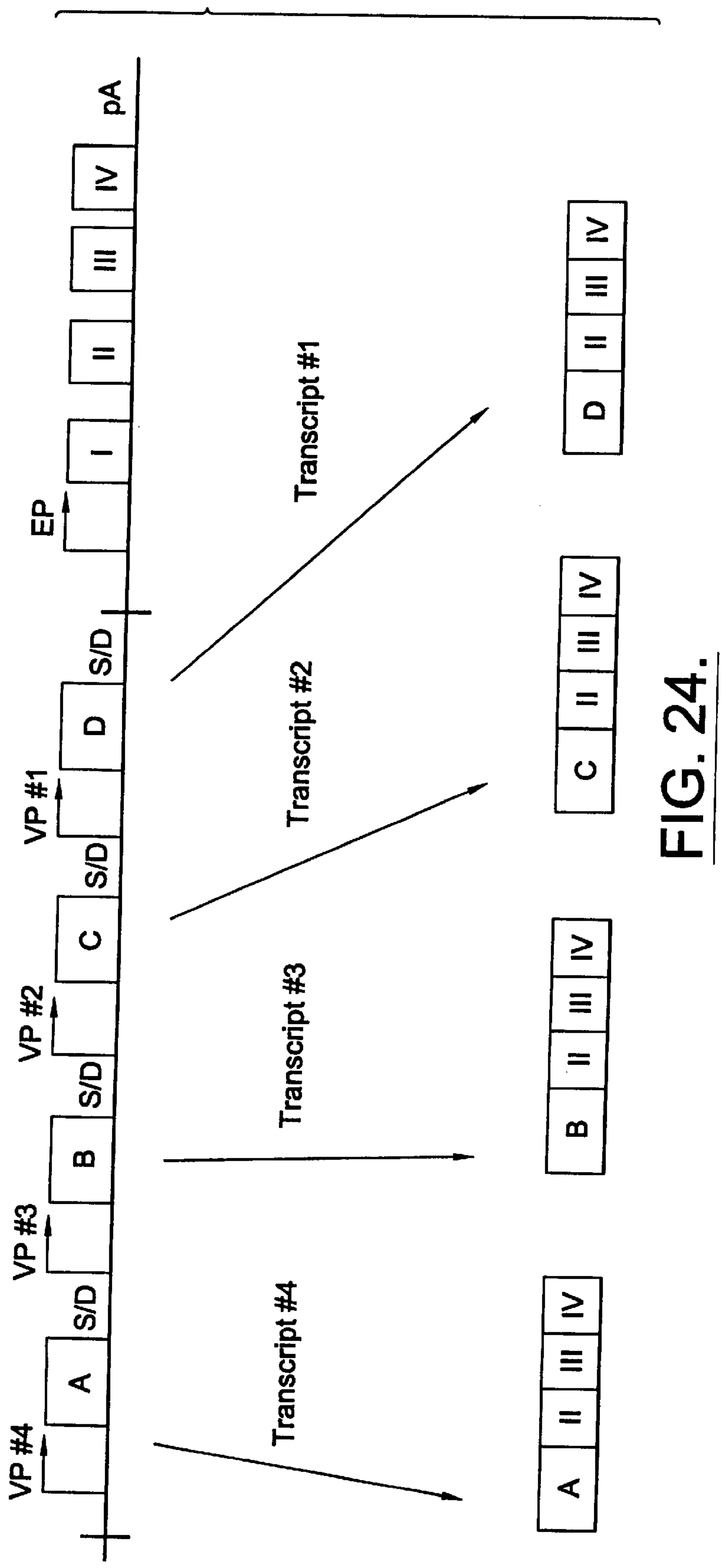
Figure 25A:
Figure 25B:
Figure 25C:
Figure 25D:

FIG. 24. Examples of transcripts produced from a multi-Promoter/Activation Exon Vector upon integration into a host cell genome upstream of an endogenous gene. Each horizontal line represents a DNA molecule. Vertical lines running through the DNA strand mark the upstream and downstream vector/cellular genome boundaries. The arrows denote promoter sequences located on the DNA molecule, and face in the direction of transcription. Transcribed regions include all sequences located downstream of each promoter. Boxes indicate exons. Hatched boxes indicate untranslated regions. The endogenous exons are numbered using roman numerals. The following designations were used: splice donor site (S/D), vector promoter #1 (VP #1), vector promoter #2 (VP#2), vector promoter #3 (VP #3), vector promoter #4 (VP#4), endogenous promoter (EP), and polyadenylation signal (pA). Individual vector activation exons are designated A, B, C, and D. Following integration, each vector encoded promoter is capable of producing a different transcript. Each transcript contains a different activation exon joined to the first downstream splice acceptor site from an endogenous gene (exon II in this example). Individual activation exons are designated by (A), (B), (C), or (D). Endogenous exons are designated by (I), (II), (III), or (IV). Generally, the coding sequence and/or reading frames, if present, are different among the activation exons. While four activation exons are illustrated in this example, any number of activation exons may be present on the integrated vector.

FIGS. 25A–25D. Examples of activation vectors useful for detection of protein-protein interactions. Each vector is illustrated schematically in its linearized form. Each horizontal line represents a DNA molecule. The arrows denote promoter sequences. Boxes indicate exons. Hatched boxes indicate untranslated regions. The following designations were used: splice donor site (S/D), neomycin resistance gene (Neo). It is also recognized that the DNA binding domain and the Activation domain may be encoded in any reading frame (relative to the splice donor site), allowing activation of endogenous genes with different reading frames.

Figure 26:
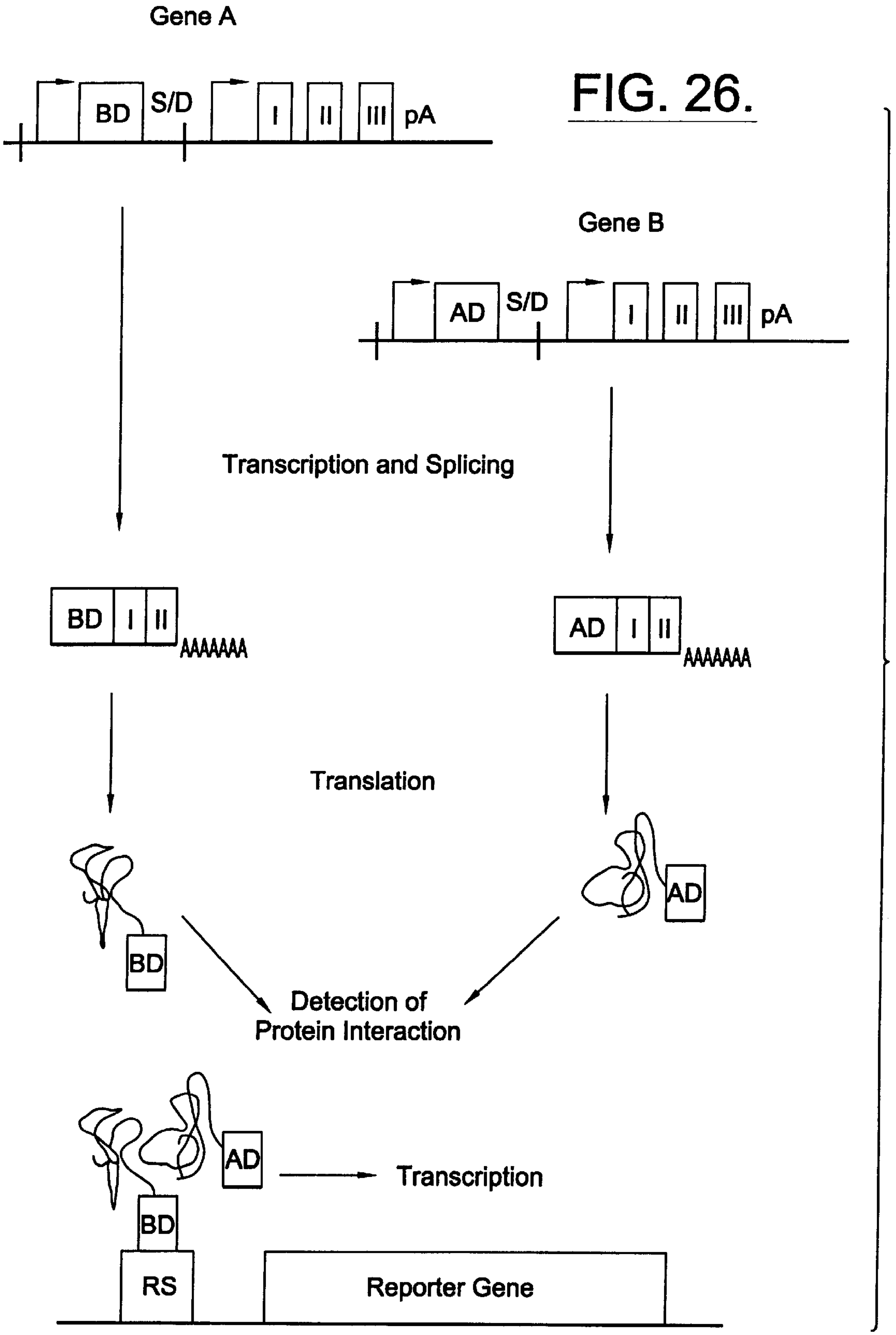
Figure 27A:
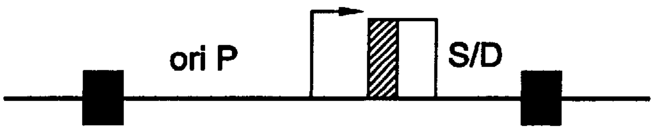
Figure 27B:
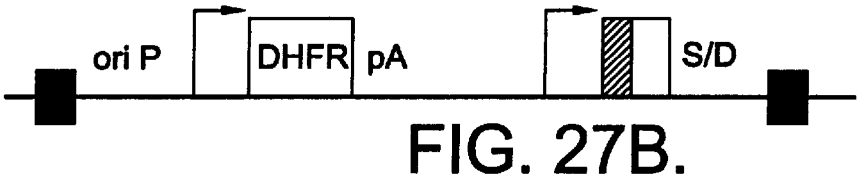
Figure 27C:
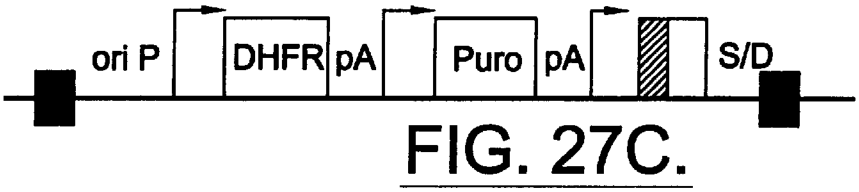
Figure 27D:
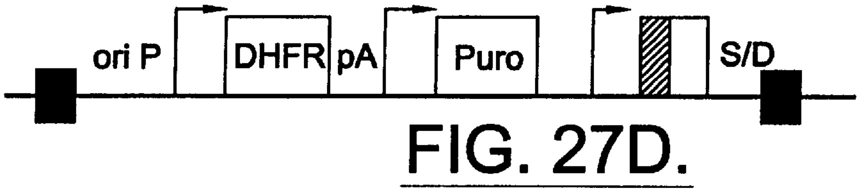
Figure 27E:
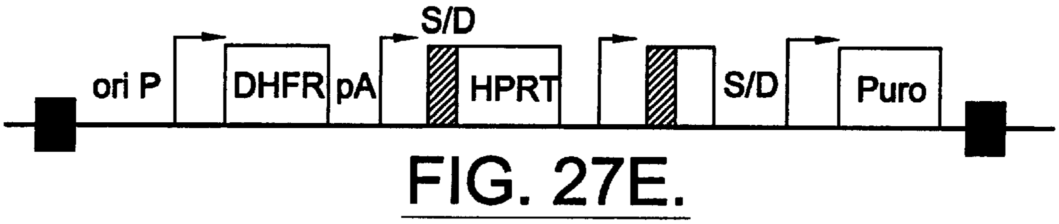

FIG. 26. Schematic illustration depicting one approach to detecting protein-protein interactions using the vectors shown in FIG. 25. Each horizontal line represents a DNA molecule. Vertical lines running through the DNA strand mark the upstream and downstream vector/cellular genome boundaries. The arrows denote promoter sequences located on the DNA molecule, and face in the direction of transcription. Transcribed regions include all sequences located downstream of each promoter. Boxes indicate exons. Hatched boxes indicate untranslated regions. The endogenous exons are numbered using roman numerals. The following designations were used: splice donor site (S/D), binding domain (BD), activation domain (AD), recognition sequence (RS), and polyadenylation signal (pA). The binding domain vector is shown integrated into the genome of a host cell, upstream of an endogenous gene, designated gene A. The activation domain vector is shown integrated into the genome of the same host cell upstream of an endogenous gene, designated gene B. Both vectors are integrated into the genome of the same host cell. Following integration, each vector is capable of producing a fusion protein containing the binding domain (or activation domain, as the case may be) and the protein encoded by the downstream endogenous gene. If the binding domain fusion protein interacts with the activation domain fusion protein, a protein complex will be formed. This complex is capable of increasing expression of a reporter gene present in the cell.

FIG. 27. Examples of activation vectors useful for in vitro and in vivo transposition. Each vector is illustrated schematically in its linearized form. Each horizontal line represents a DNA molecule. The arrows denote promoter sequences. Boxes indicate exons. Hatched boxes indicate untranslated regions. The solid boxes indicate the transposon signals. It is recognized that there is directionality to the transposon signals, and that the signals are oriented in the configuration suitable for the type of transposition reaction (integration, inversion, or deletion). The following designations were used: splice donor site (S/D), neomycin resistance gene (Neo), dihydrofolate reductase (DHFR), puromycin resistance gene (Puro), poly (A) signal (pA), and the Epstein Barr Virus origin of replication (ori P). It is also recognized that activation exon may be encode amino acids in any reading frame (relative to the splice donor site), allowing activation of endogenous genes with different reading frames.

Figure 28:
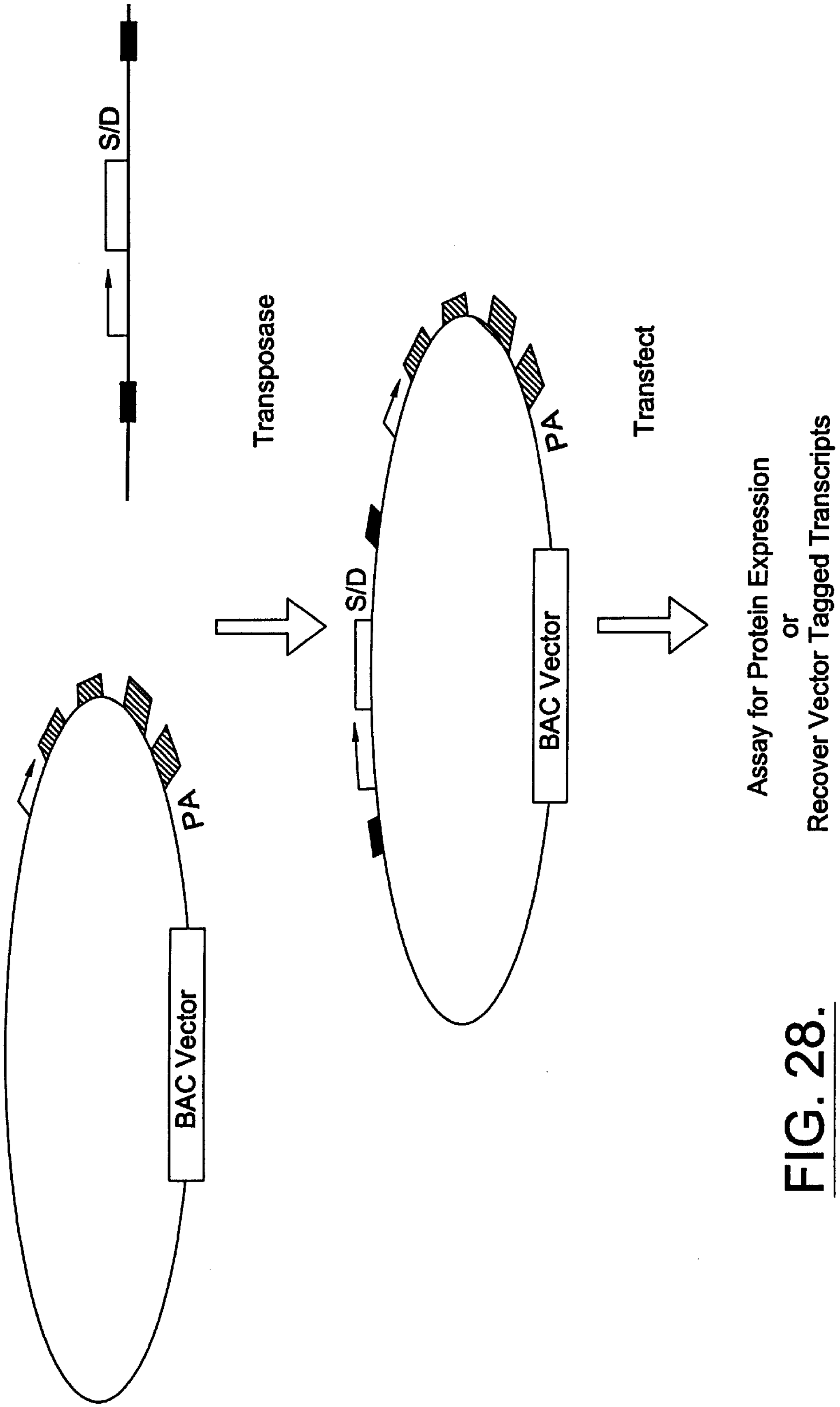

FIG. 28. Schematic illustration depicting integration of an activation vector into a cloned genomic DNA fragment by in vitro transposition. Each horizontal line represents a DNA molecule. The cloned genomic DNA is in a BAC vector. The single line represents the genomic DNA and the rectangle depicts the BAC vector sequences. The arrows denote promoter sequences located on the DNA molecule, and face in the direction of transcription. Transcribed regions include all sequences located downstream of each promoter. The vector activation exon is depicted as an open box. Exons from a gene encoded in the cloned genomic fragment are depicted as hatched boxes. The solid boxes indicate the transposon signals. It is recognized that there is directionality to the transposon signals, and that the signals are oriented in the configuration suitable for the type of transposition reaction (integration, inversion, or deletion). The following designations were used: splice donor site (S/D), and polyadenylation signal (pA). To integrate the vector into the genomic fragment, the activation vector is incubated with the cloned genomic DNA in the presence of transposase. Following integration of the activation vector into the genomic fragment, the plasmid may be transfected directly into an appropriate eukaryotic host cell to express the gene located downstream of the vector integration site. Alternatively, the BAC plasmid may be transformed into *E. coli* to produce larger quantities of plasmid for transfection into the appropriate eukaryotic host cell.

FIGS. 29A–29B. Nucleotide sequence of pRIG14.

FIGS. 30A–30C. Nucleotide sequence of pRIG19.

FIGS. 31A–31C. Nucleotide sequence of pRIG20.

FIGS. 32A–32C. Nucleotide sequence of pRIGad1.

FIGS. 33A–33D. Nucleotide sequence of pRIGbd1.

FIGS. 34A–34B. Nucleotide sequence of pUniBAC.

FIGS. 35A–35B. Nucleotide sequence of pRIG22.

Figure 36:
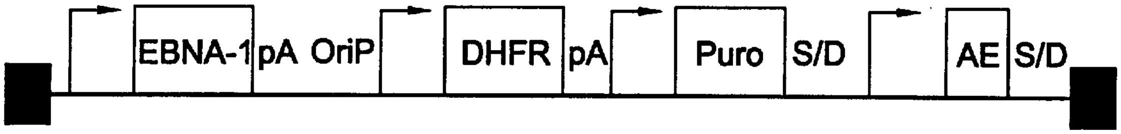

FIG. 36. Schematic diagram of pRIG-TP. The vector is shown in its linearized form. The horizontal line represents a DNA molecule. The arrows denote promoters. Open boxes indicate exons. Filled boxes represent transposon recombination signals (from Tn5-compatible with the in vitro transposition kit available from Epicentre Technologies) The following designations were used: splice donor site (S/D), puromycin resistance gene (puro), dihydrofolate reductase gene (DHFR), Epstein Barr nuclear antigen-1 replication protein (EBNA-1), Epstein Barr virus origin of replication (ori P), poly (A) signal (pA), and activation exon (AE). It is understood that the activation exon can contain any sequence capable of directing protein synthesis, including a translation start codon in any reading frame, a partial secretion signal sequence, an entire secretion signal sequence, an epitope tag, a protein, a portion of a protein, or a protein motif. The activation exon may also lack a translation start codon.

FIGS. 37A–37C. Nucleotide sequence of pRIG-T.

DETAILED DESCRIPTION OF THE INVENTION

There are great advantages to gene activation by non-homologous recombination over other gene activation procedures. Unlike previous methods of protein over-expression, the methods described herein do not require that the gene of interest be cloned (isolated from the cell). Nor do they require any knowledge of the DNA sequence or structure of the gene to be over-expressed (i.e., the sequence of the ORF, introns, exons, or upstream and downstream regulatory elements) or knowledge of a gene's expression patterns (i.e., tissue specificity, developmental regulation, etc.). Furthermore, the methods do not require any knowledge pertaining to the genomic organization of the gene of interest (i.e., the intron and exon structure).

The methods of the present invention thus involve vector constructs that do not contain target nucleotide sequences for homologous recombination. A target sequence allows homologous recombination of vector DNA with cellular DNA at a predetermined site on the cellular DNA, the site having homology for sequences in the vector, the homologous recombination at the predetermined site resulting in the introduction of the transcriptional regulatory sequence into the genome and the subsequent endogenous gene activation.

The method of the present invention does not involve integration of the vector at predetermined sites. Instead, the present methods involve integration of the vector constructs of the invention into cellular DNA (e.g., the cellular genome) by nonhomologous or "illegitimate" recombination, also called "non-targeted gene activation." In related embodiments, the present invention also concerns non-targeted gene activation. Non-targeted gene activation has a number of important applications. First, by activating genes that are not normally expressed in a given cell type, it becomes possible to isolate a cDNA copy of genes independent of their normal expression pattern. This facilitates isolation of genes that are normally expressed in rare cells, during short developmental periods, and/or at very low levels. Second, by translationally activating genes, it is possible to produce protein expression libraries without the need for cloning the full-length cDNA. These libraries can be screened for new enzymes and proteins and/or for interesting phenotypes resulting from over-expression of an endogenous gene. Third, cell-lines over-expressing a specific protein can be created and used to produce commercial quantities of protein. Thus, activating endogenous genes provides a powerful approach to discovering and isolating new genes and proteins, and to producing large amounts of specific proteins for commercialization.

The vectors described herein do not contain target sequences. A target sequence is a sequence on the vector that has homology with a sequence or sequences within the gene to be activated or upstream of the gene to be activated, the upstream region being up to and including the first functional splice acceptor site on the same coding strand of the gene of interest, and by means of which homology the transcriptional regulatory sequence that activates the gene of interest is integrated into the genome of the cell containing the gene to be activated. In the case of an enhancer integration vector for activating an endogenous gene, the vector does not contain homology to any sequence in the genome upstream or downstream of the gene of interest (or within the gene of interest) for a distance extending as far as enhancer function is operative.

The present methods, therefore, are capable of identifying new genes that have been or can be missed using conventional and currently available cloning techniques. By using the constructs and methodology described herein, unknown and/or uncharacterized genes can be rapidly identified and over-expressed to produce proteins. The proteins have use as, among other things, human therapeutics and diagnostics and as targets for drug discovery.

The methods are also capable of producing over-expression of known and/or characterized genes for in vitro or in vivo protein production.

A "known" gene is directed to the level of characterization of a gene. The invention allows expression of genes that have been characterized, as well as expression of genes that have not been characterized. Different levels of characterization are possible. These include detailed characterization, such as cloning, DNA, RNA, and/or protein sequencing, and relating the regulation and function of the gene to the cloned sequence (e.g., recognition of promoter and enhancer sequences, functions of the open reading frames, introns, and the like). Characterization can be less detailed, such as having mapped a gene and related function, or having a partial amino acid or nucleotide sequence, or having purified a protein and ascertained a function. Characterization may be minimal, as when a nucleotide or amino acid sequence is known or a protein has been isolated but the function is unknown. Alternatively, a function may be known but the associated protein or nucleotide sequence is not known or is known but has not been correlated to the function. Finally, there may be no characterization in that both the existence of the gene and its function are not known. The invention allows expression of any gene at any of these or other specific degrees of characterization.

Many different proteins (also referred to herein interchangeably as "gene products" or "expression products") can be activated or over-expressed by a single activation construct and in a single set of transfections. Thus, a single cell or different cells in a set of transfectants (library) can over-express more than one protein following transfection with the same or different constructs. Previous activation methods require a unique construct to be created for each gene to be activated.

Further, many different integration sites adjacent to a single gene can be created and tested simultaneously using a single construct. This allows rapid determination of the optimal genomic location of the activation construct for protein expression.

Using previous methods, the 5' end of the gene of interest had to be extensively characterized with respect to sequence and structure. For each activation construct to be produced, an appropriate targeting sequence had to be isolated. Usually, this must be an isogenic sequence isolated from the same person or laboratory strain of animal as the cells to be activated. In some cases, this DNA may be 50 kb or more from the gene of interest. Thus, production of each targeting construct required an arduous amount of cloning and sequencing of the endogenous gene. However, since sequence and structure information is not required for the methods of the present invention, unknown genes and genes with uncharacterized upstream regions can be activated.

This is made possible using in situ gene activation using non-homologous recombination of exogenous DNA sequences with cellular DNA. Methods and compositions (e.g., vector constructs) required to accomplish such in situ gene activation using non-homologous recombination are provided by the present invention.

DNA molecules can recombine to redistribute their genetic content by several different and distinct mechanisms, including homologous recombination, site-specific recombination, and non-homologous/illegitimate recombination. Homologous recombination involves recombination between stretches of DNA that are highly similar in sequence. It has been demonstrated that homologous recombination involves pairing between the homologous sequences along their length prior to redistribution of the genetic material. The exact site of crossover can be at any point in the homologous segments. The efficiency of recombination is proportional to the length of homologous targeting sequence (Hope, *Development* 113:399 (1991); Reddy et al., *J. Virol.* 65:1507 (1991)), the degree of sequence identity between the two recombining sequences (von Melchner et al., *Genes Dev.* 6:919 (1992)), and the ratio of homologous to non-homologous DNA present on the construct (Letson, *Genetics* 117:759 (1987)).

Site-specific recombination, on the other hand, involves the exchange of genetic material at a predetermined site, designated by specific DNA sequences. In this reaction, a protein recombinase binds to the recombination signal sequences, creates a strand scission, and facilitates DNA strand exchange. Cre/Lox recombination is an example of site specific recombination.

Non-homologous/illegitimate recombination, such as that used advantageously by the methods of the present invention, involves the joining (exchange or redistribution) of genetic material that does not share significant sequence homology and does not occur at site-specific recombination sequences. Examples of non-homologous recombination include integration of exogenous DNA into chromosomes at non-homologous sites, chromosomal translocations and deletions, DNA end-joining, double strand break repair of chromosome ends, bridge-breakage fusion, and concatemerization of transfected sequences. In most cases, non-homologous recombination is thought to occur through the joining of "free DNA ends." Free ends are DNA molecules that contain an end capable of being joined to a second DNA end either directly, or following repair or processing. The DNA end may consist of a 5' overhang, 3' overhang, or blunt end.

As used herein, retroviral insertion and other transposition reactions are loosely considered forms of non-homologous recombination. These reactions do not involve the use of homology between the recombining molecules. Furthermore, unlike site-specific recombination, these types of recombination reactions do not occur between discrete sites. Instead, a specific protein/DNA complex is required on only one of the recombination partners (i.e., the retrovirus or transposon), with the second DNA partner (i.e., the cellular genome) usually being relatively non-specific. As a result, these "vectors" do not integrate into the cellular genome in a targeted fashion, and therefore they can be used to deliver the activation construct according to the present invention.

Vector constructs useful for the methods described herein ideally may contain a transcriptional regulatory sequence that undergoes non-homologous recombination with genomic sequences in a cell to over-express an endogenous gene in that cell. The vector constructs of the invention also lack homologous targeting sequences. That is, they do not contain DNA sequences that target host cell DNA and promote homologous recombination at the target site. Thus, integration of the vector constructs of the present invention into the cellular genome occurs by non-homologous recombination, and can lead to over-expression of a cellular gene via the introduced transcriptional regulatory sequence contained on the integrated vector construct.

The invention is generally directed to methods for over-expressing an endogenous gene in a cell, comprising introducing a vector containing a transcriptional regulatory sequence into the cell, allowing the vector to integrate into the genome of the cell by non-homologous recombination, and allowing over-expression of the endogenous gene in the cell. The method does not require previous knowledge of the sequence of the endogenous gene or even of the existence of the gene. Where the sequence of the gene to be activated is known, however, the constructs can be engineered to contain the proper configuration of vector elements (e.g., location of the start codon, addition of codons present in the first exon of the endogenous gene, and the proper reading frame) to achieve maximal overexpression and/or the appropriate protein sequence.

In certain embodiments of the invention, the cell containing the vector may be screened for expression of the gene.

The cell over-expressing the gene can be cultured in vitro under conditions favoring the production, by the cell, of desired amounts of the gene product of the endogenous gene that has been activated or whose expression has been increased. If desired, the gene product can then be isolated or purified to use, for example, in protein therapy or drug discovery.

Alternatively, the cell expressing the desired gene product can be allowed to express the gene product in vivo.

The vector construct can consist essentially of the transcriptional regulatory sequence.

Alternatively, the vector construct can consist essentially of the transcriptional regulatory sequence and one or more amplifiable markers.

The invention, therefore, is also directed to methods for over-expressing an endogenous gene in a cell, comprising introducing a vector containing a transcriptional regulatory sequence and an amplifiable marker into the cell, allowing the vector to integrate into the genome of the cell by non-homologous recombination, and allowing over-expression of the endogenous gene in the cell.

The cell containing the vector is screened for over-expression of the gene.

The cell over-expressing the gene is cultured such that amplification of the endogenous gene is obtained. The cell can then be cultured in vitro so as to produce desired amounts of the gene product of the amplified endogenous gene that has been activated or whose expression has been increased. The gene product can then be isolated and purified.

Alternatively, following amplification, the cell can be allowed to express the endogenous gene and produce desired amounts of the gene product in vivo.

The vector construct can consist essentially of the transcriptional regulatory sequence and the splice donor sequence.

The invention, therefore, is also directed to methods for over-expressing an endogenous gene in a cell comprising introducing a vector containing a transcriptional regulatory sequence and an unpaired splice donor sequence into the cell, allowing the vector to integrate into the genome of the cell by non-homologous recombination, and allowing over-expression of the endogenous gene in the cell.

The cell containing the vector is screened for expression of the gene.

The cell over-expressing the gene can be cultured in vitro so as to produce desirable amounts of the gene product of the endogenous gene whose expression has been activated or increased. The gene product can then be isolated and purified.

Alternatively, the cell can be allowed to express the desired gene product in vivo.

The vector construct can consist essentially of a transcriptional regulatory sequence operably linked to an unpaired splice donor sequence and also containing an amplifiable marker.

Other activation vectors include constructs with a transcriptional regulatory sequence and an exonic sequence containing a start codon; a transcriptional regulatory sequence and an exonic sequence containing a translational start codon and a secretion signal sequence; constructs with a transcriptional regulatory sequence and an exonic sequence containing a translation start codon, and an epitope tag; constructs containing a transcriptional regulatory sequence and an exonic sequence containing a translational start codon, a signal sequence and an epitope tag; constructs containing a transcriptional regulatory sequence and an exonic sequence with a translation start codon, a signal secretion sequence, an epitope tag, and a sequence-specific protease site. In each of the above constructs, the exon on the construct is located immediately upstream of an unpaired splice donor site.

Figure 1:
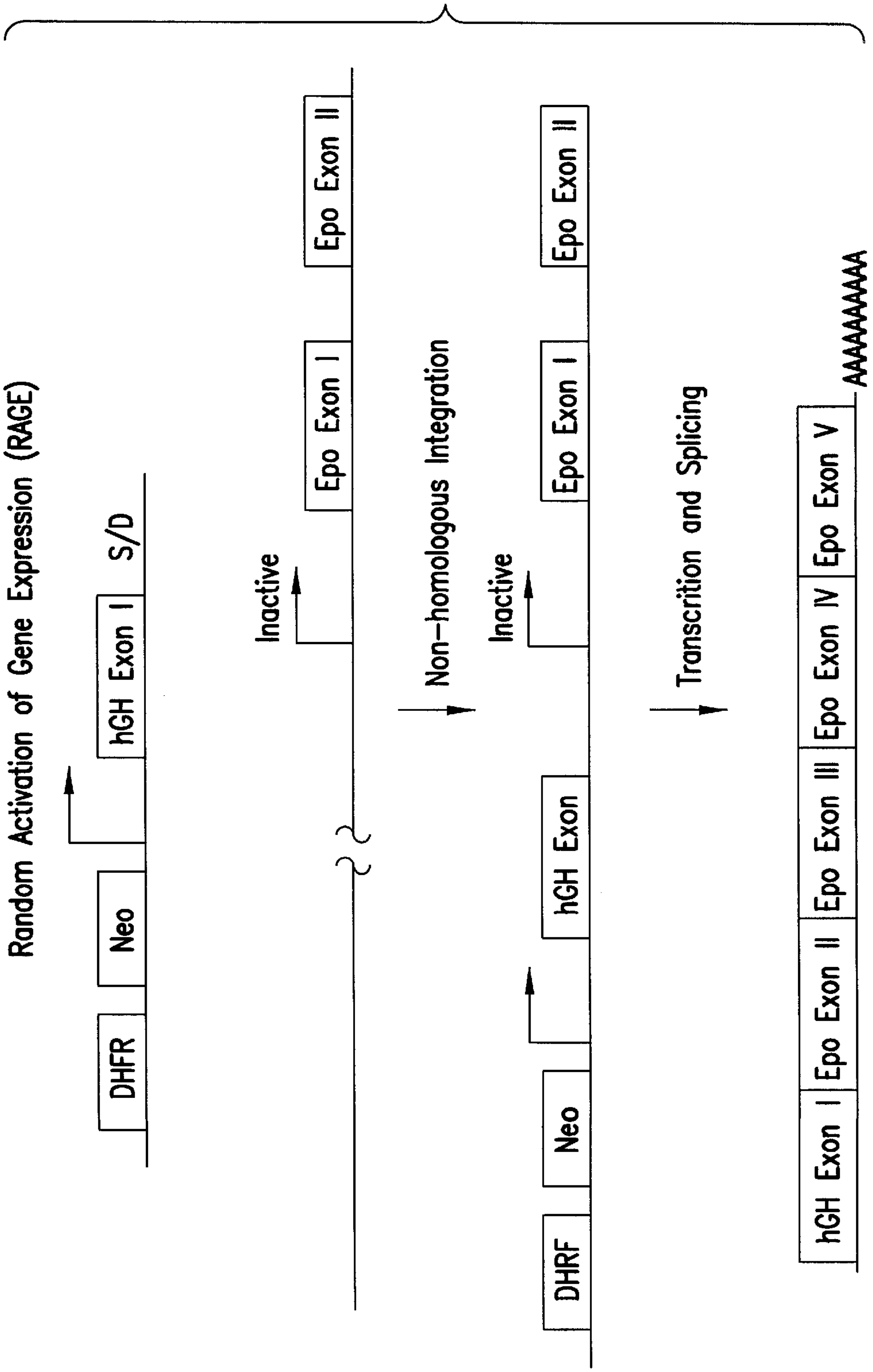
FIG. 1. Schematic diagram of gene activation events described herein. The activation construct is transfected into cells and allowed to integrate into the host cell chromosomes at DNA breaks. If breakage occurs upstream of a gene of interest (e.g., Epo), and the appropriate activation construct integrates at the break such that its regulatory sequence becomes operably linked to the gene of interest, activation of the gene will occur. Transcription and splicing produce a chimeric RNA molecule containing exonic sequences from the activation construct and from the endogenous gene. Subsequent translation will result in the production of the protein of interest. Following isolation of the recombinant cell, gene expression can be further enhanced via gene amplification.
Figure 2:
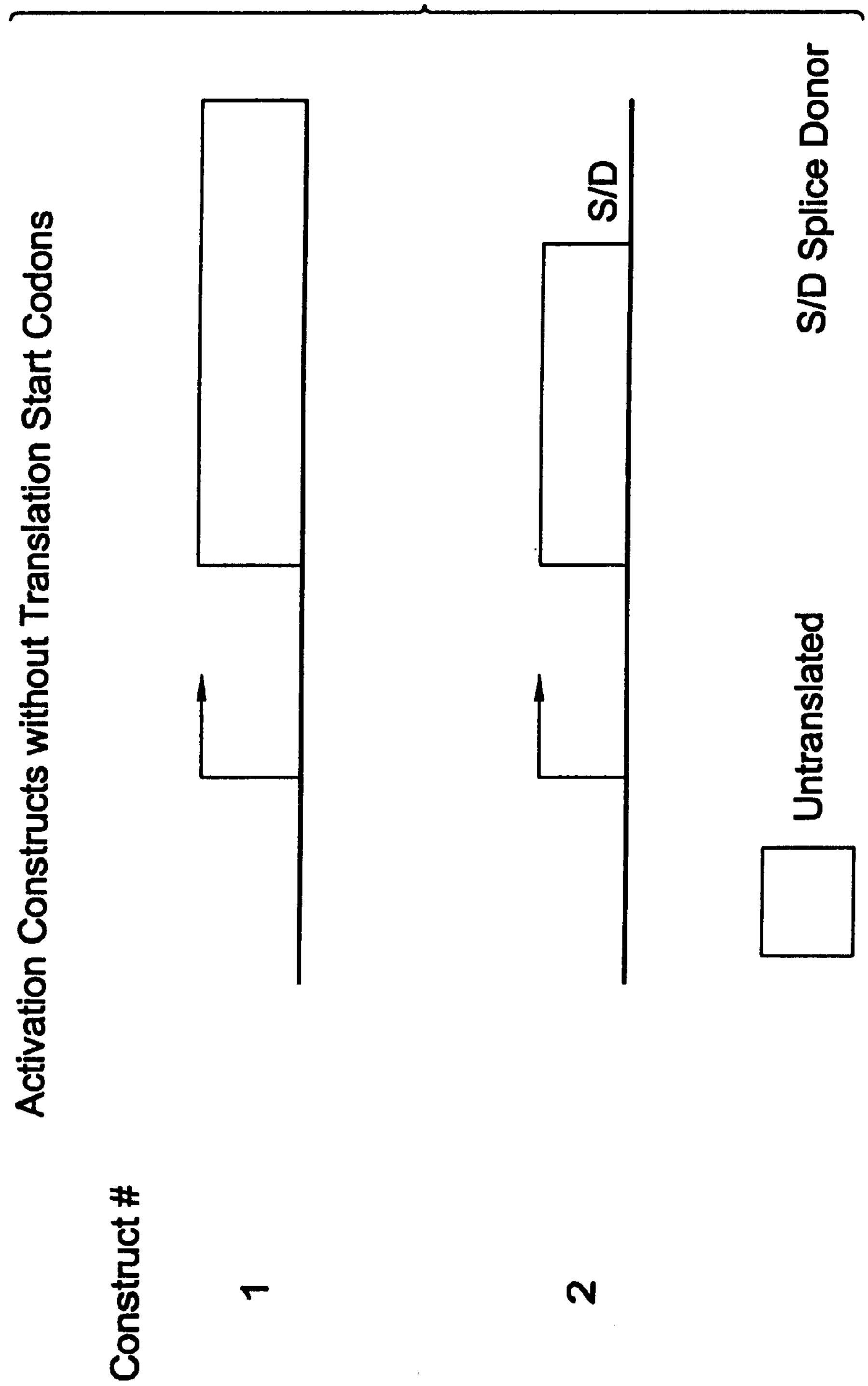
FIG. 2. Schematic diagram of non-translated activation constructs. The arrows denote promoter sequences. The exonic sequences are shown as open boxes and the splice donor sequence is indicated by S/D. Construct numbers corresponding to the description below are shown on the left. The selectable and amplifiable markers are not shown.
Figure 3:
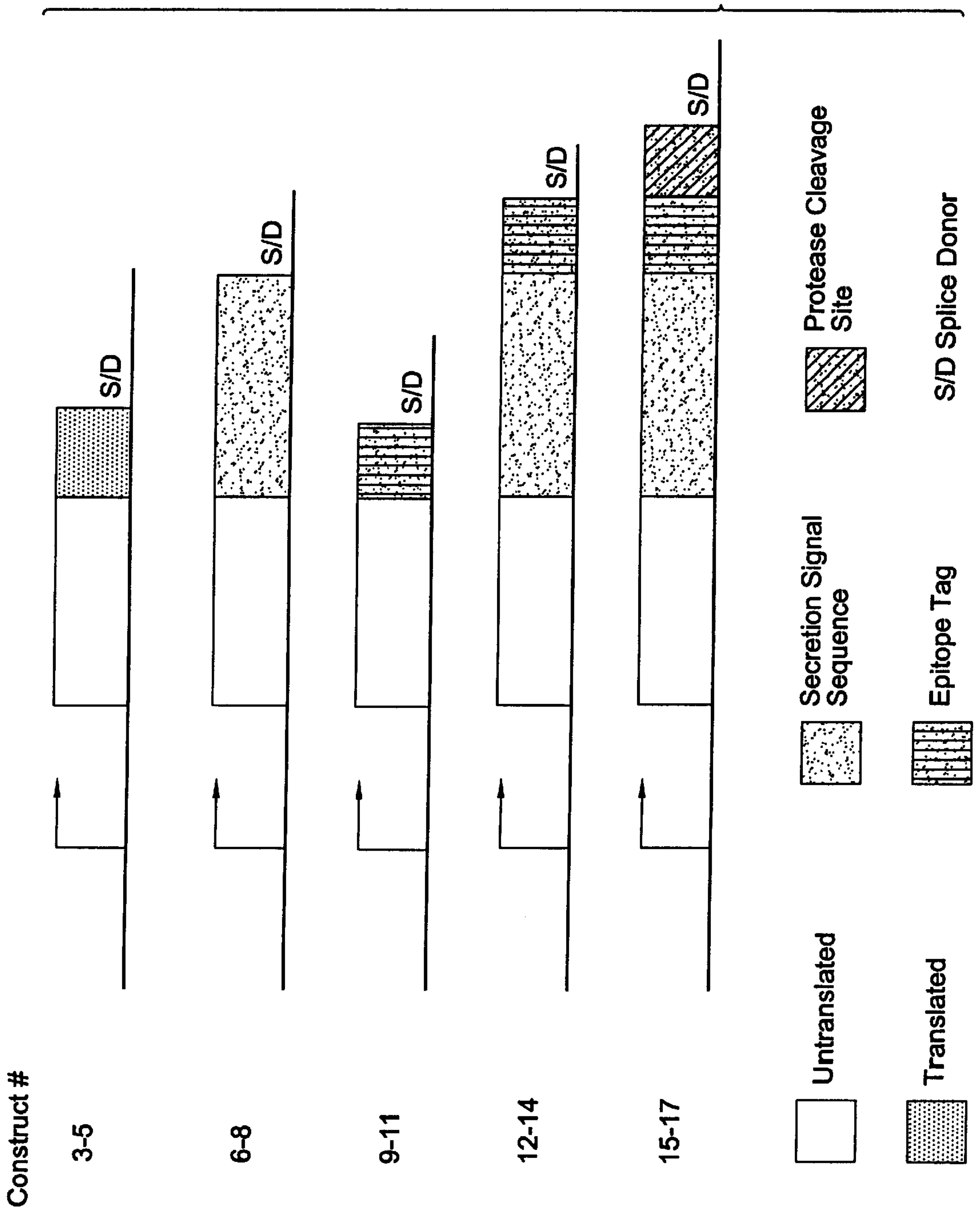
FIG. 3. Schematic diagram of translated activation constructs. The arrows denote promoter sequences. The exonic sequences are shown as open boxes and the splice donor sequence is indicated by S/D. The translated, signal peptide, epitope tag, and protease cleavage sequences are shown in the legend below the constructs. Construct numbers corresponding to the description below are shown on the left. The selectable and amplifiable markers are not shown.
Figure 4:
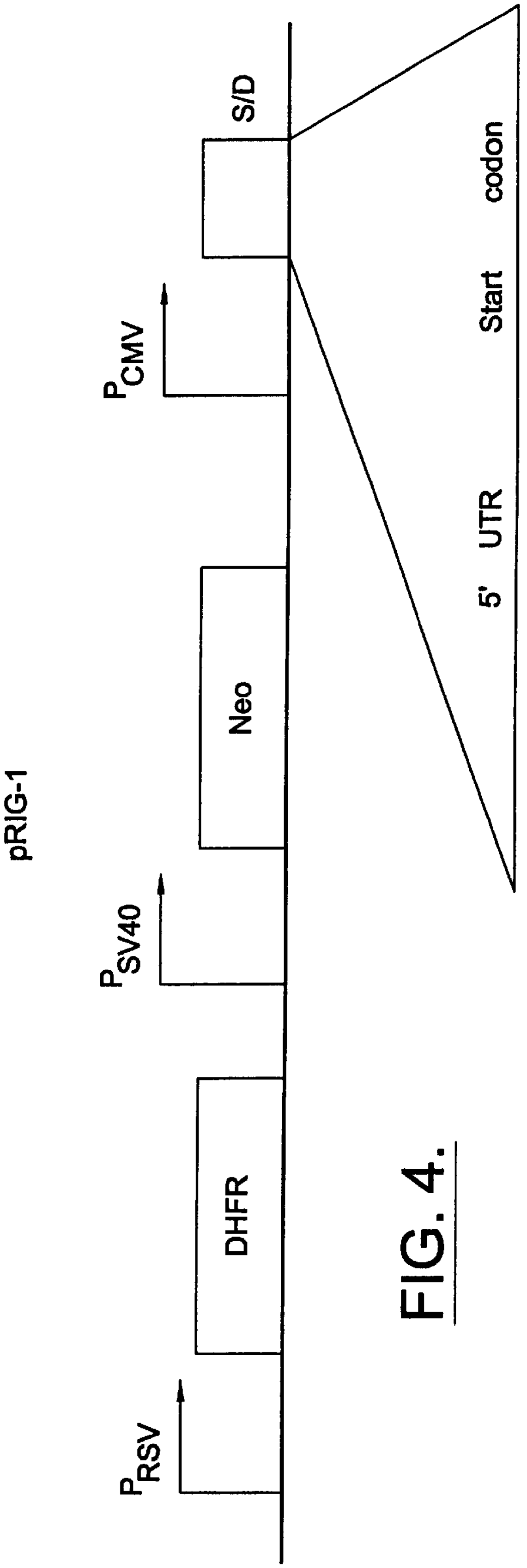
FIG. 4. Schematic diagram of an activation construct capable of activating endogenous genes.
Figure 8A:
FIGS. 8A–8F. Examples of poly(A) trap vectors. Each vector is illustrated schematically in its linearized form. Each horizontal line represents a DNA molecule. The arrows denote promoter sequences located on the DNA molecule, and face in the direction of transcription. Transcribed regions include all sequences located downstream of a promoter. Untranslated regions are designated by hatched boxes and open reading frames are designated by open boxes. The following designations were used: splice donor site (S/D), signal secretion sequence (SP), epitope tag (ET), neomycin resistance gene (Neo). In the vectors depicted in FIGS. 8B–8E, it is possible to omit the splice donor site immediately downstream of the Neo gene. In vectors lacking a splice donor site between the neo gene and the downstream promoter, the Neo transcript will utilize the splice donor site located 3' of the downstream promoter. In addition, as shown in the vectors depicted in FIGS. 8B–8E, a downstream promoter may drive expression of an exon. It is recognized that this exon, when present, may encode codons in any reading frame. Using multiple vectors, codons in each of the 3 possible reading frames can be created.
Figure 8B:
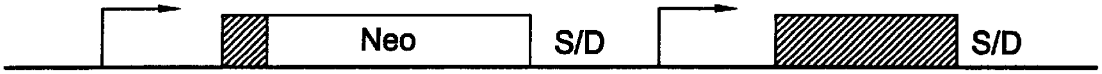
Figure 8C:
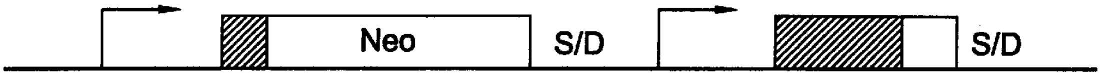
Figure 8D:
Figure 8E:
Figure 8F:
Figures 9A, 9B, 9C, 9D, 9E, 9F:
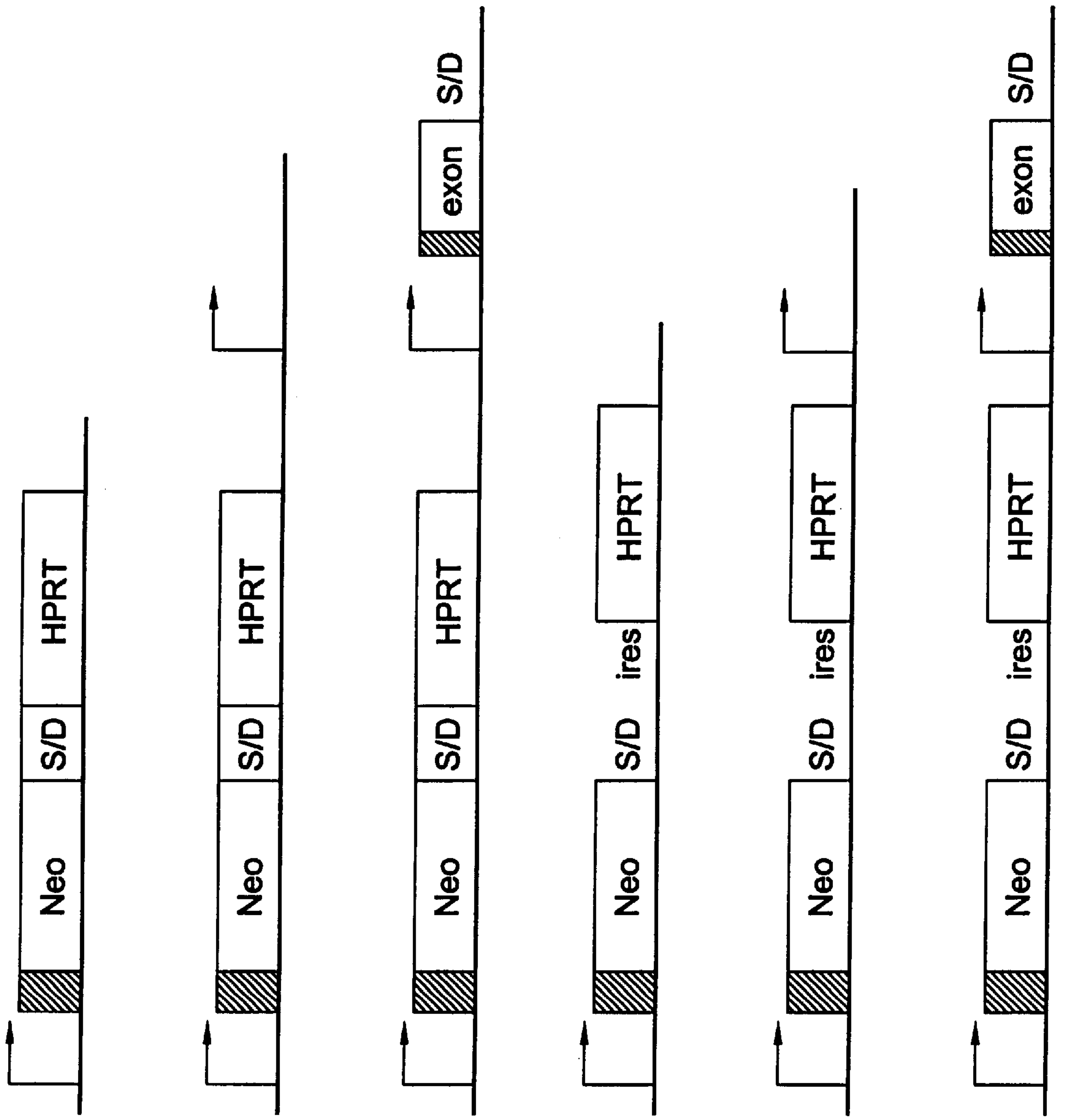
FIGS. 9A–9F. Examples of splice acceptor trap vectors containing a positive and a negative selectable marker driven from a single promoter. Each vector is illustrated schematically in its linearized form. Each horizontal line represents a DNA molecule. The arrows denote promoter sequences located on the DNA molecule, and face in the direction of transcription. Transcribed regions include all sequences located downstream of a promoter. Untranslated regions are designated by hatched boxes. Poly(A) signals are not present in these examples. As described in the specification, however, poly(A) signals may be placed on the vector 3' of either or both selectable markers. The following designations were used: splice donor site (S/D), signal secretion sequence (SP), epitope tag (ET), internal ribosome entry site (ires), hypoxanthine phosphoribosyl transferase (HPRT), and neomycin resistance gene (Neo). In these examples, Neo represents the positive selectable marker and HPRT represents the negative selectable marker. In the vectors shown in FIGS. 9C and 9F, the region designated exon contains a translation start codon. As described in the Detailed Description, the exon may encode a methionine residue, a partial signal sequence, a full signal secretion sequence, a portion of a protein, or an epitope tag. In addition, the codons may be present in any reading frame relative to the splice donor site. In other vector examples not shown, the region designated exon lacks a translation start codon.
Figure 10A:
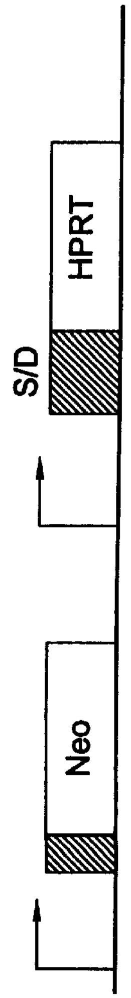
FIGS. 10A–10F. Examples of splice acceptor trap vectors containing a positive and negative selectable marker driven from different promoters. Each vector is illustrated schematically in its linearized form. Each horizontal line represents a DNA molecule. The arrows denote promoter sequences located on the DNA molecule, and face in the direction of transcription. Transcribed regions include all sequences located downstream oaf promoter. Untranslated regions are designated by hatched boxes. Poly(A) signals are not present in these examples. As described in the specification, however, poly(A) signals may be placed on the vector 3' of either or both selectable markers. The following designations were used: splice donor site (S/D), internal ribosome entry site (ires), hypoxanthine phosphoribosyl transferase (HPRT), and neomycin resistance gene (Neo). In the vectors shown in FIGS. 10A–10F, Neo represents the positive selectable marker and HPRT represents the negative selectable marker. As shown, the vectors depicted in FIGS. 10A–10F do not contain a splice donor site 3' of the Neo gene; however, in other vectors not shown, a splice donor site may be located 3' of the Neo gene to facilitate splicing of the positive selection marker to an endogenous exon. In the vectors shown in FIGS. 10C and 10F, the region designated exon contains a translation start codon. As described in the Detailed Description, the exon may encode a methionine residue, a partial signal sequence, a full signal secretion sequence, a portion of a protein, or an epitope tag. In addition, the codons may be present in any reading frame relative to the splice donor site. In other vector examples not shown, the region designated exon lacks a translation start codon.
Figure 10B:
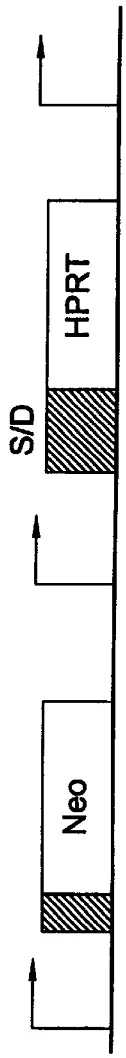
Figure 10C:
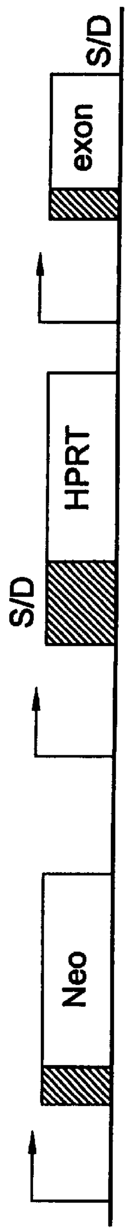
Figure 10D:
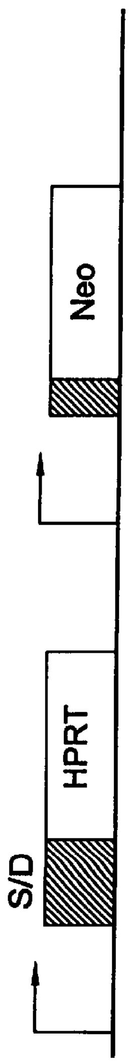
Figure 10E:
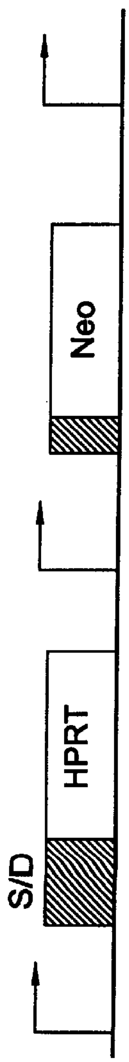
Figure 10F:
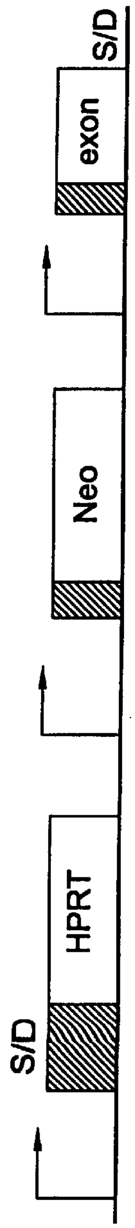

The constructs can also contain a regulatory sequence, a selectable marker lacking a poly(A) signal, an internal ribosome entry site (ires), and an unpaired splice donor site (FIG. 4). A start codon, signal secretion sequence, epitope tag, and/or a protease cleavage site may optionally be included between the ires and the unpaired splice donor sequence. When this construct integrates upstream of a gene, the selectable marker will be efficiently expressed since a poly(A) site will be supplied by the endogenous gene. In addition the downstream gene will also be expressed since the ires will allow protein translation to initiate at the downstream open reading frame (i.e. the endogenous gene). Thus, the message produced by this activation construct will be polycistronic. The advantage of this construct is that integration events that do not occur near genes and in the proper orientation will not produce a drug resistant colony. The reason for this is that without a poly(A) tail (supplied by the endogenous gene), the neomycin resistance gene will not express efficiently. By reducing the number of nonproductive integration events, the complexity of the library can be reduced without affecting its coverage (the number of genes activated), and this will facilitate the screening process.

In another embodiment of this construct, cre-lox recombination sequences can be included between the regulatory sequence and the neo start codon and between the ires and the unpaired splice donor site (between the ires and the start codon, if present). Following isolation of cells that have activated the gene of interest, the neo gene and ires can be removed by transfecting the cells with a plasmid encoding the cre recombinase. This would eliminate the production of the polycistronic message and allow the endogenous gene to be expressed directly from the regulatory sequence on the integrated activation construct. Use of Cre recombination to facilitate deletion of genetic elements from mammalian chromosomes has been described (Gu et al., *Science* 265:103 (1994); Sauer, *Meth. Enzymology* 225:890–900 (1993)).

Thus, constructs useful in the methods described herein include, but are not limited to, the following (See also FIGS. 1–4):

1) Construct with a regulatory sequence and an exon lacking a translation start codon.

2) Construct with a regulatory sequence and an exon lacking a translation start codon followed by a splice donor site.

3) Construct with a regulatory sequence and an exon containing a translation start codon in reading frame 1 (relative to the splice donor site), followed by an unpaired splice donor site.

4) Construct with a regulatory sequence and an exon containing a translation start codon in reading frame 2 (relative to the splice donor site), followed by an unpaired splice donor site.

5) Construct with a regulatory sequence and an exon containing a translation start codon in reading frame 3 (relative to the splice donor site), followed by an unpaired splice donor site.

6) Construct with a regulatory sequence and an exon containing a translation start codon and a signal secretion sequence in reading frame 1 (relative to the splice donor site), followed by an unpaired splice donor site.

7) Construct with a regulatory sequence and an exon containing a translation start codon and a signal secretion sequence in reading frame 2 (relative to the splice donor site), followed by an unpaired splice donor site.

8) Construct with a regulatory sequence and an exon containing a translation start codon and a signal secretion sequence in reading frame 3 (relative to the splice donor site), followed by an unpaired splice donor site.

9) Construct with a regulatory sequence and an exon containing (from 5' to 3') a translation start codon and an epitope tag in reading frame 1 (relative to the splice donor site), followed by an unpaired splice donor site.

10) Construct with a regulatory sequence and an exon containing (from 5' to 3') a translation start codon and an epitope tag in reading frame 2 (relative to the splice donor site), followed by an unpaired splice donor site.

11) Construct with a regulatory sequence and an exon containing (from 5' to 3') a translation start codon and an epitope tag in reading frame 3 (relative to the splice donor site), followed by an unpaired splice donor site.

12) Construct with a regulatory sequence and an exon containing (from 5' to 3') a translation start codon, a signal secretion sequence, and an epitope tag in reading frame 1 (relative to the splice donor site), followed by an unpaired splice donor site.

13) Construct with a regulatory sequence and an exon containing (from 5' to 3') a translation start codon, a signal secretion sequence, and an epitope tag in reading frame 2 (relative to the splice donor site), followed by an unpaired splice donor site.

14) Construct with a regulatory sequence and an exon containing (from 5' to 3') a translation start codon, a signal secretion sequence, and an epitope tag in reading frame 3 (relative to the splice donor site), followed by an unpaired splice donor site.

15) Construct with a regulatory sequence and an exon containing (from 5' to 3') a translation start codon, a signal secretion sequence, an epitope tag, and a sequence specific protease site in reading frame 1 (relative to the splice donor site), followed by an unpaired splice donor site.

16) Construct with a regulatory sequence and an exon containing (from 5' to 3') a translation start codon, a signal secretion sequence, an epitope tag, and a sequence specific protease site in reading frame 2 (relative to the splice donor site), followed by an unpaired splice donor site.

17) Construct with a regulatory sequence and an exon containing (from 5' to 3') a translation start codon, a signal secretion sequence, an epitope tag, and a sequence specific protease site in reading frame 3 (relative to the splice donor site), followed by an unpaired splice donor site.

18) Construct with a regulatory sequence linked to a selectable marker, followed by an internal ribosome entry site, and an unpaired splice donor site.

19) Construct 18 in which a cre/lox recombination signal is located between a) the regulatory sequence and the open reading frame of the selectable marker and b) between the ires and the unpaired splice donor site.

20) Construct with a regulatory sequence operably linked to an exon containing green fluorescent protein lacking a stop codon, followed by an unpaired splice donor site.

It is to be understood, however, that any vector used in the methods described herein can include one or more (i.e., one, two, three, four, five, or more, and most preferably one or two) amplifiable markers. Accordingly, methods can include a step in which the endogenous gene is amplified. Placement of one or more amplifiable markers on the activation construct results in the juxtaposition of the gene of interest and the one or more amplifiable markers in the activated cell. Once the activated cell has been isolated, expression can be further increased by selecting for cells containing an increased copy number of the locus containing both the gene of interest and the activation construct. This can be accomplished by selection methods known in the art, for example by culturing cells in selective culture media containing one or more selection agents that are specific for the one or more amplifiable markers contained on the genetic construct or vector.

Following activation of an endogenous gene by nonhomologous integration of any of the vectors described above, the expression of the endogenous gene may be further increased by selecting for increased copies of the amplifiable marker(s) located on the integrated vector. While such an approach may be accomplished using one amplifiable marker on the integrated vector, in an alternative embodiment the invention provides such methods wherein two or more (i.e., two, three, four, five, or more, and most preferably two) amplifiable markers may be included on the vector to facilitate more efficient selection of cells that have amplified the vector and flanking gene of interest. This approach is particularly useful in cells that have a functional endogenous copy of one or more of the amplifiable marker(s) that are contained on the vector, since the selection procedure can result in isolation of cells that have incorrectly amplified the endogenous amplifiable marker(s) rather than the vector-encoded amplifiable marker(s). This approach is also useful to select against cells that develop resistance to the selective agent by mechanisms that do not involve gene amplification. The approach using two or more amplifiable markers is advantageous in these situations because the probability of a cell developing resistance to two or more selective agents (resistance to which is encoded by two or more amplifiable markers) without amplifying the integrated vector and flanking gene of interest is significantly lower than the probability of the cell developing resistance to any single selective agent. Thus, by selecting for two or more vector encoded amplifiable markers, either simultaneously or sequentially, a greater percentage of cells that are ultimately isolated will contain the amplified vector and gene of interest.

Thus, in another embodiment, the vectors of the invention may contain two or more (i.e., two, three, four, five, or more, and most preferably two) amplifiable markers. This approach allows more efficient amplification of the vector sequences and adjacent gene of interest following activation of expression.

Examples of amplifiable markers that may be used constructing the present vectors include, but are not limited to, dihydrofolate reductase, adenosine deaminase, aspartate transcarbamylase, dihydro-orotase, and carbamyl phosphate synthase.

It is also understood that any of the constructs described herein may contain a eukaryotic viral origin of replication, either in place of, or in conjunction with an amplifiable marker. The presence of the viral origin of replication allows the integrated vector and adjacent endogenous gene to be isolated as an episome and/or amplified to high copy number upon introduction of the appropriate viral replication protein. Examples of useful viral origins include, but are not limited to, SV40 ori and EBV ori P.

The invention also encompasses embodiments in which the constructs disclosed herein consist essentially of the components specifically described for these constructs. It is also understood that the above constructs are examples of constructs useful in the methods described herein, but that the invention encompasses functional equivalents of such constructs.

The term "vector" is understood to generally refer to the vehicle by which the nucleotide sequence is introduced into the cell. It is not intended to be limited to any specific sequence. The vector could itself be the nucleotide sequence that activates the endogenous gene or could contain the sequence that activates the endogenous gene. Thus, the vector could be simply a linear or circular polynucleotide containing essentially only those sequences necessary for activation, or could be these sequences in a larger polynucleotide or other construct such as a DNA or RNA viral genome, a whole virion, or other biological construct used to introduce the critical nucleotide sequences into a cell. It is also understood that the phrase "vector construct" or the term "construct" may be used interchangeably with the term "vector" herein.

The vector can contain DNA sequences that exist in nature or that have been created by genetic engineering or synthetic processes.

The construct, upon nonhomologous integration into the genome oaf cell, can activate expression of an endogenous gene. Expression of the endogenous gene may result in production of full length protein, or in production of a truncated biologically active form of the endogenous protein, depending on the integration site (e.g., upstream region versus intron 2). The activated gene may be a known gene (e.g., previously cloned or characterized) or unknown gene (previously not cloned or characterized). The function of the gene may be known or unknown.

Examples of proteins with known activities include, but are not limited to, cytokines, growth factors, neurotransmitters, enzymes, structural proteins, cell surface receptors, intracellular receptors, hormones, antibodies, and transcription factors. Specific examples of known proteins that can be produced by this method include, but are not limited to, erythropoietin, insulin, growth hormone, glucocerebrosidase, tissue plasminogen activator, granulocyte-colony stimulating factor (G-CSF), granulocyte/macrophage colony stimulating factor (GM-CSF), macrophage colony-stimulating factor (M-CSF) interferon α, interferon β, interferon γ, interleukin-2, interleukin-3, interleukin-4, interleukin-6, interleukin-8, interleukin-10, interleukin-11, interleukin-12, interleukin-13, interleukin-14, TGF-β, blood clotting factor V, blood clotting factor VII, blood clotting factor VIII, blood clotting factor IX, blood clotting factor X, TSH-β, bone growth factor-2, bone growth factor-7, tumor necrosis factor, alpha-1 antitrypsin, anti-thrombin III, leukemia inhibitory factor, glucagon, Protein C, protein kinase C, stem cell factor, follicle stimulating hormone β, urokinase, nerve growth factors, insulin-like growth factors, insulinotropin, parathyroid hormone, lactoferrin, complement inhibitors, platelet derived growth factor, keratinocyte growth factor, hepatocyte growth factor, endothelial cell growth factor, neurotropin-3, thrombopoietin, chorionic gonadotropin, thrombomodulin, alpha glucosidase, epidermal growth factor, and fibroblast growth factor. The invention also allows the activation of a variety of genes expressing transmembrane proteins, and production and isolation of such proteins, including but not limited to cell surface receptors for growth factors, hormones, neurotransmitters and cytokines such as those described above, transmembrane ion channels, cholesterol receptors, receptors for lipoproteins (including LDLs and HDLs) and other lipid moieties, integrins and other extra-cellular matrix receptors, cytoskeletal anchoring proteins, immunoglobulin receptors, CD antigens (including CD2, CD3, CD4, CD8, and CD34 antigens), and other cell surface transmembrane structural and functional proteins that are known in the art. As one of ordinary skill will appreciate, other cellular proteins and receptors that are known in the art may also be produced by the methods of the invention.

One of the advantages of the method described herein is that virtually any gene can be activated. However, since genes have different genomic structures, including different intron/exon boundaries and locations of start codons, a variety of activation constructs is provided to activate the maximum number of different genes within a population of cells.

These constructs can be transfected separately into cells to produce libraries. Each library contains cells with a unique set of activated genes. Some genes will be activated by several different activation constructs. In addition, portions of a gene can be activated to produce truncated, biologically active proteins. Truncated proteins can be produced, for example, by integration of an activation construct into introns or exons in the middle of an endogenous gene rather than upstream of the second exon.

Use of different constructs also allows the activated gene to be modified to contain new sequences. For example, a secretion signal sequence can be included on the activation construct to facilitate the secretion of the activated gene. In some cases, depending on the intron/exon structure or the gene of interest, the secretion signal sequence can replace all or part of the signal sequence of the endogenous gene. In other cases, the signal sequence will allow a protein which is normally located intracellularly to be secreted.

The regulatory sequence on the vector can be a constitutive promoter. Alternatively, the promoter may be inducible. Use of inducible promoters will allow low basal levels of activated protein to be produced by the cell during routine culturing and expansion. The cells may then be induced to produce large amounts of the desired proteins, for example, during manufacturing or screening. Examples of inducible promoters include, but are not limited to, the tetracycline inducible promoter and the metallothionein promoter.

In preferred embodiments of the invention, the regulatory sequence on the vectors of the invention may be a promoter, an enhancer, or a repressor, any of which may be tissue specific.

The regulatory sequence on the vector can be isolated from cellular or viral genomes. Examples of cellular regulatory sequences include, but are not limited to, regulatory elements from the actin gene, metallothionein I gene, immunoglobulin genes, casein I gene, serum albumin gene, collagen gene, globin genes, laminin gene, spectrin gene, ankyrin gene, sodium/potassium ATPase gene, and tubulin gene. Examples of viral regulatory sequences include, but are not limited to, regulatory elements from Cytomegalovirus (CMV) immediate early gene, adenovirus late genes, SV40 genes, retroviral LTRs, and Herpesvirus genes. Typically, regulatory sequences contain binding sites for transcription factors such as NF-kB, SP-1, TATA binding protein, AP-1, and CAAT binding protein. Functionally, the regulatory sequence is defined by its ability to promote, enhance, or otherwise alter transcription of an endogenous gene.

In certain preferred embodiments, the regulatory sequence is a viral promoter. In particularly preferred embodiments, the promoter is the CMV immediate early gene promoter. In alternative embodiments, the regulatory element is a cellular, non-viral promoter.

In alternative preferred embodiments, the regulatory element may be or may contain an enhancer. In particularly preferred such embodiments, the enhancer is the cytomegalovirus immediate early gene enhancer. In alternative embodiments, the enhancer is a cellular, non-viral enhancer.

In alternative preferred embodiments, the regulatory element may be or may contain a repressor. In particularly preferred such embodiments, the repressor may be a viral repressor or a cellular, non-viral repressor.

The transcriptional regulatory sequence can also comprise one or more scaffold-attachment regions or matrix attachment sites, negative regulatory elements, and transcription factor binding sites. Regulatory sequences can also include locus control regions.

The invention also encompasses the use of retrovirus transcriptional regulatory sequences, e.g., long terminal repeats. Where these are used, however, they are not necessarily linked to any retrovirus sequence that materially affects the function of the transcriptional regulatory sequence as a promoter or enhancer of transcription of the endogenous gene to be activated (i.e., the cellular gene with which the transcriptional regulatory sequence recombines to activate).

The vector constructs of the invention may also comprise a regulatory sequence which is not operably linked to exonic sequences on the vector. For example, when the regulatory element is an enhancer, it can integrate near an endogenous gene (e.g., upstream, downstream, or in an intron) and stimulate expression of the gene from its endogenous promoter. By this mechanism of activation, exonic sequences from the vector are absent in the transcript of the activated gene.

Alternatively, the regulatory element may be operably linked to an exon. The exon may be a naturally occurring sequence or may be non-naturally occurring (e.g., produced synthetically). To activate endogenous genes lacking a start codon in their first exon (e.g., follicle stimulating hormone-β), a start codon is preferably omitted from the exon on the vector. To activate endogenous genes containing a start codon in the first exon (e.g., erythropoietin and growth hormone), the exon on the vector preferably contains a start codon, usually ATG and preferably an efficient translation initiation site (Kozak, *J. Mol Biol.* 196: 947 (1987)). The exon may contain additional codons following the start codon. These codons may be derived from a naturally occurring gene or may be non-naturally occurring (e.g., synthetic). The codons may be the same as the codons present in the first exon of the endogenous gene to be activated. Alternatively, the codons may be different than the codons present in the first exon of the endogenous gene. For example, the codons may encode an epitope tag, signal secretion sequence, transmembrane domain, selectable marker, or screenable marker. Optionally, an unpaired splice donor site may be present immediately 3' of the exonic sequence. When the structure of the gene to be activated is known, the splice donor site should be placed adjacent to the vector exon in a location such that the codons in the vector will be in frame with the codons of the second exon of the endogenous gene following splicing. When the structure of the endogenous gene to be activated is not known, separate constructs, each containing a different reading frame, are used.

Operably linked is defined as a configuration that allows transcription through the designated sequence(s). For example, a regulatory sequence that is operably linked to an exonic sequence indicates that the exonic sequence is transcribed. When a start codon is present on the vector, operably linked also indicates that the open reading frame from the vector exon is in frame with the open reading frame of the endogenous gene. Following nonhomologous integration, the regulatory sequence (e.g., a promoter) on the vector becomes operably linked to an endogenous gene and facilitates transcription initiation, at a site generally referred to as a CAP site. Transcription proceeds through the exonic elements on the vector (and, if present, through the start codon, open reading frame, and/or unpaired splice donor site), and through the endogenous gene. The primary transcript produced by this operable linkage is spliced to create a chimeric transcript containing exonic sequences from both the vector and the endogenous gene. This transcript is capable of producing the endogenous protein when translated.

An exon or "exonic sequence" is defined as any transcribed sequence that is present in the mature RNA molecule. The exon on the vector may contain untranslated sequences, for example, a 5' untranslated region. Alternatively, or in conjunction with the untranslated sequences, the exon may contain coding sequences such as a start codon and open reading frame. The open reading frame can encode naturally occurring amino acid sequences or non-naturally occurring amino acid sequences (e.g., synthetic codons). The open reading frame may also encode a signal secretion sequence, epitope tag, exon, selectable marker, screenable marker, or nucleotides that function to allow the open reading frame to be preserved when spliced to an endogenous gene.

Splicing of primary transcripts, the process by which introns are removed, is directed by a splice donor site and a splice acceptor site, located at the 5' and 3' ends of introns, respectively. The consensus sequence for splice donor sites is (A/C)AG GURAGU (where R represents a purine nucleotide) with nucleotides in positions 1–3 located in the exon and nucleotides GURAGU located in the intron.

An unpaired splice donor site is defined herein as a splice donor site present on the activation construct without a downstream splice acceptor site. When the vector is integrated by nonhomologous recombination into a host cell's genome, the unpaired splice donor site becomes paired with a splice acceptor site from an endogenous gene. The splice donor site from the vector, in conjunction with the splice acceptor site from the endogenous gene, will then direct the excision of all of the sequences between the vector splice donor site and the endogenous splice acceptor site. Excision of these intervening sequences removes sequences that interfere with translation of the endogenous protein.

The terms upstream and downstream, as used herein, are intended to mean in the 5' or in the 3' direction, respectively, relative to the coding strand. The term "upstream region" of a gene is defined as the nucleic acid sequence 5' of its second exon (relative to the coding strand) up to and including the last exon of the first adjacent gene having the same coding strand. Functionally, the upstream region is any site 5' of the second exon of an endogenous gene capable of allowing a nonhomologously integrated vector to become operably linked to the endogenous gene.

The vector construct can contain a selectable marker to facilitate the identification and isolation of cells containing a nonhomologously integrated activation construct. Examples of selectable markers include genes encoding neomycin resistance (neo), hypoxanthine phosphoribosyl transferase (HPRT), puromycin (pac), dihydro-orotase glutamine synthetase (GS), histidine D (his D), carbamyl phosphate synthase (CAD), dihyrofolate reductase (DHFR), multidrug resistance 1 (mdr1), aspartate transcarbamylase, xanthine-guanine phosphoribosyl transferase (gpt), and adenosine deaminase (ada).

Alternatively, the vector can contain a screenable marker, in place of or in addition to, the selectable marker. A screenable marker allows the cells containing the vector to be isolated without placing them under drug or other selective pressures. Examples of screenable markers include genes encoding cell surface proteins, fluorescent proteins, and enzymes. The vector containing cells may be isolated, for example, by FACS using fluorescently-tagged antibodies to the cell surface protein or substrates that can be converted to fluorescent products by a vector encoded enzyme.

Alternatively, selection can be effected by phenotypic selection for a trait provided by the endogenous gene product. The activation construct, therefore, can lack a selectable marker other than the "marker" provided by the endogenous gene itself In this embodiment, activated cells can be selected based on a phenotype conferred by the activated gene. Examples of selectable phenotypes include cellular proliferation, growth factor independent growth, colony formation, cellular differentiation (e.g., differentiation into a neuronal cell, muscle cell, epithelial cell, etc.), anchorage independent growth, activation of cellular factors (e.g., kinases, transcription factors, nucleases, etc.), expression of cell surface receptors/proteins, gain or loss of cell-cell adhesion, migration, and cellular activation (e.g., resting versus activated T cells).

A selectable marker may also be omitted from the construct when transfected cells are screened for gene activation products without selecting for the stable integrants. This is particularly useful when the efficiency of stable integration is high.

The vector may contain one or more (i.e., one, two, three, four, five, or more, and most preferably one or two) amplifiable markers to allow for selection of cells containing increased copies of the integrated vector and the adjacent activated endogenous gene. Examples of amplifiable markers include but are not limited to dihydrofolate reductase (DHFR), adenosine deaminase (ada), dihydro-orotase glutamine synthetase (GS), and carbamyl phosphate synthase (CAD).

The vector may contain eukaryotic viral origins of replication useful for gene amplification. These origins may be present in place of, or in conjunction with, an amplifiable marker.

The vector may also contain genetic elements useful for the propagation of the construct in micro-organisms. Examples of useful genetic elements include microbial origins of replication and antibiotic resistance markers.

These vectors, and any of the vectors disclosed herein, and obvious variants recognized by one of ordinary skill in the art, can be used in any of the methods described herein to form any of the compositions producible by those methods.

Nonhomologous integration of the construct into the genome of a cell results in the operable linkage between the regulatory elements from the vector and the exons from an endogenous gene. In preferred embodiments, the insertion of the vector regulatory sequences is used to upregulate expression of the endogenous gene. Upregulation of gene expression includes converting a transcriptionally silent gene to a transcriptionally active gene. It also includes enhancement of gene expression for genes that are already transcriptionally active, but produce protein at levels lower than desired. In other embodiments, expression of the endogenous gene may be affected in other ways such as downregulation of expression, creation of an inducible phenotype, or changing the tissue specificity of expression.

According to the invention, in vitro methods of production of a gene expression product may comprise, for example, (a) introducing a vector of the invention into a cell; (b) allowing the vector to integrate into the genome of the cell by non-homologous recombination; (c) allowing overexpression of an endogenous gene in the cell by upregulation of the gene by the transcriptional regulatory sequence contained on the vector; (d) screening the cell for overexpression of the endogenous gene; and (e) culturing the cell under conditions favoring the production of the expression product of the endogenous gene by the cell. Such in vitro methods of the invention may further comprise isolating the expression product to produce an isolated gene expression product. In such methods, any art-known method of protein isolation may be advantageously used, including but not limited to chromatography (e.g., HPLC, FPLC, LC, ion exchange, affinity, size exclusion, and the like), precipitation (e.g., ammonium sulfate precipitation, immunoprecipitation, and the like), electrophoresis, and other methods of protein isolation and purification that will be familiar to one of ordinary skill in the art.

Analogously, in vivo methods of production of a gene expression product may comprise, for example, (a) introducing a vector of the invention into a cell; (b) allowing the vector to integrate into the genome of the cell by non-homologous recombination; (c) allowing over-expression of an endogenous gene in the cell by upregulation of the gene by the transcriptional regulatory sequence contained on the vector; (d) screening the cell for over-expression of the endogenous gene; and (e) introducing the isolated and cloned cell into a eukaryote under conditions favoring the overexpression of the endogenous gene by the cell in vivo in the eukaryote. According to this aspect of the invention, any eukaryote may be advantageously used, including fungi (particularly yeasts), plants, and animals, more preferably animals, still more preferably vertebrates, and most preferably mammals, particularly humans. In certain related embodiments, the invention provides such methods which further comprise isolating and cloning the cell prior to introducing it into the eukaryote.

As used herein the phrases "conditions favoring the production" of an expression product, "conditions favoring the overexpression" of a gene, and "conditions favoring the activation" of a gene, in a cell or by a cell in vitro refer to any and all suitable environmental, physical, nutritional or biochemical parameters that allow, facilitate, or promote production of an expression product, or overexpression or activation of a gene, by a cell in vitro. Such conditions may, of course, include the use of culture media, incubation, lighting, humidity, etc., that are optimal or that allow, facilitate, or promote production of an expression product, or overexpression or activation of a gene, by a cell in vitro. Analogously, as used herein the phrases "conditions favoring the production" of an expression product, "conditions favoring the overexpression" of a gene, and "conditions favoring the activation" of a gene, in a cell or by a cell in vivo refer to any and all suitable environmental, physical, nutritional, biochemical, behavioral, genetic, and emotional parameters under which an animal containing a cell is maintained, that allow, facilitate, or promote production of an expression product, or overexpression or activation of a gene, by a cell in a eukaryote in vivo. Whether a given set of conditions are favorable for gene expression, activation, or overexpression, in vitro or in vivo, may be determined by one of ordinary skill using the screening methods described and exemplified below, or other methods for measuring gene expression, activation, or overexpression that are routine in the art.

As used herein, the phrase "activating an endogenous gene" means inducing the production of a transcript encoding the endogenous gene at levels higher than those normally found in the cell containing the endogenous gene. In some applications, "activating an endogenous gene" may also mean producing the protein, or a portion of the protein, encoded by the endogenous gene at levels higher than those normally found in the cell containing the endogenous gene.

The invention also encompasses cells made by any of the above methods. The invention encompasses cells containing the vector constructs, cells in which the vector constructs have integrated, and cells which are over-expressing desired gene products from an endogenous gene, over-expression being driven by the introduced transcriptional regulatory sequence.

Cells used in this invention can be derived from any eukaryotic species and can be primary, secondary, or immortalized. Furthermore, the cells can be derived from any tissue in the organism. Examples of useful tissues from which cells can be isolated and activated include, but are not limited to, liver, kidney, spleen, bone marrow, thymus, heart, muscle, lung, brain, testes, ovary, islet, intestinal, bone marrow, skin, bone, gall bladder, prostate, bladder, embryos, and the immune and hematopoietic systems. Cell types include fibroblast, epithelial, neuronal, stem, and follicular. However, any cell or cell type can be used to activate gene expression using this invention.

The methods can be carried out in any cell of eukaryotic origin, such as fungal, plant or animal. Preferred embodiments include vertebrates and particularly mammals, and more particularly, humans.

The construct can be integrated into primary, secondary, or immortalized cells. Primary cells are cells that have been isolated from a vertebrate and have not been passaged. Secondary cells are primary cells that have been passaged, but are not immortalized. Immortalized cells are cell lines that can be passaged, apparently indefinitely.

In preferred embodiments, the cells are immortalized cell lines. Examples of immortalized cell lines include, but are not limited to, HT1080, HeLa, Jurkat, 293 cells, KB carcinoma, T84 colonic epithelial cell line, Raji, Hep G2 or Hep 3B hepatoma cell lines, A2058 melanoma, U937 lymphoma, and W138 fibroblast cell line, somatic cell hybrids, and hybridomas.

Cells used in this invention can be derived from any eukaryotic species, including but not limited to mammalian cells (such as rat, mouse, bovine, porcine, sheep, goat, and human), avian cells, fish cells, amphibian cells, reptilian cells, plant cells, and yeast cells. Preferably, overexpression of an endogenous gene or gene product from a particular species is accomplished by activating gene expression in a cell from that species. For example, to overexpress endogenous human proteins, human cells are used. Similarly, to overexpress endogenous bovine proteins, for example bovine growth hormone, bovine cells are used.

The cells can be derived from any tissue in the eukaryotic organism. Examples of useful vertebrate tissues from which cells can be isolated and activated include, but are not limited to, liver, kidney, spleen, bone marrow, thymus, heart, muscle, lung, brain, immune system (including lymphatic), testes, ovary, islet, intestinal, stomach, bone marrow, skin, bone, gall bladder, prostate, bladder, zygotes, embryos, and hematopoietic tissue. Useful vertebrate cell types include, but are not limited to, fibroblasts, epithelial cells, neuronal cells, germ cells (i.e., spermatocytes/spermatozoa and oocytes), stem cells, and follicular cells. Examples of plant tissues from which cells can be isolated and activated include, but are not limited to, leaf tissue, ovary tissue, stamen tissue, pistil tissue, root tissue, tubers, gametes, seeds, embryos, and the like. One of ordinary skill will appreciate, however, that any eukaryotic cell or cell type can be used to activate gene expression using the present invention.

Any of the cells produced by any of the methods described are useful for screening for expression of a desired gene product and for providing desired amounts of a gene product that is over-expressed in the cell. The cells can be isolated and cloned.

Cells produced by this method can be used to produce protein in vitro (e.g., for use as a protein therapeutic) or in vivo (e.g., for use in cell therapy).

Commercial growth and production conditions often vary from the conditions used to grow and prepare cells for analytical use (e.g., cloning, protein or nucleic acid sequencing, raising antibodies, X-ray crystallography analysis, enzymatic analysis, and the like). Scale up of cells for growth in roller bottles involves increase in the surface area on which cells can attach. Microcarrier beads are, therefore, often added to increase the surface area for commercial growth. Scale up of cells in spinner culture may involve large increases in volume. Five liters or greater can be required for both microcarrier and spinner growth. Depending on the inherent potency (specific activity) of the protein of interest, the volume can be as low as 1–10 liters. 10–15 liters is more common. However, up to 50–100 liters may be necessary and volume can be as high as 10,000–15,000 liters. In some cases, higher volumes may be required. Cells can also be grown in large numbers of T flasks, for example 50–100.

Despite growth conditions, protein purification on a commercial scale can also vary considerably from purification for analytic purposes. Protein purification in a commercial practical context can be initially the mass equivalent of 10 liters of cells at approximately $10^4$ cells/ml. Cell mass equivalent to begin protein purification can also be as high as 10 liters of cells at up to $10^6$ or $10^7$ cells/ml. As one of ordinary skill will appreciate, however, a higher or lower initial cell mass equivalent may also be advantageously used in the present methods.

Another commercial growth condition, especially when the ultimate product is used clinically, is cell growth in serum-free medium, by which is intended medium containing no serum or not in amounts that are required for cell growth. This obviously avoids the undesired co-purification of toxic contaminants (e.g., viruses) or other types of contaminants, for example, proteins that would complicate purification. Serum-free media for growth of cells, commercial sources for such media, and methods for cultivation of cells in serum-free media, are well-known to those of ordinary skill in the art.

A single cell made by the methods described above can over-express a single gene or more than one gene. More than one gene can be activated by the integration of a single construct or by the integration of multiple constructs in the same cell (i.e., more than one type of construct). Therefore, a cell can contain only one type of vector construct or different types of constructs, each capable of activating an endogenous gene.

The invention is also directed to methods for making the cells described above by one or more of the following: introducing one or more of the vector constructs; allowing the introduced construct(s) to integrate into the genome of the cell by non-homologous recombination; allowing over-expression of one or more endogenous genes in the cell; and isolating and cloning the cell.

The term "transfection" has been used herein for convenience when discussing introducing a polynucleotide into a cell. However, it is to be understood that the specific use of this term has been applied to generally refer to the introduction of the polynucleotide into a cell and is also intended to refer to the introduction by other methods described herein such as electroporation, liposome-mediated introduction, retrovirus-mediated introduction, and the like (as well as according to its own specific meaning).

The vector can be introduced into the cell by a number of methods known in the art. These include, but are not limited to, electroporation, calcium phosphate precipitation, DEAE dextran, lipofection, and receptor mediated endocytosis, polybrene, particle bombardment, and microinjection. Alternatively, the vector can be delivered to the cell as a viral particle (either replication competent or deficient). Examples of viruses useful for the delivery of nucleic acid include, but are not limited to, adenoviruses, adeno-associated viruses, retroviruses, Herpesviruseses, and vaccinia viruses. Other viruses suitable for delivery of nucleic acid molecules into cells that are known to one of ordinary skill may be equivalently used in the present methods.

Following transfection, the cells are cultured under conditions, as known in the art, suitable for nonhomologous integration between the vector and the host cell's genome. Cells containing the nonhomologously integrated vector can be further cultured under conditions, as known in the art, allowing expression of activated endogenous genes.

The vector construct can be introduced into cells on a single DNA construct or on separate constructs and allowed to concatemerize.

Whereas in preferred embodiments, the vector construct is a double-stranded DNA vector construct, vector constructs also include single-stranded DNA, combinations of single- and double-stranded DNA, single-stranded RNA, double-stranded RNA, and combinations of single- and double-stranded RNA. Thus, for example, the vector construct could be single-stranded RNA which is converted to cDNA by reverse transcriptase, the cDNA converted to double-stranded DNA, and the double-stranded DNA ultimately recombining with the host cell genome.

In preferred embodiments, the constructs are linearized prior to introduction into the cell. Linearization of the activation construct creates free DNA ends capable of reacting with chromosomal ends during the integration process. In general, the construct is linearized downstream of the regulatory element (and exonic and splice donor sequences, if present). Linearization can be facilitated by, for example, placing a unique restriction site downstream of the regulatory sequences and treating the construct with the corresponding restriction enzyme prior to transfection. While not required, it is advantageous to place a "spacer" sequence between the linearization site and the proximal most functional element (e.g., the unpaired splice donor site) on the construct. When present, the spacer sequence protects the important functional elements on the vector from exonucleolytic degradation during the transfection process. The spacer can be composed of any nucleotide sequence that does not change the essential functions of the vector as described herein.

Circular constructs can also be used to activate endogenous gene expression. It is known in the art that circular plasmids, upon transfection into cells, can integrate into the host cell genome. Presumably, DNA breaks occur in the circular plasmid during the transfection process, thereby generating free DNA ends capable of joining to chromosome ends. Some of these breaks in the construct will occur in a location that does not destroy essential vector functions (e.g., the break will occur downstream of the regulatory sequence), and therefore, will allow the construct to be integrated into a chromosome in a configuration capable of activating an endogenous gene. As described above, spacer sequences may be placed on the construct (e.g., downstream of the regulatory sequences). During transfection, breaks that occur in the spacer region will create free ends at a site in the construct suitable for activation of an endogenous gene following integration into the host cell genome.

The invention also encompasses libraries of cells made by the above described methods. A library can encompass all of the clones from a single transfection experiment or a subset of clones from a single transfection experiment. The subset can over-express the same gene or more than one gene, for example, a class of genes. The transfection can have been done with a single type of construct or with more than one type of construct.

A library can also be formed by combining all of the recombinant cells from two or more transfection experiments, by combining one or more subsets of cells from a single transfection experiment or by combining subsets of cells from separate transfection experiments. The resulting library can express the same gene, or more than one gene, for example, a class of genes. Again, in each of these individual transfections, a unique construct or more than one construct can be used.

Libraries can be formed from the same cell type or different cell types.

The library can be composed of a single type of cell containing a single type of activation construct which has been integrated into chromosomes at spontaneous DNA breaks or at breaks generated by radiation, restriction enzymes, and/or DNA breaking agents, applied either together (to the same cells) or separately (applied to individual groups of cells and then combining the cells together to produce the library). The library can be composed of multiple types of cells containing a single or multiple constructs which were integrated into the genome of a cell treated with radiation, restriction enzymes, and/or DNA breaking agents, applied either together (to the same cells) or separately (applied to individual groups of cells and then combining the cells together to produce the library).

The invention is also directed to methods for making libraries by selecting various subsets of cells from the same or different transfection experiments. For example, all of the cells expressing nuclear factors (as determined by the presence of nuclear green fluorescent protein in cells transfected with construct 20) can be pooled to create a library of cells with activated nuclear factors. Similarly, cells expressing membrane or secreted proteins can be pooled. Cells can also be grouped by phenotype, for example, growth factor independent growth, growth factor independent proliferation, colony formation, cellular differentiation (e.g., differentiation into a neuronal cell, muscle cell, epithelial cell, etc.), anchorage independent growth, activation of cellular factors (e.g., kinases, transcription factors, nucleases, etc.), gain or loss of cell-cell adhesion, migration, or cellular activation (e.g., resting versus activated T cells).

The invention is also directed to methods of using libraries of cells to over-express an endogenous gene. The library is screened for the expression of the gene and cells are selected that express the desired gene product. The cell can then be used to purify the gene product for subsequent use. Expression of the cell can occur by culturing the cell in vitro or by allowing the cell to express the gene in vivo.

The invention is also directed to methods of using libraries to identify novel gene and gene products.

The invention is also directed to methods for increasing the efficiency of gene activation by treating the cells with agents that stimulate or effect the patterns of non-homologous integration. It has been demonstrated that gene expression patterns, chromatin structure, and methylation patterns can differ dramatically from cell type to cell type. Even different cell lines from the same cell type can have significant differences. These differences can impact the patterns of non-homologous integration by affecting both the DNA breakage pattern and the repair process. For example, chromatinized stretches of DNA (characteristics likely associated with inactive genes) may be more resistant to breakage by restriction enzymes and chemical agents, whereas they may be susceptible to breakage by radiation.

Furthermore, inactive genes can be methylated. In this case, restriction enzymes that are blocked by CpG methylation will be unable to cleave methylated sites near the inactive gene, making it more difficult to activate that gene using methylation-sensitive enzymes. These problems can be circumvented by creating activation libraries in several cell lines using a variety of DNA breakage agents. By doing this, a more complete integration pattern can be created and the probability of activating a given gene maximized.

The methods of the invention can include introducing double strand breaks into the DNA of the cell containing the endogenous gene to be over-expressed. These methods introduce double-strand breaks into the genomic DNA in the cell prior to or simultaneously with vector integration. The mechanism of DNA breakage can have a significant effect on the pattern of DNA breaks in the genome. As a result, DNA breaks produced spontaneously or artificially with radiation, restriction enzymes, bleomycin, or other breaking agents, can occur in different locations.

In order to increase integration efficiency and to improve the random distribution of integration sites, cells can be treated with low, intermediate, or high doses of radiation prior to or following transfection. By artificially inducing double strand breaks, the transfected DNA can now integrate into the host cell chromosome as part of the DNA repair process. Normally, creation of double strand breaks to serve as the site of integration is the rate limiting step. Thus, by increasing chromosome breaks using radiation (or other DNA damaging agents), a larger number of integrants can be obtained in a given transfection. Furthermore, the mechanism of DNA breakage by radiation is different than by spontaneous breakage.

Radiation can induce DNA breaks directly when a high energy photon hits the DNA molecule. Alternatively, radiation can activate compounds in the cell which in turn, react with and break the DNA strand. Spontaneous breaks, on the other hand, are thought to occur by the interaction between reactive compounds produced in the cell (such as superoxides and peroxides) and the DNA molecule. However, DNA in the cell is not present as a naked, deproteinized polymer, but instead is bound to chromatin and present in a condensed state. As a result, some regions are not accessible to agents in the cell that cause double strand breaks. The photons produced by radiation have wave lengths short enough to hit highly condensed regions of DNA, thereby inducing breaks in DNA regions that are under represented in spontaneous breaks. Thus, radiation is capable of creating different DNA breakage patterns, which in turn, should lead to different integration patterns.

As a result, libraries produced using the same activation construct in cells with and without radiation treatment will potentially contain different sets of activated genes. Finally, radiation treatment increases efficiency of nonhomologous integration by up to 5–10 fold, allowing complete libraries to be created using fewer cells. Thus, radiation treatment increases the efficiency of gene activation and generates new integration and activation patterns in transfected cells. Useful types of radiation include $\alpha$, $\beta$, $\gamma$, x-ray, and ultraviolet radiation. Useful doses of radiation vary for different cell types, but in general, dose ranges resulting in cell viabilities of 0.1% to >99% are useful. For HT1080 cells, this corresponds to radiation doses from a $^{137}$Cs source of approximately 0.1 rads to 1000 rads. Other doses may also be useful as long as the dose either increases the integration frequency or changes the pattern of integration sites.

In addition to radiation, restriction enzymes can be used to artificially induce chromosome breaks in transfected cells. As with radiation, DNA restriction enzymes can create chromosome breaks which, in turn, serve as integration sites for the transfected DNA. This larger number of DNA breaks increases the overall efficiency of integration of the activation construct. Furthermore, the mechanism of breakage by restriction enzymes differs from that by radiation, the pattern of chromosome breaks is also likely to be different.

Restriction enzymes are relatively large molecules compared to photons and small metabolites capable of damaging DNA. As a result, restriction enzymes will tend to break regions that are less condensed then the genome as a whole. If the gene of interest lies within an accessible region of the genome, then treatment of the cells with a restriction enzyme can increase the probability of integrating the activation construct upstream of the gene of interest. Since restriction enzymes recognize specific sequences, and since a given restriction site may not lie upstream of the gene of interest, a variety of restriction enzymes can be used. It may also be important to use a variety of restriction enzymes since each enzyme has different properties (e.g., size, stability, ability to cleave methylated sites, and optimal reaction conditions) that affect which sites in the host chromosome will be cleaved. Each enzyme, due to the different distribution of cleavable restriction sites, will create a different integration pattern.

Therefore, introduction of restriction enzymes (or plasmids capable of expressing restriction enzymes) before, during, or after introduction of the activation construct will result in the activation of different sets of genes. Finally, restriction enzyme-induced breaks increase the integration efficiency by up to 5–10 fold (Yorifuji et al., *Mut. Res.* 243:121 (1990)), allowing fewer cells to be transfected to produce a complete library. Thus, restriction enzymes can be used to create new integration patterns, allowing activation of genes which failed to be activated in libraries produced by non-homologous recombination at spontaneous breaks or at other artificially induced breaks.

Restriction enzymes can also be used to bias integration of the activation construct to a desired site in the genome. For example, several rare restriction enzymes have been described which cleave eukaryotic DNA every 50–1000 kilobases, on average. If a rare restriction recognition sequence happens to be located upstream of a gene of interest, by introducing the restriction enzyme at the time of transfection along with the activation construct, DNA breaks can be preferentially upstream of the gene of interest. These breaks can then serve as sites for integration of the activation construct. Any enzyme can be that cleaves in an appropriate location in or near the gene of interest and its site is under-represented in the rest of the genome or its site is over-represented near genes (e.g., restriction sites containing CpG). For genes that have not been previously identified, restriction enzymes with 8 bp recognition sites (e.g., NotI, SfiI, PmeI, SwaI, SseI, SrfI, SgrA1, PacI, AscI, SgfI, and Sse8387I), enzymes recognizing CpG containing sites (e.g., EagI, Bsi-WI, MluI, and BssHII) and other rare cutting enzymes can be used.

In this way, "biased" libraries can be created which are enriched for certain types of activated genes. In this respect, restriction enzyme sites containing CpG dinucleotides are particularly useful since these sites are under-represented in the genome at large, but over-represented in the form of CpG islands at the 5' end of many genes, the very location that is useful for gene activation. Enzymes recognizing these sites, therefore, will preferentially cleave at the 5' end of genic sequences.

Restriction enzymes can be introduced into the host cell by several methods. First, restriction enzymes can be introduced into the cell by electroporation (Yorifuji et al., *Mut. Res.* 243:121 (1990); Winegar et al., *Mut. Res.* 225:49 (1989)). In general, the amount of restriction enzyme introduced into the cell is proportional to its concentration in the electroporation media. The pulse conditions must be optimized for each cell line by adjusting the voltage, capacitance, and resistance. Second, the restriction enzyme can be expressed transiently from a plasmid encoding the enzyme under the control of eukaryotic regulatory elements. The level of enzyme produced can be controlled by using inducible promoters, and varying the strength of induction. In some cases, it may be desirable to limit the amount of restriction enzyme produced (due to its toxicity). In these cases, weak or mutant promoters, splice sites, translation start codons, and poly(A) tails can be utilized to lower the amount of restriction enzyme produced. Third, restriction enzymes can be introduced by agents that fuse with or permeabilize the cell membrane. Liposomes and streptolysin O (Pimplikar et al., *J. Cell Biol.* 125:1025 (1994)) are examples of this type of agent. Finally, mechanical perforation (Beckers et al., *Cell* 50:523–534 (1987)) and microinjection can also be used to introduce nucleases and other proteins into cells. However, any method capable of delivering active enzymes to a living cell is suitable.

DNA breaks induced by bleomycin and other DNA damaging agents can also produce DNA breakage patterns that are different. Thus, any agent or incubation condition capable of generating double strand breaks in cells is useful for increasing the efficiency and/or altering the sites of non-homologous recombination. Examples of classes of chemical DNA breaking agents include, but are not limited to, peroxides and other free radical generating compounds, alkylating agents, topoisomerase inhibitors, anti-neoplastic drugs, acids, substituted nucleotides, and enediyne antibiotics.

Specific chemical DNA breaking agents include, but are not limited to, bleomycin, hydrogen peroxide, cumene hydroperoxide, tert-butyl hydroperoxide, hypochlorous acid (reacted with aniline, 1-naphthylamine or 1-naphthol), nitric acid, phosphoric acid, doxorubicin, 9-deoxydoxorubicin, demethyl-6-deoxyrubicin, 5-iminodaunorubicin, adriamycin, 4'-(9-acridinylamino)methanesulfon-m-anisidide, neocarzinostatin, 8-methoxycaffeine, etoposide, ellipticine, iododeoxyuridine, and bromodeoxyuridine.

It has been shown that DNA repair machinery in the cell can be induced by pre-exposing the cell to low doses of a DNA breaking agent such as radiation or bleomycin. By pretreating cells with these agents approximately 24 hours prior to transfection, the cell will be more efficient at repairing DNA breaks and integrating DNA following transfection. In addition, higher doses of radiation or other DNA breaking agents can be used since the LD50 (the dose that results in lethality in 50% of the exposed cells) is higher following pretreatment. This allows random activation libraries to be created at multiple doses and results in a different distribution of integration sites within the host cell's chromosomes.

Screening

Once an activation library (or libraries) is created, it can be screened using a number of assays. Depending on the characteristics of the protein(s) of interest (e.g., secreted versus intracellular proteins) and the nature of the activation construct used to create the library, any or all of the assays described below can be utilized. Other assay formats can also be used.

ELISA. Activated proteins can be detected using the enzyme-linked immunosorbent assay (ELISA). If the activated gene product is secreted, culture supernatants from pools of activation library cells are incubated in wells containing bound antibody specific for the protein of interest. If a cell or group of cells has activated the gene of interest, then the protein will be secreted into the culture media. By screening pools of library clones (the pools can be from 1 to greater than 100,000 library members), pools containing a cell(s) that has activated the gene of interest can be identified. The cell of interest can then be purified away from the other library members by sib selection, limiting dilution, or other techniques known in the art. In addition to secreted proteins, ELISA can be used to screen for cells expressing intracellular and membrane-bound proteins. In these cases, instead of screening culture supernatants, a small number of cells is removed from the library pool (each cell is represented at least 100–1000 times in each pool), lysed, clarified, and added to the antibody-coated wells.

ELISA Spot Assay. ELISAspot are coated with antibodies specific for the protein of interest. Following coating, the wells are blocked with 1% BSA/PBS for 1 hour at 37° C. Following blocking, 100,000 to 500,000 cells from the random activation library are applied to each well (representing ~10% of the total pool). In general, one pool is applied to each well. If the frequency of a cell expressing the protein of interest is 1 in 10,000 (i.e., the pool consists of 10,000 individual clones, one of which expresses the protein of interest), then plating 500,000 cells per well will yield 50 specific cells. Cells are incubated in the wells at 37° C. for 24 to 48 hours without being moved or disturbed. At the end of the incubation, the cells are removed and the plate is washed 3 times with PBS/0.05% Tween 20 and 3 times with PBS/1% BSA. Secondary antibodies are applied to the wells at the appropriate concentration and incubated for 2 hours at room temperature or 16 hours at 4° C. These antibodies can be biotinylated or labeled directly with horseradish peroxidase (HRP). The secondary antibodies are removed and the plate is washed with PBS/1% BSA. The tertiary antibody or streptavidin labeled with HRP is added and incubated for 1 hour at room temperature.

FACS assay. The fluorescence-activated cell sorter (FACS) can be used to screen the random activation library in a number of ways. If the gene of interest encodes a cell surface protein, then fluorescently-labeled antibodies are incubated with cells from the activation library. If the gene of interest encodes a secreted protein, then cells can be biotinylated and incubated with streptavidin conjugated to an antibody specific to the protein of interest (Manz et al., *Proc. Natl. Acad. Sci.* (*USA*) 92:1921 (1995)). Following incubation, the cells are placed in a high concentration of gelatin (or other polymer such as agarose or methylcellulose) to limit diffusion of the secreted protein. As protein is secreted by the cell, it is captured by the antibody bound to the cell surface. The presence of the protein of interest is then detected by a second antibody which is fluorescently labeled. For both secreted and membrane bound proteins, the cells can then be sorted according to their fluorescence signal. Fluorescent cells can then be isolated, expanded, and further enriched by FACS, limiting dilution, or other cell purification techniques known in the art.

Magnetic Bead Separation. The principle of this technique is similar to FACS. Membrane bound proteins and captured secreted proteins (as described above) are detected by incubating the activation library with an antibody-conjugated magnetic beads that are specific for the protein of interest. If the protein is present on the surface of a cell, the magnetic beads will bind to that cell. Using a magnet, the cells expressing the protein of interest can be purified away from the other cells in the library. The cells are then released from the beads, expanded, analyzed, and further purified if necessary.

RT-PCR. A small number of cells (equivalent to at least the number of individual clones in the pool) is harvested and lysed to allow purification of the RNA. Following isolation, the RNA is reversed-transcribed using reverse transcriptase. PCR is then carried out using primers specific for the cDNA of the gene of interest.

Alternatively, primers can be used that span the synthetic exon in the activation construct and the exon of the endogenous gene. This primer will not hybridize to and amplify the endogenously expressed gene of interest. Conversely, if the activation construct has integrated upstream of the gene of interest and activated gene expression, then this primer, in conjunction with a second primer specific for the gene will amplify the activated gene by virtue of the presence of the synthetic exon spliced onto the exon from the endogenous gene. Thus, this method can be used to detect activated genes in cells that normally express the gene of interest at lower than desired levels.

Phenotypic Section. In this embodiment, cells can be selected based on a phenotype conferred by the activated gene. Examples of phenotypes that can be selected for include proliferation, growth factor independent growth, colony formation, cellular differentiation (e.g., differentiation into a neuronal cell, muscle cell, epithelial cell, etc.), anchorage independent growth, activation of cellular factors (e.g., kinases, transcription factors, nucleases, etc.), gain or loss of cell-cell adhesion, migration, and cellular activation (e.g., resting versus activated T cells). Isolation of activated cells demonstrating a phenotype, such as those described above, is important because the activation of an endogenous gene by the integrated construct is presumably responsible for the observed cellular phenotype. Thus, the activated gene may be an important therapeutic drug or drug target for treating or inducing the observed phenotype.

The sensitivity of each of the above assays can be effectively increased by transiently upregulating gene expression in the library cells. This can be accomplished for NF-κB site-containing promoters (on the activation construct) by adding PMA and tumor necrosis factor-α, e.g., to the library. Separately, or in conjunction with PMA and TNF-α, sodium butyrate can be added to further enhance gene expression. Addition of these reagents can increase expression of the protein of interest, thereby allowing a lower sensitivity assay to be used to identify the gene activated cell of interest.

Since large activation libraries are created to maximize activation of many genes, it is advantageous to organize the library clones in pools. Each pool can consist of 1 to greater than 100,000 individual clones. Thus, in a given pool, many activated proteins are produced, often in dilute concentrations (due to the overall size of the pool and the limited number of cells within the pool that produce a given activated protein). Thus, concentration of the proteins prior to screening effectively increases the ability to detect the activated proteins in the screening assay. One particularly useful method of concentration is ultrafiltration; however, other methods can also be used. For example, proteins can be concentrated non-specifically, or semi-specifically by adsorption onto ion exchange, hydrophobic, dye, hydroxyapatite, lectin, and other suitable resins under conditions that bind most or all proteins present. The bound proteins can then be removed in a small volume prior to screening. It is advantageous to grow the cells in serum free media to facilitate the concentration of proteins.

In another embodiment, a useful sequence that can be included on the activation construct is an epitope tag. The epitope tag can consist of an amino acid sequence that allows affinity purification of the activated protein (e.g., on immunoaffinity or chelating matrices). Thus, by including an epitope tag on the activation construct, all of the activated proteins from an activation library can be purified. By purifying the activated proteins away from other cellular and media proteins, screening for novel proteins and enzyme activities can be facilitated. In some instances, it may be desirable to remove the epitope tag following purification of the activated protein. This can be accomplished by including a protease recognition sequence (e.g., Factor IIa or enterokinase cleavage site) downstream from the epitope tag on the activation construct. Incubation of the purified, activated protein(s) with the appropriate protease will release the epitope tag from the proteins(s).

In libraries in which an epitope tag sequence is located on the activation construct, all of the activated proteins can be purified away from all other cellular and media proteins using affinity purification. This not only concentrates the activated proteins, but also purifies them away from other activities that can interfere with the assay used to screen the library.

Once a pool of clones containing cells over-expressing the gene of interest is identified, steps can be taken to isolate the activated cell. Isolation of the activated cell can be accomplished by a variety of methods known in the art. Examples of cell purification methods include limiting dilution, fluorescence activated cell sorting, magnetic bead separation, sib selection, and single colony purification using cloning rings.

In preferred embodiments of the invention, the methods include a process wherein the expression product is purified. In highly preferred embodiments, the cells expressing the endogenous gene product are cultured so as to produce amounts of gene product feasible for commercial application, and especially diagnostic and therapeutic and drug discovery uses.

Any vector used in the methods described herein can include an amplifiable marker. Thereby, amplification of both the vector and the DNA of interest (i.e., containing the over-expressed gene) occurs in the cell, and further enhanced expression of the endogenous gene is obtained. Accordingly, methods can include a step in which the endogenous gene is amplified.

Once the activated cell has been isolated, expression can be further increased by amplifying the locus containing both the gene of interest and the activation construct. This can be accomplished by each of the methods described below, either separately or in combination.

Amplifiable markers are genes that can be selected for higher copy number Examples of amplifiable markers include dihydrofolate reductase, adenosine deaminase, aspartate transcarbamylase, dihydro-orotase, and carbamyl phosphate synthase. For these examples, the elevated copy number of the amplifiable marker and flanking sequences (including the gene of interest) can be selected for using a drug or toxic metabolite which is acted upon by the amplifiable marker. In general, as the drug or toxic metabolite concentration increases, cells containing fewer copies of the amplifiable marker die, whereas cells containing increased copies of the marker survive and form colonies. These colonies can be isolated, expanded, and analyzed for increased levels of production of the gene of interest.

Placement of an amplifiable marker on the activation construct results in the juxtaposition of the gene of interest and the amplifiable marker in the activated cell. Selection for activated cells containing increased copy number of the amplifiable marker and gene of interest can be achieved by growing the cells in the presence of increasing amounts of selective agent (usually a drug or metabolite). For example, amplification of dihydrofolate reductase (DHFR) can be selected using methotrexate.

As drug-resistant colonies arise at each increasing drug concentration, individual colonies can be selected and characterized for copy number of the amplifiable marker and gene of interest, and analyzed for expression of the gene of interest. Individual colonies with the highest levels of activated gene expression can be selected for further amplification in higher drug concentrations. At the highest drug concentrations, the clones will express greatly increased amounts of the protein of interest.

When amplifying DHFR, it is convenient to plate approximately $1\times10^7$ cells at several different concentrations of methotrexate. Useful initial concentrations of methotrexate range from approximately 5 nM to 100 nM. However, the optimal concentration of methotrexate must be determined empirically for each cell line and integration site. Following growth in methotrexate containing media, colonies from the highest concentration of methotrexate are picked and analyzed for increased expression of the gene of interest. The clone(s) with the highest concentration of methotrexate are then grown in higher concentrations of methotrexate to select for further amplification of DHFR and the gene of interest. Methotrexate concentrations in the micromolar and millimolar range can be used for clones containing the highest degree of gene amplification.

Placement of a viral origin of replication(s) (e.g., ori P or SV40 in human cells, and polyoma ori in mouse cells) on the activation construct will result in the juxtaposition of the gene of interest and the viral origin of replication in the activated cell. The origin and flanking sequences can then be amplified by introducing the viral replication protein(s) in trans. For example, when ori P (the origin of replication on Epstein-Barr virus) is utilized, EBNA-I can be expressed transiently or stably. EBNA-1 will initiate replication from the integrated ori P locus. The replication will extend from the origin bi-directionally. As each replication product is created, it too can initiate replication. As a result, many copies of the viral origin and flanking genomic sequences including the gene of interest are created. This higher copy number allows the cells to produce larger amounts of the gene of interest.

At some frequency, the replication product will recombine to form a circular molecule containing flanking genomic sequences, including the gene of interest. Cells that contain circular molecules with the gene of interest can be isolated by single cell cloning and analysis by Hirt extraction and Southern blotting. Once purified, the cell containing the episomal genomic locus at elevated copy number (typically 10–50 copies) can be propagated in culture. To achieve higher amplification, the episome can be further boosted by including a second origin adjacent to the first in the original construct. For example, T antigen can be used to boost the copy number of ori P/SV40 episomes to a copy number of ~1000 (Heinzel et al., *J. Virol.* 62:3738 (1988)). This substantial increase in copy number can dramatically increase protein expression.

The invention encompasses over-expression of endogenous genes both in vivo and in vitro. Therefore, the cells could be used in vitro to produce desired amounts of a gene product or could be used in vivo to provide that gene product in the intact animal.

The invention also encompasses the proteins produced by the methods described herein. The proteins can be produced from either known, or previously unknown genes. Examples of known proteins that can be produced by this method include, but are not limited to, erythropoietin, insulin, growth hormone, glucocerebrosidase, tissue plasminogen activator, granulocyte-colony stimulating factor, granulocyte/macrophage colony stimulating factor, interferon α, interferon β, interferon γ, interleukin-2, interleukin-6, interleukin-11, interleukin-12, TGF β, blood clotting factor V, blood clotting factor VII, blood clotting factor VIII, blood clotting factor IX, blood clotting factor X, TSH-β, bone growth factor 2, bone growth factor-7, tumor necrosis factor, alpha-1 antitrypsin, anti-thrombin III, leukemia inhibitory factor, glucagon, Protein C, protein kinase C, macrophage colony stimulating factor, stem cell factor, follicle stimulating hormone β, urokinase, nerve growth factors, insulin-like growth factors, insulinotropin, parathyroid hormone, lactoferrin, complement inhibitors, platelet derived growth factor, keratinocyte growth factor, neurotropin-3, thrombopoietin, chorionic gonadotropin, thrombomodulin, alpha glucosidase, epidermal growth factor, FGF, macrophage-colony stimulating factor, and cell surface receptors for each of the above-described proteins.

Where the protein product from the activated cell is purified, any method of protein purification known in the art may be employed.

Isolation of Cells Containing Activated Membrane Protein-Encoding Genes

Genes that encode membrane associated proteins are particularly interesting from a drug development standpoint. These genes and the proteins they encode can be used, for example, to develop small molecule drugs using combinatorial chemistry libraries and high through-put screening assays. Alternatively, the proteins or soluble forms of the proteins (e.g., truncated proteins lacking the transmembrane region) can be used as therapeutically active agents in humans or animals. Identification of membrane proteins can also be used to identify new ligands (e.g., cytokines, growth factors, and other effector molecules) using two hybrid approaches or affinity capture techniques. Many other uses of membrane proteins are also possible.

Current approaches to identifying genes that encode integral membrane proteins involve isolation and sequencing of genes from cDNA libraries. Integral membrane proteins are then identified by ORF analysis using hydrophobicity plots capable of identifying the transmembrane region of the protein. Unfortunately, using this approach a gene encoding an integral membrane protein can not be identified unless the gene is expressed in the cells used to produce the cDNA library. Furthermore, many genes are only expressed in very rare cells, during short developmental windows, and/or at very low levels. As a result, these genes can not be efficiently identified using the currently available approaches.

The present invention allows endogenous genes to be activated without any knowledge of the sequence, structure, function, or expression profile of the genes. Using the disclosed methods, genes may be activated at the transcription level only, or at both the transcription and translation levels. As a result, proteins encoded by the activated endogenous gene can be produced in cells containing the integrated vector. Furthermore, using specific vectors disclosed herein, the protein produced from the activated endogenous gene can be modified, for example, to include an epitope tag. Other vectors (e.g., vectors 12–17 described above) may encode a signal peptide followed by an epitope tag. This vector can be used to isolate cells that have activated expression of an integral membrane protein (see Example 5 below). This vector can also be used to direct secretion of proteins that are not normally secreted.

Thus, the invention also is directed to methods for identifying an endogenous gene encoding a cellular integral membrane protein or a transmembrane protein. Such methods of the invention may comprise one or more steps. For example, one such method of the invention may comprise (a) introducing one or more vectors of the invention into a cell; (b) allowing the vector to integrate into the genome of the cell by non-homologous recombination; (c) allowing over-expression of an endogenous gene in the cell by upregulation of the gene by the transcriptional regulatory sequence contained on the integrated vector construct; (d) screening the cell for over-expression of the endogenous gene; and (e) characterizing the activated gene to determine its identity as a gene encoding a cellular integral membrane protein. In related embodiments, the invention provides such methods further comprising isolating the activated gene from the cell prior to characterizing the activated gene.

To identify genes that encode integral membrane proteins, vectors integrated into the genome of cells will comprise a regulatory sequence linked to an exonic sequence containing a start codon, a signal sequence, and an epitope tag, followed by an unpaired splice donor site. Upon integration and activation of an endogenous gene, a chimeric protein is produced containing the signal peptide and epitope tag from the vector fused to the protein encoded by the downstream exons of the endogenous gene. This chimeric protein, by virtue of the presence of the vector encoded signal peptide, is directed to the secretory pathway where translation of the protein is completed and the protein is secreted. If, however, the activated endogenous gene encodes an integral membrane protein, and the transmembrane region of that gene is encoded by exons located 3' of the vector integration site, then the chimeric protein will go to the cell surface, and the epitope tag will be displayed on the cell surface. Using known methods of cell isolation (for example flow cytometric sorting, magnetic bead cell sorting, immunoadsorption, or other methods that will be familiar to one of ordinary skill in the art), antibodies to the epitope tag can then be used to isolate the cells from the population that display the epitope tag and have activated an integral membrane encoding gene. These cells can then be used to study the function of the membrane protein. Alternatively, the activated gene may then be isolated from these cells using any art-known method, e.g., through hybridization with a DNA probe specific to the vector-encoded exon to screen a cDNA library produced from these cells, or using the genetic constructs described herein.

The epitope tag encoded by the vector exon may be a short peptide capable of binding to an antibody, a short peptide capable of binding to a substance (e.g., poly histidine/divalent metal ion supports, maltose binding protein/maltose supports, glutathione S-transferase/glutathione support), or an extracellular domain (lacking a transmembrane domain) from an integral membrane protein for which an antibody or ligand exists. It will be understood, however, that other types of epitope tags that are familiar to one of ordinary skill in the art may be used equivalently in accordance with the invention.

Vectors for Non-targeted Activation of Endogenous Genes

As noted above, non-targeted gene activation has a number of important applications, including activating endogenous genes in host cells which provides a powerful approach to discovering and isolating new genes and proteins, and to producing large amounts of specific proteins for commercialization. For some applications of non-targeted gene activation, it is desirable to create libraries of cells in which each member of the library contains an activation vector integrated into a unique location in the host cell genome, and in which each member of the library has activated a different endogenous gene. Furthermore, it would be desirable to remove cells from the library that contain an integrated vector, but fail to activate an endogenous gene. Since eukaryotic genomes often contain large regions that lack genes, integration of an activation vector into a region devoid of genes can occur frequently. These integrated vectors, however, fail to activate an endogenous gene, and yet are capable of conferring drug resistance on the host cells when a selectable marker (driven by a suitable promoter and followed by a polyadenylation signal) is included on the activation vector. Even more problematic for gene discovery applications, a transcript containing vector sequences is produced in these cells regardless of whether or not a gene has been activated. In cases where a gene has not been activated, these vector sequence-containing transcripts contain non-genic genomic DNA sequences. As a result, when isolating activated genes, one cannot isolate all RNA (or cDNA) molecules that are derived from the integrated vector (i.e. transcripts containing vector sequences), since many of these transcripts do not encode an endogenous gene. To overcome these difficulties, the present invention provides highly specific vectors and methods that facilitate isolation of vector-activated genes.

These vectors of the invention are useful for activating expression of endogenous genes and for isolating the mRNA and cDNA corresponding to the activated genes. One such vector reduces the number of cells in which the vector integrated into the genome but failed to activate expression from (or transcription through) an endogenous gene. By removing these cells, fewer library members can be created and screened to isolate a given number of activated genes. Furthermore, vector-containing cells that fail to activate gene expression produce an RNA molecule that can interfere with isolation of bona fide activated genes. Thus, the vectors disclosed herein are particularly useful for producing cells suitable for protein over-expression and/or for isolating cDNA molecules corresponding to activated genes. The second type of vector of the invention is useful for isolating exon I from activated endogenous genes. As a result, these vectors can be used to obtain full-length genes from activated RNA transcripts. Each of the functional vector components described herein may be used separately, or in combination with each other.

Poly(A) Trap Activation Vectors

To facilitate isolation of activated genes, the present invention provides novel gene activation vectors that are capable of producing a drug resistant colony, preferentially upon activation of an endogenous gene. Such vectors are referred to herein as "poly(A) trap vectors." Examples of poly(A) trap vectors are shown in FIGS. 8A–8F. The nucleotide sequence of one such dual poly(A) trap vector, designated pRIG21b, is shown in FIGS. 15A–15B (SEQ ID NO:19). These vectors contain a transcriptional regulatory sequence (which may be any transcriptional regulatory sequence, including but not limited to the promoters, enhancers, and repressors described herein, and which preferably is a promoter or an enhancer, and most preferably a promoter such as a CMV immediate early gene promoter, an SV40 T antigen promoter, a tetracycline-inducible promoter, or a β-actin promoter) operably linked to a selectable marker gene lacking a poly(A) signal. Since the selectable marker gene lacks a polyadenylation signal, its message will not be stable, and the marker gene product will not be efficiently produced. However, if the activation vector integrates upstream of an endogenous gene, the selectable marker can utilize the polyadenylation signal of the endogenous gene, thereby allowing production of the selectable marker protein in sufficient amounts to confer drug resistance. Thus, cells that integrate this activation vector generally form a drug resistant colony only if an endogenous gene has been activated.

The poly(A) trap activation vectors can include any selectable or screenable marker. Furthermore, the selectable marker can be expressed from any promoter that is functional in the cells used to create the integration library. Thus, the selectable marker can be expressed by viral or non-viral promoters. Optionally, an unpaired splice donor site may be included in the construct, preferably 3' of the selectable marker to allow the exon encoding the selectable marker to be spliced directly to the exons of the endogenous gene. When a downstream transcriptional regulatory sequence and a splice donor site is included on the vector, the inclusion of a splice donor site adjacent to the selectable marker results in the removal of these downstream elements from the messenger RNA.

In a related embodiment, a second transcriptional regulatory sequence (which may be any transcriptional regulatory sequence, including but not limited to the promoters, enhancers, and repressors described herein, and which preferably is a promoter or an enhancer, and most preferably a promoter) may be located downstream of, and in the same orientation as, the selectable marker. Optionally, an unpaired splice donor site may be linked to the downstream transcriptional regulatory sequence. In this configuration, the poly(A) trap vector is capable of producing a message containing the downstream vector-encoded exon spliced to endogenous exons. As described below, these chimeric transcripts can be translated into native or modified protein, depending on the nature of the vector-encoded exon.

As used herein, a "vector-encoded exon" means a region of a vector downstream of the transcriptional regulatory sequence and between the transcription start site and the unpaired splice donor site found on the vector. The vector-encoded exon is present at the 5' end of the transcript containing the endogenous gene in the fully processed message. Analogously, as used herein, a "vector-encoded intron" is the region of the vector located downstream of the unpaired splice donor site. When a linearization site is present on the vector, the vector-encoded intron is the region of the vector that is downstream of the vector-encoded exon between the unpaired splice donor site and the linearization site. The vector-encoded intron is removed from the activated gene transcript during RNA processing.

Splice Acceptor Trap (SAT) Vectors

As an alternative approach for removing cells that fail to activate an endogenous gene, the invention provides additional vectors designated herein as "Splice Acceptor Trap" (SAT) vectors. These vectors are designed to splice from a vector encoded splice donor site to an endogenous splice acceptor. Furthermore, the vectors are designed to produce a product that is toxic to the host cells (or a product that can be selected against) if splicing does not occur. Thus, these vectors facilitate elimination of cells in which the vector-encoded exon failed to splice to an endogenous exon.

The splice acceptor trap vectors can contain both a positive selectable marker and a negative selectable marker gene oriented in the same direction on the vector. As used herein, a positive selectable marker is a gene that, upon expression, produces a protein capable of facilitating the isolation of cells expressing the marker. Analogously, as used herein, a negative selectable marker is a gene that, upon expression, produces a protein capable of facilitating removal of cells expressing the marker.

The positive selectable marker and the negative selectable marker are preferably separated in the vector construct by an unpaired splice donor site. In other embodiments, however, the positive selectable marker may be fused to the negative selectable marker gene. In this configuration, an unpaired splice donor site is located between the positive and negative selectable marker, such that the reading frame of the negative selectable marker is preserved. The unpaired splice donor site is preferably located at the junction of the positive and negative selectable markers. However, the unpaired splice donor site may be located anywhere in the fusion gene such that upon splicing to an endogenous splice acceptor site, the positive selectable marker will be expressed in an active form and the negative selectable marker will be expressed in an inactive form, or not at all. In this configuration, the positive selectable marker is located upstream of the negative selectable marker.

It will also be apparent to one of ordinary skill in view of the description contained herein that the positive and negative selectable markers on the SAT vector need not be expressed as a fusion protein. In one embodiment, an internal ribosomal entry site (ires) is inserted between the positive selectable marker and the negative selectable marker. In this configuration, the unpaired splice donor site can be positioned between the two markers, or in the open reading frame of either marker gene such that, upon splicing, the positive selectable marker will be expressed in an active form and the negative selectable marker will be expressed in an inactive form, or not at all. In another embodiment, the positive selectable marker may be driven from a different transcriptional regulatory sequence than the negative selectable marker. In this configuration, the unpaired splice donor site is located in the 5' untranslated region of the negative selectable marker or anywhere in the open reading frame of the negative selectable marker such that, upon splicing, the negative selectable marker will be produced in an inactive form or not at all. Furthermore, when the positive and negative markers are driven from different transcriptional regulatory sequences, the positive selectable marker may be located upstream or downstream of the negative selectable marker, and the positive selectable marker may contain or lack a splice donor site at its 3' end.

The vectors described herein may contain any positive selectable marker. Examples of positive selectable markers useful in this invention include genes encoding neomycin (neo), hypoxanthine phosphoriosyl transferase (HPRT), puromycin (pac), dihydro-oratase, glutamine synthetase (GS), histidine D (his D), carbamyl phosphate synthase (CAD), dihydrofolate reductase (DHFR), multidrug resistance 1 (mdr1), aspartate transcarbamylase, xanthine-guaninephosphoribosyl transferase (gpt), and adenosine deaminase (ada). Alternatively, the vectors may contain a screenable marker in place of the positive selectable marker. Screenable markers include any protein capable of producing a recognizable phenotype in the host cell. Examples of screenable markers included cell surface epitopes (such as CD2) and enzymes (such as β-galactosidase).

The vectors described herein may also, or alternatively, contain any negative selectable marker that can be selected against. Examples of negative selectable markers include hypoxanthine phosphoribosyl transferase (HPRT), thymidine kinase (TK), and diptheria toxin. The negative selectable marker can also be a screenable marker, such as a cell surface protein or an enzyme. Cells expressing the negative screenable marker may be removed by, for example, Fluorescence Activated Cell Sorting (FACS) or magnetic bead cell sorting.

To isolate cells that have activated expression of an endogenous gene, the cells containing the integrated vector can be placed under the appropriate drug selection. Selection for the positive selectable marker and against the negative selectable marker can occur simultaneously. In another embodiment, selection can occur sequentially. When selection occurs sequentially, selection for the positive selectable marker can occur first, followed by selection against the negative selectable marker. Alternatively, selection against the negative selectable marker can occur first, followed by selection for the positive selectable marker.

The positive and negative markers are expressed by a transcriptional regulatory element located upstream of the translation start site of each gene. When a positive/negative marker fusion gene or an ires sequence is used, a single transcriptional regulatory element drives expression of both markers. A poly(A) signal may be placed 3' of each selectable marker. If a positive/negative fusion gene is used a single poly(A) signal is positioned 3' of the markers. Alternatively, a poly(A) signal may be excluded from the vector to provide additional specificity for a gene activation event (see dual poly(A)/splice acceptor trap below).

Dual Poly(A)/Splice Acceptor Trap Vectors

To further reduce the number of cells that lack a gene activation event, the invention also provides vectors that confers host cell survival only if the vector-encoded exon has spliced to an exon from an endogenous gene and has acquired a poly(A) signal. These vectors are designated herein as "dual poly(A)/splice acceptor trap vectors" or as "dual poly(A)/SAT vectors." By requiring both splicing and polyadenylation to occur for cell survival, cells that fail to activate an endogenous gene are more efficiently eliminated from the activation library.

The dual poly(A)/splice acceptor trap vectors contain a positive selectable marker and a negative selectable marker configured as described for the SAT vectors; however, neither gene contains a functional poly(A) signal. Thus, the positive selectable marker will not be expressed at high levels unless splicing occurs to capture an endogenous poly(A) signal. Aside from the lack of a poly(A) signal, all other features and embodiments of this type of vector are the same as those of the SAT vectors as described herein. Examples of dual poly(A)/SAT vectors are shown in FIGS. 9A–9F and 10A–10F. The nucleotide sequence of one such dual poly(A)/SAT vector, designated pRIG22b, is shown in FIGS. 16A–16B (SEQ ID NO:20).

Vectors for Activating Protein Expression from Endogenous Genes

In many applications of non-targeted gene activation, it is desirable to produce protein from the activated endogenous gene. To accomplish this, a second transcriptional regulatory sequence (which may be any transcriptional regulatory sequence, including but not limited to the promoters, enhancers, and repressors described herein, and which is preferably a promoter or an enhancer, and most preferably a promoter) can be placed downstream of the selectable marker(s) on any of the vectors described herein. When poly(A) trap vectors, SAT vectors, or dual poly(A) trap/SAT vectors are used, the downstream transcriptional regulatory sequence is positioned to drive expression in the same direction as the upstream selectable marker(s). To activate expression of full-length protein with this type of vector, however, the vector must integrate into the 5' UTR of the endogenous gene to avoid cryptic start ATG codons upstream of exon I.

Alternatively, to increase the frequency of protein expression using non-targeted gene activation, the downstream transcriptional regulatory sequence on the vector may be operably linked to an exonic sequence followed by a splice donor site. In a preferred embodiment, the vector exon lacks a start codon. This vector is particularly useful for activating protein expression from genes that do not encode the translation start codon in exon I. In an alternative preferred embodiment, the vector exon contains a start codon. Additional codons can be located between the translational start codon and the splice donor site. For example, a partial signal secretion sequence can be encoded on the vector exon. The partial signal sequence can be any amino acid sequence capable of complementing a partial signal sequence from an endogenous gene to produce a functional signal sequence. The partial sequence may encode between one and one hundred amino acids, and may be derived from existing genes, or may consist of novel sequences. Thus, this vector is useful for producing and secreting protein from genes that encode part of the endogenous signal sequence in exon I, and the remainder in subsequent exons. In another example of a vector useful for activating a particular type of endogenous gene, a functional signal sequence can be encoded on the vector exon. This vector allows protein to be produced and secreted from genes that encode a signal sequence in exon I. It can also be used to produce secreted forms of proteins that are not normally secreted.

In cases where a start codon is included on the vector exon, it can be advantageous to produce a vector in each reading frame. This is achieved by varying the number of nucleotides between the start codon and the splice donor junction site. Together, the preferred vector configurations are capable of producing protein from endogenous genes, regardless of the exon/intron structure, location of the translation start codon, or reading frame.

Vectors for Isolating Exon I from Activated Endogenous Genes

The non-targeted gene activation vectors described above are useful for activating and isolating endogenous genes and for producing protein from endogenous genes. Upon integration upstream of an endogenous gene, however each of these vectors produces a transcript that lacks exon I from the endogenous gene. Since the vectors are designed to produce a transcript containing the vector encoded exon spliced to the first splice acceptor site downstream of the vector integration site, and since the first exon of eukaryotic genes does not contain a splice acceptor site, normally, the first exon of endogenous genes will not be recovered on mRNA molecules derived from non-targeted gene activation. For some genes, such as genes that contain coding information in the first exon, there is a need to efficiently recover the first exon of the activated endogenous gene.

Figure 13:
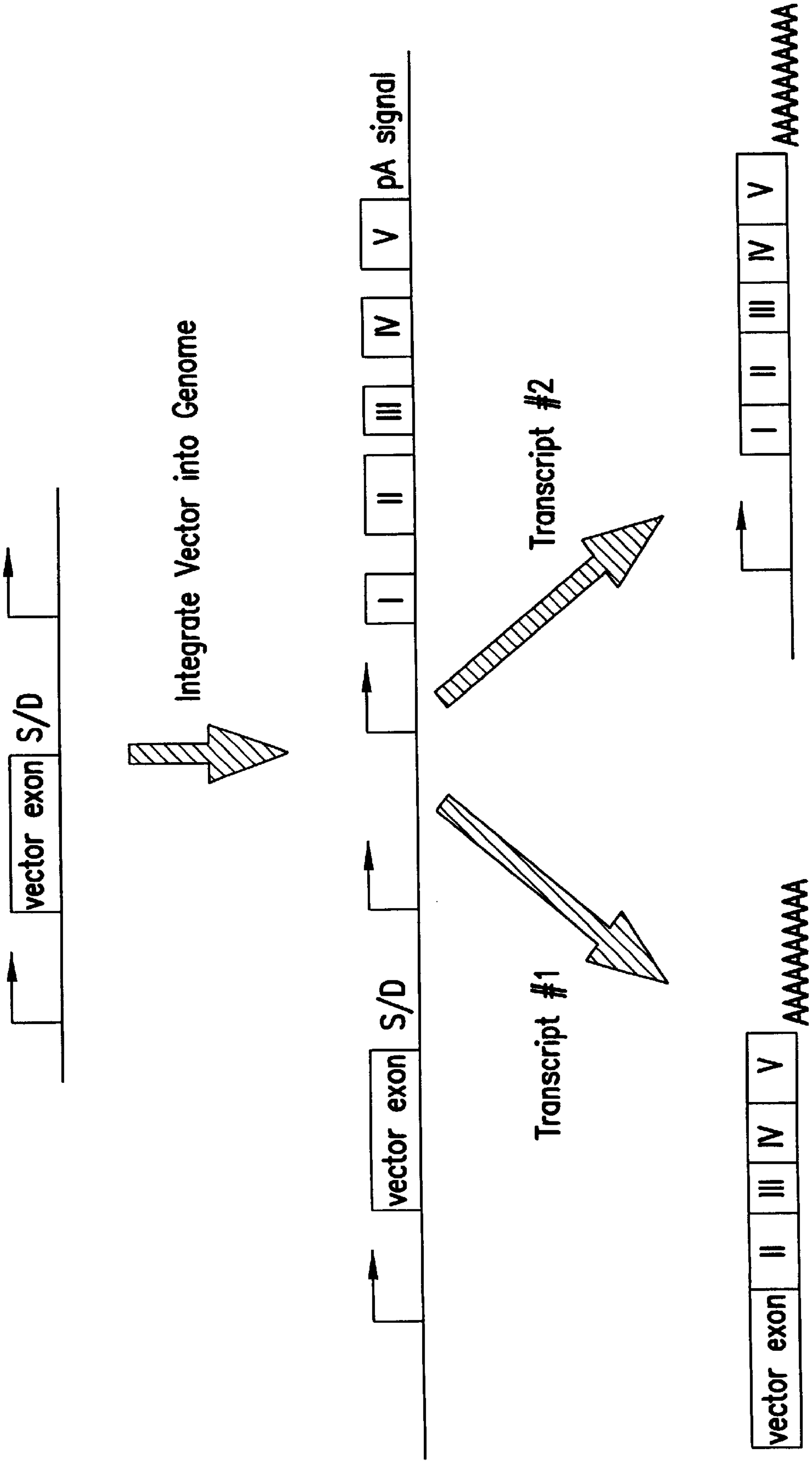
FIG. 13. Illustration depicting two transcripts produced from the integrated vectors described in FIGS. 12A–12G. DNA strands are depicted as horizontal lines. Vector DNA is shown as a black line. Endogenous genomic DNA is shown as a grey line. Rectangles depict exons. Vector-encoded exons are shown as open rectangles, while endogenous exons are shown as shaded boxes. S/D denotes a splice donor site. Following integration, the vector encoded promoters activate transcription of the endogenous gene. Transcription resulting from the upstream promoter produces a spliced RNA molecule containing the vector encoded exon joined to the second and subsequent exons from an endogenous gene. Transcription from the downstream promoter, on the other hand, produces a transcript containing the sequences downstream of the integrated joined to exon I and the subsequent exons from an endogenous gene.
Figure 17A:
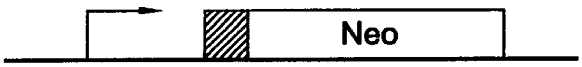
FIGS. 17A–17G. Examples of poly(A) trap vectors. Each vector is illustrated schematically in its linearized form. Each horizontal line represents a DNA molecule. The arrows denote promoter sequences located on the DNA molecule, and face in the direction of transcription. Transcribed regions include all sequences located downstream of a promoter. Boxes indicate exons. Hatched boxes indicate untranslated regions. The following designations were used: splice donor site (S/D), signal secretion sequence (SP), epitope tag (ET), neomycin resistance gene (Neo), vector promoter #1 (VP#1), and vector promoter #2 (VP#2). As shown in the vectors depicted in FIGS. 17C–17G, a promoter operably linked to an exon and an unpaired splice donor site can be positioned upstream of the selectable marker. It is recognized that this exon, when present, may encode codons a start codon in any reading frame relative to the splice donor site. To activate protein expression from genes with different reading frames, three separate vectors can be used, each with a start codon in a different reading frame relative to the splice donor site.
Figure 17B:
Figure 17C:
Figure 17D:
Figure 17E:
Figure 17F:
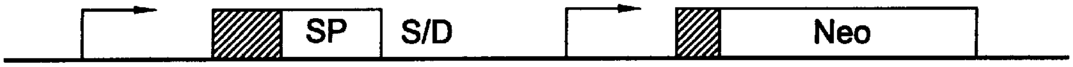
Figure 17G:

To recover the first exon of activated endogenous genes, a transcriptional regulatory sequence (which may be any transcriptional regulatory sequence, including but not limited to the promoters, enhancers, and repressors described herein, and which is preferably a promoter or an enhancer, and most preferably a promoter) is included on the activation vector downstream of a second transcriptional regulatory sequence (which may also be any transcriptional regulatory sequence, including but not limited to the promoters, enhancers, and repressors described herein, and which is preferably a promoter or an enhancer, and most preferably a promoter) which drives expression of a vector encoded exon. Thus, the upstream transcriptional regulatory sequence is linked to an unpaired splice donor site and the downstream transcriptional regulatory sequence is not linked to a splice donor site. Both transcriptional regulatory sequences are oriented to drive expression in the same direction. Examples of such exon I recovery vectors are shown in FIGS. 12A–12G. The integration of this type of vector will create at least two different types of RNA transcripts (FIG. 13). The first transcript is derived from the upstream transcriptional regulatory sequence and contains the vector exon spliced to exon II of an endogenous gene. The second transcript is derived from the downstream transcriptional regulatory sequence and contains, from 5' to 3', the region between the vector and the transcription start site of the gene, exon I, exon II, and all downstream exons. Using methods described herein, both transcripts can be recovered and analyzed, allowing the characterization of exon I from genes isolated by non-targeted gene activation.

The exon located on the activation vector can encode a selectable marker, a protein, a portion of a protein, secretion signal sequences, a portion of a signal sequence, an epitope, or nothing. When a protein is encoded by the exon, a poly(A) signal may be included downstream of the vector encoded gene. Alternatively, a poly(A) signal may be omitted. In another embodiment, a positive and negative selectable marker may be operably linked to the upstream transcriptional regulatory sequence(s). In this embodiment, the position of the unpaired splice donor site relative to the selectable markers is described above for the SAT vectors and the dual poly(A)/SAT vectors.

Gene Activation Vectors for Single-Exon and Multi-Exon Gene Trapping

As noted above, in one embodiment the poly(A) trap vectors of the invention may contain a promoter operably linked to a selectable marker followed by an unpaired splice donor site. Such vectors, when integrated into or near a gene, produce transcripts containing the selectable marker spliced onto an endogenous gene. Since the endogenous gene encodes a poly(A) signal, the resulting mRNA is polyadenylated, thereby allowing the transcript to be translated at levels sufficient to confer drug resistance on the cell containing the integrated vector.

While the vectors described above are capable of "trapping" endogenous genes, the splice donor site downstream of a selectable marker cannot be used in, and in some cases can interfere with, several potential applications for such vectors. First, these vectors cannot be used to selectively trap single exon genes, since these genes do not contain a splice acceptor site. Second, these vectors often "trap" cryptic genes, since drug resistance relies solely on vector integration upstream of a poly (A) signal. Unfortunately, cryptic poly (A) signals exist in the genome, leading to formation of drug resistant cells and creation of non-genic transcripts containing the selectable marker. These cells and transcripts can interfere with gene discovery applications using these vectors. Third, without novel modifications such as those described herein (see above), these vectors are not capable of efficiently producing protein from the activated endogenous gene. Furthermore, protein expression from an endogenous gene can be poor even when an internal ribosome entry site (ires) is included between the selectable marker and the splice donor site, since translation from an ires is generally less efficient than translation from the first start codon at the 5' end of a transcript. Thus, there is a need for vectors that are capable of more specifically trapping endogenous genes, including single exon genes, and that are capable of efficiently expressing protein from the activated endogenous genes.

Thus, in additional embodiments, the present invention provides such vectors. In one such embodiment, the vector may contain a promoter operably linked to one or more (i.e., one, two, three, four, five, or more) selectable markers, wherein the selectable marker is not followed by a splice donor site or a poly(A) signal (see FIGS. 17A–17G). In general, upon integration into a host cell genome, this vector will fail to produce sufficient quantities of selectable marker since the marker transcript will not be polyadenylated.

However, if the vector integrates in close proximity to, or into, a gene, including a single exon gene, the selectable marker will acquire a poly(A) signal from the endogenous gene, thereby stabilizing the marker transcript and conferring a drug resistant phenotype on the cell. In addition to selecting for vector integration into or near genes, vectors according to this aspect of the invention can also be used to recover exon I from the activated gene, as described in the section of this application entitled "Vectors for Isolating Exon I from Activated Endogenous Genes."

Figure 18:
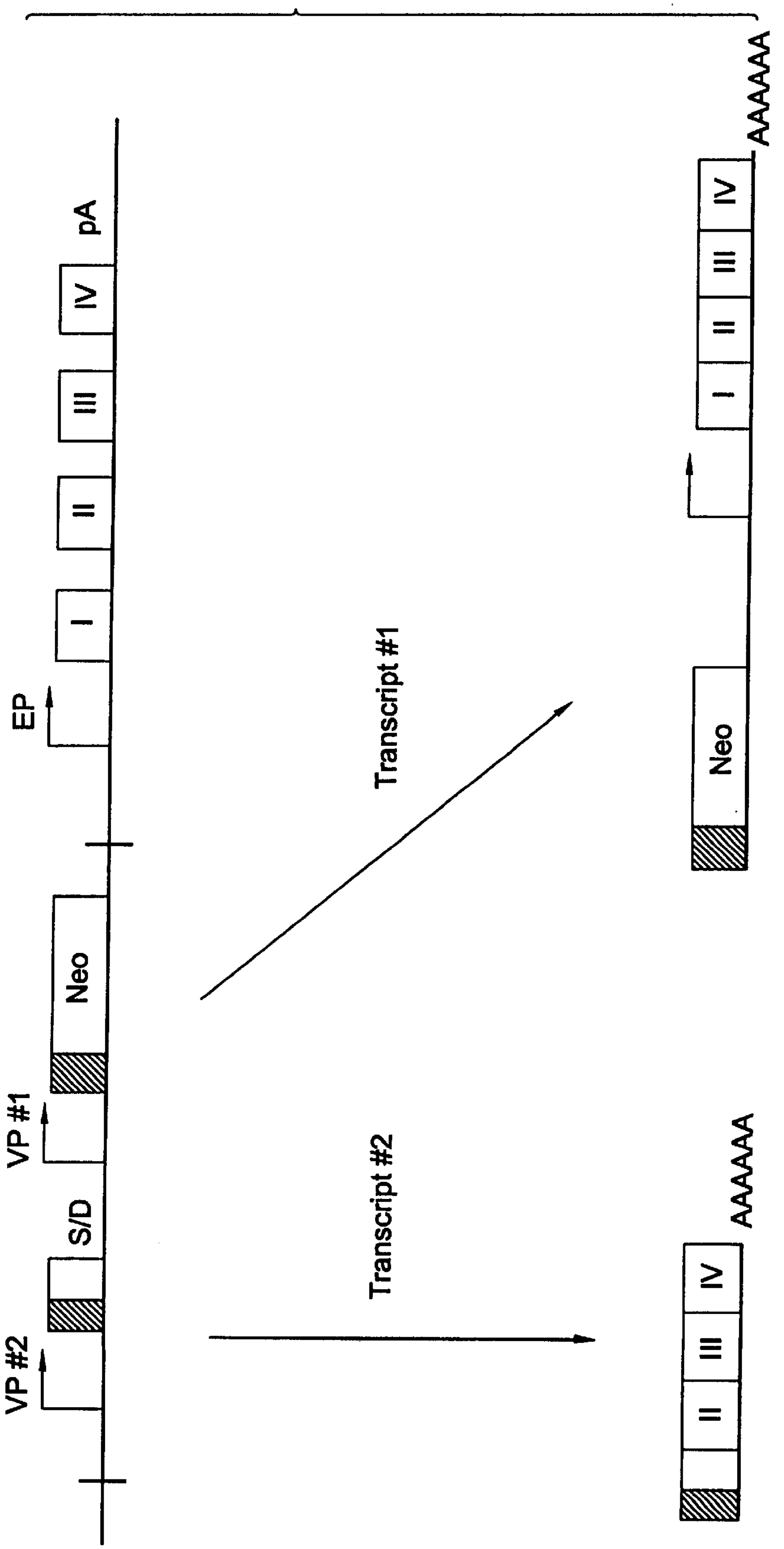
FIG. 18. Illustration of the transcripts produced by the vector from FIG. 17C upon integration into a host cell genome upstream of a multi-exon endogenous gene. Each horizontal line represents a DNA molecule. Vertical lines running through the DNA strand mark the upstream and downstream vector/cellular genome boundaries. The arrows denote promoter sequences located on the DNA molecule, and face in the direction of transcription. Transcribed regions include all sequences located downstream of a promoter. Boxes indicate exons. Hatched boxes indicate untranslated regions. The endogenous exons are numbered using roman numerals. The following designations were used: splice donor site (S/D), neomycin resistance gene (Neo), vector promoter #1 (VP#1), vector promoter #2 (VP#2), endogenous promoter (EP) and polyadenylation signal (pA). Following integration, vector promoter #1 expresses a chimeric transcript containing the Neo gene linked to the genomic sequences downstream of the integration site, including the processed (spliced) exons from the endogenous gene. Since transcript #1 contains a poly (A) signal from the endogenous gene, the Neo gene product will be efficiently produced, thereby conferring drug resistance on the cell. In addition to transcript #1, the integrated vector will generate a second transcript, designated transcript #2, originating from vector promoter #2. The structure of transcript #2 facilitates efficient translation of the protein encoded by the endogenous gene. As exemplified in FIG. 17, vectors containing alternative coding information in the vector encoded exon can be used to produce different chimeric proteins, containing, for example, signal sequences and/or epitope tags.

In a preferred embodiment, the vector can contain a second selectable marker upstream of the first selectable marker (see FIG. 18). The upstream selectable marker is preferably operably linked to a transcriptional regulatory sequence, most preferably a promoter. Optionally, an unpaired splice donor site can be positioned between the transcription start site and the translation start site of the upstream selectable marker. Alternatively, the splice donor site may be located anywhere in the open reading frame of the upstream selectable marker, such that, following vector integration into a host cell genome, and upon splicing from the vector encoded splice donor site to an endogenous exon, the upstream selectable marker will be produced in an inactive form, or not at all. By selecting for cells that produce the downstream positive selectable marker in an active form, cells containing the vector integrated into or near a gene can be isolated. Furthermore, by selecting against cells producing the upstream selectable marker in the active form, cells in which the vector transcript has spliced to an exon from a multi-exon endogenous gene can be removed. In other words, these vectors can be used to isolate cells that contain a vector integrated into a single exon gene or into the 3' most exon of a multi-exon gene since, in these instances, a splice acceptor site is absent between the vector encoded splice donor site and the endogenous poly (A) signal. Thus, the majority of cells containing activated multi-exon genes will not survive selection, and as a result, cells containing activated single exon genes will be greatly enriched in the library.

Figure 19:
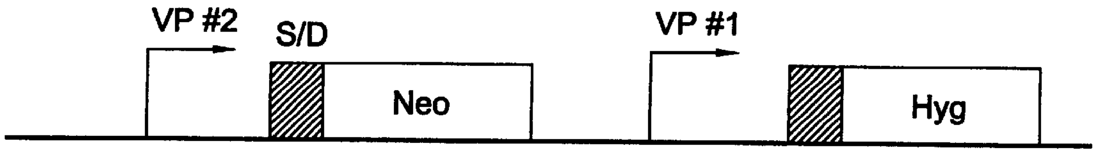
FIG. 19. Example of dual positive selectable marker vector. The vector is illustrated schematically in its linearized form. The horizontal line represents a DNA molecule. The arrows denote promoter sequences located on the DNA molecule, and face in the direction of transcription. Transcribed regions include all sequences located downstream of a promoter. Boxes indicate exons. Hatched boxes indicate untranslated regions. Poly(A) signals are not present in these examples. The following designations were used: splice donor site (S/D), hygromycin resistance gene (Hyg), neomycin resistance gene (Neo), vector promoter #1, and vector promoter #2.
Figure 20A:
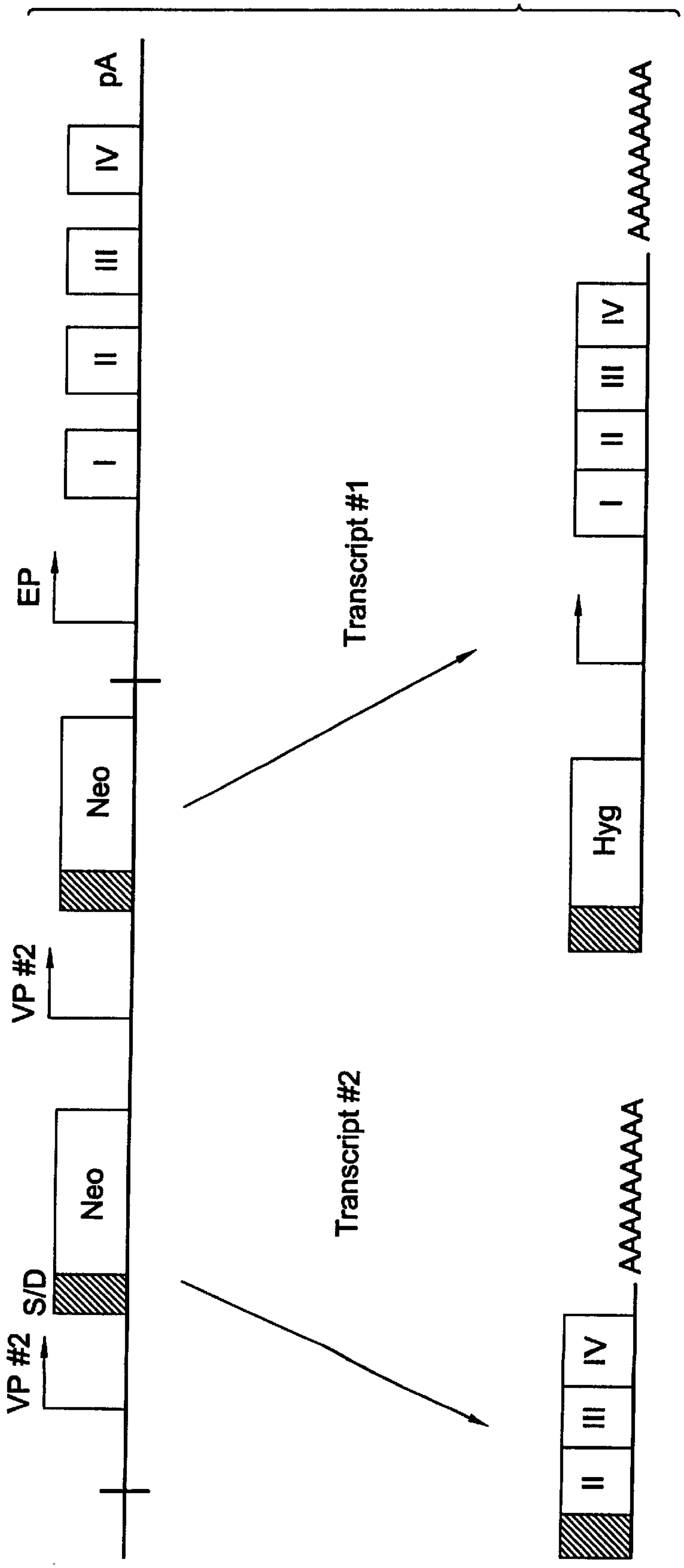
FIGS. 20A–20B. Examples of transcripts produced by a dual positive selectable marker vector integrated into a host cell genome adjacent to an endogenous gene.
Figure 20B:
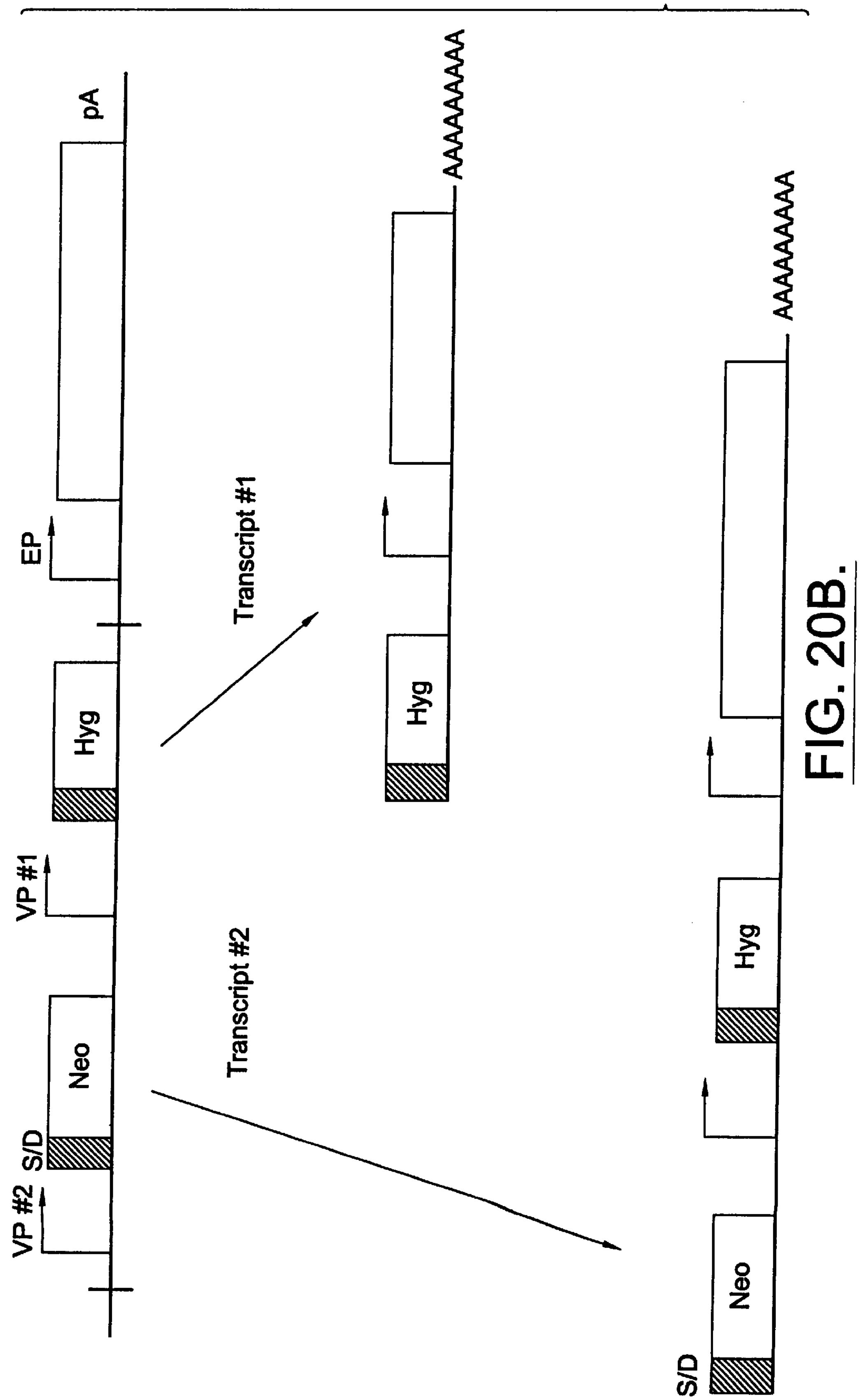

In another preferred embodiment, vectors according to this aspect of the invention may contain one or more (i.e., one, two, three, four, five, or more, and preferably one) negative selectable marker(s) upstream of the first selectable marker (see FIGS. 19A and 19B). The negative selectable marker preferably is operably linked to a promoter. Optionally, an unpaired splice donor site may be positioned between the transcription start site and the translation start site of the negative selectable marker. Alternatively, the splice donor site may be located anywhere in the open reading frame of the negative selectable marker, such that, following vector integration into a host cell genome, and upon splicing from the vector encoded splice donor site to an endogenous exon, the negative selectable marker will be produced in an inactive form, or not at all. By selecting for cells that produce the positive selectable marker in an active form and selecting against cells producing the negative selectable marker in the active form, these vectors can be used to identify cells containing the vector integrated into or upstream of an endogenous gene. Since (1) splicing to an endogenous exon and (2) acquisition of a poly (A) signal are both required for cell survival, cells containing cryptic gene trap events are reduced within the library. The reason for this is that the probability of a vector integrating next to both a cryptic splice acceptor site and a cryptic poly (A) signal is substantially less than the probability of the vector integrating next to a single cryptic site. Thus, these vectors provide a higher degree of specificity for trapping genes than previous vectors.

It will also be recognized by one of ordinary skill in view of the teachings contained herein that vectors containing positive and negative selectable markers can be used to produce protein from the activated endogenous gene. One vector configuration capable of directing protein production consists of the splice donor site positioned in the 5' UTR of the negative selectable marker. Upon splicing, a chimeric transcript containing the 5' UTR from the negative selectable marker linked to the second exon of an endogenous gene is produced. This vector is capable of activating protein production from genes that encode a translation start codon in the second or subsequent exon. Likewise, the splice donor site can be placed in the open reading frame of the negative selectable marker, in a position that does not interfere with the function of the marker unless splicing has occurred. Similar vectors containing the splice donor site positioned in different reading frames relative to the translation start codon can also be used. Upon splicing to an endogenous gene, these vectors will produce a chimeric transcript containing a start codon from the negative selectable marker fused to exon II of the activated endogenous gene. Thus, these vectors will be capable of activating protein expression from genes that encode a translation start codon in exon I. Additional positive/negative selection vector designs capable of efficiently producing protein from activated endogenous genes are described below.

Any of the vectors of the invention can contain an internal ribosome entry site (ires) 3' of the downstream selectable marker. The ires allows translation of the endogenous gene upon vector integration into an endogenous gene. Optionally, a translation start codon may be included between the selectable marker and the ires sequence. When a start codon is present, additional codons may be present on the exon. The start codon, and if present additional codons, may be present in any, and collectively all, reading frames relative to the splice donor site. Furthermore, the codons downstream of the translation start codon, if present, may encode, for example, a signal secretion signal, a partial signal sequence, a protein (including a full-length protein, a portion of a protein, a protein motif, an epitope tag, etc.), or a spacer region.

In additional preferred embodiments, any of the vectors described herein may contain, upstream of the selectable marker(s), a second transcriptional regulatory sequence (most preferably a promoter) operably linked to a exonic region, followed by an unpaired splice donor site. This upstream exon is particularly useful for expressing protein from activated endogenous genes. The exon may lack a translation start codon. Alternatively, the exon may contain a translation start codon. When a start codon is present, additional codons may be present on the exon. The start codon, and if present additional codons, may be present in any, and collectively all, reading frames relative to the splice donor site. Furthermore, the codons downstream of the translation start codon, if present, may encode, for example, a signal secretion sequence, a partial signal sequence, a protein (including a full-length protein, a portion of a protein, a protein motif, an epitope tag, etc.), or a spacer region.

Activation Vectors Useful for Detecting Protein-protein Interactions

Genetic approaches for detecting protein-protein interactions have previously been described (see, e.g., U.S. Pat. Nos. 5,283,173; 5,468,614; and 5,667,973, the disclosures of which are fully incorporated herein by reference). This approach relies on cloning a first cDNA molecule next to, and in frame with, a gene fragment encoding a DNA binding domain; and cloning a second cDNA molecule next to, and in frame with, a gene fragment encoding a transcription transactivation domain. Each chimeric gene is expressed from a promoter region located upstream of the chimeric gene. To detect expression, both chimeric genes are transfected into a reporter cell. If the first chimeric protein interacts with the second chimeric protein (via the proteins encoded by the cloned cDNA's fused to the DNA binding and transcription activation domains), then the DNA binding domain and the transcription activation domain will be joined within a single protein complex. As a result, the protein-protein interaction complex can bind to the regulatory region of the reporter gene and activate its expression.

A limitation of this previous approach is that it is only capable of detecting protein-protein interactions between genes that have been cloned as cDNA. As described herein, many genes are expressed at very low levels, in rare cell types, or during short developmental windows; and therefore, these genes are typically absent from cDNA libraries. Furthermore, many genes are too large to be isolated efficiently as full-length clones, thereby making it difficult to use these previous approaches.

The present invention is capable of activating protein expression from endogenous genes or from transfected genomic DNA. Unlike previous approaches, virtually any gene can be efficiently expressed, regardless of its normal expression pattern. Furthermore, since the present invention is also capable of modifying the protein expressed from the endogenous gene (or from the transfected genomic DNA), it is also possible to produce chimeric proteins for use in protein-protein interaction assays.

To detect protein-protein interactions by the present invention, two vectors are used. The first vector, generally referred to as BD/SD (binding domain/splice donor), contains a promoter operably linked to a polynucleotide encoding a DNA binding domain and an unpaired splice donor site. The second vector, generally referred to as AD/SD (activation domain/splice donor), contains a promoter operably linked to a polynucleotide encoding a transcription activation domain and an unpaired splice donor site. To accommodate genes that have different reading frames, the binding domain and activation domain can be encoded in each of the three possible reading frames relative to the unpaired splice donor site. In addition, BD/SD and AD/SD vectors can have other functional elements, as described herein for other vectors, including selectable markers and amplifiable markers. The vectors may also contain selectable markers oriented in a configuration that permits selection for cells in which the vector has activated a gene. Multi-promoter/activation exon vectors are also useful. Several examples of BD/SD and AD/SD vectors are illustrated in FIG. 25. An example illustrating detection of a protein-protein interaction using these vectors is depicted in FIG. 26.

The DNA binding domain of the BD/SD vector may encode any protein domain capable of binding to a specific nucleotide sequence. When a transcription activation protein is used to supply the DNA binding domain, the transcription activation domain is omitted from the BD/SD vector. Examples of genes encoding proteins with DNA binding domains include, but are not limited to, the yeast GAL4 gene, the yeast GCN4 gene, and the yeast ADR1 gene. Other genes from prokaryotic and eukaryotic sources may also be used to supply DNA binding domains.

The transcription activation domain of the AD/SD vector encodes a protein domain capable of enhancing transcription of a reporter gene when positioned near the promoter region of the reporter gene. When a transcription activation protein is used to supply the transcription activation domain, the DNA binding domain is omitted from the AD/SD vector. Examples of genes encoding proteins with transcription activation domains include, but are not limited to, the yeast GAL4 gene, the yeast GCN4 gene, and the yeast ADR1 gene. Other genes from prokaryotic and eukaryotic sources may also be used to supply transcription activation domains.

In the present invention, protein-protein interactions are detected using the BD/SD and AD/SD vectors, described above, to activate expression of genes located in stretches of genomic DNA.

In one embodiment, the BD/SD vector is integrated randomly into the genome of a reporter cell line. As with other vectors described herein, the BD/SD vectors are capable of activating protein expression from genes located downstream of the vector integration site. Since the activation exon on the BD/SD vector encodes a DNA binding domain, the activated endogenous protein will be produced as a fusion protein containing the DNA binding domain at its N-terminus. Thus, by integrating the BD/SD vector into the genome of a host cell, a library of fusion proteins can be created, wherein each protein will contain a DNA binding domain at its N-terminus.

It is also recognized that the AD/SD vector can be integrated into the genome of a reporter cell line to produce a library of cells, wherein each member of the library is expressed as a different endogenous gene fused to a transcription activation domain.

Once created, the BD/SD library may be transfected with a vector expressing a specific gene (referred to below as gene X) fused to a transcription activation domain. This allows virtually any gene encoded in the genome to be tested for an interaction to gene X. Likewise, the AD/SD library may be transfected with a vector expressing a specific gene (e.g. gene X) fused to a DNA binding domain. This allows virtually any gene encoded in the genome to be tested for an interaction to gene X. It is also recognized that the specific gene may be stably expressed in the host cell prior to construction of the BD/SD or AD/SD libraries.

In an alternative embodiment, genomic DNA is cloned into the BD/SD and/or AD/SD vector(s) downstream of the DNA binding domain and activation domain, respectively. If a gene is present and correctly oriented in the genomic DNA, then the BD/SD vector (or the AD/SD vector) will be capable of expressing the gene as a fusion protein useful for detecting protein-protein interactions. Like integration of BD/SD (or AD/SD) vectors in situ, any gene can be tested regardless of whether it has been previously isolated as a cDNA molecule.

In another embodiment, a second library is created in the cells of the first library. For example, the AD/SD vector can be integrated into cells comprising the BD/SD library. Conversely, the BD/SD vector can be integrated into cells comprising the AD/SD library. This allows all proteins expressed as binding domain fusion proteins to be tested against all activation domain fusion protein. Since the present invention is capable of expressing substantially all of the proteins (as fusions with the binding and activation domains) in a eukaryotic organism, this approach, for the first time, allows all combinations of protein-protein interactions to be tested in a single library. To survey all protein-protein interactions in an organism, the library within a library must be substantially comprehensive. For example, to detect ~50% of protein-protein interactions in an organism containing 100,000 genes, the first library must contain at least 100,000 cells, each expressing an activated gene. Within each clone of the first library, the second vector would then be used to create a library of at least 100,000 clones, each containing an activated gene. Thus, the total library would contain 100,000 clones×100,000 clones, or $10^{10}$ total clones. This assumes all genes are activated at equal frequencies, and that each gene activation event results in production of a fusion protein in frame with the activated endogenous gene. To produce libraries with greater than 50% coverage of protein-protein interactions, and/or to ensure that proteins that are activated at lower frequencies are represented, larger libraries can be created.

It is also recognized that library vs. library screens can be created in several ways. First, both libraries are produced, simultaneously or sequentially, by integrating BD/SD and AD/SD vectors into the genome of the same reporter cells. Second, a first library is created by integrating a BD/SD vector into the genome of a reporter cell, and a second library is produced by transfecting the AD/SD vector containing cloned genomic DNA. It is recognized that in this approach, the AD/SD library may be created first, followed by introduction of a BD/SD vector containing cloned genomic DNA. It is also recognized that the first library can be created by transfecting the BD/SD vector (or AD/SD vector) containing cloned genomic DNA, followed by integrating the second vector into the reporter cell genome. Third, both libraries are created, simultaneously or sequentially, by transfecting cells with a BD/SD and AD/SD vectors, wherein each vector contains a cloned fragment of genomic DNA. Fourth, it is recognized that when cloned genomic fragments are used in either the BD/SD vector or the AD/SD vector, a cDNA library may be created in the other vector and introduced into cells. This allows all of the genes present in the cDNA library to be tested for interaction with all other genes in the genome.

Since library/library screens involve the creation of large libraries of cells, it is important to maximize the frequency of gene activation and in frame fusion protein production among the members of the library. This can be accomplished in at least two ways. First, the BD/SD and AD/SD vectors can contain selectable markers in a configuration that "traps" genes. Examples of selection trap vectors are shown in FIGS. 8, 9, 10, 17, 19, 21, and 25. These vectors select for cells in which the activation vector has transcriptionally activated a gene. Second, multiple promoter/activation exon units can be included on the BD/SD and AD/SD vectors. Each promoter/activation exon unit encodes the binding domain (or activation domain) in a different reading frame relative to the unpaired splice donor site. An example of a multi-promoter/exon vector is illustrated in FIG. 23. This type of vector ensures that any gene activated at the transcription level will be produced as an in frame fusion protein from on of the promoter/activation exon units on the vector. Third, the vectors can be introduced into the reporter cells using efficient transfection procedures. In this respect, insertion of BD/SD and AD/SD vectors by retroviral integration is advantageous.

Reporter cells useful in the present invention include any cell that is capable of properly splicing the transcripts produced by the BD/SD and AD/SD vectors. The reporter cells contain a reporter gene that is expressed at higher levels in the presence of a protein-protein interaction between proteins expressed from BD/SD and AD/SD vectors. The reporter gene may be a selectable marker, such as any of the markers described herein. Alternatively, the reporter gene may be a screenable marker. Examples of useful selectable markers and screenable markers are described herein.

In the reporter cells, a minimal promoter is operably linked to the reporter gene. To allow increased expression of the reporter gene in the presence of a protein-protein interaction, a DNA binding site is positioned in or near the minimal promoter, such that the DNA binding site is recognized by the protein encoded by the DNA binding domain region of the BD/SD vector. In the absence of a protein-protein interaction, the DNA binding domain fusion protein produced from BD/SD lacks a transcription activation domain, and therefore, can not activate transcription from the minimal promoter of the reporter gene. If, however, the DNA binding domain fusion protein produced from BD/SD interacts with the activation domain fusion protein produced from the AD/SD vector, then the protein complex can activate expression of the reporter gene. Increased reporter gene expression can be detected using an assay for the screenable marker, or using drug selection for a selectable marker.

It is also recognized that other reporter systems can be used in conjunction with the present invention to detect protein-protein interactions. Specifically, any protein that contains two separable domains, each required to be in close proximity with the other to produce a biochemical or structural activity, can be used in conjunction with the present invention.

Multi-Promoter/Activation Exon Vectors

In applications of nontargeted gene activation in which the goal is to activate protein expression from an unknown gene, a collection of vectors typically must be used. Thus, in an additional embodiment, the invention provides vectors containing one or more promoter/activation exon units (see FIGS. 20A–20E).

To accommodate the variety of gene structures that exist in the genomes of eukaryotic cells, vectors according to this aspect of the invention preferably contain a transcriptional regulatory sequence (e.g., a promoter) operably linked to an activation exon with a different structure. Collectively, these activation exons are capable of activating protein expression from substantially all endogenous genes. For example, to activate protein expression from genes that encode a translation start codon in exon II (or exons downstream of exon II), one vector can contain a transcriptional regulatory sequence (e.g., a promoter) operably linked to an activation exon lacking a translation start codon. To activate protein expression from all types of genes that encode a translation start codon in exon I, three separate vectors must be used, each containing a transcriptional regulatory sequence (e.g., a promoter) operably linked to a different activation exon. Each activation exon encodes a start codon in a different reading frame. Additional activation exon configurations are also useful. For example, to activate protein expression and secretion from genes that encode a portion of their signal secretion sequence in exon I, three separate vectors must be used, each containing a transcriptional regulatory sequence (e.g., a promoter) operably linked to a different activation exon. Each activation exon encodes a partial signal sequence in a different reading frame. To activate protein expression and secretion from genes that encode their entire signal sequence in exon I, three vectors must be used, each containing a transcriptional regulatory sequence (e.g., a promoter) operably linked to a different activation exon. Each activation exon contains an entire signal secretion sequence in a different reading frame. In addition to activating expression of genes that encode secreted proteins, promoter/activation exons encoding entire signal sequences will also activate expression and secretion of proteins that are not normally secreted. This, for example, can facilitate protein purification of proteins that are normally intracellularly localized.

Other useful coding sequences can be included on the activation exon of vectors according to this aspect of the invention, including but not limited to sequences encoding proteins (including full length proteins, portions of proteins, protein motifs, and/or epitope tags). As described herein, vectors according to this aspect of the invention can be integrated, individually or collectively, into the genome of a host cell to produce a library of cells. Each member of the library will potentially overexpress a different endogenous protein. Thus, these collections of vectors make it possible to activate all or substantially all of the endogenous genes in a eukaryotic host cell.

When integrating a collection of vectors into host cells, as described above, activation of protein expression can be achieved from substantially any gene. Unfortunately, to produce protein from all endogenous genes, a large number of library members must be generated. In part, this is due to the large number of genes encoded by the host cell. In addition, using this approach, many cells will contain a vector integrated into or near an endogenous gene; however, the integrated vector will contain an activation exon with a structure that is incompatible with activating protein expression from the endogenous gene. For example, the vector exon may encode a start codon in reading frame 1 (relative to the splice junction), whereas the protein encoded by the first exon downstream of the integrated vector may be in reading frame 2 (relative to the splice junction). Thus, many library members will contain an integrated vector that has activated transcription of an endogenous gene, but that failed to produce the protein encoded by the endogenous gene.

To decrease the number of cells that fail to activate protein expression following vector integration into or near an endogenous gene, a vector containing multiple promoter/activation exons can be used. On this vector, each promoter/activation exon unit can be capable of activating protein expression from an endogenous gene with a different structure. Since a single vector comprising multiple activation exons is capable of producing multiple transcripts, each containing a different activation exon, a single vector integrated into or near a gene can be capable of activating protein expression, regardless of the structure of the endogenous gene (see FIG. 21).

Multi-promoter/activation exon vectors can contain two or more promoter/activation exons. Each promoter/activation exon unit may be followed by an unpaired splice donor site. In one such embodiment, two promoter/activation exons are included on the vector, wherein each promoter/activation exon is capable of activating protein expression from a different type of endogenous gene. In a preferred embodiment, the vector may contain three promoter/activation exons, wherein each exon encodes a translation start codon in a different reading frame. In another preferred embodiment, the vector may contain three promoter/activation exons, wherein each exon encodes a partial signal secretion sequence in a different reading frame. In yet another preferred embodiment, the vector may contain three promoter/activation exons, wherein each exon encodes an entire signal secretion sequence in a different reading frame. Additional embodiments include each of the vectors above containing a fourth promoter/activation exon, wherein the fourth activation exon does not encode a translation start codon.

Any number (e.g., one or more, two or more, three or more, four or more, five or more, etc.) of promoter/activation exon units may be included on the vector. When multiple promoter/activation exons are present on a single vector, they are preferably oriented in the same direction relative to one another (i.e., the promoters drive expression in the same direction).

The promoters that drive transcription of different activation exons may be the same as one another or one or more promoters may be different. The promoters may be viral, cellular, or synthetic. The promoters may be constitutive or inducible. Other types of promoters and regulatory sequences, recognizable to one skilled in the art or as described herein, may also be used in preparing the vectors according to this aspect of the invention.

Any of the vectors containing multiple promoter/activation exon units may optionally include one or more selectable marker(s) and/or amplifiable marker(s). The selectable and/or amplifiable markers may contain a poly(A) signal. Alternatively, the markers may lack a poly(A) signal. The selectable marker may be a positive or negative selectable marker. The selectable marker may contain an unpaired splice donor site upstream, within, or downstream of the marker. Alternatively, the selectable marker may lack an unpaired splice donor site. The selectable marker(s) and/or amplifiable marker(s), when present, may be located upstream, among, or downstream of the promoter/activation exon units. The selectable and/or amplifiable marker(s) may be located on the vector in any orientation relative to the promoter/activation exon units. When the purpose of the selectable marker is to trap endogenous genes, the selectable marker is preferably oriented in the same direction as the promoter/activation exons.

Amplifiable Markers

Any of the vectors described herein may also optionally comprise one or more (e.g., two, three, four, five, or more) amplifiable markers. Examples of amplifiable markers include those described in detail hereinabove. Preferably, the amplifiable marker(s) are located upstream of the positive/negative selectable marker(s). When using polyadenylation trap vectors, it may be advantageous to omit a polyadenylation signal from the amplifiable marker(s) to eliminate the possibility of capturing a vector-encoded poly(A) signal derived from vector concatemerization prior to integration.

When present, the amplifiable marker(s) may be located upstream of the activation transcriptional regulatory sequence (i.e. the promoter responsible for directing transcription from the vector through the endogenous gene). The amplifiable marker(s) may be present on the vector in any orientation (i.e. the open reading frame may be present on either DNA strand).

It is also understood that the amplifiable marker(s) can also be the same gene as the positive selectable marker. Examples of genes that can be used both as positive selectable markers and amplifiable markers include dihydrofolate reductase, adenosine deaminase (ada), dihydro-orotase, glutamine synthase (GS), and carbamyl phosphate synthase (CAD).

In some embodiments and for certain applications, it may be desirable to place multiple amplifiable markers on the vector. Use of more than one amplifiable marker allows dual selection, or alternatively sequential selection, for each amplifiable marker. This facilitates the isolation of cells that have amplified the vector and flanking genomic locus, including the gene of interest.

Promoters

It is understood that any promoter and regulatory element may be used on these activation vectors to drive expression of the selectable marker, amplifiable marker (if present), and/or the endogenous gene. In additional preferred embodiments, the promoter driving expression of the endogenous gene is a strong promoter. The CMV immediate early gene promoter, SV40 T antigen promoter, and β-actin promoter are examples of this type of promoter. In another preferred embodiment, an inducible promoter is used to drive expression of the endogenous genes. This allows endogenous proteins to be expressed in a more controlled fashion. The Tetracycline inducible promoter, heat shock promoter, ectdysone promoter, and metallothionein promoter are examples of this type of promoter. In yet another embodiment, a tissue specific promoter is used to drive expression of endogenous genes. Examples of tissue specific promoters include, but are not limited to, immunoglobulin promoters, casein promoter, and growth hormone promoter.

Restriction Sites

The vectors of the invention can contain one or more restriction sites located downstream of the unpaired splice donor site in the vector. These restriction sites can be used to linearize plasmid vectors prior to transfection. In the linear configuration, the activation vector contains, from 5' to 3' relative to the transcribed strand, a promoter, a splice donor site, and a linearization site.

A restriction site(s) may also be included in the vector intron to facilitate removal of vector intron-containing cDNA molecules. In this embodiment, the vector contains, from 5' to 3' relative to the transcribed strand, a promoter, a splice donor site, a restriction site, and a linearization site. By including a restriction site between the unpaired splice donor site and the linearization site, unspliced transcripts can be removed by digestion of cDNA with the appropriate restriction enzyme. cDNA molecules derived from gene activation have removed the vector intron containing the restriction site, and therefore, will not be digested. This allows gene activated transcripts to be preferentially enriched during amplification/cloning, and greatly facilitates identification and analysis of endogenous genes.

A restriction site(s) may also be included in the vector exon to facilitate cloning of activated genes. Following gene activation, mRNA is recovered from cells and synthesized into cDNA. By digesting the cDNA with a restriction enzyme that cuts in the vector exon, gene activated cDNA molecules will contain an appropriate overhang at the 5' end for subsequent cloning into a suitable vector. This facilitates isolation of gene activated cDNA molecules.

In one embodiment, the restriction site located in the vector exon is different than the restriction site(s) located in the vector intron. This facilitates removal of cDNA molecules that contain a vector intron since the digested cDNA fragments from vector intron containing transcripts can be designed to have an overhang that is incompatible with the cloning vector (see below). Alternatively, degenerate restriction sites recognized by the same enzyme may be located in the vector exon and intron. Enzymes that cleave these sites are capable of cleaving multiple sites, sites with an odd number of bases in the recognition sequence, sites with interrupted palindromes, nonpalindromic sequences, or sites containing one or more degenerate bases. In other words, restriction sites recognized by the same restriction endonuclease may be used if the enzyme produces an overhang in the vector exon that is different from the overhang produced in the vector intron. Since different overhangs are produced, a cloning vector containing a site that is compatible with the vector exon overhang, and incompatible with the vector intron overhang may be used to preferentially clone vector exon containing and vector intron lacking cDNA molecules. Examples of useful degenerate restriction sites include DNA sequences recognized by Sfi I, Acci, Afl III, SapI, Ple I, Tsp45 I, ScrF I, Tse I, PpuM I, Rsr II, and SgrA I.

The restriction site(s) located in the vector intron and/or exon can be a rare restriction site (e.g. an 8 bp restriction site) or an ultra-rare site (e.g. a site recognized by intron encoded nucleases). Examples of restriction enzymes with 8 bp recognitions sites include NotI, SfiI, PacI, AscI, FseI, PmeI, SgfI, SrfI, SbfI, Sse 8387 I, and SwaI. Examples of intron encoded restriction enzymes include I-PpoI, I-SceI, I-CeuI, PI-PspI, and PI-TliI. Alternatively, restriction sites smaller than 8 bp can be placed on the vector. For example, restriction sites composed of 7 bp, 6 bp, 5 bp, or 4 bp can be used. In general, the use of smaller the restriction recognition sites will lead to the cloning of less than full-length genes. In some cases, such as creation of hybridization probes, isolation of smaller cDNA clones may be advantageous.

Bidirectional Activation Vectors

The activation vectors described herein can also be bidirectional. When a single activation transcriptional regulatory sequence is present on the vector, gene activation occurs only when the vector integrates into an appropriate location (e.g. upstream of the gene) and in the correct orientation. That is, in order to activate an endogenous gene, the promoter on the activation construct must face the endogenous gene allowing transcription of the coding strand. As a result of this directionality requirement, only half of the integration events into a locus may result in the transcriptional activation of an endogenous gene. The other half of integration events result in the vector transcribing away from a gene of interest. Therefore, to increase the gene activation frequency by a factor of two, the present invention provides bidirectional vectors that may be used to activate an endogenous gene regardless of the orientation in which the vector integrates into the host cell genome.

Figure 11A:
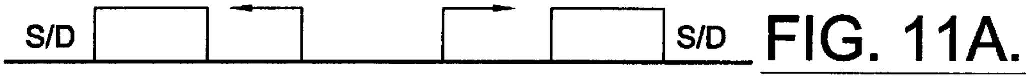
FIGS. 11A–11C. Schematic diagram of bidirectional activation vectors. The arrows denote promoter sequences. The exons are shown as checkered boxes and splice donor sites are indicated by S/D. The hatched boxes indicate exon sequences operably linked to the upstream promoter. It is understood that the exons on these vectors may be untranslated, or may contain a start codon and additional codons as described herein. As illustrated in the vectors depicted in FIGS. 11B–11C, the vectors may contain a selectable marker. In these vectors, the neomycin resistance (Neo) gene is illustrated.
Figure 11B:
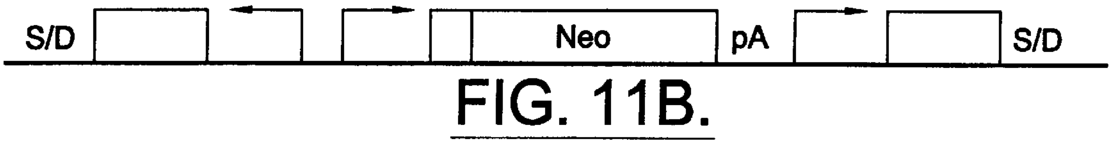
Figure 11C:
Figure 12A:
FIGS. 12A–12G. Examples of vectors useful for recovering exon I from activated endogenous genes. Each vector is illustrated schematically in its linearized form. Each horizontal line represents a DNA molecule. The arrows denote promoter sequences located on the DNA molecule, and face in the direction of transcription. Transcribed regions include all sequences located downstream of a promoter. Untranslated regions are designated by hatched boxes. Poly(A) signals are not present in the vectors depicted. As discussed in the Detailed Description, however, poly(A) signals may be placed on the vector 3' of either or both selectable markers. The following designations were used: splice donor site (S/D), internal ribosome entry site (ires), hypoxanthine phosphoribosyl transferase (HPRT), and neomycin resistance gene (Neo). In these examples, Neo represents the positive selectable marker and HPRT represents the negative selectable marker. It is also recognized that in these examples, the region designated exon, when present, lacks a translation start codon. In other examples not shown, the region designated exon contains a translation start codon. Furthermore, when the vector exon contains a translation start codon, the exon may encode a methionine residue, a partial signal sequence, a full signal secretion sequence, a portion of a protein, or an epitope tag. In addition, the codons may be present in each reading frame relative to the splice donor site.
Figure 12B:
Figure 12C:
Figure 12D:
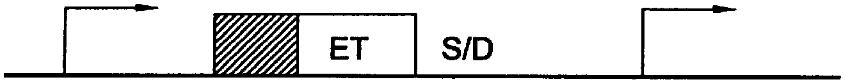
Figure 12E:
Figure 12F:
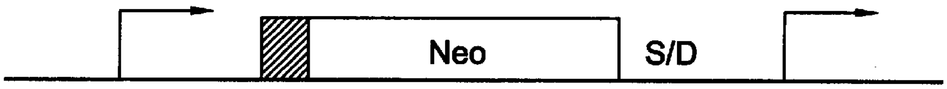
Figure 12G:
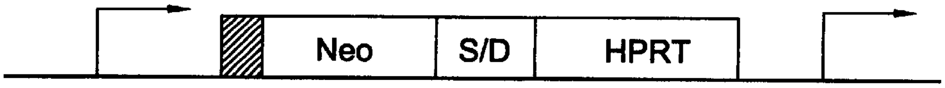

A bidirectional vector according to this aspect of the invention preferably comprises two transcriptional regulatory sequences (which may be any transcriptional regulatory sequences, including but not limited to the promoters, enhancers, and repressors described herein, and which preferably are promoters or enhancers, and most preferably promoters), two splice donor sites, and a linearization site. When a splice donor site is useful, each transcriptional regulatory sequence is operably linked to a separate splice donor site, and the transcriptional regulatory sequence/splice donor pairs may be in inverse orientation relative to each other (i.e., the first transcriptional regulatory sequence may be integrated into the host cell genome in an orientation that is inverse relative to the orientation in which the second transcriptional regulatory sequence has integrated into the host cell genome). The two opposing transcriptional regulatory sequence/splice donor sites can be separated by the linearization site. The function of the linearization site is to produce free DNA ends between the transcriptional regulatory sequence/splice donor sites (i.e. in a location suitable for activation of endogenous genes). Examples of bidirectional vectors of the invention are shown in FIGS. 11A–11C.

The two opposing transcriptional regulatory sequences may be the same transcriptional regulatory sequences or different transcriptional regulatory sequences. Optionally, a translational start codon (e.g. ATG) and one or more additional codons may be included on either or both vector encoded exons. When a translational start codon is present, either or both vector exons may encode a protein, a portion of a protein, a signal secretion sequence, a portion of a signal secretion sequence, a protein motif, or an epitope tag. Alternatively, either or both vector exons may lack a translational start codon.

The bidirectional vectors according to this aspect of the invention may optionally include one or more selectable markers and one or more amplifiable markers, including those selectable markers and amplifiable markers described in detail herein. The bidirectional vectors may also be configured as poly(A) trap, splice acceptor trap, or dual poly(A)/splice acceptor trap vectors, as described above. Other vector configurations described for unidirectional vectors may also be incorporated into bidirectional vectors.

Co-transfection of Genomic Dna with Non-targeted Activation Vectors

It is recognized that any of the vectors described herein can be integrated into, or otherwise combined with, genomic DNA prior to transfection into a eukaryotic host cell. This permits high level expression from virtually any gene in the genome, regardless of the normal expression characteristics of the gene. Thus, the vectors of the invention can be used to activate expression from genes encoded by isolated genomic DNA fragments. To accomplish this, the vector is integrated into, or otherwise combined with, genomic DNA containing at least one gene, or portion of a gene. Typically, the activation vector must be positioned within or upstream of a gene in order to activate gene expression. Once inserted (or joined), the downstream gene may be expressed (as a transcript or a protein) by introducing the vector/genomic DNA into an appropriate eukaryotic host cell. Following introduction into the host cell, the vector encoded promoter drives expression through the gene encoded in the isolated DNA, and following splicing, produces a mature mRNA molecule. Using appropriate activation vectors, this process allows protein to be expressed from any gene encoded by the transfected genomic DNA. In addition, using the methods described herein, cDNA molecules, corresponding to genes encoded by the transfected genomic DNA, can be generated and isolated.

To achieve stable expression of the activated gene, the transfected activation vector/genomic DNA can be integrated into the host cell genome. Alternatively, the transfected activation vector/genomic DNA can be maintained as a stable episome (e.g. using a viral origin of replication and/or nuclear retention function—see below). In yet another embodiment, the activated gene may be expressed transiently, for example, from a plasmid.

As used herein, the term "genomic DNA" refers to the unspliced genetic material from a cell. Splicing refers to the process of removing introns from genes following transcription. Thus, genomic DNA, in contrast to mRNA and cDNA, contains exons and introns in an unspliced form. In the present invention, genomic DNA derived from eukaryotic cells is particularly useful since most eukaryotic genes contain exons and introns, and since many of the vectors of the present invention are designed to activate genes encoded in the genomic DNA by splicing to the first downstream exon, and removing intervening introns.

Genomic DNA useful in the present invention may be isolated using any method known in the art. A number of methods for isolating high molecular weight genomic DNA and ultra-high molecular weight genomic DNA (intact and encased in agarose plugs) have been described (Sambrook et al., Molecular Cloning, Cold Spring Harbor Laboratory Press, (1989)). In addition, commercial kits for isolating genomic DNA of various sizes are also available (Gibco/BRL, Stratagene, Clontech, etc.).

The genomic DNA used in the invention may encompass the entire genome of an organism. Alternatively, the genomic DNA may include only a portion of the entire genome from an organism. For example, the genomic DNA may contain multiple chromosomes, a single chromosome, a portion of a chromosome, a genetic locus, a single gene, or a portion of a gene.

Genomic DNA useful in the invention may be substantially intact (i.e. unfragmented) prior to introduction into a host cell. Alternatively, the genomic DNA may be fragmented prior to introduction into a host cell. This can be accomplished by, for example, mechanical shearing, nuclease treatment, chemical treament, irradiation, or other methods known in the art. When the genomic DNA is fragmented, the fragmentation conditions may be adjusted to produce DNA fragments of any desirable size. Typically, DNA fragments should be large enough to contain at least one gene, or a portion of a gene (e.g. at least one exon). The genomic DNA may be introduced directly into an appropriate eukaryotic host cell without prior cloning. Alternatively, the genomic DNA (or genomic DNA fragments) may be cloned into a vector prior to transfection. Useful vectors include, but are not limited to, high and intermediate copy number plasmids (e.g. pUC, pBluescript, pACYC184, pBR322, etc.), cosmids, bacterial artificial chromosomes (BAC's), yeast artificial chromosomes (YAC's), P1 artificial chromosomes (PAC's), and phage (e.g. lambda, M13, etc.). Other cloning vectors known in the art may also be used. When genomic DNA has been cloned into a cloning vector, specific cloned DNA fragments may be isolated and used in the present invention. For example, YAC, BAC, PAC, or cosmid libraries can be screened by hybridization to identify clones that map to specific chromosomal regions. Optionally, once isolated, these clones can be ordered to produce a contig through the chromosomal region of interest. To rapidly isolate cDNA copies of the genes present in this contig, these genomic clones may be transfected, separately or en masse, with the activation vector into a host cell. cDNA containing a vector encoded exon, and lacking a vector encoded intron, can then be isolated and analyzed. Thus, since all genes present in a contig can be rapidly isolated as cDNA clones, this approach greatly enhances the speed of positional cloning approaches.

Any activation vector described herein, including derivatives recognized by those skilled in the art, may be co-transfected with genomic DNA, and therefore, are useful in the present invention. In its simplest form, the vector can contain a promoter operably linked to an exon followed by an unpaired splice donor site. Examples of other useful vectors include, but are not limited to, poly A trap vectors (e.g. vectors illustrated in FIGS. 8, 9, 11C, 12F, and 17), dual poly (A)/Splice acceptor trap vectors (e.g. vectors illustrated in FIGS. 9, 10, 12G, 19, and 21), bi-directional vectors (e.g. vectors illustrated in FIG. 11), single exon trap vectors (e.g. the vector illustrated in FIG. 19), multi-promoter/activation exon vectors (e.g. the vector illustrated in FIG. 23), vectors for isolating cDNA's corresponding to activated genes, and vectors for activating protein expression from activated genes (e.g. vectors illustrated in FIGS. 2, 3, 4, 8B–F, 9B–C, 9E–F, 10B–C, 10E–F, 11, 12, 17B–G, and 23).

The activation vector may also contain a viral origin of replication. The presence of a viral origin of replication allows vectors containing genomic fragments to be propagated as an episome in the host cell. Examples of useful viral origins of replication include ori P (Epstein Barr Virus), SV40 ori, BPV ori, and vaccinia ori. To facilitate replication from these origins, the appropriate viral replication proteins may be expressed from the vector. For example, EBV ori P and SV40 ori containing vectors may also encode and express EBNA-1 or T antigen, respectively. Alternatively, the vectors may be introduced into cells that are already expressing the viral replication protein (e.g. EBNA-1 or T antigen). Examples of cells expressing EBNA-1 and T antigen include human 293 cells transfected with an EBNA-1 expression unit (Clontech) and COS-7 cells (American Type Culture Collection; ATCC No. CRL-1651), respectively.

The activation vector may also contain an amplifiable marker. This enables cells containing increased copies of the vector and flanking genomic DNA, either episomal or integrated in the host cell genome, to be isolated. Cells containing increased copies of the vector and flanking genomic DNA express the activated gene at higher levels, facilitating gene isolation and protein production.

The activation vector and genomic DNA may be introduced into any host cell capable of splicing from the vector-encoded splice donor site to a splice acceptor site encoded by the genomic DNA. In a preferred embodiment, the genomic DNA/activation vector are transfected into a host cell from the same species as the cell from which the genomic DNA was isolated. In some instances, however, it is advantageous to transfect the genomic DNA into a host cell from a species that is different from the cell from which the genomic DNA was isolated. For example, transfection of genomic DNA from one species into a host cell of a second species can facilitate analysis of the genes activated in the transfected genomic DNA using hybridization techniques. Under high stringency hybridization, activated genes that were encoded by the transfected DNA can be distinguished from genes derived from the host cell. Transfection of genomic DNA from one species into a host cell from another species can also be used to produce protein in a heterologous cell. This may allow protein to be produced in heterologous cells that provide growth, protein modification, or manufacturing advantages.

The activation vector may be co-transfected into a host cell along with genomic DNA, wherein the vector is not attached to the genomic DNA prior to introduction into the cell. In this embodiment, the genomic DNA will become fragmented during the transfection process, thereby creating free DNA ends. These DNA ends can become joined to the co-transfected activation vector by the cell's DNA repair machinery. Following joining to the activation vector, the genomic DNA and activation vector can be integrated into the host cell genome by the process of non-homologous recombination. If, during this process, a vector becomes joined to a gene encoded by the transfected genomic DNA, the vector will activate its expression.

Alternatively, the non-targeted activation vector may be physically linked to the genomic DNA prior to transfection. In a preferred embodiment, genomic DNA fragments are ligated to the vector prior to transfection. This is advantageous because it maximizes the probability of the vector becoming operably linked to a gene encoded by the genomic DNA, and minimizes the probability of the vector integrating into the host cell genome without the heterologous genomic DNA.

In a related embodiment, the genomic DNA may be cloned into the activation vector, downstream of the activation exon. In this embodiment, cloning of large genomic fragments can be facilitated in vectors capable of accommodating large genomic fragments. Thus, the activation vector may be constructed in BAC's, YAC's, PAC's, cosmids, or similar vectors capable of propagating large fragments of genomic DNA.

Another method for joining the activation vector to genomic DNA involves transposition. In this embodiment, the activation vector is integrated into the genomic DNA by transposition or retroviral integration reactions prior to transfection into a cell. Accordingly, activation vectors can contain cis sequences necessary for facilitating transposition and/or retroviral integration. Examples of vectors containing transposon signals are illustrated in FIG. 27; however, it is recognized that any vector described herein may contain transposon signals.

Any transposition system capable of inserting foreign sequences into genomic DNA can be used in the present invention. In addition, transposons capable of facilitating inversions and deletions can also be used to practice the invention. While deletion and inversion systems do not integrate the activation vector into genomic DNA, they do allow the activation vector to change positions relative to cloned genomic DNA when the genomic DNA has been cloned into the activation vector. Thus, multiple genes within a given genomic fragment can be activated by shuffling the activation vector (by integration, inversion, or deletion) into multiple positions within, or outside of, the genomic fragment. Examples of transposition systems useful for the present invention include, but are not limited to δγ, Tn3, Tn5, Tn7, Tn9, Tn10, Ty, retroviral integration and retro-transposons (Berg et al., Mobile DNA, ASM Press, Washington D.C., pp. 879–925 (1989); Strathman et al., *Proc. Natl. Acad Sci. USA* 88:1247 (1991); Berg et al., *Gene* 113:9 (1992); Liu et al., *Nucl. Acids Res*. 15:9461 (1987), Martin et al., *Proc. Natl. Acad Sci. USA* 92:8398 (1995); Phadnis et al., *Proc. Natl. Acad Sci. USA* 86:5908 (1989); Tomcsanyi et al., *J. Bacteriol.* 172:6348 (1990); Way et al., *Gene* 32:369 (1984); Bainton et al., *Cell* 65:805 (1991); Ahmed et al., *J. Mol. Biol.* 178:941 (1984); Benjamin et al., *Cell* 59:373 (1989); Brown et al., *Cell* 49:347 (1987); Eichinger et al., *Cell* 54:955 (1988); Eichinger et al., *Genes Dev.* 4:324 (1990); Braiterman et al., *Mol. Cell. Biol.* 14:5719 (1994); Braiterman et al., *Mol. Cell. Biol.* 14:5731 (1994); York et al., *Nucl. Acids Res.* 26:1927 (1998); Devine et al., *Nucl. Acids Res.* 18:3765 (1994); Goryshin et al., *J. Biol. Chem.* 273:7367 (1998).

Using transposition, an activation vector may be integrated into any form of genomic DNA. For example, the activation vector may be integrated into either intact or fragmented genomic DNA. Alternatively, the activation vector may be integrated into a cloned fragment of genomic DNA (FIG. 28). In this embodiment, the genomic DNA may reside in any cloning vector, including high and intermediate copy number plasmids (e.g. pUC, pBluescript, pACYC184, pBR322, etc.), cosmids, bacterial artificial chromosomes (BAC's), yeast artificial chromosomes (YAC's), P1 artificial chromosomes (PAC's), and phage (e.g. lambda, M13, etc.). Other cloning vectors known in the art may also be used. As described above, genomic fragments from specific genetic loci may be isolated an used as a substrate for activation vector integration.

Following integration of the activation vector, the genomic DNA may be introduced directly into a suitable host cell for expression of the activated gene. Alternatively, the genomic DNA may be introduced into and propagated in an intermediate host cell. For example, following integration of an activation vector into a BAC genomic library, the BAC library can be transformed into *E. coli*. This allows plasmids containing the transposon to be enriched by selecting for an antibiotic resistance marker residing on the activation vector. As a result, BAC plasmids lacking an integrated activation vector will be removed by antibiotic selection.

The transposition mediated activation vector integration may occur in vitro using purified enzymes. Alternatively, the transposition reaction may occur in vivo. For example, transposition may be carried out in bacteria, using a donor strain carrying the transposon either on a vector or as integrated copies in the genome. A target of interest is introduced into the transposer host where it receives integrations. Targets bearing insertions are then recovered from the host by genetic selection. Similarly, eukaryotic host cells, such as yeast, plant, insect, or mammalian cells, can be used to carry out the transposon mediated integration of an activation vector into a fragment of genomic DNA.

Isolation of mRNA and cDNA Produced from Activated Endogenous Genes

In additional embodiments, the present invention is directed to methods for isolating genes, particularly genes contained within the genome of a eukaryotic cell, that are activated using the vectors of the invention. These methods exploit the structure of the mRNA molecules produced using the non-targeted gene activation vectors of the invention. The methods of the invention described herein allow virtually any activated gene to be isolated, regardless of whether it has been previously isolated and characterized, and regardless of whether it has a known biological activity. This is made possible by the nature of the chimeric transcripts produced from the integrated vectors of of the present invention. Using methods described herein, activation vectors can be integrated into the genome of a cell. Typically, the activation vectors, however, are integrated into the genome of many cells to produce a library of unique integration events. Each member of the library contains the vector located at a unique integration site(s), and potentially contains an activated endogenous gene. Gene activation occurs when the activation vector integrates upstream of the 3'-most exon of an endogenous gene and in an orientation capable of allowing transcription from the vector to proceed through the endogenous gene. The integration site may be in an intron or exon of the endogenous gene, or may be upstream of the transcription start site of the gene. Following integration, the activation constructs are designed to produce a transcript capable of splicing from an exon encoded by the activation vector to an exon encoded by the endogenous gene. As a result, a chimeric message is produced that contains the vector exon linked to the exons from an endogenous gene, wherein the endogenous exons are derived from the region located downstream of the vector integration site. The structure of this chimeric transcript can be exploited for gene discovery purposes. For example, the chimeric transcripts can be rapidly isolated to use as probes (to isolate the full length cDNA or genomic copy of the gene or to characterize the gene) or for direct sequencing and/or characterization.

To isolate the chimeric transcripts activated by vector insertion, cDNA is produced from a library member containing the activation event. It is also possible to isolate chimeric transcripts from pools of library members in order to increase the through-put of the procedure. cDNA can then be produced from the mRNA harvested from the activated cells. Alternatively, total RNA may be used to produce cDNA. In either case, first strand synthesis can be carried out using an oligo dT primer, an oligo dT/poly(A) signal primer, or a random primer. To facilitate cloning of the cDNA product, a poly dT based primer can be used with the structure: 5'-Primer X$(dT)_{1-100}$-3'. The oligo dT/poly(A) signal primer can have the structure 5'-$(dT)_{10-30}$-Primer X-$N_{0-6}$-TTTATT-3'. The random primer can have the structure: 5'-(Primer X)NNNNNN-3'. In each primer, Primer X is any sequence that can be used to subsequently PCR amplify target nucleic acid molecules. Where the activated gene amplification product is to be cloned, it is useful to include one or more restriction sites within the primer X sequence to facilitate subsequent cloning. Other primers recognized by those skilled in the art can be used to create first strand cDNA products, including primers that lack a Primer X region.

In accordance with the invention, the primers may be conjugated with one or more hapten molecules to facilitate subsequent isolation of nucleic acid molecules (e.g., first and/or second strand cDNA products) comprising such primers. After the primer becomes associated with the nucleic acid molecule (via incorporation during cDNA synthesis), selective isolation of the molecule containing the haptenylated primer may be accomplished using a corresponding ligand which specifically interacts with and binds to the hapten via ligand-hapten interactions. In preferred such aspects, the ligand may be bound to, for example, a solid support. Once bound to the solid support, the molecules of interest (haptenylated primer-containing nucleic acid molecules) can be separated from contaminating nucleic acids and other materials by washing the support matrix with a solution, preferably a buffer or water. Cleavage of one or more of the cleavage sites within the primer, or by treatment of the solid support containing the nucleic acid molecule with a high ionic strength elution buffer, then allows for removal of the nucleic acid molecule of interest from the solid support.

Preferred solid supports for use in this aspect of the invention include, but are not limited to, nitrocellulose, diazocellulose, glass, polystyrene, polyvinylchloride, polypropylene, polyethylene, dextran, Sepharose, agar, starch, nylon, latex beads, magnetic beads, paramagnetic beads, superparamagnetic beads or microtitre plates and most preferably a magnetic bead, a paramagnetic bead or a superparamagnetic bead, that comprises one or more ligand molecules specifically recognizing and binding to the hapten molecule on the primer.

Particularly preferred hapten molecules for use on the primer molecules of the invention, include without limitation: (i) biotin; (ii) an antibody; (iii) an enzyme; (iv) lipopolysaccharide; (v) apotransferrin; (vi) ferrotransferrin; (vii) insulin; (viii) cytokines (growth factors, interleukins or colony-stimulating factors); (ix) gp120; (x) β-actin; (xi) LFA-1; (xii) Mac-1; (xiii) glycophorin; (xiv) laminin; (xv) collagen; (xvi) fibronectin; (xvii) vitronectin; (xviii) integrins $\alpha_v\beta_1$ and $\alpha_v\beta_3$; (xix) integrins $\alpha_3\beta_1$, $\alpha_4\beta_1$, $\alpha_4\beta_7$, $\alpha_5\beta_1$, $\alpha_v\beta_1$, $\alpha_{IIb}\beta_3$, $\alpha_v\beta_3$ and $\alpha_v\beta_6$; (xx) integrins $\alpha_1\beta_1$, $\alpha_2\beta_1$, $\alpha_3\beta_1$ and $\alpha_v\beta_3$; (xxi) integrins $\alpha_1\beta_1$, $\alpha_2\beta_1$, $\alpha_3\beta_1$, $\alpha_6\beta_1$, $\alpha_7\beta_1$ and $\alpha_6\beta_5$; (xxii) ankyrin; (xxiii) C3bi, fibrinogen or Factor X; (xxiv) ICAM-1 or ICAM-2; (xxv) spectrin or fodrin; (xxvi) CD4; (xxvii) a cytokine (e.g., growth factor, interleukin or colony-stimulating factor) receptor; (xxviii) an insulin receptor; (xxix) a transferrin receptor; (xxx) $Fe^{+++}$; (xxxi) polymyxin B or endotoxin-neutralizing protein (ENP); (xxxii) an enzyme-specific substrate; (xxxiii) protein A, protein G, a cell-surface Fc receptor or an antibody-specific antigen; and (xxxiv) avidin and streptavidin. Particularly preferred is biotin.

Particularly preferred ligand molecules according to this aspect of the invention, which correspond in order to the above-described hapten molecules, include without limitation: (i) avidin and streptavidin; (ii) protein A, protein G, a cell-surface Fc receptor or an antibody- specific antigen; (iii) an enzyme-specific substrate; (iv) polymyxin B or endotoxin-neutralizing protein (ENP); (v) $Fe^{+++}$; (vi) a transferrin receptor; (vii) an insulin receptor; (viii) a cytokine (e.g., growth factor, interleukin or colony-stimulating factor) receptor; (ix) CD4; (x) spectrin or fodrin; (xi) ICAM-1 or ICAM-2; (xii) C3bi, fibrinogen or Factor X; (xiii) ankyrin; (xiv) integrins $\alpha_1\beta_1$, $\alpha_2\beta_1$, $\alpha_3\beta_1$, $\alpha_6\beta_1$, $\alpha_7\beta_1$ and $\alpha_6\beta_5$; (xv) integrin $\alpha_1\beta_1$, $\alpha_2\beta_1$, $\alpha_3\beta_1$ and $\alpha_v\beta_3$; (xvi) integrins $\alpha_3\beta_1$, $\alpha_4\beta_1$, $\alpha_4\beta_7$, $\alpha_5\beta_1$, $\alpha_v\beta_1$, $\alpha_{IIb}\beta_3$, $\alpha_v\beta_3$ and $\alpha_v\beta_6$; (xvii) integrins $\alpha_v\beta_1$ and $\alpha_v\beta_3$; (xviii) vitronectin;

(xix) fibronectin; (xx) collagen; (xxi) laminin; (xxii) glycophorin; (xxii) Mac-1; (xxiv) LFA-1; (xxv) β-actin; (xxvi) gp120; (xxvii) cytokines (growth factors, interleukins or colony-stimulating factors); (xxviii) insulin; (xxix) ferrotransferrin; (xxx) apotransferrin; (xxxi) lipopolysaccharide; (xxxii) an enzyme; (xxxiii) an antibody; and (xxxiv) biotin. Particularly preferred, for use with biotinylated primers of the invention, are avidin and streptavidin.

Following first strand synthesis, second strand cDNA synthesis may be carried out using a primer specific for the vector encoded exon. This creates double stranded cDNA from all transcripts that were derived from the vector encoded promoter. All cellular mRNA (and cDNA) produced from endogenous promoters remains single stranded since the transcript lacks a vector exon at it 5' end. Once second strand synthesis is carried out, the cDNA may be digested with a restriction enzyme, cloned into a vector, and propagated.

To facilitate cloning, cDNA molecules containing the vector exon are amplified by PCR using a primer specific for the vector exon and a primer specific for the first strand cDNA primer (e.g. Primer X). PCR amplification results in the production of variable length DNA fragments representing different locations of priming during first strand synthesis and/or amplification of multiple chimeric transcripts from different genes. These amplification products can be cloned into plasmids for characterization, or can be labeled and used as a probe.

Other amplification techniques, such as linear amplification using RNA polymerase (Van Gelder, *Proc. Natl. Acad. Sci. USA* 87:1663–1667 (1990); Eberwine, *Methods* 10:283–288 (1996)), can be used. For example, when linear amplification by RNA polymerase is used, a promoter (e.g. T7 promoter) can be placed on the vector exon. As a result, gene activated transcripts will contain the promoter sequence at the 5' end of the transcript. Alternatively, a promoter can be ligated onto the cDNA molecule following first strand and second strand synthesis. Using either strategy, RNA polymerase is then incubated with cDNA in the presence of ribonucleotide triphosphates to create RNA transcripts from the cDNA. These transcripts are then reverse transcribed to produce cDNA. Since RNA polymerase can create several thousand transcripts from a single cDNA molecule, and since each of these transcripts can be reverse transcribed into cDNA, a large amplification can be achieved. As with PCR, amplification with RNA polymerase can facilitate cloning of activated genes. Other types of amplification strategies are also possible.

In another embodiment, the vector exon containing cDNA molecules are isolated without amplification. This may be useful in instances where biases occur during amplification (for example, when one DNA fragment amplifies more efficiently than another). To produce cDNA enriched for tagged messages, RNA is isolated from the activation library. A primer (e.g. a random hexamer, oligo(dT), or hybrid primers containing a primer linked to poly(dT) or a random nucleotides) is annealed to the RNA and used to direct first strand synthesis. The first strand cDNA molecules are then hybridized to a primer specific for the vector encoded exon. This primer directs second strand synthesis. Following second strand synthesis, the cDNA may be digested with restriction enzymes that cut in the vector exon and in the first strand primer (e.g. in Primer X—see above). The second strand products may then be cloned into a useful vector to allow them to be propagated.

It will be apparent to one of ordinary skill in view of the description contained herein that the cDNA products made according to the methods of the invention may also be cloned into a cloning vector suitable for transfection or transformation of a variety of prokaryotic (bacterial) or eukaryotic (yeast, plant or animal including human and other mammalian) cells. Such cloning vectors, which may be expression vectors, include but are not limited to chromosomal-, episomal- and virus-derived vectors, e.g., vectors derived from bacterial plasmids or bacteriophages, and vectors derived from combinations thereof, such as cosmids and phagemids, BACs, MACs, YACs, and the like. Other vectors suitable for use in accordance with this aspect of the invention, and methods for insertion of DNA fragments therein and transformation of host cells with such cloning vectors, will be familiar to those of ordinary skill in the art.

Removal of Unspliced Transcription Products

In some instances, the activation vector will integrate into the genome in a region lacking genes. Alternatively, it may integrate into a region containing a gene(s), but be oriented in a manner that results in the transcription of the non-coding strand. In each of these instances, gene activated transcripts are produced that contain normally untranscribed DNA sequences next to the vector encoded exon. These sequences would complicate identification and analysis of novel genes. Therefore, it would be advantageous to selectively remove these genomic molecules.

To remove cDNA molecules that contain a vector encoded intron, the double strand cDNA is treated with a restriction enzyme that recognizes a sequence located in the vector encoded intron. Preferably, the restriction enzyme creates an overhang that is different from the overhang produced by cleavage of the vector exon. This ensures the cloning of only activated genes by preventing the cleavage products from ligating into the cloning vector.

Recovery of Exon I from Activated Endogenous Genes

To recover exon I from activated genes, specialized vectors can be used to create non-targeted gene activation libraries. In its simplest form, this vector contains, from 5' to 3', a promoter, an unpaired splice donor site, and a second promoter. The downstream promoter is oriented in the same direction as the upstream promoter. Upon integration upstream of an endogenous gene, this type of vector produces two types of transcripts. The first transcript contains the vector exon joined to exon II of the endogenous gene. Methods for isolating this transcript are described above. The second transcript contains the upstream region of the endogenous gene followed by exon I joined to exon II and other downstream exons from the endogenous gene (FIG. 6).

Using a two step process, exon I can be recovered from cells containing the integrated vector. First, vector exon containing transcripts (i.e. Transcript type #1, FIG. 13) are isolated using the methods described above. Once isolated, the 5' end of the transcript including exon II can be sequenced to determine the sequence of the flanking endogenous exons. Second, once the sequence of the flanking endogenous exons is known, PCR primers capable of annealing to exon II (or a downstream exon) of the activated gene can be developed. These primers can be used to amplify exon I from Transcript #2 (FIG. 13) using a modified form of inverse PCR (Zeiner, M., *Biotechniques* 17(6):1051–1053 (1994)). Briefly, amplification of exon I from the endogenous gene is achieved by carrying out first strand cDNA synthesis with a gene specific primer, based on the sequence information determined above. Second strand synthesis can be carried out using *E. coli* DNA polymerase I under conditions well known to those skilled in the art. The double strand cDNA is then digested with a restriction enzyme that cleaves at least once in the endogenous gene upstream of the first strand cDNA primer, and that does not cleave in the vector exon. Following digestion, the cDNA is self ligated to produce circular molecules. Using inverted PCR primers that anneal in the endogenous gene upstream of the restriction/circularization site, amplification by PCR produces a DNA product containing exon I sequences from the endogenous gene.

Method for Selecting Cells Containing Higher Levels of Gene Activated Transcripts/Protein In several embodiments of the disclosed invention, the activation vector contains an amplifiable marker (e.g. DHFR) and a viral origin of replication (e.g. EBV or P). In other embodiments, an amplifiable marker and viral origin of replication are present on a cloning vector containing a cloned fragment of genomic DNA. In yet another embodiment, the activation vector contains one element (e.g. DHFR) and a cloning vector carrying a genomic insert contains the other element (e.g. Ori P). Regardless of the initial location of the amplifiable marker and viral origin, the elements are combined on the same DNA molecule prior to or during introduction into a host cell.

In addition to the cis-acting elements, a trans-acting viral protein is generally required for efficient replication of the episomes. Examples of trans-acting viral proteins include EBNA-1 and SV40 T antigen. To promote efficient replication of episomes, the trans-acting viral protein can be expressed from the episome. Thus, the viral trans-acting protein may be expressed from the transposing activation vector, or may be positioned on the backbone of the cloning vector. Alternatively, the trans-acting viral protein may be expressed by the eukaryotic host cells into which the episome is introduced.

Once the amplifiable marker and viral origin of replication are on the same molecule and present in a host cell expressing the appropriate viral replication protein(s), the copy number of the episome can be increased. To increase the copy number of the episome, the cells can be placed under the appropriate selection For example, if DHFR is present on the episome, methotrexate may be added to the culture. The selective agent may be applied at relatively high concentrations to isolate cells in the population that already have a high episome copy number. Alternatively, the selective agent may be applied at lower concentrations, and periodically increased in concentration. Two-fold increases in drug concentration will result in step-wise increases in copy number.

To reduce the frequency of non-specific drug resistance (i.e. drug resistance that is not associated with increased copy number of the episome), more than one amplifiable marker can be placed on the vector. Inclusion of multiple amplifiable markers on the episome allows cells to be selected with multiple drugs (either simultaneously or sequentially) Since non-specific drug resistance is a relatively rare event, the probability of a cell developing non-specific drug resistance to multiple drugs is exceedingly rare. Thus, the presence of multiple amplifiable markers on the episome facilitates isolation of cells that have a high episome copy number.

Amplification of episome copy number increases the number of transcripts derived from the vector activated gene. This, in turn, facilitates isolation of cDNA molecules derived from the activated gene. Furthermore, amplification of episome copy number can dramatically increase protein expression from the activated gene. Higher levels of protein production facilitate generation of proteins for bioassay screening, cell assay screening, and manufacturing purposes.

As a result of the highly desirable characteristics described above, vectors containing a viral origin of replication and an amplifiable marker, and the use of these vectors to rapidly amplify the copy number of episomal vectors, represent a break through that extends beyond the scope of activating expression of genes present in genomic DNA. For example, these vectors can be used to over-express cDNA encoded genes to produce high levels of protein expression without the need to integrate the gene into a host cell genome with an amplifiable marker. Furthermore, like amplification of chromosomal sequences, cell possessing several hundred to several thousand episomal copies of the vector can be isolated and maintained in culture. Thus, the vectors described herein, and their uses, allow high levels of cloned genomic DNA to be propagated in mammalian cells, facilitate isolation of cDNA copies of genes present on the vector as genomic inserts, and maximize protein production from cloned cDNA and genomic copies of eukaryotic genes.

Other suitable modifications and adaptations to the methods and applications described herein will be readily apparent to one of ordinary skill in the relevant arts and may be made without departing from the scope of the invention or any embodiment thereof Having now described the present invention in detail, the same will be more clearly understood by reference to the following examples, which are included herewith for purposes of illustration only and are not intended to be limiting of the invention.

EXAMPLES

Example 1

Transfection of Cells for Activation of Endogenous Gene Expression

Method: Construction of pRIG-1

Human DHFR was amplified by PCR from cDNA produced from HT1080 cells by PCR using the primers DHFR-F1

(5' TCCTTCGAAGCTTGTCATGGTTGGT-TCGCTAAACTGCAT 3') (SEQ ID NO:1) and DHFR-R1 (5' AAACTTAAGATCGATTAATCATTCTTCT-CATATACTTCAA 3') (SEQ ID NO:2), and cloned into the T site in pTARGET™ (Promega) to create pTARGET-:DHFR. The RSV promoter was isolated from PREP9 by digestion with NheI and XbaI and inserted into the NheI site of pTARGET:DHFR to create pTgT:RSV+DHFR. Oligonucleotides JH169 (5' ATCCACCATGGCTACAGGTGAG-TACTCG 3') (SEQ ID NO:3) and JH170 (5' GATCCGAG-TACTCACCTGTAGCCATGGTGGATTTAA 3') (SEQ ID NO:4) were annealed and inserted into the I-Ppo-I and NheI sites of pTgT:RSV+DHFR to create pTgT:RSV+DHFR+Exl. A 279 bp region corresponding to nucleotides 230–508 of pBR322 was PCR amplified using primers Tet F1 (5' GGCGAGATCTAGCGCTATATGCGTTGATGCAAT 3') (SEQ ID NO:5) and Tet F2 (5' GGCCAGATCTGCTACCT-TAAGAGAGCCGAAACAAGCGCTCATGAGCCCGAA 3') (SEQ ID NO:6). Amplification products were digested with BglII and cloned into the BamHI site of pTgT:RSV+RSV+DHFR+Exl to create pRIG-1.

Transfection—Creation of pR1G-1 Gene Activation Library in HT1080 Cells

To activate gene expression, a suitable activation construct is selected from the group of constructs described above. The selected activation construct is then introduced into cells by any transfection method known in the art. Examples of transfection methods include electroporation, lipofection, calcium phosphate precipitation, DEAE dextran, and receptor mediated endocytosis. Following introduction into the cells, the DNA is allowed to integrate into the host cell's genome via non-homologous recombination. Integration can occur at spontaneous chromosome breaks or at artificially induced chromosomal breaks.

Method: Transfection of human cells with pRIG1.2x$10^9$ HH1 cells, an HPRT$^-$ subclone of HT1080 cells, was grown in 150 mm tissue culture plates to 90% confluency. Media was removed from the cells and saved as conditioned media (see below). Cells were removed from the plate by brief incubation with trypsin, added to media/10% fetal bovine serum to neutralize the trypsin, and pelleted at 1000 rpm in a Jouan centrifuge for 5 minutes. Cells were washed in 1×PBS, counted, and repelleted as above. The cell pellet was resuspended at 2.5x$10^7$ cells/ml final in 1×PBS (Gibco BRL Cat #14200–075). Cells were then exposed to 50 rads of γ irradiation from a $^{137}$Cs source. pRIG1 (FIGS. 14A–14B; SEQ ID NO:18) was linearized with BamHI, purified with phenol/chloroform, precipitated with ethanol, and resuspended in PBS. Purified and linearized activation construct was added to the cell suspension to produce a final concentration of 40 μg/ml. The DNA/irradiated cell mixture was then mixed and 400 μl was placed into each 0.4 cm electroporation cuvettes (Biorad). The cuvettes were pulsed at 250 Volts, 600 μFarads, 50 Ohms using an electroporation apparatus (Biorad). Following the electric pulse, the cells were incubated at room temperature for 10 minutes, and then placed into αMEM/10% FBS containing penicillin/streptomycin (Gibco/BRL). The cells were then plated at approximately 7x$10^6$ cells/150 mm plate containing 35 ml αMEM/10% FBS/penstrep (33% conditioned media/67% fresh media). Following a 24 hour incubation at 37° C., G418 (Gibco/BRL) was added to each plate to a final concentration of 500 μg/ml from a 60 mg/ml stock. After 4 days of selection, the media was replaced with fresh αMEM/10% FBS/penstrep/500 μg/ml G418. The cells were then incubated for another 7–10 days and the culture supernatant assayed for the presence of new protein factors or stored at −80° C. for later analysis. The drug resistant clones can be stored in liquid nitrogen for later analysis.

Example 2

Use of Ionizing Irradiation to Increase the Frequency and Randomness of DNA Integration Method: HH1 cells were harvested at 90% confluency, washed in 1×PBS, and resuspended at a cell concentration of 7.5x$10^6$ cells/ml in 1×PBS. 15 μg linearized DNA (pRIG-1) was added to the cells and mixed. 400 μl was added to each electroporation cuvette and pulsed at 250 Volts, 600 μFarads, 50 Ohms using an electroporation apparatus (Biorad). Following the electric pulse, the cells were incubated at room temperature for 10 minutes, and then placed into 2.5 ml αMEM/10% FBS/1×penstrep. 300 μl of cells from each shock were irradiated at 0, 50, 500, and 5000 rads immediately prior to or at either 1 hour or 4 hours post transfection. Immediately following irradiation, the cells were plated onto tissue culture plates in complete medium. At 24 hours post plating, G418 was added to the culture to a final concentration of 500 μg/ml. At 7 days post-selection, the culture medium was replaced with fresh complete medium containing 500 μg/ml G418. At 10 days post selection, medium was removed from the plate, the colonies were stained with Coomassie Blue/90% methanol/10% acetic acid and colonies with greater than 50 cells were counted.

Example 3

Use of Restriction Enzymes to Generate Random, Semi-random, or Targeted Breaks in the Genome Method: HHI cells were harvested at 90% confluence, washed in 1×PBS, and resuspended at a cell concentration of 7.5x$10^6$ cells/ml in 1×PBS. To test the efficiency of integration, 15 μg linearized DNA (PGK-βgeo) was added to each 400 μl aliquot of cells and mixed. To several aliquots of cells, restriction enzymes XbaI, NotI, HindIII, IppoI (10–500 units) were then added to separate cell/DNA mixture. 400 μl was added to each electroporation cuvette and pulsed at 250 Volts, 600 αFarads, 50 Ohms using an electroporation apparatus (BioRad). Following the electric pulse, the cells were incubated at room temperature for 10 minutes, and then placed into 2.5 ml αMEM/10% FBS/1× penstrep. 300 μl of 2.5 ml total cells from each shock were plated onto tissue culture plates in complete media. At 24 hours post plating, G418 was added to the culture to a final concentration of 600 μg/ml. At 7 days post-selection, the media was replaced with fresh complete media containing 600 μg/ml G418. At 10 days post selection, media was removed from the plate, the colonies were stained with Coomassie Blue/90% methanol/10% acetic acid and colonies with greater than 50 cells were counted.

Example 4

Amplification by Selecting for Two Amplifiable Markers Located on the Integrated Vector Following integration of the vector into the genome of a host cell, the genetic locus may be amplified in copy number by simultaneous or sequential selection for one or more amplifiable markers located on the integrated vector. For example, a vector comprising two amplifiable markers may be integrated into the genome, and expression of a given gene (i.e., a gene located at the site of vector integration) can be increased by selecting for both amplifiable markers located on the vector. This approach greatly facilitates the isolation of clones of cells that have amplified the correct locus (i.e., the locus containing the integrated vector).

Once the vector has been integrated into the genome by nonhomologous recombination, individual clones of cells containing the vector integrated in a unique location may be isolated from other cells containing the vector integrated at other locations in the genome. Alternatively, mixed populations of cells may be selected for amplification.

Cells containing the integrated vector are then cultured in the presence of a first selective agent that is specific for the first amplifiable marker. This agent selects for cells that have amplified the amplifiable marker either on the vector or on the endogenous chromosome. These cells are then selected for amplification of the second selectable marker by culturing the cells in the presence of a second selective agent that is specific for the second amplifiable marker. Cells that amplified the vector and flanking genomic DNA will survive this second selective step, whereas cells that amplified the endogenous first amplifiable marker or that developed nonspecific resistance will not survive. Additional selections may be performed in similar fashion when vectors containing more than two (e.g., three, four, five, or more) amplifiable markers are integrated into the cell genome, by sequential culturing of the cells in the presence of selective agents that are specific for the additional amplifiable markers contained on the integrated vector. Following selection, surviving cells are assayed for level of expression of a desired gene, and the cells expressing the highest levels are chosen for further amplification. Alternatively, pools of cells resistant to both (if two amplifiable markers are used) or all (if more than two amplifiable markers are used) of the selective agents may be further cultured without isolation of individual clones. These cells are then expanded and cultured in the presence of higher concentrations of the first selective agent (usually twofold higher). The process is repeated until the desired expression level is obtained.

Alternatively, cells containing the integrated vector may be selected simultaneously for both (if two are used) or all (if more than two are used) of the amplifiable markers. Simultaneous selection is accomplished by incorporating both selection agents (if two markers are used) or all of the selection agents (if more than two markers are used) into the selection medium in which the transfected cells are cultured. The majority of surviving cells will have amplified the integrated vector. These clones can then be screened individually to identify the cells with the highest expression level, or they can be carried as a pool. A higher concentration of each selective agent (usually twofold higher) is then applied to the cells. Surviving cells are then assayed for expression levels. This process is repeated until the desired expression levels are obtained.

By either selection strategy (i.e., simultaneous or sequential selection), the initial concentration of selective agent is determined independently by titrating the agent from low concentrations with no cytotoxicity to high concentrations that result in cell death in the majority of cells. In general, a concentration that gives rise to discrete colonies (e.g., several hundred colonies per 100,000 cells plated) is chosen as the initial concentration.

Example 5

Isolation of cDNAs Encoding Transmembrane Proteins pRIG8R1-CD2 (FIGS. 5A–5D; SEQ ID NO:7), pRIG8R2-CD2 (FIGS. 6A–6C; SEQ ID NO:8), and pRIG8R3-CD2 (FIGS. 7A–7C; SEQ ID NO:9) vectors contain the CMV immediate early gene promoter operably linked to an exon followed by an unpaired splice donor site. The exon on the vector encodes a signal peptide linked to the extra-cellular domain of CD2 (lacking an in frame stop codon). Each vector encodes CD2 in a different reading frame relative to the splice donor site.

To create a library of activated genes, $2\times10^7$ cells were irradiated with 50 rads from a $^{137}Cs$ source and electroporated with 15 μg of linearized pRIG8R1-CD2 (SEQ ID NO:7). Separately, this was repeated with pRIG8R2-CD2 (SEQ ID NO:8), and again with pRIG8R3-CD2 (SEQ ID NO:9). Following transfection, the three groups of cells were combined and plated into 150 mm dishes at $5\times10^6$ transfected cells per dish to create library #1. At 24 hours post transfection, library #1 was placed under 500 μg/ml G418 selection for 14 days. Drug resistant clones containing the vector integrated into the host cell genome were combined, aliquoted, and frozen for analysis. Library #2 was created as described above, except that $3\times10^7$ cells, $3\times10^7$ cells and $1\times10^7$ cells were transfected with pRIG8R1-CD2, pRIG8R2-CD2, and pRIG8R3-CD2, respectively.

To isolate cells containing activated genes encoding integral membrane proteins, $3\times10^6$ cells from each library were cultured and treated as follows:

Cells were trypsinized using 4 mls of Trypsin-EDTA.

After the cells had released, the trypsin was neutralized by addition of 8 ml of alpha MEM/10% FBS.

The cells were washed once with sterile PBS and collected by centrifugation at 800×g for 7 minutes.

The cell pellet was resuspended in 2 ml of alpha MEM/10% FBS. 1 ml was used for sorting while the other 1 ml was replated in alpha MEM/10% FBS containing 500 μg/ml G-418, expanded and saved.

The cells used for sorting were washed once with sterile alpha MEM/10% FBS and collected by centrifugation at 800×g for 7 minutes.

The supernatant was removed and the pellet resuspended in 1 ml of alpha MEM/10% FBS. 100 μl of these cells was removed for staining with the isotype control.

200 μl of Anti-CD2 FITC (Pharmingen catalog #30054X) was added to the 900 μl of cells while 20 μl of the Mouse $IgG_1$ isotype control (Pharmingen catalog #33814X) was added to the 100 μl of cells. The cells were incubated, on ice, for 20 minutes.

To the tube that contained the cells stained with the Anti-Human CD2 FITC, 5 ml of PBS/1% FBS were added. To the isotope control, 900 μl of PBS/1% FBS were added. The cells were collected by centrifugation at 600×g for 6 minutes.

The supernatant from the tubes was removed. The cells that had been stained with the isotype control were resuspended in 500 μl of alpha MEM/10% FBS, and the cells that had been stained with anti-CD2-FITC were resuspended in 1.5 ml alpha MEM/10% FBS.

Cells were sorted through five sequential sorts on a FACS Vantage Flow Cytometer (Becton Dickinson Immunocytometry Systems; Mountain View, Calif.). In each sort, the indicated percentage of total cells, representing the most strongly fluorescent cells (see below) were collected, expanded, and resorted. HT1080 cells were sorted as a negative control. The following populations were sorted and collected in each sort:

| | Library #1 | Library #2 | Library #3 |
|---|---|---|---|
| Sort #1 | 500,000 cells collected (top 10%) | 100,000 cells collected (top 10%) | 40,000 cells collected (top 10%) |
| Sort #2 | 300,000 cells collected (top 5%) | 220,000 cells collected (top 11%) | 14,000 cells collected (top 5%) |
| Sort #3 | 90,000 cells collected (top 5%) | 40,000 cells collected (top 10%) | 120,000 cells collected (top 10%) |
| Sort #4 | 600,000 cells collected (top 40%) | (a) 6,000 cells collected (top 5%); (b) 10,000 cells collected (next 5%) | 280,000 cells collected (top 13%) |
| Sort #5 | (a) 260,000 cells collected (top 10%); (b) 530,000 cells collected (next 25%) | (a) from group (a) of sort #4, 100,000 cells collected (top 10%), and 350,000 cells collected (next 35%); (b) from group (b) of sort #4, 120,000 cells collected (top 10%) | (Not done) |

Cells from each of the final sorts for each library were expanded and stored in liquid nitrogen.

Isolation of Activated Genes from FACS-sorted Cells

Once cells had been sorted as described above, activated endogenous genes from the sorted cells were isolated by PCR-based cloning. One of ordinary skill will appreciate, however, that any art-known method of cloning of genes may be equivalently used to isolate activated genes from FACS-sorted cells.

Genes were isolated by the following protocol:

(1) Using PolyATract System 1000 mRNA isolation kit (Promega), mRNA was isolated from $3\times10^7$ CD2+ cells (sorted 5 rounds by FACS, as described above) from libraries #1 and #2.

(2) After mRNA isolation, the concentration of mRNA was determined by diluting 0.5 μl of isolated mRNA into 99.5 µl water and measuring OD$^{260}$. 21 µg of mRNA were recovered from the CD2+ cells.

(3) First strand cDNA synthesis was then carried out as follows:
 (a) While the PCR machine was holding at 4° C., first strand reaction mixtures were set up by sequential addition of the following components:
  41 µl DEPC-treated ddH$_2$O
  4 µl 10 mM each dNTP
  8 µl 0.1 MDTT
  16 µl 5×MMLV first strand buffer (Gibco-BRL)
  5 µl (10 pmol/µl) of the consensus polyadenylation site primer GD.R1 (SEQ ID NO:10)*
  1 µl RNAsin (Promega)
  3 µl (1.25 µg/µl) mRNA.

*Note: GD.R1, 5'TTTTTTTTTTTTCGTCAGCGGCCG-CATCNNNNTTTATT 3' (SEQ ID NO:10), is a "Gene Discovery" primer for first strand cDNA synthesis of mRNA; this primer is designed to anneal to the polyadenylation signal AATAAA and downstream poly-A region. This primer will introduce a NotI site into the first strand.

Once samples had been made up, they were incubated as follows:
 (b) 70° for 1 min.
 (c) 42° hold.
  2 µl of 400 U/µl SuperScript II (Gibco-BRL; Rockville, Md.) was then added to each sample, to give a final total volume of 82 µl. After approximately three minutes, samples were incubated as follows:
 (d) 37° for 30 min.
 (e) 94° for 2 min.
 (f) 4° for 5 min.
  2 µl of 20 U/µl RNace-IT (Stratagene) was then added to each sample, and samples were incubated at 37° for 10 min.

(4) Following first strand synthesis, cDNA was purified using a PCR cleanup kit (Qiagen) as follows:
 (a) 80 µl of the first strand reaction were transferred to a 1.7 ml siliconized eppendorf tube and adding 400 µl of PB.
 (b) Samples were then transferred to a PCR clean-up column and centrifuged for two minutes at 14,000 RPM.
 (c) Columns were then disassembled, flowthrough decanted, 750 of µl PE were added to pellets, and tubes were centrifuged for two minutes at 14,000 RPM.
 (d) Columns were disassembled and flowthrough decanted, and tubes then centrifuged for two minutes at 14,000 RPM to dry resin.
 (e) cDNA was then eluted using 50 µl of EB through transferring column to a new siliconized eppendorf tube which was then centrifuged for two minutes at 14,000 RPM.

(5) Second strand cDNA synthesis was then carried out as follows:
 (a) Second strand reaction mixtures were set up at RT, through the sequential addition of the following components:

| | |
|---|---|
| ddH$_2$O | 55 µl |
| 10 × PCR buffer | 10 µl |
| 50 mM MgCl$_2$ | 5 µl |
| 10 mM dNTPs | 2 µl |
| 25 pmol/µl RIG.751-Bio* | 4 µl |
| 25 pmol/µl GD.R2** | 4 µl |
| First strand product | 20 µl |

*Note: RIG.F751-Bio, 5' Biotin-CAGATCACTAGAAGCTTTATTGCGG 3' (SEQ ID NO:11), anneals at the cap-site of the transcript expressed from pRIG vectors.

**Note: GD.R2, 5' TTTTCGTCAGCGGCCGCATC 3' (SEQ ID NO:12), is a primer used to PCR amplify cDNAs generated using primer GD.R1 (SEQ ID NO:10). GD.R2 is a sub-sequence of GD.R1 with matching sequence up to the degenerate bases preceding the polyA signal sequence.

(b) Start second strand synthesis:
  94° C. for 1 min;
  add 1 µl Taq (5 U/µl, Gibco-BRL);
  add 1 µl Vent DNA pol (0.1 U/µl, New England Biolabs).
 (c) Incubate at 63° C. for 2 min.
 (d) Incubate at 72° C. for 3 min.
 (e) Repeat step (b) four times.
 (f) Incubate at 72° C. for 6 min.
 (g) Incubate at 4° C. (hold)
 (h) END (6) 200 µl of 1 mg/ml Streptavidin-Paramagnetic Particles (SA-PMP) were then prepared by washing three times with STE.

(7) The products of the second strand reaction were added directly to the SA-PMPs and incubated at RT for 30 minutes.

(8) After binding, SA-PMPs were collected through the use of the magnet, and flowthrough material recovered.

(9) Beads were washed three times with 500 µl STE.

(10) Beads were resuspended in 50 µl of STE and collected at the bottom of the tube using the magnet. STE supernatant was then carefully pipetted off.

(11) Beads were resuspended in 50 µl of ddH$_2$O and placed into a 100° C. water bath for two minutes, to release purified cDNA from PMPs.

(12) Purified cDNA was recovered by collecting PMPs on the magnet and carefully removing the supernatant containing the cDNA.

(13) Purified products were transferred to a clean tube and centrifuged at 14,000 RPM for two minutes to remove all of the residual PMPs.

(14) A PCR reaction was then carried out to specifically amplify RIG activated cDNAs, as follows:
 (a) PCR reaction mixtures were set up at RT, through the sequential addition of the following components:

| | |
|---|---|
| H$_2$O | 59 µl |
| 10 × PCR buffer | 10 µl |
| 50 mM MgCl$_2$ | 5 µl |
| 10 mM dNTPs | 2 µl |
| 25 pmol/µl RIG.F781* | 2 µl |
| 25 pmol/µl GD.R2 | 2 µl |
| second strand product | 20 µl |

-continued

*Note:
RIG.F781, 5' ACTCATAGGCCATAGAGGCCTATCA-CAGTTAAATTGCTAACGCAG 3' (SEQ ID NO:13), anneasl downstream of GD.F1 GD.F3, GD.F5-Bio, and RIG.F751-Bio, and adds an SfiI site for 5' cloning of cDNAs. This primer is used in nested PCR amplification of RIG Exon1 specific second strand cDNAs.

(b) Start thermal cycler:
94° C. for 3 min;
add 1 $\mu$l of Taq (5 U/$\mu$l; Gibco-BRL);
add 1 $\mu$l of 0.1 U/$\mu$l Vent DNA polymerase (New England Biolabs)

PCR was then carried out by 10 cycles of steps (c) to (e):
(c) 94° C. for 30 sec.
(d) 60° C. for 40 sec.
(e) 72° C. for 3 min.

PCR was then completed by carrying out the following steps:
(f) 94° C. for 30 sec.
(g) 60° C. for 40 sec.
(h) 72° C. for 3 min.
(i) 72° C. +20 sec each cycle for 10 cycles
(j) 72° C. for 5 min
(k) 4° C. hold.

(15) After elution of library material with 50 $\mu$l EB, samples were digested by adding 10 $\mu$l of NEB Buffer 2, 40 $\mu$l of $dH_2O$ and 2 $\mu$l of SfiI and digesting for 1 hour at 50° C., to cut the 5' end of the cDNA at the SfiI site encoded by the forward primer (RIG.F781; SEQ ID NO:13).

(16) Following SfiI digestion, 5 $\mu$l of 1M NaCl and 2 $\mu$l of NotI were added to each sample, and samples digested for one hour at 37° C., to cut the 3' end of the cDNA at the NotI site encoded by the first strand primer (GD.R1; SEQ ID NO:10).

(17) The digested cDNA was then separated on a 1% low melt agarose gel. cDNAs ranging in size from 1.2 Kb to 8 Kb were excised from the gel.

(18) cDNA was recovered from the excised agarose gel using Qiaex II Gel Extraction (Qiagen). 2 $\mu$l of cDNA (approximately 30 mg) was ligated to 7 $\mu$l (35 ng) of pBS-HSB (linearized with SfiI/NotI) in a total volume of 10 $\mu$l of 1×T4 ligase buffer (NEB), using 400 units of T4 DNA ligase (NEB).

(19) 0.5 $\mu$l of the ligation reaction mixture from step (18) was transformed into *E. coli* DH10B.

(20) 103 colonies/0.5 $\mu$l ligated DNA were recovered.

(21) These colonies were screened for exons using the primers M13F20 and JH182 (RIG Exon 1 specific) through PCR in 12.5 $\mu$l volumes as follows:

(a) 100 $\mu$l of LB (with selective antibiotic) were dispensed into the appropriate number of 96-well plates.

(b) Single colonies were picked and inoculated into individual wells of the 96-well plate, and the plate placed into a 37° C. incubator for 2–3 hours without shaking.

(c) A PCR reaction "master mix" was prepared on ice, as follows:

| # of 96-Well Plates: Total # of 12.5 $\mu$l PCR rxns: | 1 Plate 96 | 2 Plates 192 | 3 Plates 288 | 4 Plates 384 |
|---|---|---|---|---|
| $dH_2O$ | 755 $\mu$l | 1.47 ml | 2.20 ml | 2.94 ml |
| 5 × PCR Premix-4 | 250 $\mu$l | 500 $\mu$l | 750 $\mu$l | 1.0 ml |
| F Primers premix (25 pmol/$\mu$l) | 10 $\mu$l | 20 $\mu$l | 30 $\mu$l | 40 $\mu$l |
| R Primers premix (25 pmol/$\mu$l) | 10 $\mu$l | 20 $\mu$l | 30 $\mu$l | 40 $\mu$l |
| RNace-It Cocktail | 3.2 $\mu$l | 6.3 $\mu$l | 9.6 $\mu$l | 12.8 $\mu$l |
| Taq Polymerase (5 U/$\mu$l) | 3.2 $\mu$l | 6.3 $\mu$l | 9.6 $\mu$l | 12.8 $\mu$l |
| Total Volume (ml) | 1.01 | 2.02 | 3.03 | 4.04 |

(d) 10 $\mu$l of the master mix were dispensed into each well of the PCR reaction plate.

(e) 2.5 $\mu$l from each 100 $\mu$l *E. coli* culture were transferred into the corresponding wells of the PCR reaction plate.

(f) PCR was performed, using typical PCR cycle conditions of:
(i) 94° C./2 min. (Bacterial lysis and plasmid denaturation)
(ii) 30 cycles of 92° C. denaturation for 15 sec; 60° C. primer annealing for 20 sec; and 72° C. primer extension for 40 sec
(iii) 72° C. final extension for 5 min.
(iv) 4° C. hold.

(g) Bromophenol blue was then added to the PCR reaction; samples were mixed, centrifuged, and then the entire reaction mix was loaded onto an agarose gel.

23) Of 200 clones screened, 78% were positive for the vector exon. 96 of these clones were grown as minipreps and purified using a Qiagen 96-well turbo-prep following the Qiagen Miniprep Handbook (April 1997).

24) Many duplicate clones were eliminated though simultaneous digestion of 2 $\mu$l of DNA with NotI, Bam HI, XhoI, XbaI, HindIII, EcoRI in NEB Buffer 3, in a total volume of 22 $\mu$l, followed by electrophoresis on a 1% agarose gel.

Results:

Two different cDNA libraries were screened using this protocol. In the first library (TMT#1), eight of the isolated activated genes were sequenced. Of these eight genes, four genes encoded known integral membrane proteins and six were novel genes. In the second library (TMT#2), 11 isolated activated genes were sequenced. Of these 11 genes, one gene encoded a known integral membrane protein, one gene encoded a partially sequenced gene homologous to an integral membrane protein, and nine were novel genes. In all cases where the isolated gene correspond to a characterized known gene, that gene was an integral membrane protein.

Exemplary significant alignments (obtained from GenBank) for genes isolated from each library are shown below:

TMT#1 Significant Alignments:

179761|gb|M76559|HUMCACNLB Human neuronal DHP-sensitive
voltage-dependent, calcium channel alpha-2b subunit mRNA
complete CDs.
Length=3600

>gi|3183974|emb|Y10183|HSMEMD *H. sapiens* mRNA for MEMD protein Length=4235

TMT#2 Significant Alignments:

>gi|476590|gb|U06715|HSU06715 Human cytochrome B561, HCYTO B561, mRNA, partial CDs. Length=2463

>gi|2184843lgb|AA4599591AA459959 zx66cO1.sl Soares total fetus $N_b$2HF8 9w Homo sapiens cDNA clone 796414 3' similar to gb:J03171 INTERFERON-ALPHA RECEPTOR PRECURSOR (HUMAN); Length =431

Example 6

Activation of Endogenous Genes using a Poly(A) Trap Vector

HT1080 cells ($1\times10^7$ cells) were irradiated with 50 rads using a $^{137}$Cs source and electroporated with 15 μg linearized pRIG14 (FIGS. 29A–29B. Following transfection, the cells were plated into a 150 mm dish at $5\times10^6$ cells/dish. At 24 hours, puromycin was added to 3 μg/ml. The cells were incubated at 37° C. for 12 days in the presence of 3 μg/ml puromycin. The media was replaced every 5 days. At 12 days, the number of colonies was counted, and the cells were trypsinized and replated onto a new dish. The cells were grown to 90% confluency and harvested for frozen storage and gene isolation. Typically, 1000–3000 colonies were produced per $1\times10^7$ cells transfected.

Example 7

Activation of Endogenous Genes Using a Dual Poly(A) Trap/SA T Vector $1\times10^7$ HHI cells (HPRT-minus HT1080 cells) were irradiated with 50 rads using a $^{137}$Cs source and electroporated with 15 μg linearized pRIG-22. Following transfection, the cells were plated into a 150 mm dish at $5\times10^6$ cells/dish. At 24 hours, neomycin was added to 500 μg/ml G481. The cells were incubated at 37° C. for 4 days in the presence of 500 μg/ml G418. The media was replaced with fresh media containing 500 μg/ml G418 and AgThg and grown in the presence of both drugs for an additional 7 days. Alternatively, as a control for HPRT activity, the media was replaced with fresh media containing 500 μg/ml G418 and HAT (available from Life Technologies, inc., Rockville, Md., and used at manufacturer's recommended concentration) and grown in the presence of both drugs for an additional 7 days. At 12 days post transfection, the number of colonies was counted, and the cells were trypsinized and replated onto a new dish.

The cells were grown to 90% confluency and harvested for frozen storage and gene isolation. Typically, cells subjected to G418/AgThg selection produced 1000–3000 colonies per $1\times10^7$ cells transfected. In contrast, cells subjected to G418/HAT selection produced approximated 100 colonies per $1\times10^7$ cells transfected.

Example 8

Isolation of Activated Genes

Non-targeted gene activation vectors are integrated into the genome of a eukaryotic cells using the methods of the invention. By integrating the vector into multiple cells, a library is created in which cells are expressing different vector activated genes. RNA is isolated from these cells using a commercial RNA isolation kit. In this example, RNA is isolated from cells using Poly(A) Tract 1000 (Promega). The RNA is converted into cDNA, amplified, size fractionated, and cloned into a plasmid for analysis and sequencing. A brief description of this process is presented.

1) Place 4 ml GTC Extraction buffer (Poly(A) tract 1000 Kit-Promega) in a 15 ml polycarbonate screw cap tube and add 168 μl 2-mercaptoethanol and place in a 70° C. water bath.
2) Place 8 ml dilution buffer in a 15 ml polycarbonate screw cap tube for every pellet processed and add 168 μl 2-mercaptoethanol and place in a 70° C. water bath.
3) Remove from −80° C. storage cell pellets ($1\times10^7$–$1\times10^8$ cells) containing non-targeted gene activation vector integrated into their genome. Pipette 4 ml GTC Extraction buffer immediately onto cell pellet. Pipette up-and-down several times until the pellet is resuspended and transfer into a 15 ml snap cap polypropylene tube.
4) Add the 8 ml dilution buffer and mix by inversion.
5) Add 10 μl (500 pmol) of the biotinlylated oligo dT primer and mix.
6) Let sit at 70° C. for 5 minutes inverting every couple of minutes to ensure even heating.
7) Centrifuge in a Sorvall HB-6 rotor at 7800 rpm (10 k×g) at 25° C. for 10 minutes. During this period of time wash 6 ml Strepavidin-Paramagnetic particles (SA-PMPs) 3× with 6 ml 0.5×SSC through use of the Poly(A) Tract system 1000 magnet.
8) After 3 washes resuspend the SA-PMPs in 6 ml 0.5×SSC.
9) Pipette to remove the supernatant from the RNA prep and add to the resuspended SA-PNPs (Be careful when removing supernatant so that you do not disrupt the pellet).
10) Let the SA-PMP/RNA mix and incubate for 2 minutes at room temperature.
11) Capture the magnetic beads through use of the Poly (A) Tract system 1000 magnet. Note that it takes some time for all of the beads to pellet due to the high viscosity of the liquid.
12) Pour off the supernatant and resuspend the beads in 1.7 ml of 0.5×SSC using a 2 ml pipette and transfer to a 2 ml screw cap tube.
13) Capture the SA-PMPs using the magnet and remove the supernatant by pipetting with a P1000.
14) Add 1.7 ml 0.5×SSC and invert the tube several times to mix.
15) Repeat steps 14 and 15 two more times.
16) Resuspend the SA-PMPs in 1 ml of nuclease free water and invert several times to mix.
17) Capture the SA-PMPs and pipette off the mRNA.
18) Place 0.5 ml of the mRNA into each of two siliconized eppendorf tubes and add 50 μl of DEPC-treated 3M NaOAc solution and 0.55 ml of isopropanol. Invert several times to mix and place at −20° C. for at least 4 hours.
19) Centrifuge the mRNA for 10 minutes at max RPM (14 k).
20) Carefully pipette off the supernatants and wash pellets with 200 μl 80% ethanol through re-centrifugation for 2 minutes at 14K RPM. Note that the pellets are often brown or tan in color. This color results from residual SA-PMPs.
21) Remove wash and let pellets air dry for not more than 10 minutes at room temperature.

22) Resuspend pellets in 5 μl each and combine into a single tube.

23) Centrifuge at 14K RPM for 2 minutes to remove the residual SA-PMPs and carefully remove the mRNA.

24) Determine the concentration of mRNA by diluting 0.5 μl into 99.5 μl water and measuring OD 260. Note that 1 OD 260=40 μg RNA.

25) Set up first strand reaction for both the test sample and the negative control (HT1080) through the sequential addition of the following components while the PCR machine is holding at 4° C.:

Step 1:
42 μl DEPC-treated $ddH_2O$
4 μl 10 mM each dNTP
8 μl 0.1 M DTT
16 μl 5×MMLV 1st strand buffer
5 μl (10 pmol/μl) GDR1
1 μl RNAsin (Promega)
4 μl (1.25 μg/μl) mRNA.

Step 2: 70°/1 min
Step 3: 42°/hold
Step 4: After 1 minute add 2 μl SUPERSCRIPT II® (Life Technologies, Inc.; Rockville, Md.) and incubate at 37° C. for 30 min
Step 5: 94°/2 min
Step 6: 4°/∞
Step 7: Add 2 μl RNase and incubate at 37° C. for 10 min
Step 8: 4°/∞

26) Analyze 8 μl of cDNA on a 1% agarose gel to check for cDNA synthesis and purify remaining cDNA using the PCR cleanup kit from Qiagen by transferring the 70 μl first strand reaction to a 1.5 ml siliconized eppendorf tube and adding 400 μl PB.

27) Transfer to a PCR clean-up column and centrifuge 2 minutes at max RPM.

28) Disassemble column and pour out Flow through. Add 750 μl PE and centrifuge 2 minutes at max RPM.

29) Disassemble column and pour out Flow throught then centrifuge 2 minutes at max RPM to dry resin.

30) Elute using 50 μl of EB through transferring column to a new siliconized eppendorf tube and centrifuging for 2 minutes at max RPM.

31) Second Strand cDNA synthesis set up at RT:

| | |
|---|---|
| $H_2O$ | 8.5 μl |
| 10 × PCR buffer | 5 μl |
| 50 mM $MgCl_2$ | 2.5 μl |
| 10 mM dNTPs | 1 μl |
| 25 pmol/μl GDF5Bio | 10 μl |
| 25 pmol/μl GDR2 | 10 μl |
| First strand product | 15 μl |

Step 9: 94° C./1 min.
Step 10: 60° C./10 min.
Add 0.25 μl Taq polymerase
Step 11: 60° C./2 min.
Step 12: 72° C./10 min.
Step 13: 94° C./1 min.
Step 14: min go to "Step 11" four more times
Step 15: 60° C./2 min
Step 16: 72° C./10 min
Step 17: END 32) Prepare 100 μl of SA-PMPs by washing 3× with STE and collection using a magnet. After the final wash, resuspend the beads in 150 μl STE.

33) Purify the products of the second strand reaction using the PCR cleanup kit from Qiagen. Elute in 50 μl EB and add he products of the second strand reaction to 150 μl of the PMPs.

34) Mix gently at RT for 30 minutes.

35) After binding collect SA-PMPs through use of a magnet and recover flow through material (SAVE THIS MATERIAL!)

36) Wash the beads 3× with 500 μl STE and 1× with NEB 2 (1×).

37) Resuspend the beads in 100 μl NEB 2 (1×).

38) Add 2 μl SfiI and digest at 50° C. for 30 minutes with gentle mixing every 10 minutes.

39) Recover purified cDNA through use of a magnet and carefully removing the supernatant.

40) Transfer the products to a new tube and centrifige at maximum RPM for 2 minutes to remove all of the beads.

41) Set up a PCR reaction to specifically amplify RAGE activated cDNAs:

| | |
|---|---|
| $H_2O$ | 37 μl |
| 10 × PCR buffer | 10 μl |
| 10 mM dNTPs | 2 μl |
| 25 pmol/μl GDF 781 | 10 μl |
| 25 pmol/μl GDR2 | 10 μl |
| Second strand product | 25 μl |

Step 1: 94° C./2 min.
Step 2: 94° C./45 sec.
Step 3: 60° C./10 min.
Add 0.5 μl Taq Polymerase
Step 4: 72° C./10 min.
Step 6: 60° C./2 min.
Step 7: 72° C./10 min.
Step 8: Cycle to step 5, 8 more times
Step 9: 94° C./45 sec.
Step 10: 60° C./2 min.
Step 11: 72° C./10 min.+20 sec each cycle
Step 12: Cycle to step 9, 14 more times
Step 13: 72° C./5 min.
Step 14: 4° C. hold 42) Check specificity of PCR amplification of HT1080 versus library material through analysis on a 1% agarose gel. If there is a high specificity of cDNA amplification, then use Qiagen PCR clean up kit to purify PCR products.

43) After elution of library material with 50 μl EB add 10 μl NEB2, 40 μl $dH_2O$ and 2 μl SfiI and digest for 1 hour at 50° C.

44) Add 5 μl of 1 M NaCl and 2 μl of NotI and digest for 1 hour at 37° C.

45) Prepare and run a 1% L.M. agarose gel and run library material on gel. After visualization of material, cut out fragments ranging in size from 500 bp to 10 Kb.

46) Recover the library DNA from agarose using Qiaex II Gel Extraction Protocol (Qiagen) and elute DNA in 10 μl EB. Ligate 5 μl of this material to 4 μl pBS-HSB (SfiI/NotI) or pBS-SNS in a total volume of 10 μl.

47) Transform *E. coli* with 0.5 μl ligated DNA per 40 μl cells.

48) Pick colonies, grow overnight in LB, isolate plasmids.

49) Analyze gene activated cDNA inserts by restriction digest and DNA sequencing.

Example 9

Isolation of Activated Genes from Subtracted cDNA Pools

Purified mRNAs from non-transfected HT1080 cells was prepared using the Poly-A Tract 1000 system (Promega), as described in Example 8 steps 1–24, and were biotinylated using EZ-Link™ Biotin LC-ASA reagent (Pierce), as follows:

1.) 25 μl DEPC-treated dH$_2$O and 15 μl containing 10 μg of HT1080 mRNA was added into a siliconized microfuge tube and held on ice.
2.) Working under subdued light, 40 μl of prepared LC-ASA stock reagent (1 mg/ml in 100% ethanol) was added into the reaction tube.
3.) A UV light (365 nm wavelength) was positioned 5 cm above the microfuge tube and used to irradiate the reaction mix for 15 minutes.
4.) Unlinked biotin reagent was removed from the labeled HT1080 mRNA by passing the reaction mix through an RNase-free MicroSpin P-30 column (BioRad), as prescribed by the manufacturer.

HT1080 cells were transfected with a poly(A) trap pRIG activation vector and grown under selective media to produce a population of drug resistant colonies, as described in Example 1. Purified mRNAs were prepared from the pooled colonies using the Promega Poly-A Tract 1000 system, as described in Example 8. First strand cDNA was prepared from 5 μg of this mRNA using oligo GD.R1 (TTTTTTTTTTTTCGTCAGCGGCCGCATCNNNNTTTATT) (SEQ ID NO:10), as described in Example 8, Step 25. The reaction mix was passed through a Qiagen PCR Quick Clean-up column and the purified 1st strand cDNA was recovered in 100 μl EB.

The subtractive hybridization of biotinylated HT1080 mRNAs (subtractor population) and 1st strand cDNAs prepared from the superpool of pRIG-transfected colonies (target population) was performed as follows:

1.) 9 μg of biotinylated mRNA was added into a 0.5 ml microfuge tube containing 0.5 μg 1st strand cDNA.
2.) 1/100×volume of 10 mg/ml glycogen, 1/10×volume of 3 M sodium acetate, pH 5.5, and 2.6×volume of 100% ethanol were added into the tube and mixed.
3.) The tube was placed at −80° C. for 1 hr, then spun in a refrigerated microfuge for 20 minutes.
4.) The pellet of precipitated nucleic acids was drained, washed once with 70% ethanol, then air-dried.
5.) The pellet was solvated in 5 μl HBS (50 mM HEPES, pH 7.6; 2 mM EDTA; 0.2% SDS; 500 mM NaCl) and overlayered with 5 μl light mineral oil, then heated to 95° C. for 2 minutes followed by 68° C. for 24 hours.
6.) The reaction mix was diluted with 100 μl HB (HBS without SDS) and extracted once with 100 μl chloroform to remove the oil.
7.) The diluted hybridization mix was added to 300 μl streptavidin-coated paramagnetic particles (Promega) which had been pre-washed 3× in 300 μl HB.
8.) The mix was incubated 10 minutes at room temperature and the SA-PMP's and bound Biotin-mRNA:DNA hybrids were removed from solution by magnetic capture.
9.) Steps 7 and 8 were repeated once.
10.) The cleared solution was subjected to one additional round of subtractive hybridization and magnetic removal of captured hybrids (Steps 1–9), with the following exceptions:
  Step 6: the hybridization reaction was diluted with 2×PCR Buffer (40 mM Tris-HCl, pH 8.4; 100 mM KCl).
  Step 7: PMPs were pre-washed in 1×PCR Buffer The twice-subtracted 1st strand cDNA was used to generate 2nd strand cDNA by combining 45 μl of 1st strand cDNA with 7 μl dH$_2$O, 5 μl 50 mM MgCl$_2$, 2 μl premix of 10 mM each dNTP, 1 μl 10×PCR Buffer, 20 μl of 12.5 pmol/μl GD19F1-Bio (5' Biotin-CTCGTTTAGTGCGGCCGCTCAGATCACTGAATTCT GACGACCT) (SEQ ID NO:14), 20 μl of 12.5 pmol/μl GD.R2 (TTTTCGTCAGCGGCCGCATC) (SEQ ID NO:12), and 0.5 μl Taq Polymerase, with thermocycling as described in Example 8, Step 31. The second strand cDNA product was amplified and further processed for the production of an E. coli-based cDNA library, as described in Example 8, steps 32–49.

Example 10

Selective Capture of RIG-activated Transcripts

HT1080 cells were transfected with pRIG19 activation vector (FIGS. 30A–30C) and cultured for 2 weeks in selective media, as described in Example 6. Total RNA was prepared from a pellet comprised of $10^8$ cells using TRIzol® Reagent (Life Technologies, Inc.; Rockville, Md.) following the manufacturer's protocol, and was dissolved in 720 μl of DEPC-treated dH$_2$O (dH$_2$O$^{DEPC}$) Contaminating genomic DNA was eliminated from the RNA preparation by mixing 80 μl NEB 10×Buffer 2, 8 μl Promega RNasin, and 20 μl RQ1 Promega RNase-free DNase, incubating at 37° C. for 30 minutes, extracting sequentially with equal volumes of phenol:chlorofom(1:1) and chloroform, mixing with 1/10× volume sodium acetate (pH 5.5), precipitating the RNA with 2×volume of 100% ethanol, and solvating the dried RNA pellet in dH$_2$O$^{DEPC}$ to a final concentration of 4.8 μg/μl.

mRNA transcripts derived from pRIG19-activated genes were selectively captured from the pool of total cellular RNAs by mixing in a 2 ml RNase-free microfuge tube 150 μl total RNA, 150 μl HBDEPC (50 mM HEPES, pH 7.6; 2 mM EDTA; 500 mM NaCl), 3 μl Promega RNasin, and 2.5 μl (25 pmol/μl) oligo GD19.R1-Bio (see Table 1), then incubating at 70° C. for 5 minutes followed by 50° C. for 15 minutes. One ml of Promega streptavidin coated paramagnetic particles (SA-PMPs) was magnetically captured and washed 3× each with 1.5 ml of 0.5×SSC, and the SA-PMPs were left without being resuspended. The warm oligo:RNA hybridization reaction was added directly into the tube containing the semi-dry SA-PMPs. After incubating for 10 minutes at room temperature the SA-PMPs were washed 3× with 1 ml 0.5×SSC.

TABLE 1

| Primer and Oligonucleotide Sequences | | |
| --- | --- | --- |
| Primer/Oligo Name | Sequence | SEQ ID NO: |
| Forward PCR Primers GD19.F1-Bio | 5'Biotin-CTCGTTTAGTGCGG-CCGCTCAGATCACTGAATTC TGACGACCT | 14 |
| GD19.F2-Bio | 5'Biotin-CTCGTTTAGTGGCG-CGCCAGATCACTGAATTCTG ACGACCT | 15 |

TABLE 1-continued

Primer and Oligonucleotide Sequences

| | Primer/Oligo Name | Sequence | SEQ ID NO: |
|---|---|---|---|
| | GD19.F2 | GACCTACTGATTAACGGCC-ATA | 16 |
| Reverse PCR Primers | GD.R1 | TTTTTTTTTTTTCGTCAGCG-GCCGCATCNNNNTTTATT | 10 |
| | GD.R2 | TTTTCGTCAGCGGCCGCATC | 12 |
| mRNA Capture Oligo | GD19.R1-Bio | TCGTCAGAATTCAGTGAT-CT-3'Biotin | 17 |

After the final magnetic capture, the SA-PMP's were suspended in 190 µl dH$_2$ODEPC and incubated at 68° C. for 15 minutes. PMPs were immobilized by exposure to a magnetic and the cleared solution containing RIG-activated transcripts was transferred to a microfuge tube. 63 µl of captured RIG-activated transcript were transferred to a PCR tube where first and second strand cDNA synthesis was performed using PCR program "1+2CDNA", as follows:

Step 1: 4° C./∞: Add into the PCR tube containing the RIG-activated transcripts 20 µl 5×GibcoBRL RT Buffer, 1 µl Promega RNasin, 10 µl 100 mM DTT, 5 µl dNTP premix at 10 mM each, 1 µl oligo GD.R1 (see Table 1) at 25 pmol/µl.

Step 2: 70° C./3 minutes

Step 3: 42° C./10 minutes

Step 4: Add 2.5 µl SUPERSCRIPT II® (Life Technologies, Inc.), then incubate at 37° C./1 hour Step 5: 94° C./2 minutes Step 6: 4° C./∞.

To the 1st strand cDNA mix, 2 µl of Stratagene RNase-It was added and the mixture was incubated at 37° C. for 15 minutes. 600 µl of Qiagen PB reagent was added to the reaction, then transferred to a Qiagen PCR clean-up column and processed according to the manufacturer's protocol. cDNA was eluted from the column in 50 µl EB and transferred to a PCR tube. The second strand cDNA reaction was performed using oligos GD19.F2-Bio (Table 1) and GD.R2 (Table 1) as described in Example 9. The second strand product was captured on Promega SA-PMPs as described in Example 9, with the exception that the final suspension of SA-PMPs was in 1×NEB 4 Buffer and the captured cDNAs were cleaved from the particles using restriction endonuclease Asc I. Amplification of the second strand cDNA products using oligos GD19.F2 and GD.R2, digestion of the amplified cDNAs using endonucleases SfiI and NotI, and size selection of cDNAs prior to cloning were all performed as described in Example 9. The final cDNA cleanup was achieved by eluting the cDNA pool off a Qiagen PCR Cleanup column in 30 µl EB. 11 µl of cDNA was mixed with 4 µl 5×GibcoBRL Ligase Buffer, 4 µl pGD5 vector DNA previously prepared by digestion with SfiI, NotI, and CIP. 1 µl T4 DNA Ligase was added, and the reaction mix was incubated at 16° C. overnight. 1 µl of ligation reaction was used to transform electro-competent E. coli DH10B cells, which were subsequently plated on LB agar plates containing 12.5 µg/ml chloramphenicol. Typically, 60 to 80 bacterial colonies were recovered per µl of ligation mix transformed.

Example 11

Selective Capture of RIG-activated Transcripts

HT1080 cells were transfected with pRIG19 activation vector and cultured for 2 weeks in selective media, as described in Example 6. Total RNA was prepared from a pellet comprised of $10^8$ cells using TRIzol® Reagent (Life Technologies, Inc.) following the manufacturer's protocol, and was dissolved in 720 µl of DEPC treated dH$_2$O (dH$_2$O$^{DEPC}$). Contaminating genomic DNA was eliminated from the RNA preparation by mixing 80 µl NEB 10×Buffer 2, 8 µl Promega RNasin, and 20 µl RQ1 Promega RNase-free DNase, incubating at 37° C. for 30 minutes, extracting sequentially with equal volumes of phenol:chlorofom (1:1) and chloroform, mixing with 1/10×volume sodium acetate (pH 5.5), precipitating the RNA with 2×volume of 100% ethanol, and solvating the dried RNA pellet in dH2ODEPC to a final concentration of 4.8 µg/µl.

mRNA transcripts derived from pRIG19-activated genes were selectively captured from the pool of total cellular RNAs by mixing in a 2 ml RNase-free microfuge tube 150 µl total RNA, 150 µl HBDEPC (50 mM HEPES, pH 7.6; 2 mM EDTA; 500 mM NaCl), 3 µl Promega RNasin, and 2.5 µl (25 pmol/µl) oligo GD19.R1-Bio (see Table 1), then incubating at 70° C. for 5 minutes followed by 50° C. for 15 minutes. One ml of Promega streptavidin coated paramagnetic particles (SA-PMPs) was magnetically captured and washed 3×each with 1.5 ml of 0.5×SSC, and the SA-PMPs were left without being resuspended. The warm oligo:RNA hybridization reaction was added directly into the tube containing the semi-dry SA-PMPs. After incubating for 10 minutes at room temperature the SA-PMPs were washed 3× with 1 ml 0.5×SSC. After the final magnetic capture the SA-PMP's were suspended in 190 µl dH$_2$O$^{DEPC}$ and incubated at 68° C. for 15 minutes. PMPs were immobilized by exposure to a magnetic and the cleared solution containing RIG-activated transcripts was transferred to a microfuge tube. 63 µl of captured RIG-activated transcript were transferred to a PCR tube where first and second strand cDNA synthesis was performed using PCR program "1+2CDNA", as follows:

Step 1: 4° C./∞: Add into the PCR tube containing the RIG-activated transcripts 20 µl 5×GibcoBRL RT Buffer, 1 µl Promega RNasin, 10 µl 100 mM DTT, 5 µl dNTP premix at 10 mM each, 1 µl oligo GD.R1 (see Table 1) at 25 pmol/µl.

Step 2: 70° C./3 minutes

Step 3: 42° C./10 minutes

Step 4: Add 2.5 µl SUPERSCRIPT II® (Life Technologies, Inc.), then incubate at 37° C./1 hour Step 5: 94° C./2 minutes Step 6: 60° C./∞; while holding temperature, the following were added: 2 µl 50 mM MgCl$_2$, 1 µl oligo GD19.F1-Bio (Table 1) at 25 pmol/µl, and 2 µl Stratagene RNace-It. After 10 minutes, 0.5 µl Taq DNA Polymerase (Life Technologies, Inc.) was added and the cycling was continued:

Step 7: 72° C./10 minutes

Step 8: 4° C./∞.

The 100 µl volume cDNA reaction mix was transferred to a 1.5 ml siliconized microfluge tube and extracted sequentially with equal volumes of phenoi:chloroform (1:1) and chloroform, and the aqueous phase was transferred to a new tube and place in speed-vac for 5 minutes at 37° C. Restriction digestion of the cDNA was performed by adding 74 µl dH$_2$O, 20 µl NEB 10×Buffer 2, 2 µl 1 mg/ml BSA, 4 µl SfiI and incubating at 50° C. for 1 hour, then adding 10 µl 1 M NaCl, 4 µl NotI and incubating an additional 37° C. for 1 hour. The reaction mix was extracted sequentially with equal volumes of phenol:chloroform (1:1) and chloroform, then cDNAs were precipitated by adding 1/100×volume 10 mg/ml glycogen, 1/30×volume 3 M sodium acetate (pH 7.5), 2×volume 100% absolute ethanol, and freezing at −80° C. for 1 hour. The cDNA pellet was washed once with 70% ethanol and air dried for 15 minutes, then solvated in 5 μl $dH_2O$, 1 μl 10×NEB Ligase Buffer, 4 μl pGD5 vector DNA previously prepared by digestion with SfiI, NotI, and CIP. 0.5 μl T4 DNA Ligase was added, and the reaction mix was incubated at 16° C. overnight. 10 μl $dH_2O$ was added to the ligation reaction and 0.5 μl was used to transform electrocompetent *E. coli* DH10B cells. Typically, 6 to 10 colonies per μl of transformed ligation mix were observed.

Example 12

Ligation of Activation Vectors to Genomic DNA and Transfection into Human Cells

Genomic DNA was harvested from a human cell line, HT1080 ($10^8$ cells), according to published procedures (Sambrook et al., *Molecular Cloning*, Cold Spring Harbor Laboratory Press, (1989)). The isolated genomic DNA was digested with BamHI under conditions that resulted in incomplete digestion. This was accomplished by titrating the amount of BamHI in the reaction. Each reaction contained 10 μg genomic DNA and BamHI at a concentration of either 0.01, 0.02, 0.04, 0.08, 0.16, 0.32, 0.64, 1.28, 2.56, 5.62, or 11.24 units. After a one hour incubation at 37° C., the reactions were stopped by phenol extraction, followed by ethanol precipition. The digested DNA from each reaction was separated by agarose gel electrophoresis. Reactions containing DNA predominantly in the range of 10 kb to 400 kb were combined for ligation to the activation vector. The pooled, digested genomic DNA was then added to BamHI linearized activation vector in 1×ligation buffer. Ligase (Life Technologies, Inc., 40 units) was added and the ligation reaction was incubated at 16° C. for 24 hours. Following ligation, the genomic DNA/activation vector was transfected into HT1080 cells using LIPOFECTIN® (Life Technologies, Inc.) according to the manufacturer's procedures. Optionally, the HT1080 cells were irradiated prior to or after transfection. When cells were irradiated, doses in the range of 0.1 rads to 200 rads were found to be particularly useful. Following transfection, cells were grown in complete media. At 36 hours post-transfection, G418 (300 μg/ml) were added to the media. At 10–14 days post selection, the drug resistant clones were pooled, expanded, and harvested. Total RNA or mRNA was collected from the harvested cells. cDNA derived from vector activated genes was then synthesized and isolated using the methods described herein (see, e.g., Example 8 supra).

Example 13

Co-transfections of BAC Contig Clones with the Activation Vector

Genomic libraries were created in pUniBAC (FIGS. 34A–34B) according to published procedures (Shizuya et al., *Proc. Natl. Acad. Sci. USA* 89:8794 (1992)). Typically, the size of genomic fragments can be between 1 kb and 500 kb, and preferably between 50 kb and 500 kb. The BAC library was propagated in *E. coli*. To prepare plasmids for transfection, the library was plated onto LB agar plates containing 12.5 μg/ml chloramphenicol. Approximately 1000 clones were present on each 150 mm plate. Following growth and selection, the colonies from each plate were eluted from the agar plate through the addition of LB and pooled. Each pool (~10,000 clones) was grown in 1 liter LB/12.5 μg/ml chloramphenicol overnight. BAC plasmids were then isolated from each pool using a commercial kit (Qiagen).

Purified BAC clones were digested with I-Ppo-I which cleaves a unique site in the BAC vector flanking the cloning site. Since I-Ppo-I is an ultra-rare cutter, it will not digest the vast majority of genomic DNA inserts. Following digestion, the linearized genomic library clones were cotransfected into HT1080 cells using LIPOFECTIN® (Life Technologies, Inc.) according to the manufacturer's directions. Briefly, 10 μg of BAC genomic DNA was combined with 1 μg of linearized pRIG20 (FIGS. 31A–31C) in α-MEM (no serum). 5 μg of LIPOFECTIN® was added to the DNA and the mixture was incubated at room temperature for 15 minutes. The DNA/LIPOFECTIN® mixture was then added to $10^5$ HT1080 cells in a 6 well dish. The cells were incubated with the DNA/LIPOFECTIN® in serum free α-MEM for 12 hours, washed, and placed in α-MEM/10% FBS for 36 hours. To select for cells that had integrated the vector and genomic DNA, the transfected cells were replated into a 10 cm dish and incubated in the presence of 300 μg/ml G418 for 10 days. Drug resistant clones were expanded and harvested to allow isolation of the activated cDNA molecules as described herein in Example 8.

Example 14

In vitro Integration of Activation Vector into Purified Genomic DNA and Transfection of the Integration Products into Host Cells Genomic DNA was isolated and cloned into the Bacterial Artificial Chromosome, pUniBAC (FIGS. 34A–34B), using published procedures (Sambrook et al., *Molecular Cloning*, Cold Spring Harbor Laboratory Press, (1989); Shizuya et al., *Proc. Natl. Acad. Sci. USA* 89:8794 (1992)). Following ligation of the genomic inserts into pUniBAC, the plasmids were transformed into the *E. coli* strain DH10B (Life Technologies, Inc.) and selected on tetracycline. Individual bacterial clones were combined into pools containing approximately 1000 members. Each pool was grown to saturation in 1 liter LB/tetracycline. pUniBAC plasmids containing genomic DNA inserts were isolated from the bacteria using a commercial kit (Qiagen).

For each pool of UniBAC clones, 2 μg of the library were incubated with 50 ng of the activation vector pRIG-T and 1 unit of mutant Tn5 transposase for 2 hours at 37° C. (transposase available from Epicentre Technologies). Following incubation, the pUniBAC clones were transformed into DH10B cells and selected on chloramphenicol. All colonies from each pool were combined and grown in 1 liter LB/chloramphenicol. Plasmids were harvested using Qiagen Tip-500 columns according to the manufacturer's instructions.

For each pool, 20 μg of the library was transfected into $2 \times 10^6$ HT1080 cells with 30 μg Ex-gen 500 (MBI Fermentas) according to the manufacturer's instructions. At 48 hours post-transfection, the cells were placed into media containing 3 μg/ml puromycin. After 10 days of growth in the presence of puromycin, drug resistant clones were pooled, expanded and harvested for gene discovery. To isolate vector activated genes, mRNA from each pool of cells was isolated, converted to cDNA, and cloned into plasmids as described in Example 8. Individual cDNA clones were analyzed by restriction digestion and sequencing.

Example 15

Creation of Protein Expression Libraries from Cloned Genomic DNA

A genomic library containing genomic DNA inserts (100 kb avg. size) was created in pUniBAC as described in Examples 13 and 14. (Note: In some embodiments of the invention, the genomic fragments are cloned into the linearization site of an activation vector, wherein the activation vector is preferably a YAC, BAC, PAC, or Cosmid based vector.) In this example, the activation vector, pRIG-TP, was integrated into the BAC genomic library using in vitro transposition as described in Example 14. pRIG-TP is shown in FIG. 36. Following integration, the library plasmids were transformed into *E. coli* and BAC vectors containing an integrated pRIG-TP vector were selected for on chloramphenicol plates. Colonies were pooled and grown to saturation in LB/Tetracycline. BAC plasmids were harvested using a commercial kit (Qiagen).

For each transfection, 20 ug of the BAC library was transfected into $2\times10^6$ HT1080 cells using 30 ug Ex-gen 500 (MBI Fermentas) according to the manufacturer's instructions. At 48 hours post transfection, the cells were placed into mdia containing 3 ug/ml puromycin. After 10 days of selection, drug resistant clones were pooled and expanded. The expaned pools of drug resistant clones were divided into separate groups for freezing, protein production, and episome amplification.

To isolate and test activated secreted proteins, culture supernatants were harvested and saved at −80° C. until used in specific assays. Activated intracellular proteins were harvested from cell lysates (prepared by any method known in the art) and used in in vitro assays.

To amplify the copy number of the BAC episomes, the cells were selected with increasing concentrations of methotrexate. In these experiments, the initial methotrexate concentration was 20 nM. Methotrexate concentrations were doubled every 7 days until cells resistant to 5 $\mu$M were obtained. At each methotrexate concentration, a portion of cells were removed for storage and protein production. Activated secreted and intracellular proteins were harvested from these cells as described for the non-methotrexate selected cells.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A eukaryotic cell in vitro comprising a vector construct, said vector construct comprising in operable linkage:

(a) a transcriptional regulatory sequence, (b) an exon comprising an exon comprising a nucleic acid sequence encoding a partial signal sequence that can complement a partial signal sequence in an endogenous cellular gene to produce a functional signal sequence, and (c) an unpaired splice donor site that defines the 3' end of the exon in (b), wherein said vector construct does not contain a targeting sequence.

2. A eukaryotic cell in vitro comprising a vector construct, said vector construct comprising operable linkage:

(a) a transcriptional regulatory sequence, (b) a nucleic acid sequence encoding a partial signal sequence that can complement a partial signal sequence in an endogenous cellular gene to produce a functional signal sequence, and (c) an unpaired splice donor site that defines the 3' end of the exon in (b), wherein said vector construct does not contain a targeting sequence, and wherein said vector construct further comprises one or more amplifiable markers.

3. The cell of claim 1, wherein said vector construct has integrated into the genome of said cell.

4. The cell of claim 2, wherein said vector construct has integrated into the genome of said cell.

5. A eukaryotic cell in vitro comprising a vector construct, said vector construct comprising in operable linkage:

(a) a transcriptional regulatory sequence, (b) an exon comprising a nucleic acid sequence encoding a partial signal sequence that can complement a partial signal sequence in an endogenous cellular gene to produce a functional signal sequence, and (c) an unpaired splice donor site that defines the 3' end of the exon in (b), wherein said vector construct does not contain a targeting sequence, wherein said vector construct has integrated into the genome of said cell, wherein said endogenous cellular gene is over-expressed in said cell by upregulation of the gene in said cell by said transcriptional regulatory sequence on said vector construct.

6. The cell of claim 1, wherein said cell is an isolated cell.

7. The cell of claim 2, wherein said cell is an isolated cell.

8. A method for making a eukaryotic cell containing a vector construct, said method comprising introducing into a eukaryotic cell in vitro a vector construct comprising in operable linkage:

(a) a transcriptional regulatory sequence, (b) an exon comprising a nucleic acid sequence encoding a partial signal sequence that can complement a partial signal sequence in an endogenous cellular gene to produce a functional signal sequence, and (c) an unpaired splice donor site that defines the 3' end of the exon in (b), wherein said vector construct does not contain a targeting sequence.

9. A method for producing an expression product of an endogenous cellular gene or portion thereof comprising:

(a) introducing into a eukaryotic cell in vitro a vector construct comprising in operable linkage:

(1) a transcriptional regulatory sequence, (2) an exon comprising a nucleic acid sequence encoding a partial signal sequence that can complement a partial signal sequence in an endogenous cellular gene to produce a functional signal sequence, and (3) an unpaired splice donor site that defines the 3' end of the exon in (2);

(b) maintaining said cell under conditions suitable for integrating said vector construct into the genome of said cell by non-homologous recombination such that the sequences of (1), (2) and (3) are opetably linked to said endogenous cellular gene; and (c) maintaining said cell produced in step (b) under conditions suitable for over-expressing, by means of said integrated transcriptional regulatory sequence, said endogenous cellular gene, or portion thereof, in said cell, thereby producing said expression product.

10. The method of claim 9, wherein said over-expressing is accomplished in vitro.

11. The method of claim 9, further comprising isolating said expression product produced by said cell following over-expression.

12. A eukaryotic cell library comprising a collection of cells in vitro transformed with a vector construct comprising in operable linkage:

(a) a transcriptional regulatory sequence, (b) an exon comprising a nucleic acid sequence encoding a partial signal sequence that can complement a partial signal sequence in an endogenous cellular gene to produce a functional signal sequence, and (c) an unpaired splice donor site that defines the 3' end of the exon in (b), wherein said vector construct is integrated into the genomes of said cells by non-homologous recombination and wherein said vector construct does not contain a targeting sequence.

13. A method of obtaining a gene product from a library of eukaryotic cells in vitro, said gene product being produced by up-regulation of an endogenous cellular gene by a vector construct comprising in operable linkage:

(a) a transcriptional regulatory sequence, (b) an exon comprising a nucleic acid sequence encoding a partial signal sequence that can complement a partial signal sequence in an endogenous cellular gene to produce a functional signal sequence, and (c) an unpaired splice donor site that defines the 3' end of the exon in (b), said method comprising screening the library of claim 12 for expression of said gene product, selecting from said library a cell that over-expresses said gene product, and obtaining said gene product produced by said selected cell.

14. The method of claim 8, further comprising introducing double strand breaks into the genome of said cell prior to or simultaneously with integration of said vector construct.

15. The method of claim 9, further comprising introducing double strand breaks into the genome of said cell prior to or simultaneously with integration of said vector construct.

16. A method for producing an expression product of an endogenous cellular gene or portion thereof in a cell comprising:

(a) introducing into at least one eukaryotic cell in vitro a vector construct comprising in operable linkage:

(1) a transcriptional regulatory sequence, (2) an exon comprising a nucleic acid sequence encoding a partial signal sequence that can complement a partial signal sequence in an endogenous cellular gene to produce a functional signal sequence, and (3) an unpaired splice donor site that defines the 3' end of the exon in (2);

(b) maintaining said cell under conditions suitable for integrating said vector construct into the genome of said cell by non-homologous recombination such that the sequences of (1), (2) and (3) are operably linked to said endogenous cellular gene;

(c) maintaining said cell produced in step (b) under conditions suitable for over-expressing said endogenous cellular gene or portion thereof in said cell by up-regulation of said gene in said cell by said transcriptional regulatory sequence; and (d) culturing said cell in serum-free medium, resulting in production of said expression product.

17. A method of identifying a protein product over-expressed by an endogenous cellular gene or portion thereof, said method comprising:

(a) introducing into at least one eukaryotic cell in vitro a vector construct comprising in operable linkage:

(1) a transcriptional regulatory sequence, (2) an exon comprising a nucleic acid sequence encoding a partial signal sequence that can complement a partial signal sequence in an endogenous cellular gene to produce a functional signal sequence, and (3) an unpaired splice donor site that defines the 3' end of the exon in (2);

(b) maintaining said cell under conditions suitable for integrating said vector construct into the genome of said cell by non-homologous recombination such that the sequences of (1), (2) and (3) are operably linked to said endogenous cellular gene;

(c) culturing said cell in serum-free medium under conditions that allow over-expression of said endogenous cellular gene or a portion thereof in said cell by up-regulation of said gene in said cell by said transcriptional regulatory sequence, thereby producing cell-conditioned media; and (d) screening said cell-conditioned media for the presence of the protein product of over-expression of said gene or portion thereof, thereby identifying said protein product.

18. The method of claim 17, further comprising concentrating said cell-conditioned media prior to screening in (d).

19. The method of any one of claims 11 and 16–18, wherein said endogenous gene encodes a transmembrane protein and wherein said method includes an assay for said transmembrane protein.

20. A vector construct comprising in operable linkage:

(a) a transcriptional regulatory sequence, (b) an exon comprising a nucleic acid sequence encoding a partial signal sequence that can complement a partial signal sequence in an endogenous cellular gene to produce a functional signal sequence, and (c) an unpaired splice donor site that defines the 3' end of the exon in (b), said vector construct further comprising one or more transposition signals.

21. A vector construct comprising in operable linkage:

(a) a transcriptional regulatory sequence, (b) an exon comprising a nucleic acid sequence encoding a partial signal sequence that can complement a partial signal sequence in an endogenous cellular gene to produce a functional signal sequence, and (c) an unpaired splice donor site that defines the 3' end of the exon in (b), said vector construct further comprising one or more viral origins of replication.

22. A vector construct comprising in operable linkage:

(a) a transcriptional regulatory sequence, (b) an exon comprising a nucleic acid sequence encoding a partial signal sequence that can complement a partial signal sequence in an endogenous cellular gene to produce a functional signal sequence, and (c) an unpaired splice donor site that defines the 3' end of the exon in (b), said vector construct further comprising one or more viral replication protein-coding sequences.

23. The vector construct of claim 21, wherein said viral origin of replication is selected from the group consisting of Epstein Barr virus ori P and SV40 ori.

24. A eukaryotic cell comprising the vector construct of claim 20.

25. A eukaryotic cell comprising the vector construct of claim 21.

26. A eukaryotic cell comprising the vector construct of claim 22.

27. The cell of any one of claims 24–26, wherein said host cell is an isolated cell.

28. A library of eukaryotic cells comprising the vector construct of claim 20.

29. A library of eukaryotic cells comprising the vector construct of claim 21.

30. A library of eukaryotic cells comprising the vector construct of claim 22.

31. A method for activation of an endogenous cellular gene in a cell comprising:

(a) transfecting a eukaryotic cell in vitro with a vector construct comprising in operable linkage:

(1) a transcriptional regulatory sequence, (2) an exon comprising a nucleic acid sequence encoding a partial signal sequence that can complement a partial signal sequence in an endogenous cellular gene to produce a functional signal sequence, and (3) an unpaired splice donor site that defines the 3' end of the exon in (2); and (b) culturing said cell under conditions suitable for non-homologous integration of said vector construct into the genome of said cell, wherein said integration results in the activation of said endogenous cellular gene in the genome of said cell by means of said transcriptional regulatory sequence.

32. A method for identifying an endogenous cellular gene containing an exon by identifying a cDNA made from an RNA expression product of that gene, said method comprising:

(a) transfecting a plurality of eukaryotic cells in vitro with a vector construct comprising in operable linkage:

(1) a transcriptional regulatory sequences, (2) an exon comprising a nucleic acid sequence encoding a partial signal sequence that can complement a partial signal sequence in an endogenous cellular gene to produce a functional signal sequence, and (3) an unpaired splice donor site that defines the 3' end of the exon in (2), wherein said vector construct does not contain a targeting sequence;

(b) culturing said cells under conditions suitable for integration of the vector construct into the genome of the host cell;

(c) selecting for cells in which said vector construct has integrated into the genomes of said cells;

(d) isolating RNA from said selected cells;

(e) producing cDNA from said isolated RNA; and (f) identifying cDNA that contains both vector and exon sequence, thereby identifying said gene containing said exon.

33. The method of claim 32, wherein said identification in (f) is accomplished by hybridizing said cDNA to sequences on the vector construct.

34. The method of claim 32, wherein said identification in (f) is accomplished by sequencing said cDNA.

35. A method for activating expression from an endogenous cellular gene comprising:

(a) introducing into a eukaryotic cell in vitro a vector construct comprising in operable linkage:

(1) a transcriptional regulatory sequence, (2) an exon comprising a nucleic acid sequence encoding a partial signal sequence that can complement a partial signal sequence in an endogenous cellular gene to produce a functional signal sequence, and (3) an unpaired splice donor site that defines the 3' end of the exon in (2);

(b) introducing DNA breaks in the chromosome of said cell prior to or following introduction of said vector construct; and (c) maintaining said cell under conditions suitable for integrating said vector construct, by non-homologous recombination, into said chromosome so as to result in the formation of an operable linkage between said transcriptional regulatory sequence on said vector construct and said endogenous cellular gene, whereby said endogenous cellular gene is activated by said transcriptional regulatory sequence on said vector construct.

36. The method of claim 35 further comprising isolating said cell after step (c).

37. The method of any of claims 8, 9, 13, 31 and 35, wherein said vector construct further comprises one or more amplifiable markers.

38. The method of any of claims 9, 10, 13, 16, 17, 18, 31 and 35, wherein said transcriptional regulatory sequence is a promoter.

39. The method of claim 38, wherein said promoter is a viral promoter.

40. The method of claim 39, wherein said viral promoter is the cytomegalovirus immediate early promoter.

41. The method of claim 38, wherein said promoter is a non-viral promoter.

42. The method of claim 38, wherein said promoter is an inducible promoter.

43. The method of any of claims 8, 9, 13, 31 and 35, wherein said cell is a mammalian cell.

44. The method of claim 43 wherein said mammalian cell is selected from the group consisting of human, murine, rat, bovine, porcine, and ovine cells.

45. The method of claim 44 wherein said mammalian cell is a human cell.

46. The method of claim 44 wherein said mammalian cell is a murine cell.

47. The method of any of claims 8, 9, 13, 31, 32 and 35, wherein said cell in vitro is in culture.

48. The cell of claim 5, wherein said vector construct further comprises one or more amplifiable markers.

49. The cell of any of claims 1, 2 or 5, wherein said transcriptional regulatory sequence is a promoter.

50. The cell of claim 49, wherein said promoter is a viral promoter.

51. The cell of claim 50, wherein said viral promoter is the cytomegalovirus immediate early promoter.

52. The cell of claim 49, wherein said promoter is a non-viral promoter.

53. The cell of claim 49, wherein said promoter is an inducible promoter.

54. The cell of any of claims 1, 2 or 5, wherein said cell is a mammalian cell.

55. The cell of claim 54 wherein said mammalian cell is selected from the group consisting of human, murine, rat, bovine, porcine, and ovine cells.

56. The cell of claim 55 wherein said mammalian cell is a human cell.

57. The cell of claim 56 wherein said mammalian cell is a murine cell.

58. A method for expressing a gene or portion thereof, comprising:

(a) obtaining genomic DNA, comprising one or more genes, or a portion of said one or more genes from one or more eukaryotic cells;

(b) introducing into a eukaryotic cell in vitro said genomic DNA and a vector construct, said vector construct comprising a transcriptional regulatory sequence that is operably linked to an exon encoding a partial signal sequence that can complement a partial signal sequence in said genomic DNA and an unpaired splice donor site that defines the 3' end of said exon;

(c) selecting for a cell containing said genomic DNA and said vector; and (d) culturing said cell under conditions suitable for expression of said gene or portion thereof, wherein said gene or portion thereof is present on said genomic DNA and said expression results from the operable linkage between said transcriptional regulatory sequence in said vector construct and said gene or portion thereof.

* * * * *

UNITED STATES PATENT AND TRADEMARK OFFICE

CERTIFICATE OF CORRECTION

PATENT NO. : 6,361,972 B1
DATED : March 26, 2002
INVENTOR(S) : John J. Harrington It is certified that error appears in the above-identified patent and that said Letters Patent is hereby corrected as shown below:

Title page,
Item [75], please delete the inventors "Bruce Shert and Stephen Rundlett."

Signed and Sealed this

Nineteenth Day of August, 2003

JAMES E. ROGAN
*Director of the United States Patent and Trademark Office*

UNITED STATES PATENT AND TRADEMARK OFFICE

CERTIFICATE OF CORRECTION

PATENT NO. : 6,361,972 B1 Page 1 of 1
DATED : March 26, 2002
INVENTOR(S) : John J. Harrington It is certified that error appears in the above-identified patent and that said Letters Patent is hereby corrected as shown below:

Title page,
Item [75], please delete the inventors "Bruce Sherf and Stephen Rundlett."

This certificate supersedes Certificate of Correction issued August 19, 2003.

Signed and Sealed this

Sixth Day of April, 2004

JON W. DUDAS
*Acting Director of the United States Patent and Trademark Office*

UNITED STATES PATENT AND TRADEMARK OFFICE

CERTIFICATE OF CORRECTION

PATENT NO. : 6,361,972 B1
DATED : March 26, 2002
INVENTOR(S) : John J. Harrington It is certified that error appears in the above-identified patent and that said Letters Patent is hereby corrected as shown below:

Column 186,
Line 62, insert -- in -- before “operable”
Line 64, insert -- an exon comprising -- before “a nucleic acid sequence”

Column 187,
Line 53, change “opetably” to -- operably --

Column 188,
Lines 38 and 63, change “at least one” to -- a --

Column 189,
Line 64, delete “host”

Column 190,
Line 28, change “sequences” to -- sequence --

Signed and Sealed this

Fifth Day of October, 2004

JON W. DUDAS
*Director of the United States Patent and Trademark Office*